US006211234B1

(12) United States Patent
Astles et al.

(10) Patent No.: US 6,211,234 B1
(45) Date of Patent: Apr. 3, 2001

(54) SUBSTITUTED PHENYL COMPOUNDS

(75) Inventors: Peter Charles Astles; Mark Francis Harper; Neil Victor Harris; Iain McFarlane McLay; Roger John Aitchison Walsh; Richard Alan Lewis; Christopher Smith; Barry Porter; Clive McCarthy, all of Dagenham (GB)

(73) Assignee: Rhone-Poulenc Rorer Limited, Eastbourne (GB)

( * ) Notice: Subject to any disclaimer, the term of this patent is extended or adjusted under 35 U.S.C. 154(b) by 0 days.

(21) Appl. No.: 08/640,922

(22) PCT Filed: Nov. 14, 1994

(86) PCT No.: PCT/GB94/02499

§ 371 Date: Jun. 27, 1997

§ 102(e) Date: Jun. 27, 1997

(87) PCT Pub. No.: WO95/13262

PCT Pub. Date: May 18, 1995

(30) Foreign Application Priority Data

Nov. 12, 1993 (GB) .................................................. 9323382
Feb. 22, 1994 (GB) .................................................. 9403363
May 27, 1994 (GB) .................................................. 9410750

(51) Int. Cl.$^7$ .......................... C07C 59/68; C07C 59/90; A61K 31/216; A61K 31/277
(52) U.S. Cl. .......................... 514/520; 514/521; 514/522; 514/568; 514/570; 558/411; 558/414; 558/415; 558/423
(58) Field of Search .................................. 514/520, 521, 514/522, 568, 570; 558/414, 411, 415, 422, 425, 423

(56) References Cited

PUBLICATIONS

Patent US 2,792,418 Filing Date Dec. 21, 1954, Issue Date May 14, 1957 Inventor Druey, Isler Title Acyl–Butyric Acids.
Patent US 3,914,166 Filing Date Nov. 29, 1954, Issue Date Oct. 21, 1975 Inventor Rudolph, Heinze, Fuhr, Schnell Title Butyric Acid Derivatives as Novel Photosensitizers.
Patent EP 0 051 819 Filing Date Oct. 29, 1981, Issue Date May 19, 1982 Inventor Shinma, Fujiu, Umeda, Ohtsuka, Ishitsuka, Suhara Title Tetra–substituierte Benzoiderivate, deren Herstellung und pharmazeutische Preparate damit.
Patent EP 0 068 250 Filing Date Jun. 12, 1982, Issue Date Jan. 5, 1983 Inventor Boshagen, Horlein, Reinhardt, Seuter, Perzborn Title Dioxybenzoletherderivate, diese enthaltende Arzneimittel, Verfahren zuihrer Herstellung und ihre Verwendung.
Patent EP 0 072 926 Filing Date Jul. 23, 1982, Issue Date Mar. 2, 1983 Inventor Jonas, Minck, Enenkel, Schliep Title 2–Aryl–imidazopyridine.

Patent US 4,590,291 Filing Date Jun. 7, 1982, Issue Date May 20, 1986 Inventor Boshagen, Horlein, Rinhardt, Seuter, Persborn Title Thrombin Inhibitory New Dihydroxybenzene Ether Derivatives.
Patent CA 1 206 964 Filing Date Oct. 20, 1981, Issue Date Jul. 2, 1986 Inventor Shinma, Fujiu, Umeda, Ohtsuka, Ishitsuka, Suhara Title Tetra–Substituted Benzene Derivatives.
Patent US 4,616,090 Filing Date Sep. 19, 1982, Issue Date Oct. 7, 1986 Inventor Jonas Title 2–Arylimidazopyridines Intermediates.
Patent EP 0 248 594 Filing Date May 28, 1987, Issue Date Dec. 9, 1987 Inventor Wachter, Ferro Title Pharmacologically active 1,5–diaryl–3–substitute–pyrazoles and method for synthesizing the same.
Patent EP 0 419 905 Filing Date Sep. 5, 1990, Issue Date Apr. 3, 1991 Inventor Abe, Okamoto, Tagami, Hibi, Nagakawa, Hirota et al. Title Quinone derivatives and pharmacological use.
Patent US 5,210,239 Filing Date Aug. 31, 1990, Issue Date May 11, 1993 Inventor Abe, Okamoto, Tagami, Hibi, Nagakawa, Hirota et al. Title Quinone Derivatives and Pharmacological Use.
Patent WO 94/02474 Filing Date Jul. 15, 1993, Issue Date Feb. 3, 1994 Inventor Bryan, Elliott Title Endothelin Receptor Antagonists.

(List continued on next page.)

*Primary Examiner*—Mukund J. Shah
*Assistant Examiner*—Deepak R. Rao
(74) *Attorney, Agent, or Firm*—Ronald G. Ort

(57) ABSTRACT

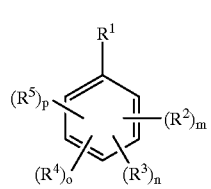

(I)

Compounds of formula (I) are described wherein $R^1$ is hydrogen, -(lower alkyl)$_q$(CO$_2$R$^6$ or OH), —CN, —C(R$^7$)=NOR$^8$, NO$_2$, —O(lower alkyl)R$^9$, —C≡C—R$^{10}$, —CR$^{11}$=C(R$^{12}$)(R$^{13}$), —C(=O)CH$_2$C(=O)CO$_2$H, —CO(R$^{14}$), alkylthio, alkylsulphinyl, alkylsulphonyl, carbamoyl, thiocarbamoyl, substituted carbamoyl, substituted thiocarbamoyl, sulphamoyl or an optionally substituted nitrogen-containing ring, m, n, o and p are independently zero or 1 and $R^2$, $R^3$, $R^4$ and $R^5$ are various groups; and physiologically acceptable salts, N-oxides and prodrugs thereof. The compounds have endothelin antagonist activity and are useful as pharmaceuticals.

20 Claims, No Drawings

OTHER PUBLICATIONS

Patent US 5,385,942 Filing Date Mar. 1, 1993, Issue Date Jan 31, 1995 Inventor Abe, Okamoto, Tagami, Hibi, Nagakawa, Hirota et al. Title Quinone Derivatives and Pharmacological Use.

Patent US 5,536,874 Filing Date Nov. 30, 1994, Issue Date Jul. 16, 1996 Inventor Sheldon, Maat, Papadogianakis Title Process for PReparing Arylacetic Acid and Arylproponic Acid Derivatives.

Patent US 5,538,991 Filing Date Sep. 14, 1994, Issue Date Jul. 23, 1996 Inventor Ashton, Chang, Greenlee Title Endothelin Antagonists Bearing 5–Membered Heterocyclic Amides.

SUBSTITUTED PHENYL COMPOUNDS

This application is a 371 of PCT/GB94/02499 filed Nov. 14, 1994.

FIELD OF THE INVENTION

This invention is directed to substituted phenyl compounds, their preparation, pharmaceutical compositions containing these compounds, and their pharmaceutical use in the treatment of disease states associated with endothelin peptides.

Endothelins are a family of peptides, mainly synthesized and released by endothelial cells. The term endothelin (ET) refers to a family of homologous 21-amino acid peptides found in three distinct isoforms: ET-1, ET-2 and ET-3, and in the present specification the term "endothelin" is intended to refer to any or all of the isoforms of endothelin. Each endothelin isopeptide is encoded by a distinct gene with a distinct chromosomal locus for each human gene.

Receptor subtypes $ET_A$ and $ET_B$ specific for endothelin have been identified (H. Arai, et al., *Nature*, 348, 730 (1990) and T. Sakurai et al., *Nature*, 348, 732 (1990)). ET-1 and ET-2 bind more potently than ET-3 to $ET_A$, and stimulation of this receptor subtype promotes vasoconstriction. ET-1, ET-2 and ET-3 bind with equal affinity to $ET_B$ receptors, and stimulation of this receptor subtype can evoke vasodilation or promote vasoconstriction.

Thus, endothelin is an important potent vasoconstrictor producing long-lasting effects in arteries and veins. Consequently, endothelin causes profound actions on the cardiovascular system in particular the coronary, renal, mesenteric and cerebral circulation. Other biological activities by endothelin are also observed. Thus, disease states associated with a physiologically detrimental excess of endothelin are treatable according to the invention.

Intravenous infusion of ET-1 to rats causes a transient hypotensive effect, followed by a sustained increase in blood pressure. Even low doses of endothelin, which alone are without pressor actions, potentiate the effects of other vasoconstrictor agents. Significantly elevated plasma immunoreactive ET-1 levels have been reported in patients with disorders such as myocardial infarction including acute myocardial infarction, coronary heart disease, unstable angina including vasospastic angina, preeclampsia, essential and pulmonary hypertension and congestive heart failure.

Renal blood vessels are particularly sensitive to the vasoconstrictor effect of ET. It produces a marked reduction in renal blood flow accompanied by reductions in glomerular filtration rate, urine volume and urinary sodium and potassium excretion. Endothelin is also mitogenic for mesangial cells. Thus, endothelin has a role in a number of renal disorders such as acute renal insufficiency and chronic renal insufficiency and cyclosporin induced nephrotoxicity. Furthermore, erythropoetin causes endothelin release and that release plays a role in renal complications and hypertension occurring as side effects in dialysis patients.

Endothelin induces a proliferative response in vascular smooth muscle cells and this, combined with observations of elevated circulating levels of ET-1 in atherosclerosis, indicates that endothelin contributes to the pathogenesis of this and related diseases. Levels of endothelin are also elevated after angioplasty and is implicated in the high level of restenosis after percutaneous transluminal angioplasty.

The cerebral vasculature is very sensitive to the pressor actions of the endothelins. A single intrathecal injection of ET-1 in dogs leads to a prolonged constriction of the basilar artery. Hypoxia and ischaemia are potent stimuli for increased release of endothelin by endothelial cells, while the secretion of endogenous vasodilators such as $PGI_2$ and endothelial derived relaxant factor are reduced. Therefore, endothelin plays an important role in cerebral ischaemia such as stroke and subarachnoid hemorrhage.

Endothelin is a potent contractor of isolated airway tissue including human bronchus. In addition, endothelin has been shown to induce eicosanoid release, possess mitogenic properties for airway smooth muscle and has pronounced inflammatory actions. All of these actions confirm an important role for endothelin in pulmonary pathophysiology and in asthma and related conditions.

Endothelin levels are elevated during septic shock and other endotoxin induced conditions such as disseminated intravascular coagulation, migraine, gastrointestinal disorders such as ulceration and irritable bowel syndrome, Raynauds disease and haemangioendothelioma.

Normal bone remodelling involves the coupling of osteoclast and osteoblast functions, an imbalance of these events leading to pathophysiological bone loss. Both cell types produce endothelin and possess endothelin receptors. Antagonists of selected actions of endothelin would therefore be useful in the treatment of clinical conditions of bone loss, such as osteoporosis.

Endothelin-1 is produced in the human prostrate and endothelin receptors have been identified in this tissue. Since endothelin is a paracrine contractile and proliferative factor in the prostrate gland, a role is indicated for endothelin in benign prostatic hyperplasia.

The further actions of endothelin on neurotransmitter release are also observed, indicating a role in certain disorders of the central nervous system.

SUMMARY OF THE INVENTION

This invention is directed to compounds useful for inhibiting the production or physiological effects of endothelin in the treatment of a patient suffering from a disease state associated with a physiologically detrimental excess of endothelin. Thus, according to a first aspect of the present invention, we provide a compound of formula I as follows:

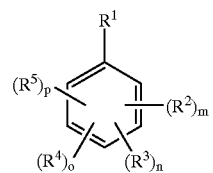

wherein
$R^1$ is hydrogen, -(lower alkyl)$_q$(CO$_2$R$^6$ or OH), —CN, —C(R$^7$)=NOR$^8$, —NO$_2$, —O(lower alkyl)R$^9$, —C≡C—R$^{10}$, —CR$^{11}$=C(R$^{12}$)(R$^{13}$), —C(=O)CH$_2$C(=O)CO$_2$H, —CO(R$^{14}$), alkylthio, alkylsulphinyl, alkylsulphonyl, carbamoyl, thiocarbamoyl, substituted carbamoyl, substituted thiocarbamoyl, sulphamoyl or an optionally substituted nitrogen-containing ring;

$R^2$ is aryl lower alkoxy, heteroaryl lower alkoxy, aryl lower alkylthio or heteroaryl lower alkylthio;

$R^3$ is hydroxy, alkoxy, aryloxy, cycloalkyl(lower alkyl)oxy, cycloalkenyl(lower alkyl)oxy, aryl lower alkoxy, heteroaryl lower alkoxy, aryl lower alkylthio, heteroaryl lower alkylthio or aralkynyl;

$R^4$ is —Y—CH($R^{15}$)(alkyl or alkenyl)$R^{16}$;

$R^5$ is alkyl, alkenyl or halo;

$R^6$, $R^7$, $R^{17}$, $R^{18}$ and $^{19}$ are independently hydrogen or alkyl;

$R^8$ is hydrogen, aralkyl or -(lower alkyl)$CO_2R^{17}$;

$R^9$ is —CN, —$CO_2R^{19}$, —$CH_2OH$, or carbamoyl;

$R^{10}$ is —$CO_2H$ or carboxyphenyl;

$R^{11}$ is hydrogen, alkyl or aralkyl;

$R^{12}$ and $R^{13}$ are independently hydrogen, —$CO_2R^{18}$, —CN, aryl lower alkyl, heteroaryl lower alkyl or —NHC(=O)aryl, provided that one of $R^{12}$ and $R^{13}$ is —$CO_2H$;

$R^{14}$ is hydrogen, alkyl, -(lower alkyl)carboxy, aralkenyl, heteroaralkenyl or carboxy;

$R^{15}$ is aryl or heteroaryl;

$R^{16}$ is carboxy or acid isostere;

Y is oxygen or carbonyl; and m, n, o, p and q are independently zero or 1, with the provisos that (i) when o is zero then m and n are both 1 (ii) when o is 1 then at least one of m and n is 1 (iii) when o is zero then $R^1$ cannot represent hydrogen, or a pharmaceutically acceptable salt, N-oxide or prodrug thereof.

DETAILED DESCRIPTION OF THE INVENTION

As used above, and throughout the description of the invention, the following terms, unless otherwise indicated, shall be understood to have the following meanings:

Definitions

"Patient" includes both human and other mammals.

"Pharmaceutically acceptable salt" means a salt form of the parent compound of formula I which is relatively innocuous to a patient when used in therapeutic doses so that the beneficial pharmaceutical properties of the parent compound of formula I are not vitiated by side-effects ascribable to a counter ion of that salt form. Pharmaceutically acceptable salt also includes a zwitterion or internal salt of the compound of formula I.

"Alkyl" means an aliphatic hydrocarbon group which may be straight or branched having about 1 to about 6 carbon atoms in the chain. Preferred alkyl groups have 1 to about 4 carbon atoms in the chain, especially 1 to about 2 carbon atoms. Branched means that one or more lower alkyl groups such as methyl, ethyl or propyl are attached to a linear alkyl chain. "Lower alkyl" means about 1 to about 4 carbon atoms in the chain which may be straight or branched. The alkyl group may be independently substituted by one or more halo, cycloalkyl or cycloalkenyl. Exemplary alkyl groups include methyl, fluoromethyl, trifluoromethyl, cyclohexylmethyl, ethyl, n-propyl, ipropyl, n-butyl, t-butyl, n-pentyl and pentafluoroethyl.

"Alkenyl" means an aliphatic hydrocarbon group containing a carbon-carbon double bond and which may be straight or branched having about 2 to about 6 carbon atoms in the chain. Preferred alkenyl groups have 2 to about 3 carbon atoms in the chain. Branched means that one or more lower alkyl groups such as methyl or ethyl are attached to a linear alkenyl chain. "Lower alkenyl" means about 2 to about 4 carbon atoms in the chain which may be straight or branched. The alkenyl group may be independently substituted by one or more halo, cycloalkyl or cycloalkenyl. Exemplary alkenyl groups include ethenyl, propenyl, n-butenyl, i-butenyl, 3-methylbut-2-enyl, n-pentenyl, hexenyl or cyclopentylethenyl.

"Alkynyl" means an aliphatic hydrocarbon group containing a carbon-carbon triple bond and which may be straight or branched having about 2 to about 6 carbon atoms in the chain. Preferred alkynyl groups have 2 to about 3 carbon atoms in the chain. Branched means that one or more lower alkyl groups such as methyl are attached to a linear alkynyl chain. "Lower alkynyl" means about 2 to about 4 carbon atoms. An exemplary alkynyl groups is ethynyl.

"Alkylenedioxy" means an —O-alkyl-O— group in which the alkyl group is as previously described. Exemplary alkylenedioxy groups include methylenedioxy and ethylenedioxy.

"Cycloalkyl" means a saturated mono- or multicyclic ring system of about 3 to about 10 carbon atoms. The cycloalkyl group may be substituted by one or more halo or alkyl. Preferred monocyciic cycloalkyl rings include cyclopentyl, fluorocyclopentyl and cyclohexyl; more preferred is cyclohexyl. Exemplary multicyclic cycloalkyl rings include 1-decalin and norbornyl.

"Cycloalkenyl" means a non-aromatic monocyclic or multicyclic ring system containing a carbon-carbon double bond and having about 3 to about 10 carbon atoms. Exemplary monocyclic cycloalkenyl rings include cyclopentenyl or cyclohexenyl; preferred is cyclohexenyl. An exemplary multicyclic cycloalkenyl ring is norbornylenyl. The cycloalkenyl group may be independently substituted by one or more halo or alkyl.

"Aryl" means aromatic carbocyclic radical containing about 6 to about 10 carbon atoms. Exemplary aryl include phenyl or naphthyl, or phenyl or naphthyl substituted with one or more aryl group substituents which may be the same or different, where "aryl group substituent" includes alkyl, preferably lower alkyl, halo for example chloro, bromo or fluoro, $CF_3$, amino, (lower alkyl)$_q CO_2 R^{11}$, carbamoyl, thiocarbamoyl, substituted carbamoyl, substituted thiocarbamoyl, nitro, cyano, alkoxy, preferably lower alkoxy, hydroxy and alkylenedioxy, where q, $R^{11}$, alkoxy, alkyl, alkylenedioxy, carbamoyl, thiocarbamoyl, substituted carbamoyl and substituted thiocarbamoyl, are as defined herein.

"Heteroaryl" means about a 5- to about a 10-membered aromatic monocyclic or multicyclic hydrocarbon ring system in which one or more of the carbon atoms in the ring system is/are element(s) other than carbon, for example nitrogen, oxygen or sulfur. The "heteroaryl" may also be substituted by one or more aryl group substituents, or aryl, heteroaryl, aralkyl or hydroxyalkyl. Exemplary heteroaryl groups include pyrazinyl, pyrazolyl, tetrazolyl, furanyl, (2- or 3-)thienyl, (2-, 3- or 4-)pyridyl, imidazoyl, pyrimidinyl, isoxazolyl, thiazolyl, isothiazolyl, quinolinyl, indolyl, isoquinolinyl, oxazolyl and 1,2,4-oxadiazolyl. Preferred heteroaryl groups include pyridyl, isothiazolyl and thienyl.

"Optionally substituted nitrogen-containing ring" means a 5- or 6-membered ring containing at least one nitrogen atom and optionally containing one or more additional heteroatoms selected from nitrogen, oxygen and sulphur in addition to the carbon atom(s) present. The ring system may be unsaturated or partially saturated and may optionally be substituted, for example by any of the groups $Y^1$, $CO_2R^{20}$ or R as defined hereinafter. Exemplary nitrogen-containing ring systems include tetrazolyl, substituted tetrazolyl, 1,2,4-oxadiazolyl, substituted isoxazolyl, isothiazolyl, substituted thiazolyl, pyrazolyl, substituted pyrazolyl, pyridyl, oxazolyl, substituted oxazolyl and dihydrooxazolyl.

"Prodrug" means a compound, for example an ester, which is convertible in vivo by metabolic means (e.g. by hydrolysis) to a compound of formula I.

"Substituted pyrazolyl" means a group of the following formula,

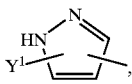

wherein $Y^1$ is hydroxymethyl, carbamoyl, substituted carbamoyl, thiocarbamoyl, substituted thiocarbamoyl or -(lower alkyl)$_k$CO$_2$R$^{20}$, wherein k is 0 or 1 and R$^{20}$ is hydrogen and alkyl, and alkyl, carbamoyl, substituted carbamoyl, thiocarbamoyl and substituted thiocarbamoyl are as defined herein. The substituted pyrazolyl may also be C- or N-substituted by lower alkyl, aryl, heteroaryl, aralkyl or -(lower alkyl)$_k$CO$_2$R$^{20}$. The substituted pyrazolyl group is preferably bonded at its 3-position to the phenyl depicted in formula I. The substituted pyrazolyl wherein R$^{17}$ is hydrogen is preferred. The $Y^1$ moiety is preferably substituted at the 5-position. Exemplary substituted pyrazolyl groups include 5-(carboxy)pyrazol-3-yl, N-methyl-5-(carboxymethyl)pyrazol-3-yl, 5-(hydroxymethyl)pyrazol-3-yl, N-phenyl-5-(carboxy)pyrazol-3-yl, N-(1- or 2-)-benzyl-5-(carboxy)pyrazol-3-yl and 2-(2-pyridyl)pyrazol-3-yl.

"Substituted isoxazolyl" means a group of the following formula,

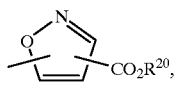

wherein R$^{20}$ is hydrogen and alkyl. The substituted isoxazolyl wherein R$^{20}$ is hydrogen is preferred. The substituted isoxazolyl is preferably bonded at its 3-position to the phenyl depicted in formula I. The carboxy moiety is preferably substituted at the 5-position.

"Substituted oxazolyl" means a group of the following formula,

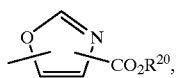

wherein R$^{20}$ is hydrogen and alkyl. The substituted oxazolyl wherein R$^{20}$ is hydrogen is preferred. The oxazolyl group is preferably bonded at its 2-position to the phenyl depicted in formula I. The carboxy moiety is preferably substituted at the 4-position.

"Substituted thiazolyl" means a group of the following formula,

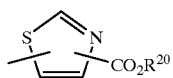

wherein R$^{20}$ is hydrogen and alkyl. The substituted thiazolyl wherein R$^{20}$ is hydrogen is preferred. The thiazolyl group is preferably bonded at its 2-position to the phenyl group depicted in formula I. The moiety —CO$_2$R$^{20}$ is preferably in the 4-position of the thiazolyl ring.

"Substituted tetrazolyl" means a group of the following formulae

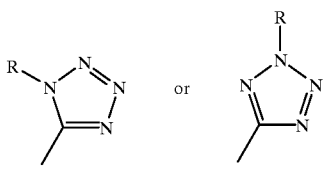

where R is alkyl, hydroxyalkyl or (lower alkyl)CO$_2$R$^{11}$, wherein alkyl and R$^{11}$ are as defined herein.

"Aralkyl" means an aryl-alkyl- group in which the aryl and alkyl are as previously described. Preferred aralkyls are aryl lower alkyls. Exemplary aralkyl groups include benzyl and phenethyl.

"Aralkenyl" means an aryl-alkenyl- group in which the aryl and alkenyl are as previously described. Preferred aralkenyls are aryl lower alkenyls. An exemplary aralkenyl group is styryl.

"Aralkynyl" means an aryl-alkynyl- group in which the aryl and alkynyl are as previously described. Preferred aralkynyls are aryl lower alkynyls. An exemplary aralkenyl group is phenylethynyl.

"Heteroaralkyl" means an heteroaryl-alkyl- group in which the heteroaryl and alkyl are as previously described. Preferred heteroaralkyls are heteroaryl lower alkyls. Exemplary heteroaralkyl groups include pyrid(2- or 3-)ylmethyl, pyrid(2- or 3-)ylethyl, thienylethyl, thienylmethyl, indol-3-ylmethyl or furylmethyl.

"Heteroaralkenyl" means an heteroaryl-alkenyl- group in which the heteroaryl and alkenyl are as previously described. Preferred heteroaralkenyls are heteroaryl lower alkenyls. An exemplary heteroaralkenyl group is 3-(2-pyridyl)prop-2-enyl.

"Alkoxy" means an alkyl-O— group in which the alkyl group is as previously described. Preferred alkoxy groups are lower alkoxy groups having 1 to about 3 carbon atoms. Exemplary alkoxy groups include methoxy, ethoxy, n-propoxy, i-propoxy, n-butoxy, t-butoxy and hexyloxy.

"Aryloxy" means an aryl-O— group in which the aryl group is as previously described. Exemplary aryloxy groups include phenoxy and naphthoxy.

"Aralkyloxy" means an aralkyl-O— group in which the aralkyl groups is as previously described. Preferred aralkyloxys are aryl lower alkoxys. Exemplary aralkyloxy groups include benzyloxy, phenylethoxy, phenylpropyloxy, (1- or 2-naphthalene)ethoxy and (o-tolyl)ethoxy; preferred are 1-phenylethoxy and 1-(o-tolyl)ethoxy.

"Heteroaralkyloxy" means an heteroaryl-alkyl-O— group in which the heteroaryl and alkyl are as previously described. Preferred heteroaralkyloxys are heteroaryl lower alkoxys. Exemplary heteroaralkyloxy groups include pyrid (2- or 3-)ylethoxy, pyrid(2- or 3-)ylmethoxy, thienylmethoxy and thienylethoxy.

"Alkylthio" means alkyl-S— in which the alkyl is as previously described. Preferred alkylthios are lower alkylthios. An exemplary alkylthio group is methylthio.

"Alkylsulphinyl means alkyl-SO— in which the alkyl is as previously described. Preferred alkylsulphinyls are lower alkylsulphinyls. An exemplary alkylsulphinyl group is methylsulphinyl.

"Alkoxycarbonyl" means an alkyl-O—CO— group. Exemplary alkoxycarbonyl groups include methoxy- and ethoxycarbonyl.

"Halo" means fluoro, chloro, bromo, or iodo. Preferred are fluoro, chloro or bromo, and more preferred are fluoro or chloro.

"Carbamoyl" means —CONH$_2$.

"Substituted Carbamoyl" means —CONY$^2$Y$^3$ in which Y$^2$ and Y$^3$ are independently hydrogen, alkyl, cyano(lower alkyl), aryalkyl, heteroaralkyl, carboxy(lower alkyl), carboxy(aryl substituted lower alkyl), carboxy(carboxy substituted lower alkyl), carboxy(hydroxy substituted lower alkyl), carboxy(heteroaryl substituted lower alkyl), carbamoyl(lower alkyl), alkoxycarbonyl(lower alkyl) or alkoxycarbonyl(aryl substituted lower alkyl), provided that only one of Y$^2$ and Y$^3$ may be hydrogen and when one of Y$^2$ and Y$^3$ is carboxy(lower alkyl), carboxy(aryl substituted lower alkyl), carbamoyl(lower alkyl), alkoxycarbonyl(lower alkyl) or alkoxycarbonyl(aryl substituted lower alkyl) then the other of Y$^2$ and Y$^3$ is hydrogen or alkyl. Preferred for Y$^2$ and Y$^3$ are independently hydrogen, alkyl, cyano(lower alkyl), aryalkyl, heteroaralkyl, carboxy(lower alkyl), carboxy(aryl substituted lower alkyl) and carbamoyl(lower alkyl).

"Thiocarbamoyl" means —CSNH$_2$.

"Substituted thiocarbamoyl" means —CSNY$^2$Y$^3$ in which Y$^2$ and Y$^3$ are as defined above.

"Alkoxycarbonyl(lower alkyl) means alkoxy-CO-lower alkyl in which the alkoxy and lower alkyl are as previously described.

"Carboxy(aryl substituted lower alkyl)" means a lower alkyl group substituted by an aryl moiety and a carboxy moiety, wherein the alkyl and aryl moieties are as defined herein.

"Alkoxycarbonyl(aryl substituted lower alkyl)" means a lower alkyl group substituted by an aryl moiety and an alkoxy moiety, wherein the alkyl, aryl and alkoxy moieties are as defined herein.

"Aryl lower alkylthio" means aryl-lower alkyl-S— in which the aryl and lower alkyl are as previously described.

"Heteroaryl lower alkylthio" means heteroaryl-lower alkyl-S— in which the heteroaryl and lower alkyl are as previously described.

"Acid isostere" means a group which is significantly ionised at physiological pH. Examples of suitable acid isosteres include sulpho, phosphono, alkylsulphonylcarbamoyl, tetrazolyl, arylsulphonylcarbamoyl or heteroarylsulphonylcarbamoyl.

Preferred Embodiments

A compound of formula I is preferred for use in treating a disease state associated with a physiologically detrimental excess of endothelin.

Disease states associated with pathological conditions that are modulated by inhibiting endothelin are also preferably treated with a compound of formula I.

According to the compound aspect of the invention, preferred compounds are described by formula I wherein $R^1$ is hydrogen, -(lower alkyl)$_q$(CO$_2$H or OH), —CN, —C(R$^7$)=NOR$^8$, —NO$_2$, —O(lower alkyl)R$^9$, —C≡C—R$^{10}$, —CR$^{11}$=C(R$^{12}$)(R$^{13}$), —C(=O)CH$_2$C(=O)CO$_2$H, —CO(R$^{14}$), alkylthio, alkylsulphinyl, carbamoyl, thiocarbamoyl, substituted carbamoyl, tetrazolyl, substituted tetrazolyl, 1,2,4-oxadiazolyl, substituted isoxazolyl, pyrazolyl, substituted pyrazolyl, pyridyl, isothiazolyl, oxazolyl, substituted oxazolyl or dihydrooxazolyl;

$R^2$ is aryl lower alkoxy or heteroaryl lower alkoxy;

$R^4$ is —O—CH(aryl)(alkyl)R$^{16}$;

$R^5$ is halo;

$R^8$ is hydrogen or -(lower alkyl)CO$_2$H;

$R^9$ is —CN, —CO$_2$H or carbamoyl;

$R^{10}$ is —CO$_2$H;

$R^{12}$ and $R^{13}$ are independently hydrogen, —CO$_2$H, —CN or —NHC(=O)aryl, provided that one of $R^{12}$ and $R^{13}$ is —CO$_2$H;

$R^{14}$ is hydrogen, alkyl, -(lower alkyl)carboxy, heteroarylalkenyl or carboxy; and m, o and p are 1 and n is zero.

According to another compound aspect of the invention, preferred compounds are described by formula I wherein $R^1$ is hydrogen, -(lower alkyl)$_q$(CO$_2$H or OH), —CN, —C(R$^7$)=NOR$^8$, —NO$_2$, —O(lower alkyl)R$^9$, —C≡C—R$^{10}$, —CR$^{11}$=C(R$^{12}$)(R$^{13}$), —C(=O)CH$_2$C(=O)CO$_2$H, —CO(R$^{14}$), alkylthio, alkylsulphinyl, carbamoyl, thiocarbamoyl, substituted carbamoyl, tetrazolyl, substituted tetrazolyl, 1,2,4-oxadiazolyl, substituted isoxazolyl, pyrazolyl, substituted pyrazolyl, pyridyl, oxazolyl, substituted oxazolyl or dihydrooxazolyl;

$R^2$ is aryl lower alkoxy or heteroaryl lower alkoxy;

$R^4$ is —O—CH(aryl)(alkyl)R$^{16}$;

$R^8$ is hydrogen, aralkyl or -(lower alkyl)CO$_2$H $R^9$ is —CN, —CO$_2$H, —CH$_2$OH, or carbamoyl;

$R^{10}$ is —CO$_2$H;

$R^{12}$ and $R^{13}$ are independently hydrogen, —CO$_2$H, —CN, or —NHC(=O)aryl, provided that one of $R^{12}$ and $R^{13}$ is —CO$_2$H;

$R^{14}$ is hydrogen, alkyl, -(lower alkyl)carboxy, heteroarylalkenyl or carboxy; and m and o are 1 and n and p are zero.

According to yet another compound aspect of the invention, preferred compounds are described by formula I wherein $R^1$ is -(lower alkyl)$_q$(CO$_2$H or OH), —CN, —C(R$^7$)=NOR$^8$, —NO$_2$, —O(lower alkyl)R$^9$, —C≡C—R$^{10}$, —CR$^{11}$=C(R$^{12}$)(R$^{13}$), —C(=O)CH$_2$C(=O)CO$_2$H, —CO(R$^{14}$), carbamoyl, thiocarbamoyl, substituted carbamoyl, tetrazolyl, substituted tetrazolyl, substituted isoxazolyl, substituted pyrazolyl or substituted oxazolyl;

$R^2$ is aryl lower alkoxy or heteroaryl lower alkoxy;

$R^3$ is hydroxy, alkoxy, aryl lower alkoxy, heteroaryl lower alkoxy or aralkynyl;

$R^8$ is hydrogen, aralkyl or -(lower alkyl)CO$_2$H;

$R^9$ is —CN, —CO$_2$H, —CH$_2$OH, or carbamoyl;

$R^{10}$ is —CO$_2$H;

$R^{12}$ and $R^{13}$ are independently hydrogen, —CO$_2$H, —CN, aryl lower alkyl, heteroaryl lower alkyl or —NHC(=O)aryl, provided that one of $R^{12}$ and $R^{13}$ is —CO$_2$H;

$R^{14}$ is hydrogen, alkyl, -(lower alkyl)carboxy, heteroarylalkenyl or carboxy;

m and n are 1; and o and p are zero.

More preferred compounds according to the present invention where o is 1 include those wherein $R^1$ is —CO$_2$H, —C≡CCO$_2$H, —C(R$^{11}$)=CHCO$_2$H, —(CH$_2$)$_2$CO$_2$H, —O(lower alkyl)CO$_2$H, —C(=O)NH(lower alkyl)CO$_2$H, (carboxy)pyrazolyl, (carboxy)(lower alkyl)pyrazolyl, (alkoxycarbonyl)pyrazolyl, —CN, —NO$_2$, (carboxy)oxazolyl, (carboxy)isoxazolyl, pyrazolyl, formyl, oxazolyl, 1,2,4-oxadiazolyl, acetyl, carboxymethoxyimino, dihydrooxazolyl, pyndyl, carboxamide, thiocarboxamide, pyridylpyrazolyl, cyano(lower alkyl)carboxamide, carboxamidopyrazolyl, isothiazolyl and oxime, wherein $R^{11}$ is hydrogen or lower alkyl. Further preferred compounds where o is 1 are those wherein $R^1$ is CN, NO$_2$, substituted pyrazolyl [e.g. (carboxy)pyrazolyl, (carboxy)(lower alkyl) pyrazolyl, (alkoxycarbonyl)pyrazolyl, pyridylpyrazolyl or carboxamidopyrazolyl], substituted oxazolyl [e.g.(carboxy)oxazolyl] and substituted isoxazolyl [e.g.(carboxy)isoxazolyl], especially where $R^1$ is CN.

More preferred compounds according to the present invention where o is zero include those wherein $R^1$ is —CO$_2$H, —C≡CCO$_2$H, —C(R$^{11}$)=CHCO$_2$H, —C(=O)

NH(lower alkyl)CO$_2$H, (carboxy)pyrazolyl, (carboxy) (lower alkyl)pyrazolyl and (carboxy)oxazolyl, wherein R$^{11}$ is hydrogen or lower alkyl.

Further preferred compounds where o is zero are those wherein R$^1$ is —C(=O)NH(lower alkyl)CO$_2$H, (carboxy) pyrazolyl and (carboxy)(lower alkyl)pyrazolyl.

According to a further compound aspect of the invention, preferred compounds where o is zero are those wherein R$^2$ and R$^3$ are substituted on the phenyl moiety at the (2- and 4-) positions relative to R$^1$.

According to a further compound aspect of the invention, preferred compounds where o is 1 are those wherein R$^2$ or R$^3$ is substituted on the phenyl moiety at the 4-position relative to R$^1$ and R$^4$ is substituted on the phenyl moiety at the 2-position relative to R$^1$; more preferred R$^2$ is substituted on the phenyl moiety at the 4-position relative to R$^1$.

According to a further compound aspect of the invention, preferred compounds where p is 1 are those wherein R$^5$ is substituted on the phenyl moiety at the ortho position relative to R$^1$.

According to another compound aspect of the invention, preferred compounds are those wherein R$^2$ and R$^3$ are independently aryl lower alkoxy or heteroaryl lower alkoxy, particularly where R$^2$ and R$^3$ are independently heteroaryl lower alkoxy. When o is 1 only one of R$^2$ and R$^3$ is preferably present.

According to another compound aspect of the invention, preferred compounds where o is 1 are those wherein R$^{15}$ is aryl; more preferably phenyl or particularly phenyl substituted at the ortho position relative to the attachment of the phenyl group to the rest of the R$^4$ moiety, and is optionally further substituted.

According to another compound aspect of the invention, preferred compounds where R$^{15}$ is a substituted phenyl include those wherein the phenyl moiety is substituted by one or more (e.g. 1, 2 or 3) substituents selected from lower alkyl (e.g. methyl), halo (e.g. chloro), CN, lower alkoxy (e.g. methoxy) or CF$_3$.

According to the compound aspect of the invention, preferred compounds where o is zero are those wherein R$^2$ is 1-(aryl)ethoxy, more preferred 1-(o-tolyl)ethoxy, and R$^3$ is benzyloxy, (3-thienyl)methoxy, (3-pyridyl)methoxy and (4-isothiazolyl)methoxy.

According to the compound aspect of the invention, preferred compounds where o is 1 are those wherein R$^2$ is heteroaryl lower alkoxy, more particularly heteroarylmethoxy. Exemplary heteroarylmethoxy groups include pyridylmethoxy (e.g. 3-pyridylmethoxy), thienylmethoxy (e.g. 3-thienylmethoxy) and isothiazolylmethoxy (e.g. 4-isothiazolylmethoxy).

According to another compound aspect of the invention, preferred compounds where o is 1 are those wherein Y is oxygen.

According to another compound aspect of the invention, preferred compounds are those wherein o is 1 and n is zero.

According to another compound aspect of the invention, preferred compounds where o is 1 are those wherein R$^4$ is —Y—CH(R$^{15}$)(C$_{1-3}$alkyl)R$^{16}$ in which Y, R$^{15}$ and R$^{16}$ are as defined hereinbefore, especially where R$^{16}$ is carboxy.

It is to be understood that the present invention is intended to cover all combinations of particular and preferred groupings as defined herein.

A particular group of compounds of the present invention are compounds of formula Ia as follows:

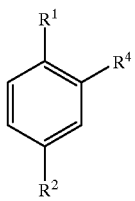

Ia wherein R$^1$, R$^2$ and R$^4$ are as defined previously.

Compounds of formula Ia in which R$^1$ represents CN, NO$_2$, substituted pyrazolyl, substituted oxazolyl, substituted isoxazolyl, and especially CN, are preferred.

Compounds of formula Ia in which R$^2$ represents heteroaryl lower alkoxy, more particularly a heteroarylmethoxy group such as pyridylmethoxy (e.g. 3-pyridylmethoxy), thienylmethoxy (e.g. 3-thienylmethoxy) and isothiazolylmethoxy (e.g. 4-isothiazolylmethoxy), are also preferred.

Compounds of formula Ia in which R$^4$ represents —OCH(R$^{15}$)(alkyl)R$^{16}$, more particularly where R$^{15}$ is aryl and R$^{16}$ is carboxy, are also preferred. Within —OCH(R$^{15}$)(alkyl)R$^{16}$, R$^{15}$ is preferably phenyl substituted in the ortho position relative to the attachment of the phenyl group to the rest of the R$^4$ moiety by a lower alkyl (e.g. methyl) or chloro substituent and is optionally further substituted by one or more halo, CF$_3$, lower alkyl, CN or lower alkoxy groups. Within —OCH(R$^{15}$)(alkyl)R$^{16}$, the alkyl portion is preferably C$_{1-3}$alkylene, more preferably —CH$_2$CH$_2$—.

A preferred group of compounds of the present invention are compounds of formula Ib:

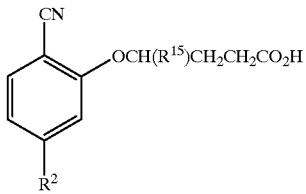

Ib wherein R$^2$ and R$^{15}$ are as defined previously. Particularly preferred are compounds of formula Ib wherein R$^2$ is heteroarylmethoxy and R$^{15}$ is aryl (e.g. phenyl substituted in the ortho position by lower alkyl such as methyl or chloro, and is optionally further substituted by one or more, e.g. 1, 2 or 3, substituents selected from halo, lower alkyl, CN, CF$_3$ and lower alkoxy).

Prefered compounds of formulae Ia and Ib above are those wherein the chiral centre associated with the carbon atom α to the oxygen atom within the R$^4$ group has the (R) configuration.

Compounds of formula Ib wherein R$^2$ is pyridylmethoxy (e.g. 3-pyridylmethoxy), thienylmethoxy (e.g. 3-thienylmethoxy) or isothiazolylmethoxy (e.g. 4-isothiazolylmethoxy) are particularly preferred.

A further particular group of compounds of the invention are compounds of formula I wherein o is 1, R$^4$ is —Y—CH (R$^{15}$)(alkyl or alkenyl)R$^{16}$ in which Y, R$^{15}$ and R$^{16}$ are as defined in formula I and the groups R$^1$, (R$^2$)$_m$, (R$^3$)$_n$ and (R$^5$)$_p$ comprise phenyl substituents wherein the central phenyl ring is substituted by one or more substituents selected from alkoxy, cycloalkyl(lower alkyl)oxy, arylalkoxy or heteroarylalkoxy and is optionally further substituted by one or more substituents selected from halogen atoms and alkyl, hydroxy, alkanoyl, cyano, carboxy, carbamoyl, alkylcarbamoyl, dialkylcarbamoyl, sulphamoyl, alkylsulphamoyl, dialkylsulphamoyl and pyrazolyl groups.

Another particular group of compounds of the invention are compounds of formula I wherein m and n are 1, o is zero, $R^1$ is -(lower alkyl)$_q$CO$_2$H, CH$_2$OH, CN, —C($R^7$)=NOH, NO$_2$, —O(lower alkyl)$R^9$, —CH≡C—$R^{10}$, —CH=C($R^{12}$)($R^{13}$), —C(=O)NH(lower alkyl)CO$_2$H, —C(=O)CH$_2$C(=O)CO$_2$H, —CO($R^{14}$), tetrazolyl, substituted tetrazolyl, substituted isoxazolyl or substituted pyrazolyl, $R^2$ is aryl lower alkoxy or heteroaryl lower alkoxy, $R^3$ is hydroxy, alkoxy, phenoxy, cycloalkyl(lower alkyl)oxy, cycloalkenyl(lower alkyl)oxy, aryl lower alkoxy or heteroaryl lower alkoxy, $R^5$ is alkyl or alkenyl, $R^7$ is hydrogen or alkyl, $R^9$ is CN, CO$_2$H, CH$_2$OH or CONH$_2$, $R^{10}$ is CO$_2$H or carboxyphenyl, $R^{12}$ and $R^{13}$ are independently hydrogen, CO$_2$H, CN, aryl lower alkyl, heteroaryl lower alkyl or NHCOaryl provided that one of $R^{12}$ and $R^{13}$ is CO$_2$H, $R^{14}$ is hydrogen, alkyl or carboxy lower alkyl, and p and q are independently zero or 1.

Particular compounds for use according to the invention are selected from the following:

A 2-Benzyloxy-4-(4-chlorobenzyloxy)benzoic acid;
B 2-Benzyloxy-4-(3-phenylpropyloxy)benzoic acid;
C 2,4-Di-(4-chlorobenzyloxy)benzoic acid;
D 2-Benzyloxy-4-(2-(3-indolyl)ethoxy)benzoic acid;
E 2-Hydroxy-4-benzyloxybenzoic acid;
F 2-(3-Phenylpropyloxy)-4-benzyloxybenzoic acid;
G 2-Benzyloxy-4-(2-naphthylmethoxy)benzoic acid;
H 2-Benzyloxy-4-(1-naphthylmethoxy)benzoic acid;
I 2-Benzyloxy-4-(3,4-methylenedioxybenzyloxy)benzoic acid;
J 2-(2-Pyridylmethoxy)-4-benzyloxybenzoic acid;
K 2-(2-Phenylethoxy)-4-benzyloxybenzoic acid;
L 2-Cyclohexylmethoxy-4-benzyloxybenzoic acid;
M 2-(4-Chlorobenzyloxy)-4-benzyloxybenzoic acid;
N 2-Benzyloxy-4-(2-phenylethoxy)benzoic acid;
O 2-Benzyloxy-4-(4-isopropylbenzyloxy)benzoic acid;
p 2-Benzyloxy-4-(4-nitrobenzyloxy)benzoic acid;
Q 2-Benzyloxy-4-(4-fluorobenzyloxy)benzoic acid;
R 4-Benzyloxy-2-(methylpropoxy)benzoic acid;
S 2-(4-Pyridylmethoxy)-4-benzyloxybenzoic acid;
T 2-Benzyloxy-4-(3,4-dichlorobenzyloxy)benzoic acid;
U 2-Benzyloxy-4-(4-methoxybenzyloxy)benzoic acid;
V 2-Benzyloxy-4-(3-methoxybenzyloxy)benzoic acid;
W 2,4-Dibenzyloxybenzoic acid;
X (E)-3-(2,4-Dibenzyloxyphenyl)prop-2-enoic acid;
Y 3-(2,4-Dibenzoyloxyphenyl)prop-2-ynoic acid;
Z N-(2,4-Dibenzyloxybenzoyl)glycine;
AA N-(4-Benzyloxy-2-(1-o-tolylethoxy)benzoyl)glycine;
AB 3-(2,4-Dibenzyloxyphenyl)-pyrazole-5-carboxylic acid;
AC 2-Benzyl-5-(4-benzyloxyphenyl)-2H-pyrazole-3-carboxylic acid;
AD 1-Benzyl-5-(4-benzyloxyphenyl)-2H-pyrazole-3-carboxylic acid;
AE 5-(2,4-Dibenzyloxyphenyl)-2H-tetrazole;
AF (Z)-2-Benzoylamino-3-(2,4-dibenzyloxyphenyl)acrylic acid;
AG (E)-2-Benzoylamino-3-(2,4-dibenzyloxyphenyl)acrylic acid;
AH E-2-Benzyl-3-(2,4-dibenzyloxyphenyl)acrylic acid;
AI (E)-3-(2,4-Dibenzyloxyphenyl)-2-cyanoacrylic acid;
AJ 3-(2,4-Dibenzyloxyphenyl)isoxazole-5-carboxylic acid;
AK 4-(2,4-Dibenzyloxyphenyl)-2,4-dioxobutanoic acid;
AL 2,4-Dibenzyloxybenzaldehyde oxime;
AM 2,4-Dibenzyloxybenzaldehyde;
AN 2,4-Dibenzyloxybenzyl alcohol;
AO 2,4-Dibenzyloxybenzonitrile;
AP 2,4-Dibenzyloxynitrobenzene;
AQ 2,4-Dibenzyloxyacetophenone;
AR 2,4-Dibenzyloxyphenol;
AS 2,4-Dibenzyloxyacetophenone oxime;
AT 2-Benzyloxy-4-phenylethynylbenzoic acid;
AU 2-(2,4-Dibenzyloxyphenoxy)ethanol hemihydrate;
AV 2-(2,4-Dibenzyloxyphenoxy)acetamide;
AW (RS)-5-(3-Benzyloxyphenyl)-5-oxo-4-phenylpentanoic acid;
AX (RS)-5-(3-Benzyloxyphenyl)-4-(2-chlorophenyl)-5-oxopentanoic acid;
AY (RS)-5-(3-Benzyloxyphenyl)-4-(2-methoxyphenyl)-5-oxopentanoic acid;
AZ (RS)-5-(3-Benzyloxyphenyl)-4-(2-methylphenyl)-5-oxopentanoic acid;
BA (RS)-5-(3-Benzyloxyphenyl)-4-(2-ethylphenyl)-5-oxopentanoic acid;
BB (RS)-5-(3-Benzyloxyphenyl)-4-(2-chloro-6-fluorophenyl)-5-oxopentanoic acid;
BC (RS)-5-(3-Benzyloxyphenyl)-4-(2,6-dichlorophenyl)-5-oxopentanoic acid;
BD (RS)-5-(3-Benzyloxyphenyl)-4-(4-methoxyphenyl)-5-oxopentanoic acid;
BE (RS)-5-(3-benzyloxyphenyl)-4-(3,4-dichlorophenyl)-5-oxopentanoic acid;
BF (RS)-5-(3-Benzyloxyphenyl)-4-(4-chlorophenyl)-5-oxopentanoic acid;
BG (RS)-5-(3-Benzyloxyphenyl)-4-(4-methylphenyl)-5-oxopentanoic acid;
BH (RS)-5-(3-Benzyloxyphenyl)-4-(3-chlorophenyl)-5-oxopentanoic acid;
BI (RS)-5-(3-Benzyloxyphenyl)-4-(3-methoxyphenyl)-5-oxopentanoic acid;
BJ (RS)-5-(4-Benzyloxyphenyl)-5-oxo-4-phenylpentanoic acid;
BK (RS)-4-(3-Benzyloxyphenyl)-4-oxo-3-phenylbutanoic acid;
BL (RS)-6-(3-Benzyloxyphenyl)-6-oxo-5-phenylhexanoic acid;
BM (RS)-7-(3-Benzyloxyphenyl)-7-oxo-6-phenylheptanoic acid;
BN (RS)-6-(3-Benzyloxyphenyl)-6-oxo-5-phenylhex-2-enoic acid;
BO (RS)-5-(3-Benzyloxyphenyl)-5-oxo-4-(2-pyridyl)pentanoic acid;
BP (3RS,4RS)-5-(3-Benzyloxyphenyl)-3-methyl-5-oxo-4-phenylpentanoic acid;
BQ (2RS,4RS)-5-(3-Benzyloxyphenyl)-2-methyl-5-oxo-4-phenylpentanoic acid;
BR (RS)-5-(3-Methoxyphenyl)-4-(2-methylphenyl)-5-oxopentanoic acid;
BS (RS)-5-[3-(2-Methoxybenzyloxy)phenyl]-5-oxo-4-phenylpentanoic acid;
BT (RS)-5-[3-(3,4-Methylenedioxybenzyloxy)phenyl]-5-oxo-4-phenylpentanoic acid;
BU (RS)-4-(2-Methylphenyl)-5-[3-(2-methylpropoxy)phenyl]-5-oxopentanoic acid;
BV (RS)-5-[3-(4-Chlorobenzyloxy)phenyl]-4-(2-methylphenyl)-5-oxopentanoic acid;
BW (RS)-5-(3-Cyclopentylmethoxyphenyl)-4-(2-methylphenyl)-5-oxopentanoic acid;
BX (RS)-5-[3-(3-Thienylmethoxy)phenyl]-4-(2-methylphenyl)-5-oxopentanoic acid;
BY (RS)-5-[3-(2-Fluorobenzyloxy)phenyl]-4-(2-methylphenyl)-5-oxopentanoic acid;
BZ (RS)-5-[3-(2-Furylmethoxy)phenyl]-4-(2-methylphenyl)-5-oxopentanoic acid;

CA (RS)-5-[3-(3-Furylmethoxy)phenyl]-4-(2-methylphenyl)-5-oxopentanoic acid;
CB (RS)-5-[3-(3-Chlorobenzyloxy)phenyl]-4-(2-methylphenyl)-5-oxopentanoic acid;
CC (RS)-5-[3-(4-Methoxybenzyloxy)phenyl]-4-(2-methylphenyl)-5-oxopentanoic acid;
CD (RS)-4-(2-Methylphenyl)-5-oxo-5-[3-(2-pyridylmethoxy)phenyl]pentanoic acid;
CE (RS)-4-(2-Methylphenyl)-5-oxo-5-[3-(2-thienylmethoxy)phenyl]pentanoic acid;
CF (RS)-5-(2-Methyl-3-benzyloxyphenyl)-4-(2-methylphenyl)-5-oxopentanoic acid;
CG (RS)-5-(3,5-Dibenzyloxyphenyl)-4-(2-methylphenyl)-5-oxopentanoic acid;
CH (RS)-5-[3-(3-Methoxybenzyloxy)phenyl]-4-(2-methylphenyl)-5-oxopentanoic acid;
CI (RS)-5-[3-(3-Aminobenzyloxy)phenyl]-4-(2-methylphenyl)-5-oxopentanoic acid;
CJ (RS)-5-[3-(3-Isothiazolylmethoxy)phenyl]-4-(2-methylphenyl)-5-oxopentanoic acid;
CK (RS)-5-(3-benzyloxy-5-hydroxyphenyl)-4-(2,3-dimethylphenyl)-5-oxopentanoic acid;
CL (RS)-5-(3-Benzyloxy-4-methylphenyl)-4-(2-methylphenyl)-5-oxopentanoic acid;
CM (RS)-4-(2-Methylphenyl)-5-oxo-5-[3-(4-pyridylmethoxy)phenyl]pentanoic acid;
CN (RS)-4-(2-Methylphenyl)-5-[3-(3-methyl-2-thienylmethoxy)phenyl]-5-oxopentanoic acid;
CO (RS)-4-(2-Methylphenyl)-5-oxo-5-[3-(3-pyridylmethoxy)phenyl]pentanoic acid;
CP (RS)-5-(3-Benzyloxyphenyl)-4-(2,5-dimethylphenyl)-5-oxopentanoic acid;
CQ (RS)-5-(3-Benzyloxy-6-hydroxyphenyl)-4-(2-methylphenyl)-5-oxopentanoic acid;
CR (RS)-5-(3-Benzyloxyphenyl)-4-(3-methylpyrid-4-yl)-5-oxopentanoic acid;
CS (RS)-5-[3-(1,2,4-Oxadiazol-3-ylmethoxy)phenyl]-4-(2-methylphenyl)-5-oxopentanoic acid;
CT Methyl (RS)-5-(3-benzyloxyphenyl)-5-oxo-4-phenylpentanoate;
CU Methyl (RS)-5-[3-(benzyloxy)phenyl]-4-(2-chlorophenyl)-5-oxopentanoate;
CV Methyl (RS)-5-[3-(benzyloxy)phenyl]-4-(2-methoxyphenyl)-5-oxopentanoate;
CW Methyl (RS)-5-[3-(benzyloxy)phenyl]-4-(2-methylphenyl)-5-oxopentanoate;
CX Methyl (RS)-5-[3-(benzyloxy)phenyl]-4-(2-ethylphenyl)-5-oxopentanoate;
CY Methyl (RS)-5-[3-(benzyloxy)phenyl]-4-(2-chloro-6-fluorophenyl)-5-oxopentanoate;
CZ Methyl (RS)-5-[3-(benzyloxy)phenyl]-4-(2,6-dichlorophenyl)-5-oxopentanoate;
DA Methyl (RS)-5-[3-(benzyloxy)phenyl]-4-(3,4-dichlorophenyl)-5-oxopentanoate;
DB Methyl (RS)-5-[3-(benzyloxy)phenyl]-4-(4-chlorophenyl)-5-oxopentanoate;
DC Methyl (RS)-5-[3-(benzyloxy)phenyl]-4-(4-methylphenyl)-5-oxopentanoate;
DD Methyl (RS)-5-[3-(benzyloxy)phenyl]-4-(3-chlorophenyl)-5-oxopentanoate,
DE Methyl (RS)-5-[3-(benzyloxy)phenyl]-4-(3-methoxyphenyl)-5-oxopentanoate;
DF Methyl (RS)-5-(4-benzyloxyphenyl)-5-oxo-4-phenylpentanoate;
DG Methyl (RS)-5-(3-benzyloxyphenyl)-5-oxo-4-(2-pyridyl)pentanoate,
DH Methyl (3RS,4RS)-5-(3-benzyloxyphenyl)-3-methyl-5-oxo-4-phenylpentanoate;
DI Methyl (2RS,4RS)-5-(3-benzyloxyphenyl)-2-methyl-5-oxo-4-phenylpentanoate;
DJ Methyl (RS)-5-[3-(2-methoxybenzyloxy)phenyl]-5-oxo-4-phenylpentanoate;
DK Methyl (RS)-5-[3-(3,4-methylenedioxybenzyloxy)phenyl]-5-oxo-4-phenylpentanoate;
DL Methyl (RS)-5-(3-benzyloxy-2-methylphenyl)-4-(2-methylphenyl)-5-oxopentanoate;
DM Methyl (RS)-5-(3,5-benzyloxyphenyl)-4-(2-methylphenyl)-5-oxopentanoate;
DN Methyl (RS)-5-(3-benzyloxy-4-methylphenyl)-4-(2-methylphenyl)-5-oxopentanoate;
DO Methyl (RS)-5-(3-benzyloxyphenyl)-4-(2,5-dimethylphenyl)-5-oxopentanoate;
DP Methyl (RS)-4-(3-benzyloxyphenyl)-4-oxo-3-phenylbutanoate;
DQ Ethyl (RS)-6-(3-benzyloxyphenyl)-6-oxo-5-phenylhexanoate;
DR Ethyl (RS)-7-(3-benzyloxyphenyl)-7-oxo-6-phenylheptanoate;
DS Ethyl (RS)-6-(3-benzyloxyphenyl)-6-oxo-5-phenylhex-2-enoate;
DT Methyl (RS)-5-[3-(4-chlorobenzyloxy)phenyl]-4-(2-methylphenyl)-5-oxopentanoate;
DU Ethyl (RS)-5-[3-(4-chlorobenzyloxy)phenyl]-4-(2-methylphenyl)-5-oxopentanoate;
DV Methyl (RS)-5-(3-cyclopentylmethoxyphenyl)-4-(2-methylphenyl)-5-oxopentanoate;
DW Methyl (RS)-4-(2-methylphenyl)-5-oxo-5-[3-(3-thienylmethoxy)phenyl]pentanoate;
DX Methyl (RS)-5-[3-(2-fluorobenzyloxy)phenyl]-4-(2-methylphenyl)-5-oxopentanoate;
DY Methyl (RS)-5-[3-(2-furylmethoxy)phenyl]-4-(2-methylphenyl)-5-oxopentanoate;
DZ Methyl (RS)-5-[3-(3-furylmethoxy)phenyl]-4-(2-methylphenyl)-5-oxopentanoate;
EA Methyl (RS)-5-[3-(3-chlorobenzyloxy)phenyl]-4-(2-methylphenyl)-5-oxopentanoate;
EB Methyl (RS)-5-[3-(4-methoxybenzyloxy)phenyl]-4-(2-methylphenyl)-5-oxopentanoate;
EC Methyl (RS)-4-(2-methylphenyl)-5-oxo-5-[3-(2-pyridylmethoxy)-phenyl]pentanoate;
ED Methyl (RS)-4-(2-methylphenyl)-5-oxo-5-[3-(2-thienylmethoxy)-phenyl]pentanoate;
EE Methyl (RS)-5-[3-(3-methoxybenzyloxy)phenyl]-4-(2-methylphenyl)-5-oxopentanoate;
EF Methyl (RS)-5-[3-(3-isothiazolylmethoxy)phenyl]-5-oxo-4-(2-methylphenyl)pentanoate;
EG Methyl (RS)-5-[3-(4-pyridylmethoxy)phenyl]-5-oxo-4-(2-methylphenyl)pentanoate;
EH Methyl (RS)-5-[3-(3-nitrobenzyloxy)phenyl]-5-oxo-4-(2-methylphenyl)pentanoate;
EI Methyl (RS)-5-[3-(3-pyridylmethoxy)phenyl]-5-oxo-4-(2-methylphenyl)pentanoate;
EJ Methyl (RS)-5-(3-methoxyphenyl)-4-(2-methylphenyl)-5-oxopentanoate;
EK Methyl (RS)-5-(3-isopropoxyphenyl)-4-(2-methylphenyl)-5-oxopentanoate;
EL Methyl (RS)-5-[3-(1,2,4-oxadiazol-3-yl-methoxy)phenyl]-4-(2-methylphenyl)-5-oxo-pentanoate;
EM Methyl (RS)-5-[3-(3-methyl-2-thienylmethoxy)-phenyl]-4-(2-methylphenyl)-5-oxopentanoate;
EN Methyl (RS)-5-[3-(3-aminobenzyloxy)phenyl]-5-oxo-4-(2-methylphenyl)pentanoate;
EO Ethyl (RS)-5-[3-benzyloxy-5-(4-methoxybenzyloxy)phenyl]-4-(2-methylphenyl)-5-oxopentanoate;
EP (RS)-5-(3-Benzyloxy-5-hydroxyphenyl)-4-(2-methylphenyl)-5-oxopentanoic acid;

EQ 5-[4-(3-Benzyloxyphenyl)-4-oxo-3-phenylbutyl]-1H-tetrazole;

ER 5-[3-(3-Benzyloxyphenyl)-3-oxo-2-(2-methylphenyl)propyl]-1H-tetrazole;

ES (RS)-4-(3-Benzyloxyphenyl)-3-(2-methylphenyl)-4-oxobutylsulphonic acid;

ET (RS)-4-[3-(3-Thienylmethoxy)phenyl]-3-(2-methylphenyl)-4-oxobutylsulphonic acid;

EU (RS)-6-(3-Benzyloxyphenyl)-5-(2-methyl-phenyl)-3,4-dihydro-1,2-oxathiine-2,2-dioxide;

EV (RS)-6-(3-(3-Thienylmethoxy)phenyl)-5-(2-methylphenyl)-3,4-dihydro-1,2-oxathiine-2,2-diocide;

EW Ethyl (RS)-4-(3-benzyloxyphenyl)-3-(2-methylphenyl)-4-oxobutylphosphonate;

EX Diethyl (RS)-4-(3-benzyloxyphenyl)-3-(2-methylphenyl)-4-oxobutylphosphonate;

EY (RS)-4-(3-Benzyloxyphenoxy)-4-phenylbutanoic acid;

EZ (RS)-4-(2-Carboxy-5-benzyloxyphenoxy)-4-phenylbutanoic acid;

FA (RS)-4-[2-(N-Ethylcarbamoyl)-5-benzyloxy-phenoxy]-4-phenylbutanoic acid;

FB (RS)-4-(2-Acetyl-5-benzyloxyphenoxy)-4-phenylbutanoic acid;

FC (RS)-4-[3-(3-Thienylmethoxy)phenoxy)]-4-phenylbutanoic acid;

FD (RS)-4-(3-Benzyloxy)phenoxy-4-(2-methylphenyl)butanoic acid;

FE (RS)-4-[2-Acetyl-5-(3-thienylmethoxy)phenoxy]-4-(2-methylphenyl)butanoic acid;

FF (RS)-4-[2-Acetyl-5-(3-thienylmethoxy)phenoxy]-4-phenylbutanoic acid;

FG (RS)-4-[2-Acetyl-5-(3-pyridylmethoxy)-phenoxy]-4-phenylbutanoic acid;

FH (RS)-4-[2-Carbamoyl-5-benzyloxyphenoxy]-4-phenylbutanoic acid;

FI (RS)-4-[2-Cyano-5-benzyloxyphenoxy]-4-phenyl-butanoic acid;

FJ (RS)-4-[2-(N,N-Dimethylcarbamoyl)-5-benzyloxyphenoxy]-4-phenylbutanoic acid;

FK (RS)-4-[2-(3-Pyrazolyl)-5-(3-thienylmethoxy)phenoxy]-4-(2-methylphenyl)butanoic acid FL (RS)-4-[2-Cyano-5-(3-thienylmethoxy)phenoxy]-4-(2-methylphenyl)butanoic acid;

FM Ethyl (RS)-4-(3-benzyloxyphenoxy)-4-phenylbutanoate;

FN Ethyl (RS)-4-(2-methoxycarbonyl-5-benzyloxyphenoxy)-4-phenylbutanoate;

FO Ethyl (RS)-4-[(3-benzyloxy)phenoxy]-4-(2-methylphenyl)butanoate;

FP Ethyl (RS)-4-[3-(3-thienylmethoxy)phenoxy]-4-phenylbutanoate;

FQ Ethyl (RS)-4-[2-acetyl-5-(3-thienylmethoxy)-phenoxy)]-4-phenylbutanoate;

FR Ethyl (RS)-4-[2-(N-ethylcarbamoyl)-5-benzyloxyphenoxy]-4-phenylbutanoate;

FS Ethyl (RS)-4-[2-acetyl-5-(3-thienylmethoxy)-phenoxy]-4-(2-methylphenyl)butanoate;

FT Ethyl (RS)-4-[2-acetyl-5-(3-pyridylmethoxy)phenoxy]-4-phenylbutanoate;

FU Ethyl (RS)-4-[2-carbamoyl-5-benzyloxyphenoxy]-4-phenylbutanoate;

FV Ethyl (RS)-4-[2-N,N-dimethylcarbamoyl-5-benzyloxyphenoxy]-4-phenylbutanoate;

FW Ethyl (RS)-4-[2-carbamoyl-5-(3-thienyl-methoxy)phenoxy]-4-(2-methylphenyl)butanoate FX Ethyl (RS)-4-(2-acetyl-5-benzyloxyphenoxy)-4-phenylbutanoate;

FY Ethyl (RS)-4-(2-cyano-5-benzyloxyphenoxy)-4-phenylbutanoate;

FZ Ethyl (RS)-4-[2-cyano-5-(3-thienylmethoxy)-phenoxy]-4-(2-methylphenyl)butanoate;

GA Ethyl (RS)-4-[2-(3-pyrazolyl)-5-(3-thienylmethoxy)phenoxy]-4-(2-methylphenyl)butanoate;

GB (R)-5-(3-Benzyloxyphenyl)-4-(2-methylphenyl)-5-oxopentanoic acid;

GC (S)-5-(3-Benzyloxyphenyl)-4-(2-methylphenyl)-5-oxopentanoic acid;

GD (R)-4-[2-Acetyl-5-(3-thienylmethoxy)phenoxy]-4-(2-methylphenyl)butanoic acid, GE (S)-4-[2-Acetyl-5-(3-thienylmethoxy)phenoxy]-4-(2-methylphenyl)butanoic acid.

GF (RS)-4-[2-Acetyl-5-(5-pyrimidinylmethoxy)phenoxy]-4-(2-methylphenyl)butanoic acid;

GG (RS)-4-(2-Methylphenyl)-4-[2-(2-pyridyl)-5-(3-thienylmethoxy)-phenoxy]butanoic acid;

GH (RS)-4-(2-Methylphenyl)-4-[2-{3-(2-pyridyl)pyrazol-5-yl}-5-(3-thienylmethoxy)phenoxy]butanoic acid;

GI (RS)-4-(2-Methylphenyl)-4-[2-thiocarbamoyl-5-(3-thienylmethoxy)-phenoxy]butanoic acid;

GJ (E)-(RS)-4-(2-Methylphenyl)-4-[2-{3-(2-pyridyl)prop-2-enoyl}-5-(3-thienylmethoxy)phenoxy]butanoic acid;

GK Ethyl (RS)-4-[2-acetyl-5-(5-pyrimidinylmethoxy)phenoxy]-4-(2-methyl-phenyl)butanoate, GL Ethyl (RS)-4-(2-methylphenyl)-4-[2-(2-pyridyl)-5-(3-thienylmethoxy)-phenoxy]butanoate;

GM Ethyl (RS)-4-(2-methylphenyl)-4-[2-{3-(2-pyridyl)pyrazol-5-yl}-5-(3-thienylmethoxy)phenoxy]butanoate;

GN Ethyl (RS)-4-(2-methylphenyl)-4-[5-(3-thienylmethoxy)-2-thiocarbamoyl-phenoxy]butanoate;

GO (RS)-4-[5-Benzyloxy-2-(methylthio)phenoxy]-4-phenylbutanoic acid;

GP (E)-(RS)-4-[5-Benzyloxy-2-(2-carboxyethenyl)phenoxy]-4-(2-methyl-phenyl)butanoic acid;

GQ (RS)-4-[2-(1-Methyl-2-carboxyethenyl)-5-(3-thienylmethoxy)phenoxy]-4-(2-methylphenyl)-butanoic acid;

GR (RS)-4-[5-Benzyloxy-2-hydroxyiminomethylphenoxy]-4-(2-methylphenyl)butanoic acid;

GS (RS)-4-[2-{N-(Carboxymethoxy)iminomethyl}-5-(3-thienylmethoxy)-phenoxy]-4-(2-methylphenyl)butanoic acid;

GT (RS,RS)-4-[2-(1-Hydroxyethyl)-5-(3-thienylmethoxy)phenoxy]-4-(2-methylphenyl)butanoic acid;

GU (RS)-4-(2-Methylphenyl)-4-[2-(propen-2-yl)-5-(3-thienylmethoxy)phenoxy]butanoic acid;

GV (RS)-4-[2-(5-Carboxy-3-pyrazolyl)-5-(3-pyridylmethoxy)phenoxy]-4-(2-methylphenyl)-butanoic acid;

GW (RS)-4-[2-(5-Carboxy-3-pyrazolyl)-5-(3-thienylmethoxy)phenoxy]-4-(2-methylphenyl)-butanoic acid;

GX (RS)-4-[2-Acetyl-5-(3-thienylmethoxy)phenoxy]-4-(2-bromophenyl)butanoic acid;

GY (RS)-4-(2-Methylphenyl)-4-[2-nitro-5-(3-thienylmethoxy)phenoxy]butanoic acid;

GZ (RS,RS)-4-(2-Methylphenyl)-4-[2-methyl-sulphinyl-5-(3-thienylmethoxy)phenoxy]butanoic acid;

HA (RS)-4-[2-Acetyl-5-(3-thienylmethoxy)-phenoxy]-4-(2-chloro-6-fluorophenyl)butanoic acid;

HB (RS)-4-(5-Benzyloxy-2-formylphenoxy)-4-(2-methylphenyl)butanoic acid;

HC (RS)-4-[2-Formyl-5-(3-thienylmethoxy)-phenoxy]-4-(2-methylphenyl)butanoic acid;

HD (RS)-4-(2-Methylphenyl)-4-[5-(3-thienylmethoxy)-2-(trifluoroacetyl)phenoxy]butanoic acid;

HE (RS)-4-(2-Methylphenyl)-4-[2-pentafluoroethyl-5-(3-thienylmethoxy)phenoxy]butanoic acid;

HF (RS)-4-[2-Cyano-3-methyl-5-(3-thienylmethoxy)phenoxy]-4-(2-methylphenyl)butanoic acid;

HG (RS)-4-[2-Carbamoyl-5-(3-thienylmethoxy)phenoxy]-4-(2-methylphenyl)butanoic acid;

HH (RS)-4-[2-{N-(3-Imidazol-1-ylpropyl)carbamoyl}-5-(3-thienylmethoxy)phenoxy]-4-(2-methylphenyl)butanoic acid;

HI (RS)-4-[2-{N-(2-Carboxyethyl)carbamoyl}-5-(3-thienylmethoxy)phenoxy]-4-(2-methylphenyl)butanoic acid;

HJ (RS)-4-[2-{N-(Carboxymethyl)carbamoyl}-5-(3-thienylmethoxy)phenoxy]-4-(2-methylphenyl)-butanoic acid;

HK (RS)-4-[2-(N-(2-Cyanoethyl)carbamoyl}-5-(3-thienylmethoxy)phenoxy]-4-(2-methylphenyl)-butanoic acid;

HL (RS)-4-[2-(5-Carboxy-1-methyl-3-pyrazolyl)-5-(3-thienylmethoxy)phenoxy]-4-(2-methylphenyl)butanoic acid;

HM (RS)-4-[2-{N-(Carbamoylmethyl)carbamoyl}-5-(3-thienylmethoxy)phenoxy]-4-(2-methylphenyl)butanoic acid;

HN (RS)-4-[2-{N-(Methoxycarbonylmethyl)-carbamoyl}-5-(3-thienylmethoxy)phenoxy]-4-(2-methylphenyl)butanoic acid;

HO Ethyl (RS)-4-[5-benzyloxy-2-(methylthio)phenoxy]-4-phenylbutanoate;

HP Ethyl (RS)-4-(2-methylphenyl)-4-[2-methylthio-5-(3-thienylmethoxy)phenoxy]butanoate;

HQ Ethyl (RS)-4-[2-acetyl-5-(3-thienylmethoxy)-phenoxy]-4-(2-chloro-6-fluorophenyl)butanoate;

HR Ethyl (RS)-4-(5-benzyloxy-2-formylphenoxy)-4-(2-methylphenyl)butanoate;

HS Ethyl (RS)-4-[2-formyl-5-(3-thienylmethoxy)-phenoxy]-4-(2-methylphenyl)butanoate;

HT Ethyl (RS)-4-[5-(3-thienylmethoxy)-2-trifluoroacetylphenoxy]-4-(2-methylphenyl)butanoate;

HU Ethyl (RS)-4-[2-carbamoyl-3-methyl-5-(3-thienylmethoxy)phenoxy]-4-(2-methylphenyl)-butanoate;

HV Ethyl (RS)-4-[2-acetyl-5-(3-thienylmethoxy)phenoxy]-4-(2-bromophenyl)butanoate;

HW Ethyl (RS)-4-(2-methylphenyl)-4-[2-nitro-5-(3-thienylmethoxy)phenoxy]butanoate;

HX Ethyl (RS)-4-[2-{N-methoxycarbonylmethyl)carbamoyl}-5-(3-thienylmethoxy)phenoxy]-4-(2-methylphenyl)butanoate;

HY Ethyl (RS)-4-[2{-(N-(3-imidazol-1-ylpropyl)carbamoyl}-5-(3-thienylmethoxy)phenoxy]-4-(2-methylphenyl)butanoate;

HZ Ethyl (RS)-4-[2-{N-(2-cyanoethyl)carbamoyl}-5-(3-thienylmethoxy)phenoxy]-4-(2-methylphenyl)-butanoate;

IA Ethyl (RS)-4-[2-{N-cyanomethyl)carbamoyl}-5-(3-thienylmethoxy)phenoxy]-4-(2-methylphenyl)-butanoate;

IB Ethyl (RS)-4-[2-{N-(2-methoxycarbonylethyl)carbamoyl}-5-(3-thienylmethoxy)phenoxy]-4-(2-methylphenyl)butanoate;

IC Ethyl (RS,RS)-4-(2-methylphenyl)-4-[2-methylsulphinyl-5-(3-thienylmethoxy)phenoxy)butanoate;

ID Ethyl (E)-(RS)-4-(2-methylphenyl)-4-[2-(2-methoxycarbonylethenyl)-5-benzyloxyphenoxy]-butanoate;

IE Ethyl (RS)-4-[2-(2-methoxycarbonyl-1-methylethenyl)-5-(3-thienylmethoxy)phenoxy]-4-(2-methylphenyl)butanoate;

IF Ethyl (RS)-4-(5-benzyloxy-2-hydroxyiminomethylphenoxy)-4-(2-methylphenyl)butanoate;

IG Ethyl (RS)-4-[2-hydroxyiminomethyl-5-(3-thienylmethoxy))phenoxy]-4-(2-methylphenyl)-butanoate;

IH (RS)-4-[2-{N-(ethoxycarbonylmethoxy)iminomethyl}-5-(3-thienylmethoxy)phenoxy]-4-(2-methylphenyl)butanoate;

II Ethyl (RS,RS)-4-[2-(1-hydroxyethyl)-5-(3-thienylmethoxy)-phenoxy]-4-(2-methylphenyl)-butanoate;

IJ Ethyl (RS)-4-(2-methylphenyl)-4-[2-(propen-2-yl)-5-(3-thienylmethoxy)phenoxy]butanoate;

IK Ethyl (RS)-4-[2-(5-ethoxycarbonyl-3-pyrazolyl)-5-(3-pyridylmethoxy)phenoxy]-4-(2-ethylphenyl)butanoate;

IL Ethyl (RS)-4-[2-(5-ethoxycarbonyl-3-pyrazolyl)-5-(3-thienylmethoxy)phenoxy]-4-(2-methylphenyl)butanoate;

IM Ethyl (RS)-4-(2-methylphenyl)-4-[2-pentafluoroethyl-5-(3-thienylmethoxy)phenoxy]-butanoate;

IN Ethyl (RS)-4-[2-cyano-3-methyl-5-(3-thienylmethoxy)phenoxy]-4-(2-methylphenyl)butanoate.

IO Methyl (RS)-4-[2-(5-methoxycarbonyl-1-methyl-3-pyrazolyl)-5-(3-thienylmethoxy)phenoxy]-4-(2-methylphenyl)butanoate;

IP (RS)-N-[4-{2-Cyano-5-(3-thienylmethoxy)-phenoxy}-4-(2-methylphenyl)butanoyl]benzenesulphonamide;

IQ (R)-4-[2-Cyano-5-(3-thienylmethoxy)phenoxy]-4-(2-methylphenyl)butanoic acid;

IR (S)-4-[2-Cyano-5-(3-thienylmethoxy)phenoxy]-4-(2-methylphenyl)butanoic acid;

IS (R)-4-[2-Cyano-5-(3-pyridylmethoxy)phenoxy]-4-(2-methylphenyl)butanoic acid;

IT Dicyclohexylammonium (R)-4-[2-cyano-5-(3-pyridylmethoxy)phenoxy]-4-(2-methylphenyl)butanoate;

IU (S)-4-[2-Cyano-5-(3-thienylmethoxy)phenoxy]-4-(2-methylphenyl)butanoic acid;

IV (RS)-5-(3-Benzylthiophenyl)-4-(2-methylphenyl)-5-oxopentanoic acid hemihydrate;

IW (RS)-4-(2-Methylphenyl)-5-oxo-(1-oxopyrid-3-ylmethoxy)pentanoic acid hemihydrate;

IX (RS)-4-[2-(Benzyloxyiminomethyl)-5-(3-thienylmethoxy)phenoxy]-4-(2-methylphenyl)butanoic acid hydrate;

IY (RS)-4-(2-Carboxycarbonyl-5-(3-thienylmethoxy)phenoxy)-4-(2-methylphenyl)butanoic acid;

IZ (R)-4-[2-Benzoyl-5-(pyridin-3-ylmethoxy)phenoxy]-4-(2-methylphenyl)butyric acid;

JA (RS)-3-[3-(3-Carboxy-1-(2-methylphenyl)propoxy)-4-nitrophenoxymethyl]benzoic acid;

JB (RS)-4-{5-[3-(2-Carboxyethyl) benzyloxy]-2-cyanophenoxy}-4-(2-methylphenyl)butanoic acid;

JC (RS)-4-[2-(4,5-Dihydrooxazol-2-yl)-5-(3-thienylmethoxy)phenoxy]-4-(2-methylphenyl)butanoic acid;

JD (RS)-4-[2-((1R)-1-Carboxy-2-phenylethylcarbamoyl)-5-(3-thienylmethoxy)-phenoxy]-4-(2-methylphenyl)butanoic acid;

JE (RS)-4-[2-((1S)-1-Carboxy-2-phenylethylcarbamoyl)-5-(3-thienylmethoxy)-phenoxy]-4-(2-methylphenyl)butanoic acid;

JF (RS)-4-[2-(Oxazol-2-yl)-5-(3-thienylmethoxy)phenoxy]-4-(2-methylphenyl)butanoic acid;

JG (RS)-2-[2-(3-Carboxy-1-(2-methylphenyl)propoxy)-4-(3-thienylmethoxy)benzoylamino]acrylic acid;

JH (RS)-4-[2-(4-Carboxyoxazol-2-yl)-5-(3-thienylmethoxy)phenoxy]-4-(2-methylphenyl)butanoic acid;
JI (RS)-4-(2-Chloro-6-fluorophenyl)-4-(2-cyano-5-(3-thienylmethoxy)phenoxy)butanoic acid;
JJ (R)-4-(2-Methylphenyl)-4-(2-nitro-5-(3-pyridylmethoxy)phenoxy)butanoic acid;
JK (RS)-4-(2-Cyano-5-(3-thienylmethoxy)phenoxy)-4-(2,5-dimethylphenyl) butanoic acid;
JL (RS)-4-(Benzo[1,3]dioxol-4-yl)-4-[2-cyano-5-(3-pyridylmethoxy)phenoxy]butanoic acid;
JM (RS)-4-[2-Cyano-5-(3-pyridylmethoxy)phenoxy]-4-(2,3-dimethylphenyl)butanoic acid;
JN (RS)-4-[2-Cyano-5-(3-pyridylmethoxy)phenoxy]-4-(5-hydroxy-2-methylphenyl)-butanoic acid;
JO (RS)-5-[2-Cyano-5-(3-thienylmethoxy)-phenoxy]-5-(2-methylphenyl)pentanoic acid;
JP (RS)-4-(2-Cyano-3-fluoro-5-(3-thienylmethoxy)phenoxy)-4-(2-methylphenyl)butanoic acid;
JQ (RS)-2,4-Dioxo-4-[2-(1-(2-methylphenyl)ethoxy)-4-(3-thienylmethoxy)phenyl]butanoic acid;
JR (RS)-4-[2-(5-Ethoxycarbonylpyrazol-3-yl)-5-(3-thienylmethoxy)phenoxy]-4-(2-methylphenyl)butanoic acid;
JS (R)-4-[2-(5-Ethoxycarbonylpyrazol-3-yl)-5-(3-pyridylmethoxy)phenoxy]-4-(2-methylphenyl)butanoic acid;
JT (R)-4-[2-(5-Carboxypyrazol-3yl)-5-(pyrid-3-ylmethoxy)phenoxy]-4-(2-methylphenyl)butanoic acid;
JU (RS)-3-(2-Cyano-5-(3-pyridylmethoxy)phenoxy)-2,2-difluoro-3-(2-methylphenyl)propanoic acid;
JV (RS)-4-[2-(5-Carboxyisoxazol-3-yl)-5-(3-thienylmethoxy)phenoxy]-4-(2-methylphenyl)butanoic acid;
JW (R)-4-[2-(5-Methoxycarbonylpyrazol-3-yl)-5-(3-pyridylmethoxy)phenoxy]-4-(2-methylphenyl)butanoic acid;
JX (R)-4-[2-(5-Carbamoylpyrazoly-3-yl)-5-(3-pyridylmethoxy)phenoxy]-4-(2-methylphenyl)butanoic acid;
JY (RS)-4-[(2-Acetyl-5-(3-thienylmethoxy)phenoxyl]-4-(2-cyanophenyl)butanoic acid;
JZ (R)-4-[(2-Cyano-5-(isothiazol-4-ylmethoxy)phenoxy]-4-(2-methylphenyl)butanoic acid;
KA 3-(2,4-Dibenzyloxy)phenyl propanoic acid;
KB 2,4-Dibenzyloxyphenoxyacetic acid;
KC (R)-4-[2-Nitro-5-(thiophen-3-ylmethoxy)phenoxy]-4-(2-methylphenyl)butyric acid;
KD (R,S)-N-{4-[2-Cyano-5-(thiophen-3-ylmethoxy)phenoxy]-4-(2-methylphenyl)butyryl}methane sulphonamide;
KE (R,S)-N-{4-[2-Cyano-5-(thiophen-3-ylmethoxy)phenoxy]-4-(2-methylphenyl)butyryl}trifluoromethane sulphonamide;
KF (R,S)-4-[2-(3-Carboxypropionyl)-5-(thiophen-3-ylmethoxy)phenoxy]-4-(2-methylphenyl)butyric acid;
KG (R,S)-4-[2-(1,2,4-Oxadiazol-3-yl)-5-(thiophen-3-ylmethoxy)phenoxy]-4-(2-methylphenyl)butyric acid; and
KH (R,S)-4-[2-(Thiazol-2-yl)-5-(thiophen-3-ylmethoxy)phenoxy]-4-(2-methylphenyl)butyric acid.

The letters A to KH are allocated to compounds for easy reference in this specification.

Preferred species according to the invention are those identified hereinbefore as compounds FE, FK, FL, GG, GH, GI, GJ, GS, GV, GW, GY, HA, HC, HF, HG, HI, HJ, HK, HL, HM, HN, IQ, IS, IY, JC, JF, JG, JH, JI, JJ, JK, JL, JM, JO, JP, JQ, JR, JS, JT, JV, JW, JX, JZ, KC, KD, KE, KF, KG and KH, and their pharmaceutically acceptable salts, N-oxides and prodrugs.

Especially preferred according to the invention is that species identified hereinbefore as compound IS and its pharmaceutically acceptable salts, N-oxide and prodrugs.

Compounds of formula I may be prepared by the application or adaptation of known methods, which means methods used heretofore or described in the literature.

Thus, according to a feature of the present invention, compounds of formula I containing a carboxy moiety are prepared by hydrolysis of the corresponding compound of formula I containing an alkoxycarbonyl moiety. The hydrolysis may be by alkaline hydrolysis using a base, such as alkali hydroxide or carbonate, for example, NaOH, LiOH, KOH or $K_2CO_3$, in the presence of an aqueous/organic solvent mixture, using organic solvents such as dioxan, THF or methanol, at a temperature from about ambient to about reflux. The hydrolysis may also be by acid hydrolysis using an inorganic acid, such as HCl, in the presence of an aqueous/inert organic solvent mixture, using organic solvents such as dioxan, THF, at a temperature from about 50° C. to about 80° C. or where alkoxy moiety of the alkoxycarbonyl (ester) group is t-butoxy then one may use trifluoroacetic acid at about ambient temperature.

According to a further feature of the present invention, compounds of formula I, wherein $R^1$ is —C≡$CO_2$H, and $R^2$, $R^3$, $R^4$, $R^5$, m, n, o and p are as hereinbefore defined, are prepared by the reaction of compounds of the formula II,

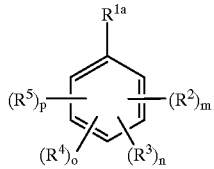

II wherein $R^{1a}$ is —CH=$CBr_2$, and $R^2$, $R^3$, $R^4$, $R^5$, m, n, o and p are as hereinbefore defined, with n-butyl lithium in an inert solvent, such as tetrahydrofuran, at about −70° C., followed by reaction with carbon dioxide at about −40° C.

According to a further feature of the present invention, compounds of formula I substituted by a carbamoyl or substituted carbamoyl group are prepared by the reaction of compounds of the formula I having the corresponding alkoxycarbonyl (ester) group with concentrated aqueous ammonium hydroxide solution or the appropriate alkylamine, dialkylamine or aminoalkanol, optionally in an inert organic solvent, such as methanol, or aqueous mixture thereof, preferably at a temperature from about 0° C. to about reflux temperature, and optionally under high pressure. Alternatively compounds of formula I substituted by a carbamoyl group are prepared by the reaction of compounds of the formula I having the corresponding carboxy group with an inorganic halogenating agent, such as $SOCl_2$, $PCl_3$, $PBr_3$ or $PCl_5$ to form the corresponding acid halide (—COX, wherein X' is halo, preferably chloro or bromo), which is then reacted with $NH_3$ preferably in the presence of a base such as potassium carbonate or a tertiary amine, such as triethylamine or pyridine, optionally in an inert solvent, for example dichloromethane, dimethylformamide, or an ether, such as diethyl ether or tetrahydrofuran, preferably at a temperature from about 0° C. to about reflux temperature. Alternatively, an acid halide wherein X' is chloro is prepared by reacting oxaiyl chloride with a carboxy moiety. The reaction preferably takes place in an inert solvent, such as methylene chloride, at a temperature from about 0° C. to about reflux.

According to a further feature of the present invention, compounds of formula I, wherein $R^1$ is —C≡$CR^{10}$, and $R^2$, $R^3$, $R^4$, $R^5$, m, n, o and p are as hereinbefore defined, are prepared by hydrolyzing the ester product of the reaction of compounds of formula III,

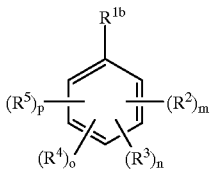

III wherein $R^{1b}$ is iodo, and $R^2$, $R^3$, $R^4$, $R^5$, m, n, o and p are as hereinbefore defined, with compounds of the formula IV $R^{10a}Q^1$   IV wherein $R^{10a}$ is alkoxycarbonyl or alkoxycarbonylphenyl, and $Q^1$ is ethynyl. Preferably the reaction is carried out with the aid of a catalyst, such as tetrakis(triphenylphosphine) palladium, and cuprous iodide, preferably with the aid of a base such as a tertiary amine, such as triethylamine, preferably in a solvent such as dimethylformamide, at a temperature from about room temperature to about 100° C.

As another example, compounds of formula I wherein $R^1$ contains or is a -alkylOH moiety, are prepared by the reduction of the corresponding compounds of formula I wherein $R^1$ contains or is an alkoxycarbonyl or formyl or acetyl moiety by reaction with an alkali metal hydride, such as lithium aluminum hydride or sodium borohydride respectively, preferably in an inert solvent, such as tetrahydrofuran or methanol, preferably at about room temperature.

According to a further feature of the present invention, compounds of formula I wherein $R^1$ is —CH=CHCO$_2$H are prepared by the reaction of compounds of formula I wherein $R^1$ is —CHO with diethyl phosphonoacetic acid in the presence of a base such as sodium hydride or n-butyl lithium. The reaction preferably takes place in an inert solvent, such as tetrahydrofuran, at a temperature from about -70° C. to about room temperature. Alternatively compounds of formula I wherein $R^1$ is —CH=CHCO$_2$H are prepared by the reaction of compounds of formula I. wherein $R^1$ is —CHO with malonic acid in the presence of a base such as piperidine in a solvent such as pyridine, at a temperature from about 50 to about 200° C.

According to a further feature of the present invention, compounds of formula I wherein $R^1$ is -alkenyl (carbonylalkoxy or alkyl) are prepared by the reaction of compounds of formula I, wherein $R^1$ is —CHO or —C(alkyl)=O with a compound of the formula V $[(Q^2)_3PCH_2Q^3]^+X^-$   V wherein $Q^2$ is aryl, such as phenyl, $Q^3$ is (alkoxycarbonyl- or alkyl) and X is halo, preferably bromo, with a base such as an alkali metal alkoxide, such as potassium t-butoxide. The reaction is preferably carried out in an inert solvent, such as tetrahydrofuran, at a temperature from about 0° C. to about reflux temperature. The alkoxycarbonyl moiety of the —CH=CH(carbonylalkoxy) group formed according to this method may be hydrolyzed to the corresponding —CH=CHCO$_2$H group as described herein.

Alternatively, compounds of formula I as described herein except for comprising hydroxy or carboxy moieties, are prepared by reacting compounds of the formula VIIa

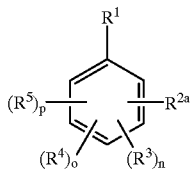

VIIa wherein $R^{2a}$ is hydroxy, wherein $R^1$ and $R^3$ are as described herein except for being or having thereon hydroxy or carboxy moieties, and $R^4$ is as described herein except for having thereon hydroxy moieties or acidic hydrogen atoms, such as carboxy, phosphonic or sulphonic groups, and $R^5$, n, o, and p are as described herein, with compounds of formula VIIIa $Q^4OH$   VIIIa wherein $Q^4$ is aryl lower alkyl or heteroaryl lower alkyl except for having thereon hydroxy or carboxy moieties. The reaction is carried out in the presence of a triarylphosphine, such as triphenylphosphine, and a dialkyl ester, such as the diisopropyl or diethyl ester, of azodicarboxylic acid, preferably in an inert solvent such as tetrahydrofuran, preferably at a temperature from about 0° C. to about room temperature.

Alternatively, compounds of formula I as described herein except for comprising hydroxy or carboxy moieties, are prepared by reaction with compounds of the formula VIIa as described herein, with compounds of formula IXa $Q^4X$   IXa wherein $Q^4$ is as described herein but with the exclusion of moieties containing hydroxy groups, or acidic hydrogen atoms, such as in carboxy groups, and X is a leaving group, such as halo or alkylsulphonyloxy, such as methanesulphonyloxy, or arylsulphonyloxy, such as p-toluenesulphonyloxy. The reaction is carried out in the presence of a base, such as sodium hydride or alkali metal alkoxide, such as potassium tert-butoxide, in an inert solvent, such as a ketone, such as acetone or methyl ethyl ketone, or a dipolar aprotic solvent, such as dimethylformamide, at a temperature from about room temperature to about 100° C. Additionally, since VIIa may have a mercapto group in place of the free hydroxyl of $R^{2a}$, as described herein regarding introduction of mercapto moieties on phenyl groups, regarding introduction of mercapto moieties, then the reaction of VIIa bearing such a mercato group with $Q^4X$ would result in the introduction of a $Q^4S$— moiety, for example benzylthio, in place of $R^{2a}$.

Compounds of formula I, wherein $R^1$ is as described herein except for comprising hydroxy or carboxy moieties, are prepared by reacting compounds of the formula VIIb

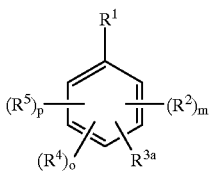

VIIb wherein $R^{3a}$ is hydroxy, wherein $R^1$ and $R^2$ are as described herein except for having thereon hydroxy or carboxy moieties, and $R^4$ is as described herein except for having thereon hydroxy moieties or acidic hydrogen atoms, such as in carboxy, phosphonic or sulphonic groups, and $R^5$, o, and p are as described herein, with compounds of formula VIIIb $$Q^5OH \qquad\qquad VIIIb$$

wherein $Q^5$ is alkyl, cycloalkyl(lower alkyl), cycloalkenyl (lower alkyl), aryl lower alkyl or heteroaryl lower alkyl except for having thereon hydroxy or carboxy moieties. The reaction is carried out in the presence of a triarylphosphine, such as triphenylphosphine, and a dialkyl ester, such as the diisopropyl or diethyl ester, of azodicarboxylic acid, preferably in an inert solvent such as tetrahydrofuran, preferably at a temperature from about 0° C. to about room temperature.

Alternatively, compounds of formula I as described herein except for comprising hydroxy or carboxy moieties, are prepared by reaction with compounds of the formula VIIa as described herein, with compounds of formula IXb $$Q^5X \qquad\qquad IXb$$

wherein $Q^5$ is as described herein but with the exclusion of moieties containing hydroxy groups, or acidic hydrogen atoms, such as in carboxy groups, and X is a leaving group, such as halo or alkylsulphonyloxy, such as methanesulphonyloxy, or arylsulphonyloxy, such as p-toluenesulphonyloxy. The reaction is carried out in the presence of a base, such as sodium hydride or alkali metal alkoxide, such as potassium tert-butoxide, in an inert solvent, such as a ketone, such as acetone or methyl ethyl ketone, or a dipolar aprotic solvent, such as dimethylformamide, at a temperature from about room temperature to about 100° C. Additionally, since VIIb may have a mercapto group in place of the free hydroxyl of $R^{3a}$, as described herein regarding introduction of mercapto moieties on phenyl groups, then the reaction of VIIA bearing such a mercato group with $Q^5X$ would result in the introduction of a $Q^5S$— moiety, for example benzylthio, in place of $R^{3a}$.

Alternatively, compounds of formula I as described herein except for comprising hydroxy or carboxy moieties, are prepared by reacting compounds of the formula VIIc VIIc

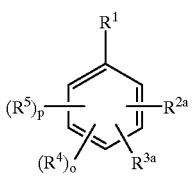

wherein $R^{2a}$ and $R^{3a}$ are hydroxy, wherein $R^1$ is as described herein except for being or having thereon hydroxy or carboxy moieties, and $R^4$ is as described herein except for having thereon hydroxy moieties or acidic hydrogen atoms, such as carboxy, phosphonic or sulphonic groups, and $R^5$, o, and p are as described herein, with compounds of formula IXa $$Q^4X \qquad\qquad IXa$$

wherein $Q^4$ is as described herein but with the exclusion of moieties containing hydroxy groups, or acidic hydrogen atoms, such as in carboxy groups, and X is a leaving group, such as halo or alkylsulphonyloxy, such as methanesulphonyloxy, or arylsulphonyloxy, such as p-toluenesulphonyloxy. The reaction is carried out in the presence of a base, such as sodium hydride or alkali metal alkoxide, such as potassium tert-butoxide, in an inert solvent, such as a ketone, such as acetone or methyl ethyl ketone, or a dipolar aprotic solvent, such as dimethylformamide, at a temperature from about room temperature to about 100° C. Additionally, since VIIc may have a mercapto group in place of the free hydroxyls of $R^{2a}$ and/or $R^{3a}$, as described herein regarding introduction of mercapto moieties on phenyl groups, then the reaction of VIIc bearing such a mercato group with $Q^4X$ would result in the introduction of a $Q^5S$— moiety, for example benzylthio, in place of $R^{3a}$ and/or $R^{2a}$.

Thus, according to a feature of the present invention, compounds of formula I, as hereinbefore defined but with the exclusion of groups having thereon hydroxy moieties or acidic hydrogen atoms, such as carboxy, phosphonic or sulphonic groups, are prepared by the reaction of compounds of formula X

X

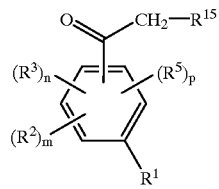

wherein $R^1$, $R^2$, $R^3$, $R^5$, $R^{15}$, m, n and p are as hereinbefore defined but with the exclusion of groups being or having thereon hydroxy moieties or acidic hydrogen atoms, such as carboxy groups, with compounds of formulae XI or XII $$X^1\text{-(alkyl)-}R^{16a} \qquad\qquad XI$$

or $$X^1\text{—}CH_2\text{—}(C_{2\text{-}5}\text{ alkenyl})\text{—}R^{16a} \qquad\qquad XII$$

wherein $X^1$ is halo, such as chloro or, preferably, bromo, and $R^{16a}$ is esterified carboxy, in the presence of an alkali metal alkoxide, such as potassium tert-butoxide. The reaction preferably takes place in an inert solvent, such as tetrahydrofuran, at temperatures from about −40° C. to about reflux.

According to a further feature of the present invention, compounds of formula I, as hereinbefore defined but with the exclusion of groups having thereon hydroxy moieties or acidic hydrogen atoms, such as carboxy, phosphonic or sulphonic groups, are prepared by the reaction of compounds of formula X with compounds of formulae XIII $$CH_2\text{=}CH\text{—}R^{16b} \qquad\qquad XIII$$

wherein $R^{16b}$ represents esterified carboxy, sulphonic or phosphonic, in the presence of a base, for example an alkali metal alkoxide, such as potassium tert-butoxide. The reaction preferably takes place in an inert solvent, such as tetrahydrofuran, at temperatures from about room temperature to about reflux.

Compounds of formula I, wherein $R^1$ is as described herein except for comprising hydroxy or carboxy moieties, are prepared by reacting compounds of the formula VIId

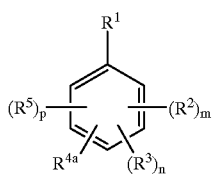

VIId wherein $R^{4a}$ is hydroxy, wherein $R^1$, $R^2$ and $R^3$ are as described herein except for being or having thereon hydroxy or carboxy moieties, and $R^5$, m, n and p are as described herein, with compounds of formula XIV

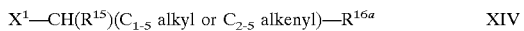

XIV wherein $X^1$ is a leaving group, such as halo or alkylsulphonyloxy, such as methanesulphonyloxy, or arylsulphonyloxy, such as p-toluenesulphonyloxy, and $R^{15}$ and $R^{16a}$ are as herein defined, in the presence of an alkali metal alkoxide, such as potassium tert-butoxide. The reaction preferably takes place in an inert solvent, such as a ketone, such as acetone or methyl ethyl ketone, or a dipolar aprotic solvent, such as dimethylformamide, at a temperature from about room temperature to about reflux.

Compounds of formula I, wherein $R^1$ is as described herein except for being or having thereon a OH, $CO_2H$ or NH group, may be prepared by reacting compounds of formula VIId wherein $R^{4a}$ is hydroxy, with compounds of formula XIVa

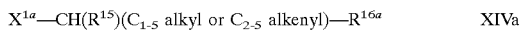

XIVa wherein $X^{1a}$ is hydroxy and $R^{16a}$ is esterified carboxy. The reaction is carried out in the presence of a triarylphosphine, such as triphenylphosphine, and a dialkyl ester, such as diisopropyl or diethyl ester, of azodicarboxylic acid, preferably in an inert solvent, such as tetrahydrofuran, preferably at a temperature from about 0° C. to about room temperature. The reaction may be particularly suitable for the preparation of compounds with defined chirality at the carbon to which $R^{15}$ is attached.

Compounds of formula I, wherein $R^1$ is as described herein may also be prepared by reacting compounds of formula VIId wherein $R^{4a}$ is fluorine with alkali metal salts of compounds of formula XIVa wherein $X^{1a}$ is hydroxy and $R^{16a}$ is carboxy or esterified carboxy. The reaction preferably takes place in an inert solvent such as THF at a temperature between about room temperature and the reflux temperature. The reaction may be particularly suitable for the preparation of compounds with defined chirality at the carbon to which $R^{15}$ is attached.

Compounds of formula XIVa, where $X^{1a}$ is hydroxy and $R^{16a}$ is $CO_2tBu$, and with defined chirality at the carbon to which $R^{15}$ is attached, may be prepared by reduction of the corresponding ketones with bis[(1S,2R,3S,5S)-pinan-3-yl]chloroborane, or bis[(1R,2R,3R,5R)-pinan-3-yl]chloroborane, in an inert solvent, such as diethyl ether, at a temperature between about −40° C. and about room temperature.

According to a further feature of the present invention, compounds of formula I, wherein $R^1$ or $R^2$ is tetrazolyl, are prepared by the reaction of the corresponding compounds of formula I, wherein $R^1$ or $R^{16}$ is —CN, with a source of trimethyltin azide, such as sodium azide and trimethyltin chloride, in an inert solvent, such as toluene, preferably at about the reflux temperature.

According to a further feature of the present invention, compounds of formula I containing an amino moiety, are preferably prepared by the reduction of the corresponding compounds of formula I containing a nitro moiety. When compounds of formula I contain alkyl moieties rather than alkenyl or alkynyl moieties, the reduction is preferably carried out by means of catalytic hydrogenation, such as using a palladium on carbon catalyst. Preferably the reaction is carried out in an inert solvent, such as an alkyl alkanoate ester, at or near room temperature. When the starting material of formula I contains an ester moiety, the ester used as reaction medium is preferably chosen so as to avoid transesterification, such as methyl esters of formula I are preferably reduced in a solvent which is a methyl ester, such as methyl acetate. When the compound of formula I contains an alkenyl or alkynyl moieties, the reduction is preferably carried out in a system such as iron and hydrochloric acid, in the presence of a solvent such as an alkanol. When the starting material of formula I is an ester, the alkanol used as reaction medium is preferably chosen so as to avoid transesterification, such as methyl esters of formula I are preferably reduced in the presence of methanol and ethyl esters of formula I are preferably reduced in the presence of ethanol.

According to a further feature of the present invention, compounds of formula I containing a hydroxyaryl group are prepared from the corresponding compounds of formula I containing an arylmethoxy group, such as a p-methoxybenzyloxy group, by reaction with 2,3-dichloro-5,6-dicyano-1,4-benzoquinone in an inert solvent system, such as dichloromethane and tert-butanol, preferably in the presence of a buffer (pH about 6 to 8), such as a phosphate buffer, preferably at about room temperature, or are prepared from the corresponding compounds of formula I containing an arylmethoxy group such as a benzyloxy group instead of the said hydroxy group, by hydrogenolysis, for example in solution in a mixture of an alkanol and an alkyl alkanoate ester, containing dilute hydrochloric acid, in the presence of a catalyst of palladium on carbon. When the starting material of formula I is an ester, the alkanol and ester used as reaction medium are preferably chosen so as to avoid transesterification, such as methyl esters of formula I are preferably hydrogenolysed in a solvent which is a mixture of methanol and a methyl ester, such as methyl acetate.

According to a further feature of the present invention, compounds of general formula I containing a cyano group are prepared from the corresponding compounds of formula I containing a carbamoyl group by heating with an alkanoic acid anhydride, such as acetic anhydride.

According to a further feature of the present invention, compounds of general formula I containing a pyrazolyl group are prepared from the corresponding compounds of formula I containing an alkylcarbonyl group, such as acetyl group, by reaction with an alkyl formate, such as ethyl formate, in the presence of sodium hydride, followed by treatment with dilute hydrochloric acid and then with hydrazine hydrate.

According to a further feature of the present invention, for preparing compounds of formula I wherein $R^1$ contains a substituted carbamoyl having the nitrogen thereof substituted by a cyano(lower alkyl), aryalkyl, heteroaralkyl, alkoxycarbonyl(lower alkyl) or alkoxycarbonyl(aryl substituted lower alkyl) moiety may be prepared by reacting the corresponding compounds of formula I wherein $R^1$ contains a carboxy moiety with cyano(lower alkyl)$NH_2$, such as aminopropionitrile, aryalkyl$NH_2$, such as benzylamine, heteroaralkyl$NH_2$, such as aminomethyl-pyridine, alkoxycarbonyl(lower alkyl)$NH_2$, such as glycine methyl ester, or alkoxycarbonyl(aryl substituted lower alkyl)$NH_2$, such as phenylalanine ethyl ester, in the presence of an activating agent such as 1-(3-dimethylamino-propyl)-3-ethylcarbodiimide in an inert solvent such as dimethylformamide, and preferably takes place in the presence of a catalyst, such as 1-hydroxy-benzatriazole, at a temperature from about 0° C. to about 60° C.

Alternatively, according to a further feature of the present invention, compounds of formula I wherein $R^1$ contains a substituted carbamoyl having the nitrogen thereof substituted by a cyano(lower alkyl), aryalkyl, heteroaralkyl, alkoxycarbonyl(lower alkyl) or alkoxycarbonyl(aryl substituted lower alkyl) moieties may be prepared by reacting the corresponding compounds of formula I wherein $R^1$ contains a carboxy moiety that is converted to an acid halide as hereinbefore described, with cyano(lower alkyl)$NH_2$, aryalkyl$NH_2$, heteroaralkyl$NH_2$, alkoxycarbonyl(lower alkyl)$NH_2$ or alkoxycarbonyl(aryl substituted lower alkyl) $NH_2$, in the presence of a base, such as triethylamine in an inert solvent, such as dichloromethane, at a temperature from about 0° C. to about reflux.

According to a further feature of the present invention, for preparing compounds of formula I wherein $R^{16}$ is arylsulphonylcarbamoyl or heteroarylsulphonylcarbamoyl may be prepared by reacting the corresponding compounds of formula I wherein $R^{16}$ is carboxy with an activating agent such as N,N-carbonyldiimidazole in an inert solvent such as dichloromethane followed by reaction with an arylsulphonamide, alkylsulphonamide or heteroarylsulphonamide in dimethylformamide at or near room temperature.

Compounds of formula I, wherein $R^1$ is alkoxycarbonylpyrazolyl, and preferably Y is an oxygen atom and carboxy moieties thereon are esterified, are prepared by reaction of compounds of the formula I, wherein $R^1$ —C(=O)$CH_3$, and preferably Y is an oxygen atom and carboxy moieties thereon are esterified, with diethyl oxalate, in an inert solvent, such as toluene, in the presence of an alkali metal hydride, such as sodium hydride, or an alkali metal alkoxide, such as potassium ethoxide, at temperatures from room temperature to about reflux temperature, to prepare compounds of formula I wherein $R^1$ is —COCH$_2$COCO$_2$alkyl, which may be treated as a crude product with hydrazine hydrate in an inert solvent such as ethanol and in the presence of acetic acid, at a temperature from about ambient to about reflux to yield the alkoxycarbonylpyrazole. The pyrazolyl nitrogen atom may be further substituted by reacting it with a lower alkyl halide or aralkyl halide or a lower alky ester of a haloalkanoic acid, e.g. ethyl bromoacetate, in an inert solvent, such as DMF or THF, in the presence of base, such as potassium carbonate or sodium hydride, at temperatures between room temperature and the reflux temperature.

According to a further feature of the present invention compounds of formula I wherein $R^1$ is oxazolyl or alkoxycarbonyloxazolyl, and preferably Y is an oxygen atom and carboxy moieties thereon are esterified, may be prepared by the oxidation of the corresponding dihydrooxazole or alkoxycarbonyldihydrooxazole, with nickel peroxide or 2,3-dichloro-5,6-dicyanobenzoquinone, in an inert solvent, such as toluene, at a temperature at or about reflux.

Compounds of formula I or VIId wherein $R^1$ is dihydrooxazole or alkoxycarbonyldihydrooxazolyl, and preferably Y is an oxygen atom and carboxy moieties thereon are esterified, may be prepared by reaction of compounds of formula I or VIIc wherein $R^1$ is HOCH$_2$CH$_2$NHC(=O)— or HOCH$_2$CH(CO$_2$alkyl)NHC(=O)—, with thionyl chloride in an inert solvent, such as dichloromethane, at a temperature at or about room temperature. Alternatively this dehydration reaction can be performed by reaction with Burgess reagent [(methoxycarbonylsulphamoyl) triethylammonium hydroxide, inner salt] in an inert solvent such as tetrahydrofuran at a temperature at or about reflux.

According to a further feature of the present invention compounds of formula I wherein $R^1$ is alkoxycarbonylisoxazolyl, and preferably Y is an oxygen atom and carboxy moieties thereon are esterified, may be prepared by reaction of compounds of formula I wherein $R^1$=—C(=O)CH$_3$ and preferably Y is an oxygen atom and carboxy moieties thereon are esterified, with diethyl oxalate, in an inert solvent, such as toluene, in the presence of an alkali metal hydride, such as sodium hydride, at a temperature from room temperature to about reflux temperature, to prepare compounds of formula I wherein $R^1$ is —C(=O) CH$_2$COCO$_2$alkyl, which may be treated as a crude product with hydoxylamine hydrochloride, in the presence of an acid, such as hydrochloric acid, at a temperature from room temperature to about reflux temperature to yield the alkoxycarbonylisoxazole.

According to a further feature of the present invention compounds of formula I wherein $R^1$ is thiazolyl, and preferably Y is an oxygen atom and carboxy moieties thereon are esterified, may be prepared by reaction of compounds of formula I wherein $R^1$ is —C(=S)NH$_2$ and preferably Y is an oxygen atom and carboxy moieties thereon are esterified, with chloroacetaldehyde, in an inert solvent, such as aqueous ethanol, at a temperature from room temperature to about reflux temperature.

According to a further feature of the present invention compounds of formula I wherein $R^1$ is oxadiazolyl, and preferably Y is an oxygen atom and carboxy moieties thereon are esterified, may be prepared by reaction of compounds of formula I wherein $R^1$ is —CN and preferably Y is an oxygen atom and carboxy moieties thereon are esterified, with hydoxylamine hydrochloride, in an inert solvent, such as aqueous ethanol, in the presence of an alkali metal hydroxide, such as sodium hydroxide, at a temperature from room temperature to about reflux temperature, followed by treatment with trimethyl orthoformate, at a temperature from room temperature to about reflux temperature.

Compounds of formula I wherein $R^1$ is alkylsulphinyl, are prepared by oxidising compounds of the formula I wherein $R^1$ is alkylthio. The reaction preferably takes place in an inert solvent, such as acetone, in the presence an oxidising agent, such as potassium peroxymonosulfate, at temperatures between about 0° C. and room temperature.

Compounds of formula I wherein $R^1$ is alkylthio are prepared by alkylating the corresponding compounds of formula I wherein $R^1$ is mercapto. The reaction preferably takes place in an inert solvent, such as acetone, in the presence of potassium carbonate with an alkyl halide at temperatures between about room temperature and the reflux temperature of the solvent.

Compounds of formula I, wherein $R^1$ —CH=NHOH, and preferably Y is oxygen and carboxy moieties thereon are esterified, are prepared by reacting compounds of formula I, wherein $R^1$ is formyl, and preferably Y is oxygen and carboxy moieties thereon are esterified, with hydroxylamine hydrochloride, in the presence of a base, such as pyridine, at temperatures from about room temperature to about reflux.

Compounds of formula I, wherein $R^1$ is —CH=NHOalkylCO$_2$alkyl, and preferably Y is oxygen and carboxy moieties thereon are esterified, are prepared by reacting compounds of formula I, wherein $R^1$—CH=NHOH, and preferably Y is oxygen and carboxy moieties thereon are esterified, with an alkyl bromoalkanoate, such as ethyl bromoacetate, in the presence of an alkali metal hydride, such as sodium hydride. The reaction is preferably carried out in anert solvent, such as dimethylformamide, at temperatures from about room temperature to about 80° C.

Compounds of formula I, having a CF$_2$alkyl wherein the alkyl may be halogenated as defined, such as trifluoromethyl, Y is oxygen atom and carboxy moieties thereon are esterified, are prepared by reacting compounds of the formula I, wherein $R^1$ is —C(=O)alkyl, Y is oxygen atom and carboxy moieties thereon are esterified, with diethylaminosulfur trifluoride. The reaction is preferably carried out in an inert solvent, such as dichloromethane, at a temperature between about −5° C. and room temperature.

Compounds of formula I, wherein $R^1$ is —C(=O)NHalkylCONH$_2$ or —C(=O)NHalkylCO$_2$alkyl, are prepared by reacting compounds of the formula I, wherein $R^1$ is —C(=O)NHalkylCN, with potassium carbonate in alkylOH at room temperature.

Compounds of formula I, wherein $R^1$ is —C(=O)(alkenylaryl or alkenylheteroaryl), are prepared by reaction of compounds of the formula I, wherein $R^1$—C(=O)CH$_3$, with (aryl or heteroaryl)carboxaldehyde, in the presence of aqueous sodium hydroxide. The reaction is preferably carried out in an alcohol, such as ethanol, at about room temperature.

As another example, compounds of formula I containing a thiocarbamoyl group are prepared from the corresponding compounds of formula I containing a carbamoyl group, by reaction with phosphorus pentasulfide or 2,4-bis(4-methoxyphenyl)-1,3-dithia-2,4-diphosphetane-2,4-disulfide, preferably in a solvent such as pyridine or toluene, and preferably at a temperature from about 0° C. to about reflux.

As another example according to the invention, the compounds of formula I wherein a heteroaryl group thereon contains one or more nitrogen ring atoms, can be converted to the corresponding N-oxides preferably by means of reaction with a mixture of hydrogen peroxide and an organic acid, e.g. acetic acid, preferably at about room temperature to about 90° C. Alternatively, the oxidation is carried out by reaction with hydrogen peroxide in the presence of sodium tungstate at temperatures between room temperature and about 60° C. This latter method is preferred for compounds of formula I containing an acid-labile group, such as a carbon-carbon double bond.

As another example according to the invention, the compounds of formula I containing a cyano moiety, may be prepared the corresponding compound of formula I containing a formyl group by reacting with diammonium hydrogen phosphate and an alkylnitrate, such as n-propyl nitrate, in an organic acid solvent, such as glacial acetic acid, at about reflux.

As another example according to the invention, the compounds of formula I containing a hydroxy moiety on a phenyl moiety, may be prepared from the corresponding compound of formula I containing a formyl group on a phenyl moiety by reacting with hydrogen peroxide.

The compounds of the present invention are useful in the form of the free base or acid or in the form of a pharmaceutically acceptable salt thereof. All forms are within the scope of the invention.

Where the compound of the present invention is substituted with a basic moiety, acid addition salts are formed and are simply a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects on endothelin inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention are those derived from the following acids: mineral acids such as hydrochloric acid, sulfuric acid, phosphoric acid and sulfamic acid; and organic acids such as acetic acid, citric acid, lactic acid, tartaric acid, malonic acid, methanesufonic acid, ethanesulfonic acid, benzenesulfonic acid, p-toluenesulfonic acid, cyclohexylsulfamic acid, quinic acid, and the like. The corresponding acid addition salts comprise the following: hydrohalides, such as hydrochloride and hydrobromide, sulfate, phosphate, nitrate, sulfamate, acetate, citrate, lactate, tartarate, malonate, oxalate, salicylate, propionate, succinate, fumarate, maleate, methylene-bis-β-hydroxynaphthoates, gentisates, mesylates, isethionates and di-p-toluoyltartrates, methanesulfonate, ethanesulfonate, benzenesulfonate, p-toluenesulfonate, cyclohexylsulfamate and quinate, respectively.

According to a further feature of the invention, acid addition salts of the compounds of this invention are prepared by reaction of the free base with the appropriate acid, by the application or adaptation of known methods. For example, the acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

The parent compounds of this invention can be regenerated from the acid addition salts by the application or adaptation of known methods. For example, parent compounds of the invention can be regenerated from their acid addition salts by treatment with an alkali, such as aqueous sodium bicarbonate solution or aqueous ammonia solution.

Where the compound of the invention is substituted with an acidic moiety, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the animal organism in pharmaceutical doses of the salts, so that the beneficial inhibitory effects on endothelin inherent in the free acid are not vitiated by side effects ascribable to the cations. Pharmaceutically acceptable salts, including for example alkali and alkaline earth metal salts, within the scope of the invention are those derived from the following bases: sodium hydride, sodium hydroxide, potassium hydroxide, calcium hydroxide, aluminum hydroxide, lithium hydroxide, magnesium hydroxide, zinc hydroxide, ammonia, ethylenediamine, dicyclohexylamine, N-methyl-glucamine, lysine, arginine, ornithine, choline, N,N'-dibenzylethylenediamine, chloroprocaine, diethanoiamine, procaine, N-benzylphenethylamine, diethylamine, piperazine, tris(hydroxymethyl)aminomethane, tetramethylammonium hydroxide, and the like.

Metal salts of compounds of the present invention may be obtained by contacting a hydride, hydroxide, carbonate or similar reactive compound of the chosen metal in an aqueous or organic solvent with the free acid form of the compound. The aqueous solvent employed may be water or it may be a mixture of water with an organic solvent, preferably an alcohol such as methanol or ethanol, a ketone such as acetone, an aliphatic ether such as tetrahydrofuran, or an ester such as ethyl acetate. Such reactions are normally conducted at ambient temperature but they may, if desired, be conducted with heating.

Amine salts of compounds of the present invention may be obtained by contacting an amine in an aqueous or organic solvent with the free acid form of the compound. Suitable aqueous solvents include water and mixtures of water with alcohols such as methanol or ethanol, ethers such as tetrahydrofuran, nitrites such as acetonitrile, or ketones such as acetone. Amino acid salts may be similarly prepared.

The parent compounds of this invention can be regenerated from the base addition salts by the application or adaptation of known methods. For example, parent compounds of the invention can be regenerated from their base addition salts by treatment with an acid, such as hydrochloric acid.

As will be self-evident to those skilled in the art, some of the compounds of this invention do not form stable acid addition salts. However, acid addition salts are most likely to be formed by compounds of this invention having a nitrogen-containing heteroaryl group.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

It will be apparent to those skilled in the art that certain compounds of formula I can exhibit isomerism, for example geometrical isomerism and optical isomerism. Geometrical isomers include the cis and trans forms of compounds of the invention having an alkenyl moiety. Optical isomers contain asymmetric centers. These asymmetric centers may independently be in either the R or S configuration. All isomers within formula I, and their mixtures, are within the scope of the invention.

Such isomers can be separated from their mixtures, by the application or adaptation of known methods, for example chromatographic techniques and recrystallization techniques, or they are separately prepared from the appropriate isomers of their intermediates, for example by the application or adaptation of methods described herein.

The starting materials and intermediates may be prepared by the application or adaptation of known methods. Methods for preparing starting materials and intermediates are described in the Reference Examples or by chemical equivalents thereof.

According to a further example of the present invention, compounds of formula X are prepared by reacting solutions of Grignard reagents, derived by the reaction of compounds of formula XV

wherein $X^1$ and $R^{15}$ are as hereinbefore defined, with magnesium in an ethereal solvent, such as diethyl ether, with compounds of the formula XVI

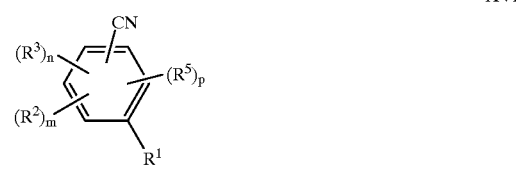

wherein $R^1$, $R^2$, $R^3$, $R^5$, $R^{15}$, n, m, and p, are as hereinbefore defined. The reaction is followed by heating to the reflux temperature, followed by reaction with dilute hydrochloric acid.

According to a further example of the present invention, compounds of formula XVII

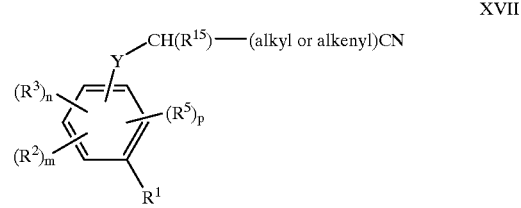

wherein $R^1$, $R^2$, $R^3$, $R^5$, $R^{15}$, n, m, and p, are as hereinbefore defined, and Y is carbonyl, are prepared by reacting compounds of formula XVIII

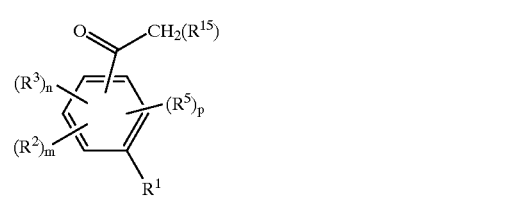

wherein $R^1$, $R^2$, $R^3$, $R^5$, $R^{15}$, n, m, and p, are as hereinbefore defined, with compounds of formula XIX

wherein $X^1$ is as hereinbefore defined, in the presence of an alkali metal alkoxide, such as potassium tert-butoxide. The reaction preferably takes place in an inert solvent, such as tetrahydrofuran, at temperatures between −40° C. and the reflux temperature of the reaction mixture.

Alternatively, compounds of formula XVIIa,

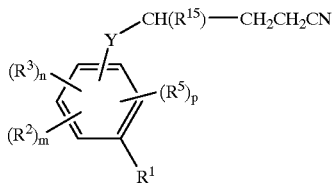

XVIIa wherein $R^1$, $R^2$, $R^3$, $R^5$, $R^{15}$, n, m, and p, are as hereinbefore defined, and Y is carbonyl, are prepared by reacting of compounds of formula XVIII, with acrylonitrile, in the presence of a base, for example an alkali metal alkoxide, such as potassium tert-butoxide. The reaction preferably takes place in an inert solvent, such as tetrahydrofuran, at temperatures between room temperature and the reflux temperature of the reaction mixture.

Compounds of formula VII(a) or VII(b), as hereinbefore defined, are prepared from compounds of formula VIIc, as hereinbefore defined, by reaction with compounds of formula IXb, as hereinbefore defined, in the presence of a base, for example an alkali metal alkoxide, such as potassium tert-butoxide.

Alternatively, salts, such as alkali metal salts, of the compounds of formula VIIc, are prepared from compounds of formula VIIc by known methods beforehand or in situ, for example by reaction with an alkali metal carbonate, alkoxide or hydride), are used for the reaction with the compounds of formula IXb. The reaction preferably takes place in an inert solvent, such as a ketone, such as acetone or methyl ethyl ketone, or a dipolar aprotic solvent, such as dimethylformamide, at temperatures between room temperature and the reflux temperature of the reaction mixture.

Alternatively, compounds of formula VII(a) or VII(b), as hereinbefore defined, are prepared from compounds of formula VIIc, as hereinbefore defined, by reaction with compounds of formula VIIIb, as hereinbefore defined, in the presence of a triarylphosphine, such as triphenylphosphine, and a dialkyl ester, such as the diisopropyl or diethyl ester, of azodicarboxylic acid, preferably in an inert solvent such as tetrahydrofuran, preferably at temperatures between 0° C. and room temperature.

According to a further feature of the invention compounds of formula VIIc, wherein $R^1$ is pyridyl, $R^{2a}$ and $R^{3a}$ are hydroxy, and o and p are zero, may be prepared by reaction of compounds of formula VIIc, wherein $R^1$ is pyridyl, $R^{2a}$ and $R^{3a}$ are methoxy, and o and p are zero, with pyridine hydrochloride at a temperature of about 160° C.

Compounds of formula VIIc, wherein $R^1$ is pyridyl, $R^{2a}$ and $R^{3a}$ are methoxy, and o and p are zero, may be prepared by reacting solutions of Grignard reagents derived by reaction of a bromodimethoxybenzene, such as 1-bromo-2,4-dimethoxybenzene with magnesium in an inert solvent, such as tetrahydrofuran, with a bromopyridine, such as 2-bromopyridine, in the presence of bis-triphenylphosphinepalladium(II) chloride at a temperature about the reflux temperature.

Compounds of formula XIV as hereinbefore defined except that $R^{16a}$ is an esterified carboxy, and $X^1$ is a chlorine atom are prepared by the reaction of compounds of formula XX

 XX wherein $R^{15}$ is as hereinbefore defined, with [(1-ethoxy-cyclopropyloxy)trimethyl]silane, in the presence of titanium (IV) chloride. The reaction preferably takes place in an inert solvent, such as dichloromethane, at temperatures between about 0° C. and about room temperature.

Compounds corresponding to compounds of formula I wherein $R^1$ is mercapto are prepared by reaction of compounds of the formula XXI

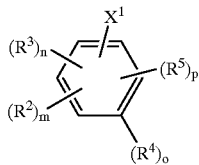

XXI wherein $R^2$, $R^3$, $R^5$, $R^{15}$, $X^1$, n, m, o and p, are as hereinbefore defined, with sodium hydrogensulphide at temperatures between room temperature and the reflux temperature of the solvent.

Nitrohalophenyl, preferably nitrofluorophenyl, compounds optionally substituted alkoxy, cycloalkyloxy arylalkoxy, e.g.arylmethoxy, or heteroarylalkoxy, such as a heteroarylalkoxy group, may be reacted with an alkali metal hydroxide or hydrogensulphide, such as KOH or KSH to prepare the corresponding hydoxynitrophenyl or mercaptonitrophenyl compounds, such as the precursors VIIa, VIIb or VIIc. The reaction preferably takes place in an alcohol, such as t-butanol, at reflux temperature. Alternatively, compounds of the formula $Q^4$(OH or SH) may be reacted with the nitrohalophenyl under the aforesaid conditions to introduce $Q^4O$— or $Q^4S$— moieties on the phenyl moiety in place of the halo groups.

Intermediates for preparing compounds of formula I having a free hydroxyl group thereon, may be prepared from the compound wherein the hydroxyl moiety is protected by a —$CH_2OCH_2CH_2Si(CH_3)_3$ moiety that is removed by hydrochloric acid or tetrabutylammonium fluoride. The reaction is preferably carried out in an inert solvent, such as THF, at a temperature from about room temperature to about reflux.

Intermediates, for preparing compounds of formula I, having a protected hydroxy moiety may be prepared from the corresponding compounds having a free hydroxyl moiety by reaction with 2-(trimethylsilyl)ethoxymethyl chloride. The reaction is preferably carried out in an inert solvent, such as DMF, in the presence of sodium hydride at room temperature.

The following Examples illustrate the preparation of the compounds according to the invention and the Reference Examples illustrate the preparation of the intermediates.

In the nuclear magnetic resonance (NMR) spectra, chemical shifts are expressed in ppm relative to tetramethylsilane. Abbreviations have the following meanings:

s=singlet, d=doublet, t=triplet, q=quartet, m=multiplet, dd=doublet of doublets.

EXAMPLE 1

Compound A–W

A solution of methyl 2-benzyloxy-4-(4-chlorobenzyloxy) benzoate (1.88 g) in dioxan (37 mL) and 1M NaOH (12.5 mL) is refluxed for 4 hours. The solution is evaporated, the residue diluted with water, and brought to pH 1 with 2M HCl. The precipitate is extracted with ethyl acetate, washed with water, dried and evaporated. The residue is recrystallized from ethyl acetate to yield 2-benzyloxy-4-(4-chlorobenzyloxy)benzoic acid (0.8 g, 44%) as colourless crystals, m.p. 150–152° C. ¹H NMR (DMSO) 5.15 (2H,s), 5.2(2H,s), 6.7(1H,d), 6.8(1H,s), 7.3–7.5(9H,m), 7.7(1H,d).

By proceeding in a similar manner, but using the appropriate amount of an ester precursor, there are prepared:

2-Benzyloxy-4-(3-phenylpropyloxy)benzoic acid. m.p. 74–75° C.;
2,4-Di-(4-chlorobenzyloxy)benzoic acid. m.p. 147–149° C.;
2-Benzyloxy-4-(2-(3-indolyl)ethoxy)benzoic acid. m.p. 68–69° C.;
2-Hydroxy-4-benzyloxybenzoic acid. m.p. 182° C.;
2-(3-Phenylpropyloxy)-4-benzyloxybenzoic acid. m.p. 101–102° C.;
2-Benzyloxy-4-(2-naphthylmethoxy)benzoic acid. m.p. 134–136° C.;
2-Benzyloxy-4-(1-naphthylmethoxy)benzoic acid. m.p. 145–147° C.;
2-Benzyloxy-4-(3,4-methylenedioxybenzyloxy)benzoic acid. m.p. 112–114° C.;
2-(2-Pyridylmethoxy)-4-benzyloxybenzoic acid. m.p. 147–148° C.;
2-(2-Phenylethoxy)-4-benzyloxybenzoic acid. m.p. 100–101° C.;
2-Cyclohexylmethoxy-4-benzyloxybenzoic acid. m.p. 99–100° C.;
2-(4-Chlorobenzyloxy)-4-benzyloxybenzoic acid. m.p. 145–146° C.;
2-Benzyloxy-4-(2-phenylethoxy)benzoic acid. m.p. 116–118° C.;
2-Benzyloxy-4-(2-methylpropoxy)benzoic acid. m.p. 162–164° C.;
2-Benzyloxy-4-(4-nitrobenzyloxy)benzoic acid. m.p. 203–205° C.;
2-Benzyloxy-4-(4-fluorobenzyloxy)benzoic acid. m.p. 130–132° C.;
4-Benzyloxy-2-(2-methylpropoxy)benzoic acid. m.p. 96° C.;
2-(4-Pyridylmethoxy)-4-benzyloxybenzoic acid. m.p. 180–181° C.;
2-Benzyloxy-4-(3,4-dichlorobenzyloxy)benzoic acid. m.p. 149–150° C.;
2-Benzyloxy-4-(4-methoxybenzyloxy)benzoic acid. m.p. 127–129° C.;
2-Benzyloxy-4-(3-methoxybenzyloxy)benzoic acid. m.p. 104–105° C.; and
2,4-Dibenzyloxybenzoic acid. m.p. 220–222° C.

EXAMPLE 2

Compound X

To a solution of 2.5 M n-butyl lithium (3.64 mL) in dry tetrahydrofuran (THF) (20 mL) that is cooled to −70° C. under nitrogen is added a solution of diethyl phosphonoacetic acid (0.89 g) in THF (5 mL). After 30 minutes a solution of 2,4-dibenzyloxybenzaldehyde (1.46 g) in THF (5 mL) is slowly added to the cooled solution so as to maintain the temperature. The resulting mixture is stirred at −70° C. for 3 hours and then at 25° C. for 18 hours. The resulting suspension is treated with water, the THF is removed in vacuo, the residue is extracted with ethyl acetate, the extract is dried and evaporated. The residual solid is recrystallized from isopropanol to yield (E)-3-(2,4-dibenzyloxyphenyl)prop-2-enoic acid as colourless crystals (0.6 g), m.p. 153–155° C. H NMR (DMSO) 5.15 (2H,s), 5.21(2H,s), 6.4(1H,d,J=16 Hz), 6.7(1H,d), 6.85(1H,s), 7.3–7.5(10H,m), 7.6(1H,d), 7.8(1H,d,J=16 Hz).

EXAMPLE 3

Compound Y

A solution of 1-(2,4-dibenzyloxyphenyl)-2,2-dibromoethylene (4.85 g) in dry THF (100 mL) is treated with 2.5 M n-butyl lithium (9 mL) at −70° C. under nitrogen. The mixture is stirred for 45 minutes at −70° C. and then at 25° C. for 45 minutes. The mixture is then cooled to −40° C., treated with solid $CO_2$ (10 g) and then stirred at 25° C. for 24 hours. The solution is evaporated, the residue taken up in water. and the pH is adjusted to pH 14 with 1 M NaOH. The water is washed with pentane, the pH adjusted to pH 1 and extracted with dichloromethane. The extract is washed with brine, dried and evaporated. The residue is recrystallized from ethyl acetate/pentane to yield 3-(2,4-dibenzoyloxyphenyl)prop-2-ynoic acid as yellow crystals (1.5 g, 42%), m.p. 125° C. (dec.). H NMR (DMSO) 5.15 (2H,s), 5.25(2H,s), 6.7(1H,d), 6.85(1H,s), 7.3–7.5(11H,m).

EXAMPLE 4

Compound Z and AA

A solution of methyl N-(2,4-dibenzyloxybenzoyl)glycinate (900 mg) in methanol (20 mL) is treated with 1 M NaOH (20 mL) and stirred at 25° C. for 2 hours. The solution is evaporated, the residue diluted with water, brought to pH 1 and extracted with ethyl acetate. The extract is dried and evaporated. The residue is recrystallized from methanol to yield N-(2,4-dibenzyloxybenzoyl)glycine as a colourless solid (300 mg), m.p. 183° C. H NMR ($CDCl_3$) 4.15(2H,d), 5.05 (2H,s), 5.2(2H,s), 6.6(1H,s), 6.7(1H,d), 7.3–7.5(10H,m), 8.2(1H,d), 8.4(1H,t).

By proceeding in a similar manner, but using the appropriate amount of an ester precursor, there is prepared N-(4-Benzyloxy-2-(1-o-tolylethoxy)benzoyl)glycine, m.p. 168–169° C.

EXAMPLE 5

Compound AB

A solution of ethyl 3-(2,4-dibenzyloxyphenyl)-pyrazole-5-carboxylate (1.5 g) in methanol (20 mL) and THF(10 mL) is treated with aqueous 10% KOH (7.5 mL) and refluxed for 2 hours. The solution is evaporated, brought to pH 1 with 1 M HCl, and the precipitate filtered. The solid is purified by flash chromatography on silica, eluting with dichloromethane/methanol (98:2). Fractions homogeneous in the required product are combined and evaporated. The residue is recrystallized from ethyl acetate to give 3-(2,4-dibenzyloxyphenyl)-pyrazole-5-carboxylic acid as colourless crystals (0.13 g), m.p. 218–219° C. ¹H NMR ($CDCl_3$) 5.1 (2H,s), 5.2(2H,s), 6.68(1H,d), 6.72(1H,s), 7.3–7.5(11H, m), 7.7(1H,d).

EXAMPLE 6

Compounds AC and AD

A solution of ethyl 2-benzyl-5-(4-benzyloxyphenyl)-2H-pyrazole-3-carboxylate (1.2 g) in methanol (125 mL) is treated with 10% aqueous potassium hydroxide solution (10 mL, w/v) and the mixture is heated to reflux for 2 hours. The reaction mixture is evaporated in vacuo, stirred with 1N hydrochloric acid (50 mL) and extracted with ethyl acetate (100 mL). The organic phase is dried over magnesium sulphate, evaporated in vacuo, and the residue crystallised from a mixture of ethyl acetate and cyclohexane to give 2-benzyl-5-(4-benzyloxyphenyl)-2H-pyrazole-3-carboxylic acid (0.55 g), m.p. 207–208° C. [Elemental analysis:- C,75.2; H,5.20; N,7.30%. Calculated:- C,75.0; H,5.20; N,7.30%].

By proceeding in a similar manner but replacing the ethyl 2-benzyl-5-(4-benzyloxyphenyl)-2H-pyrazole-3-carboxylate by ethyl 1-benzyl-5-(4-benzyloxyphenyl)-2H-pyrazole-3-carboxylate there is prepared 1-benzyl-5-(4-benzyloxyphenyl)-2H-pyrazole-3-carboxylic acid hydrate, m.p. 141–146° C. [Elemental analysis:- C,74.2; H,5.13;

N,7.10%. Calculated for $C_{24}H_{20}N_2O_3.0.2H_2O$:- C,74.3; H,5.26; N,7.20%].

EXAMPLE 7
Compound AE

A suspension of 2,4-dibenzyloxybenzonitrile (1.89 g) in dry toluene (200 mL) is treated with trimethyltin chloride (6 g) and sodium azide (2 g). The mixture is stirred at reflux for 3 days, evaporated and the residue partitioned between dichloromethane (250 mL) and water (165 mL). The organic phase is washed with brine (165 mL), dried over magnesium sulphate and evaporated. The resulting semi-solid is triturated with ether (30 mL) and the solid washed with pentane and crystallised from a mixture of ethyl acetate and pentane to give 5-(2,4-dibenzyloxyphenyl)-2H-tetrazole hydrate (1.55 g) as a white solid, m.p. 178–179° C. [Elemental analysis:- C,69.7; H,5.02; N,15.4%. Calculated for $C_{21}H_{18}N_4O_2.0.2H_2O$:- C,68.68; H,5.12; N,15.48%].

EXAMPLE 8
Compounds AF and AG

A mixture of methyl (Z)-2-benzoylamino-3-(2,4-dibenzyloxyphenyl)acrylate (1.6 g) and aqueous potassium hydroxide in methanol (35 mL, 15%) is stirred and heated at 60° C. for 6 hours. The reaction mixture is diluted with water (20 mL), acidified to pH 1 by addition of concentrated hydrochloric acid and the resulting solid filtered. Recrystallisation fro ethyl acetate gives (Z)-2-benzoylamino-3-(2,4-dibenzyloxyphenyl)acrylic acid (0.72 g) as a white solid, m.p. 212–213° C. [Elemental analysis:- C,75.2; H,5.28; N,2.83%. Calculated :- C,75.1; H,5.26; N,2.92%].

By proceeding in a similar manner but replacing the methyl Z-2-benzoylamino-3-(2,4-dibenzyloxyphenyl) acrylate by the appropriate quantity of methyl (E)-2-benzoylamino-3-(2,4-dibenzyloxyphenyl)acrylate there is prepared (E)-2-benzoylamino-3-(2,4-dibenzyloxyphenyl) acrylic acid, m.p. 149–150° C. [Elemental analysis:- C,74.8; H,5.24; N,2.84%. Calculated;- C,75.1; H,5.26; N,2.92%].

EXAMPLE 9
Compound AH

A mixture of ethyl (E)-2-benzyl-3-(2,4-dibenzyloxyphenyl)acrylate (1.5 g) and aqueous potassium hydroxide in methanol (50 mL, 15%) is stirred and heated at reflux for 3 hours. The reaction mixture is diluted with water (30 mL) plus 3 N potassium hydroxide solution (5 mL), acidified to pH 1 by addition of concentrated hydrochloric acid and the resulting solid filtered. Recrystallisation from a mixture of ethyl acetate and pentane gives E-2-benzyl-3-(2, 4-dibenzyloxyphenyl)acrylic acid (1.13 g) as a white solid, m.p. 175–176° C. [Elemental analysis:- C,79.7; H,5.72%. Calculated:- C,80.0; H,5.82%].

EXAMPLE 10
Compound Al

A solution of methyl (E)-3-(2,4-dibenzyloxyphenyl)-2-cyanoacrylate (400 mg) in tetrahydrofuran (20 mL) containing 0.5 N aqueous lithium hydroxide solution (4 mL) is stirred at ambient temperature for 2 hours. The reaction is concentrated under reduced pressure and the residue taken up in water. This solution is acidified to pH 1 and extracted with diethyl ether. The organic layer is dried over magnesium sulphate, filtered and concentrated under reduced pressure to leave (E)-3-(2,4-dibenzyloxyphenyl)-2-cyanoacrylic acid hydrate as a yellow solid (30 mg). [Elemental analysis:- C, 71.43; H, 5.25; N, 3.47%; Calculated for $C_{24}H_{19}NO_4.H_2O$:- C, 71.40; H, 4.81; N, 3.72%].

EXAMPLE 11
Compound AJ

A solution of ethyl 3-(2,4-dibenzyloxyphenyl)isoxazole-5-carboxylate (2.2 g) in hot methanol (100 mL) is treated with 10% aqueous potassium hydroxide solution (10 mL w/v) and the mixture is heated to reflux for 2 hours. The reaction mixture is evaporated to low bulk, stirred with 1 N hydrochloric acid (50 mL) for 15 minutes and filtered. The resulting solid is washed with water, dried and crystallised from ethyl acetate to give 3-(2,4-dibenzyloxyphenyl) isoxazole-5-carboxylic acid (1 g), in the form of a white solid, m.p. 192–193° C. [Elemental analysis:- C,71.7; H,4.67; N,3.34%. Calculated:- C,71.8; H,4.77; N,3.49%].

EXAMPLE 12
Compound AK

A solution of ethyl 4-(2,4-dibenzyloxyphenyl)-2,4-dioxobutanoate (2 g) in methanol (100 mL) is treated with 10% aqueous potassium hydroxide (10 mL) and the mixture stirred at room temperature for 18 hours. The reaction mixture is evaporated to low bulk and the residue partitioned between ethyl acetate (100 mL) and 1 N hydrochloric acid (50 mL). The organic phase is washed with water, dried over magnesium sulphate and evaporated in vacuo. The residue iscrystallised from a mixture of ethyl acetate and cyclohexane to give 4-(2,4-dibenzyloxyphenyl)-2,4-dioxobutanoic acid (0.6 g), in the form of a white solid, m.p. 160–164° C. [Elemental analysis:- C,71.3; H,4.93%. Calculated:- C,71.3; H,4.99%].

EXAMPLE 13
Compound AL

A mixture of 2,4-dibenzyloxybenzaldehyde (2 g), hydroxylamine hydrochloride (0.45 g) and pyridine (0.53 mL) in ethanol (20 mL) is heated at reflux for 1 hour. The solvent is then removed in vacuo, the residue dissolved in ethyl acetate and the solution washed with 1 N hydrochloric acid then with brine. Removal of the solvent in vacuo gives a beige coloured solid which crystallises from a mixture of ether and petroleum ether to give 2,4-dibenzyloxybenzaldehyde oxime in the form of a white solid, m.p., 130° C. [Elemental analysis:- C,76.1; H,5.75; N,4.28%. Calculated:- C,75.7; H,5.74; N,4.20%].

EXAMPLE 14
Compound AM

A mixture of 2,4-dihydroxybenzaldehyde (17.5 g), potassium carbonate (42 g) and benzyl bromide (35 mL) in dimethyl formamide (100 mL) is stirred at room temperature for 18 hours. The reaction mixture is poured into vigorously stirred ice-water (300 mL) and stirring is continued for 30 minutes. The resulting brown solid is filtered and dried to give 2,4-dibenzyloxybenzaldehyde (28.5 g), m.p. 80–81° C. [Elemental analysis:- C,79.5; H,6.10%. Calculated:- C,79.2; H,5.70%].

EXAMPLE 15
Compound AN

A solution of 2,4-dibenzyloxybenzaldehyde (2.26 g) in methanol (20 mL) is treated portionwise with sodium borohydride (0.268 g) over 5 minutes.

Water (5 mL) is added dropwise to the reaction mixture. The resulting white solid is filtered, dried and crystallised from a mixture of ether and petroleum ether to give 2,4-dibenzyloxybenzyl alcohol as a white solid, m.p. 87° C. [Elemental analysis:- C,79.0; H,6.42%. Calculated:- C,78.7; H,6.29%].

EXAMPLE 16
Compound AO

A mixture of 2,4-dibenzyloxybenzaldehyde (1.59 g), diammonium hydrogen phosphate (3.5 g) and n-propyl nitrate (15 mL) in glacial acetic acid (5 mL) is refluxed for 15 hours. The reaction mixture is evaporated to dryness in vacuo and the residue is stirred with water (100 mL). The insoluble material is filtered and dried at 50° C. to yield 2,4-dibenzyloxybenzonitrile as a tan coloured solid (0.6 g, 40%), m.p. 100° C. [Elemental analysis:- C,79.8; H,5.47; N,4.48%. Calculated:- C,80.0; H,5.43; N,4.44%].

EXAMPLE 17
Compound AP

Benzyl alcohol (5.4 g) is added slowly to a stirred suspension of sodium hydride (2 g, 60% dispersion in mineral oil) in dry dimethylformamide (100 mL). The mixture is stirred for 30 minutes then 2,4-difluoronitrobenzene (3.2 g) is added in one portion. The resulting black solution is stirred at room temperature for 18 hours ,evaporated and the residue partitioned between ether (200 mL) and water (100 mL). The organic phase is washed thoroughly with water, dried and evaporated. The residue is triturated with hot ethanol (50 mL) and the mixture cooled in an ice-bath. The insoluble material is purified by filtration through a bed of silica eluting with a mixture of dichloromethane and petroleum ether, b.p.40–60° C., (1:1 v/v). The filtrate is evaporated and the solid crystallised from ethanol to give 2,4-dibenzyloxynitrobenzene (2.3 g) as a cream coloured solid, m.p. 101–103° C. [Elemental analysis:- C,71.4; H,5.07; N,4.09%. Calculated:- C,71.6; H,5.11; N,4.18%].

EXAMPLE 18
Compound AQ

A mixture of 2,4-dihydroxyacetophenone (15.2 g), potassium carbonate (30.4 g), potassium iodide (0.5 g) and benzyl bromide (37.6 g) in dimethyl formamide (200 mL) is stirred at room temperature for 18 hours. The reaction mixture is filtered and the insoluble material washed with a little dimethyl formamide. The combined filtrate plus washings are evaporated to dryness and the residue partitioned between ether and water. The organic phase is dried over magnesium sulphate, evaporated and the residual pink-red coloured solid crystallised from cyclohexane to give 2,4-dibenzyloxyacetophenone (28.4 g) as a pale pink coloured powder, m.p. 64–65° C. [Elemental analysis:- C,79.5; H,5.94%. Calculated:- C,79.5; H,6.07%].

EXAMPLE 19
Compound AR

Concentrated sulphuric acid (2–3 drops) is added to a stirred solution of dibenzyloxybenzaldehyde (1.5 g) in methanol (50 mL), resulting in a thick precipitate. The mixture is stirred for 5 minutes then hydrogen peroxide (1 g; 27.5% in water) is added in one portion and stirring is continued for 2 hours. The resulting brown solution is treated with 10% aqueous sodium sulphite solution (10 mL) then evaporated to low bulk. The residue is treated with water (50 mL), the solid washed with water, dried and crystallised from cyclohexane, with charcoal treatment, to give 2,4-dibenzyloxyphenol (0.3 g) as a white powder, m.p. 82–83° C. [Elemental analysis:- C,78.2; H,5.79%. Calculated:- C,78.4; H,5.92%].

EXAMPLE 20
Compound AS

A mixture of 2,4-dibenzyloxyacetophenone (6.6 g), hydroxylamine hydrochloride (2.8 g) and pyridine (10 mL) in ethanol (100 mL) is heated at reflux for 1 hour, The clear solution is cooled in an ice-bath and the solid filtered. The solid is washed with ice-cold ethanol then with ether to give 2,4-dibenzyloxyacetophenone oxime (5.4 g) as a white solid, m.p. 150° C. [Elemental analysis:- C,76.3; H,6.10; N,4.02%. Calculated:- C,76.1; H,6.09; N,4.03%]

EXAMPLE 21
Compound AT

A stirred solution of benzyl 2-benzyloxy-4-phenylethynylbenzoate (2 g) and 1 N sodium hydroxide (5 mL) in dioxan (80 mL) is heated at reflux for 1 hour. The reaction mixture is evaporated, the residue dissolved in water (6 mL) and the solution washed twice with ethyl acetate (20 mL). The pH of the aqueous phase is adjusted to pH 1 by addition of 2 N hydrochloric acid and resulting solid is filtered and washed well with water to give 2-benzyloxy-4-phenylethynylbenzoic acid (0.6 g), m.p. 125–127° C. [Elemental analysis:- C,80.2; H,4.86%. Calculated:- C,80.5; H,4.91%].

EXAMPLE 22
Compound AU

Ethyl (2,4-dibenzyloxyphenoxy)acetate (3.9 g) is added in small portions to a stirred suspension of lithium aluminium hydride (0.21 g) in dry tetrahydofuran (100 mL) with ice-cooling. The mixture is allowed to warm to room temperature and stirred for a further 30 minutes. The reaction mixture is cooled in an ice-bath and water is added dropwise. After stirring for 1 hour the mixture is filtered through hyflo and the insolubles washed with tetrahydrofuran. Evaporation of the combined filtrate plus washings and crystallisation of the resulting solid from petroleum ether (bp 40–60° C.) containing a little ethyl acetate gives 2-(2, 4-dibenzyloxy-phenoxy)ethanol hemihydrate (1.8 g) as a white solid, m.p. 47–52° C. [Elemental analysis:- C,73.3; H,6.25%. Calculated for $C_{22}H_{22}O_4.0.5H_2O$:- C,73.5; H,6.45%].

EXAMPLE 23
Compound AV

A mixture of ethyl (2,4-dibenzyloxyphenoxy)acetate (2 g), concentrated ammonia (25 mL) and methanol (50 mL) is stirred at room temperature for 18 hours. The reaction mixture is diluted with water (50 mL) then evaporated to low bulk and filtered. The solid is washed with water and dried to give 2-(2,4-dibenzyloxyphenoxy)acetamide (1.1 g) as a white powder, m.p. 120° C. [Elemental analysis:- C,73.1; H,5.78; N,3.79%. Calculated:- C,72.7; H,5.83; N,3.85%].

EXAMPLE 24
Compounds AW–AZ, BA–BZ, and CA–CQ (i) A mixture of methyl (RS)-5-(3-benzyloxyphenyl)-5-oxo-4-phenylpentanoate (11.6 g),sodium hydroxide (60 mL; 1 N) and 1,4-dioxane is stirred at ambient temperature for 18 hours. The reaction mixture is then concentrated to dryness and dissolved in water (50 mL), acidified to pH 1 by treatment with concentrated hydrochloric acid, and extracted with chloroform. The organic layer is dried over magnesium sulphate, filtered and concentrated under reduced pressure to leave an oil. Trituration with a mixture of pentane and diethyl ether (1:1 v/v) and recrystallisation of the resulting solid with a mixture of diethyl ether and pentane gives (RS)-5-(3-benzyloxyphenyl)-5-oxo-4-phenylpentanoic acid (5.1 g), in the form of a white solid, m.p. 127–129° C. [Elemental analysis:-: C,76.9;H,5.94%; Calculated:- C,76.98;H,5.92%]. (ii) By proceeding in a similar manner but replacing the methyl (RS)-5-(3-benzyloxyphenyl)-5-oxo-4-phenylpentanoate by the appropriate quantity of methyl (RS)-5-(3-benzyloxyphenyl)-4-(2-chlorophenyl)-5-oxopentanoate and using 15% potassium hydroxide in methanol at reflux, there is prepared (RS)-5-(3-benzyloxyphenyl)-4-(2-chlorophenyl)-5-oxopentanoic acid in the form of a white solid after recrystallisation from ethyl acetate and pentane, m.p. 131–132° C. [Elemental analysis:- C,70.8;H,5.17;Cl,8.7%; Calculated; C,70.5;H,5.18;Cl, 8.67%]. (iii) By proceeding in a similar manner but replacing the methyl (RS)-5-(3-benzyloxyphenyl)-5-oxo-4-phenylpentanoate by the appropriate quantity of methyl (RS)-5-(3-benzyloxyphenyl)-4-(2-methoxyphenyl)-5-oxopentanoate and using 15% potassium hydroxide in methanol at reflux for 1 hour, there is prepared (RS)-5-(3-benzyloxyphenyl)-4-(2-methoxyphenyl)-5-oxopentanoic acid in the form of a white solid after trituration with diisopropyl ether and pentane and recrystallisation from ethyl acetate, m.p. 143–144° C. [Elemental analysis:- C,74.3;H,6.10%. Calculated:- C,74.24;H,6.10%]. (iv) By proceeding in a similar manner but replacing the methyl (RS)-5-(3-benzyloxyphenyl)-5-oxo-4-phenylpentanoate by the appropriate quantity of methyl (RS)-5-(3-benzyloxyphenyl)-4-(2-methylphenyl)-5-oxopentanoate and using 15% potassium hydroxide in methanol at reflux for 1.5 hours, there is prepared (RS)-5-(3-benzyloxyphenyl)-4-(2-methylphenyl)-5-oxopentanoic acid in the form of a pale yellow solid after recrystallisation from a mixture of ethyl acetate and pentane, m.p. 121–122° C. [Elemental analysis:- C,77.3;H,6.28%. Calculated:- C,77.3; H,6.23%]. (v) By proceeding in a similar manner but replacing the methyl (RS)-5-(3-benzyloxyphenyl)-5-oxo-4-phenylpentanoate by the appropriate quantity of methyl (RS)-5-(3-benzyloxyphenyl)-4-(2-ethylphenyl)-5-oxopentanoate and using 15% potassium hydroxide in methanol at reflux for 2.5 hours, there is prepared (RS)-5-(3-benzyloxyphenyl)-4-(2-ethylphenyl)-5-oxopentanoic acid in the form of a white solid after recrystallisation from a mixture of ethyl acetate and pentane, m.p. 85–86° C. [Elemental analysis:- C,77.0;H,6.38%; Calculated:- C,77.58;H,6.51%]. (vi) By proceeding in a similar manner but replacing the methyl (RS)-5-(3-benzyloxyphenyl)-5-oxo-4-phenylpentanoate by the appropriate quantity of methyl (RS)-5-(3-benzyloxyphenyl)-4-(2-chloro-6-fluorophenyl)-5-oxopentanoate and using 15% potassium hydroxide in methanol at reflux for 1 hour, there is prepared (RS)-5-(3-benzyloxyphenyl)-4-(2-chloro-6-fluorophenyl)-5-oxopentanoic acid in the form of a white solid after trituration with diisopropyl ether/pentane and recrystallisation from ethyl acetate/pentane, m.p. 95–96° C. [Elemental analysis:- C,67.5; H,4.72;Cl,8.20%. Calculated:- C,67.53; H,4.72; Cl,8.31%]. (vii) By proceeding in a similar manner but replacing the methyl (RS)-5-(3-benzyloxyphenyl)-5-oxo-4-phenyl-pentanoate by the appropriate quantity of methyl (RS)-5-(3-benzyloxyphenyl)-4-(2,6-dichlorophenyl)-5-oxopentanoate and using 15% potassium hydroxide in methanol at reflux for 30 minutes, there is prepared (RS)-5-(3-benzyloxyphenyl)-4-(2,6-dichlorophenyl)-5-oxopentanoic acid in the form of a white solid after trituration with a mixture of diisopropyl ether and pentane and recrystallisation from a mixture of ethyl acetate and pentane, m.p. 113–114° C. [Elemental analysis:- C,64.6;H,4.43; Cl,15.70%. Calculated:- C,65.02;H,4.55; Cl,15.99%]. (viii) By proceeding in a similar manner but replacing the methyl (RS)-5-(3-benzyloxyphenyl)-5-oxo-4-phenylpentanoate by the appropriate quantity of methyl (RS)-5-(3-benzyloxyphenyl)-4-(4-methoxyphenyl)-5-oxopentanoate and using 15% potassium hydroxide in methanol at reflux for 1.5 hours, there is prepared (RS)-5-(3-benzyloxyphenyl)-4-(4-methoxyphenyl)-5-oxopentanoic acid in the form of a white solid after trituration with pentane, m.p. 74° C. [Elemental analysis:- C 74.3;H 5.95%. Calculated:- C 74.24; H,5.98%]. (ix) By proceeding in a similar manner but replacing the methyl (RS)-5-(3-benzyloxyphenyl)-5-oxo-4-phenylpentanoate by the appropriate quantity of methyl (RS)-5-(3-benzyloxyphenyl)-4-(3,4-dichlorophenyl)-5-oxopentanoate and using 15% potassium hydroxide in methanol at reflux for 3 hours, there is prepared (RS)-5-(3-benzyloxyphenyl)-4-(3,4-dichlorophenyl)-5-oxopentanoic acid in the form of a yellow solid after trituration from pentane, m.p. 87–88° C. [Elemental analysis:- C,64.50;H,4.51;Cl,15.60%. Calculated:- C,65.02;H,4.55;Cl,15.99%]. (x) By proceeding in a similar manner but replacing the methyl (RS)-5-(3-benzyloxyphenyl)-5-oxo-4-phenylpentanoate by the appropriate quantity of methyl (RS)-5-(3-benzyloxyphenyl)-4-(4-chlorophenyl)-5-oxopentanoate and using 15% potassium hydroxide in methanol at reflux for 1 hour, there is prepared (RS)-5-(3-benzyloxyphenyl)-4-(4-chlorophenyl)-5-oxopentanoic acid in the form of a white solid after chromatography on silica gel using a mixture of ethyl acetate and pentane (1:1 v/v) and trituration of the resulting solid with diisopropyl ether, m.p. 91° C. [Elemental analysis:- C,70.4;H,5.14; Cl,8.6%. Calculated:- C,75.5;H,5.17;Cl, 8.67%]. (xi) By proceeding in a similar manner but replacing the methyl (RS)-5-(3-benzyloxyphenyl)-5-oxo-4-phenylpentanoate by the appropriate quantity of methyl (RS)-5-(3-benzyloxyphenyl)-4-(4-methylphenyl)-5-oxopentanoate and using 15% potassium hydroxide in methanol at reflux for 3.5 hours, there is prepared (RS)-5-(3-benzyloxyphenyl)-4-(4-methylphenyl)-5-oxopentanoic acid in the form of a white solid after recrystallisation from a mixture of diisopropyl ether and pentane, m.p. 105–106° C. [Elemental analysis:- C,77.1;H,6.17%. Calculated:- C,77.3;H,6.23%]. (xii) By proceeding in a similar manner but replacing the methyl (RS)-5-(3-benzyloxyphenyl)-5-oxo-4-phenylpentanoate by the appropriate quantity of methyl (RS)-5-(3-benzyloxyphenyl)-4-(3-chlorophenyl)-5-oxopentanoate and using 15% potassium hydroxide in methanol at reflux for 1.5 hours, there is prepared (RS)-5-(3-benzyloxyphenyl)-4-(3-chlorophenyl)-5-oxopentanoic acid in the form of a white solid after trituration with a mixture of diethyl ether and pentane and recrystallisation from a mixture of ethyl acetate and pentane, m.p. 110–111° C. [Elemental analysis:- C,70.3;H,5.10;Cl,8.50%. Calculated:- C,70.5;H,5.18;Cl,8.67%]. (xiii) By proceeding in a similar manner but replacing the methyl (RS)-5-(3-benzyloxyphenyl)-5-oxo-4-phenylpentanoate by the appropriate quantity of methyl (RS)-5-(3-benzyloxyphenyl)-4-(3-methoxyphenyl)-5-oxopentanoate and using 15% potassium hydroxide in methanol at reflux for 1 hour, there is prepared (RS)-5-(3-benzyloxyphenyl)-4-(3-methoxyphenyl)-5-oxopentanoic acid in the form of a white solid after trituration with a mixture of diisopropyl ether and pentane and recrystallisation from a mixture of ethyl acetate and pentane, m.p. 94–95° C. [Elemental analysis:- C,73.0;H,5.93%; Calculated for $C_{25}H_{24}O_5 \cdot 0.25AcOEt$:- C,73.22; H,6.14%]. (xiv) By proceeding in a similar manner but replacing the methyl (RS)-5-(3-benzyloxyphenyl)-5-oxo-4-phenylpentanoate by the appropriate quantity of methyl (RS)-5-(4-benzyloxyphenyl)-5-oxo-4-phenylpentanoate, there is prepared (RS)-5-(4-benzyloxyphenyl)-5-oxo-4-phenylpentanoic acid in the form of a white solid after trituration with pentane, m.p. 147–149° C. [Elemental analysis:- C,77.4;H,6.06%. Calculated:- C,76.98; H,5.92%]. (xv) By proceeding in a similar manner but replacing the methyl (RS)-5-(3-benzyloxyphenyl)-5-oxo-4-phenylpentanoate by the appropriate quantity of methyl (RS)-4-(3-benzyloxyphenyl)-4-oxo-3-phenylbutanoate, there is prepared (RS)-4-(3-benzyloxyphenyl)-4-oxo-3-phenylbutanoic acid in the form of a white solid after recrystallisation from a mixture of ethyl acetate and pentane, m.p. 150–152° C. [Elemental analysis:- C,76.7;H,5.67%. Calculated:- C,76.65; H,5.59%]. (xvi) By proceeding in a similar manner but replacing the methyl (RS)-5-(3-benzyloxyphenyl)-5-oxo-4-phenylpentanoate by the appropriate quantity of ethyl (RS)-6-(3-benzyloxyphenyl)-6-oxo-5-phenylhexanoate, there is prepared (RS)-6-(3-benzyloxyphenyl)-6-oxo-5-phenylhexanoic acid in the form of a white solid after trituration with pentane and recrystallisation from a mixture of ethyl acetate and cyclohexane, m.p. 107–109° C. [Elemental analysis:- C,77.0;H,6.22%. Calculated:- C,77.3;H,6.23%]. (xvii) By proceeding in a similar manner but replacing the methyl (RS)-5-(3-benzyloxyphenyl)-5-oxo-4-phenylpentanoate by ethyl (RS)-7-(3-benzyloxyphenyl)-7-oxo-6-phenylheptanoate, there is prepared (RS)-7-(3-benzyloxyphenyl)-7-oxo-6-phenylheptanoic acid in the form of an orange oil after chromatography on silica gel eluting with a mixture of pentane and ethyl acetate (8:1 v/v). [Elemental analysis:- C,77.2:H,66%; Calculated:- C,77.59; H,6.51%]. (xviii) By proceeding in a similar manner but replacing the methyl (RS)-5-(3-benzyloxyphenyl)-5-oxo-4-phenylpentanoate by the appropriate quantity of ethyl (RS)-6-(3-benzyloxyphenyl)-6-oxo-5-phenylhex-2-enoate, there is prepared (RS)-6-(3-benzyloxyphenyl)-6-oxo-5-phenylhex-2-enoic acid in the form of an oil after chromatography on silica gel eluting with a mixture of pentane and ethyl acetate (1:4 v/v). [Elemental analysis:- C,75.6;H,5.87%. Calculated:- C,75.96;H,5.73%]. (xix) By proceeding in a similar manner but replacing the methyl (RS)-5-(3-benzyloxyphenyl)-5-oxo-4-phenylpentanoate by the appropriate quantity of methyl (RS)-5-(3-benzyloxyphenyl)-5-oxo-4-(2-pyridyl)pentanoate and acidifying to pH 4.5 rather than pH 1 prior to extraction, there is prepared (RS)-5-(3-benzyloxyphenyl)-5-oxo-4-(2-pyridyl)pentanoic acid in the form of a white solid after chromatography on silica gel eluting with a mixture of pentane and ethyl acetate (1:1 v/v) followed by trituration with pentane, m.p. 99–104° C. [Elemental analysis:- C,73.2;H,5.91; N,3.5%. Calculated:- C,73.58;H,5.64;N,3.73%]. (xx) By proceeding in a similar manner but replacing the methyl (RS)-5-(3-benzyloxyphenyl)-5-oxo-4-phenylpentanoate by the appropriate quantity of methyl (3RS,4RS)-5-(3-benzyloxyphenyl)-3-methyl-5-oxo-4-phenylpentanoate, there is prepared (3RS,4RS)-5-(3-benzyloxyphenyl)-3-methyl-5-oxo-4-phenylpentanoic acid in the form of a white solid after trituration with pentane, m.p. 68–70° C. [Elemental analysis:- C,77.0; H,6.28%. Calculated:- C,77.29;H,6.22%]. (xxi) By proceeding in a similar manner but replacing the methyl (RS)-5-(3-benzyloxyphenyl)l-5-oxo-4-phenylpentanoate by methyl (2RS,4RS)-5-(3-benzyloxyphenyl)-2-methyl-5-oxo-4-phenylpentanoate, there is prepared (2RS,4RS)-5-(3-benzyloxyphenyl)-2-methyl-5-oxo-4-phenylpentanoic acid in the form of a white solid after recrystallisation from a mixture of ethyl acetate and pentane, m.p. 98–100° C. [Elemental analysis:- C,77.0;H,6.13%. Calculated:- C,77.29; H,6.22%]. (xxii) By proceeding in a similar manner, but replacing the methyl (RS)-5-(3-benzyloxyphenyl)-5-oxo-4-phenylpentanoate by the appropriate quantity of methyl (RS)-5-(3-methoxyphenyl)-4-(2-methylphenyl)-5-oxopentanoate, and carrying out the reaction at 60° C. for 3 hours, there is prepared (RS)-5-(3-methoxyphenyl)-4-(2-methylphenyl)-5-oxopentanoic acid, in the form of a white solid, m.p. 108–110° C. [Elemental analysis:- C,72.7; H,6.42%; Calculated:- C,73.1;H,6.45%]. (xxiii) By proceeding in a similar manner but replacing the methyl (RS)-5-(3-benzyloxyphenyl)-5-oxo-4-phenylpentanoate by the appropriate quantity of methyl (RS)-5-[3-(2-methoxybenzyloxy)phenyl]-5-oxo-4-phenylpentanoate, there is prepared (RS)-5-[3-(2-methoxybenzyloxy)phenyl]-5-oxo-4-phenylpentanoic acid in the form of a white solid after trituration with a mixture of pentane, ethyl acetate and acetic acid (72/28/1) and trituration with pentane, m.p. 111–113° C. [NMR(CDCl$_3$):- 2.1–2.5(4H,m),3.9(3H,s), 4.6(1H,t),5.1(2H,s),6.9–7.6 (13H)]. (xxiv) By proceeding in a similar manner but replacing the methyl (RS)-5-(3-benzyloxyphenyl)-5-oxo-4-phenylpentanoate by the appropriate quantity of methyl (RS)-5-[3-(3,4-methylenedioxybenzyloxy)phenyl]-5-oxo-4-phenylpentanoate, there is prepared (RS)-5-[3-(3,4-methylenedioxybenzyloxy)phenyl]-5-oxo-4-phenylpentanoic acid, m.p. 92–94° C. [Elemental analysis:- C,71.4;H,5.46%. Calculated:- C,71.8;H,5.29%]. (xxv) By proceeding in a similar manner, but replacing the methyl (RS)-5-(3-benzyloxyphenyl)-5-oxo-4-phenylpentanoate by the appropriate quantity of methyl (RS)-4-(2-methylphenyl)-5-[3-(2-methylpropoxy)phenyl]-5-oxopentanoate, and carrying out the reaction for 18 hours, there is prepared (RS)-4-(2-methylphenyl)-5-[3-(2-methylpropoxy)phenyl]-5-oxopentanoic acid, in the form of a white solid after recrystallisation from a mixture of ethyl acetate and hexane, m.p. 96–98° C. [Elemental analysis:- C,74.0;H,7.3%; Calculated:- C,74.5;H,7.39%]. (xxvi) By proceeding in a similar manner but replacing the methyl (RS)-5-(3-benzyloxyphenyl)-5-oxo-4-phenylpentanoate by the appropriate quantity of methyl (RS)-5-[3-(4-chlorobenzyl-oxy)phenyl]-4-(2-methylphenyl)-5-oxopentanoate, there is prepared (RS)-5-[3-(4-chlorobenzyl-oxy)phenyl]-4-(2-methylphenyl)-5-oxopentanoic acid, m.p. 131–133° C. [Elemental analysis; C,71.2;H,5.48%. Calculated:- C,71.0;H,5.48%]. (xxvii) By proceeding in a similar manner but replacing the methyl (RS)-5-(3-benzyloxyphenyl)-5-oxo-4-phenylpentanoate by the appropriate quantity of methyl (RS)-5-(3-cyclopentylmethoxyphenyl)-4-(2-methylphenyl)-5-oxopentanoate, there is prepared (RS)-5-(3-cyclopentylmethoxyphenyl)-4-(2-methylphenyl)-5-oxopentanoic acid, m.p. 104–105° C. [Elemental analysis:- C,75.7;H,7.60%. Calculated:- C,75.8; H,7.42%]. (xxviii) By proceeding in a similar manner but replacing the methyl (RS)-5-(3-benzyloxyphenyl)-5-oxo-4-phenylpentanoate by the appropriate quantity of methyl (RS)-5-[3-(3-thienylmethoxy)- phenyl]-4-(2-methylphenyl)-5-oxopentanoate, there is prepared (RS)-5-[3-(3-thienylmethoxy)phenyl]-4-(2-methylphenyl)-5-oxopentanoic acid hydrate, m.p. 94–98° C. [Elemental analysis:- C,67.1;H,5.60%. Calculated for C$_{23}$H$_{22}$O$_4$S.H$_2$O:- C,67.1; H,5.85%]. (xxix) By proceeding in a similar manner but replacing the methyl (RS)-5-(3-benzyloxy-phenyl)-5-oxo-4-phenylpentanoate by the appropriate quantity of methyl (RS)-5-[3-(2-fluorobenzyl-oxy) phenyl]-4-(2-methylphenyl)-5-oxopentanoate, there is prepared (RS)-5-[3-(2-fluorobenzyl-oxy)phenyl]-4-(2-methylphenyl)-5-oxopentanoic acid, m.p. 108–110C. [Elemental analysis:- C, 73.5;H,5.65%. Calculated:- C,73.9;H,5.70%]. (xxx) By proceeding in a similar manner but replacing the methyl (RS)-5-(3-benzyloxyphenyl)-5-oxo-4-phenylpentanoate by the appropriate quantity of methyl (RS)-5-[3-(2-furylmethoxy)phenyl]-4-(2- methylphenyl)-5-oxopentanoate, there is prepared (RS)-5-[3-(2-furylmethoxy)phenyl]-4-(2-methylphenyl)-5-oxopentanoic acid, m.p. 92–94° C. [Elemental analysis:- C,72.9;H,5.81%. Calculated:- C,73.0;H,5.86%]. (xxxi) By proceeding in a similar manner but replacing the methyl (RS)-5-(3-benzyloxyphenyl)-5-oxo-4-phenylpentanoate by the appropriate quantity of methyl (RS)-5-[3-(3-furylmethoxy)phenyl]- 4-(2-methylphenyl)-5-oxopentanoate, there is prepared (RS)-5-[3-(3-furylmethoxy)phenyl]-4-(2-methylphenyl)-5-oxopentanoic acid, m.p. 83–85° C. [Elemental analysis:- C,72.6;H,5.66%. Calculated:- C,73.0; H,5.86%]. (xxxii) By proceeding in a similar manner but replacing the methyl (RS)-5-(3-benzyloxyphenyl)-5-oxo-4-phenylpentanoate by the appropriate quantity of methyl (RS)-5-[3-(3-chlorobenzyl-oxy)phenyl]-4-(2-methylphenyl)-5-oxopentanoate, there is prepared (RS)-5-[3-(3-chlorobenzyl-oxy)phenyl]-4-(2-methylphenyl)-5-oxopentanoic acid, m.p. 103–105° C. [Elemental analysis:- C,71.1;H,5.45%. Calculated:- C,71;H, 5.48%]. (xxxiii) By proceeding in a similar manner but replacing the methyl (RS)-5-(3-benzyloxyphenyl)-5-oxo-4-phenylpentanoate by the appropriate quantity of methyl (RS)-5-[3-(4-methoxy-benzyloxy)phenyl]-4-(2-methylphenyl)-5-oxopentanoate, there is prepared (RS)-5-[3-(4-methoxybenzyloxy)phenyl]-4-(2-methylphenyl)-5-oxopentanoic acid, m.p. 132–133° C. [Elemental analysis; C,74.4;H,6.25%. Calculated:- C,74.4;H,6.25%]. (xxxiv) By proceeding in a similar manner but replacing the methyl (RS)-5-(3-benzyloxyphenyl)-5-oxo-4-phenylpentanoate by the appropriate quantity of methyl (RS)-4-(2-methylphenyl)-5-oxo-5-(3-(2-pyridylmethoxy)phenyl)pentanoate, there is prepared (RS)-4-(2-methylphenyl)-5-oxo-5-(3-(2-pyridylmethoxy)phenyl)pentanoic acid, m.p. 152–154° C. [Elemental analysis:- C,74.0;H,5.95%. Calculated:- C,74.0;H,5.95%]. (xxxv) By proceeding in a similar manner but replacing the methyl (RS)-5-(3-benzyloxyphenyl)-5-oxo-4-phenylpentanoate by the appropriate quantity of methyl (RS)-4-(2-methylphenyl)-5-oxo-5-[3-(2-thienylmethoxy)phenyl]pentanoate, there is prepared (RS)-4-(2-methylphenyl)-5-oxo-5-[3-(2-thienylmethoxy)phenyl]-pentanoic acid, m.p. 96–98° C. [Elemental analysis:- C,70.1; H,5.67%. Calculated:- C,70.0;H,5.62%]. (xxxvi) By proceeding in a similar manner, but replacing the methyl (RS)-5-(3-benzyloxyphenyl)-5-oxo-4-phenylpentanoate by the appropriate quantity of methyl (RS)-5-(2-methyl-3-benzyloxyphenyl)-4-(2-methylphenyl)-5-oxopentanoate, and carrying out the reaction for 18 hours, there is prepared (RS)-5-(2-methyl-3-benzyloxyphenyl)-4-(2-methylphenyl)-5-oxopentanoic acid, in the form of a white solid after recrystallisation from ethyl acetate, m.p. 177–178° C. [Elemental analysis:- C,77.7; H,6.54%; Calculated:- C,77.6;H,6.51%]. (xxxvii) By proceeding in a similar manner, but replacing the methyl (RS)-5-(3-benzyloxyphenyl)-5-oxo-4-phenylpentanoate by the appropriate quantity of methyl (RS)-5-(3,5-dibenzyloxyphenyl)-4-(2-methylphenyl)-5-oxopentanoate, and using a solution of potassium hydroxide in methanol (15% w/v) at reflux for 1.5 hours, and subjecting to flash chromatography on silica gel, eluting with a mixture of ethyl acetate and pentane (2:3 v/v), there is prepared (RS)-5-(3,5-dibenzyloxyphenyl)-4-(2-methylphenyl)-5-oxo-pentanoic acid, in the form of a pale yellow oil. [Elemental analysis:- C,76.6;H,6.08%; Calculated for $C_{32}H_{30}O_5$.0.25AcOEt:- C,76.7;H,6.24%]. (xxxviii) By proceeding in a similar manner but replacing the methyl (RS)-5-(3-benzyloxyphenyl)-5-oxo-4-phenylpentanoate by the appropriate quantity of methyl (RS)-5-[3-(3-methoxybenzyloxy)phenyl]-4-(2-methylphenyl)-5-oxopentanoate, there is prepared (RS)-5-[3-(3-methoxybenzyloxy)phenyl]-4-(2-methylphenyl)-5-oxopentanoic acid, m.p. 72–74° C. [Elemental analysis:- C,74.6;H,6.27%. Calculated:- C,74.6; H,6.26%]. (xxxix) By proceeding in a similar manner but replacing the methyl (RS)-5-(3-benzyloxyphenyl)-5-oxo-4-phenylpentanoate by the appropriate quantity of methyl (RS)-5-[3-(3-aminobenzyloxy)-phenyl]-4-(2-methylphenyl)-5-oxopentanoate, there is prepared (RS)-5-[3-(3-aminobenzyloxy)phenyl]-4-(2-methylphenyl)-5-oxopentanoic acid in the form of an oil. [Elemental analysis:- C,73.9; H,6.34;N,3.43%. Calculated:- C,74.4;H, 6.24; N,3.47%]. (xxxx) By proceeding in a similar manner but replacing the methyl (RS)-5-(3-benzyloxyphenyl)-5-oxo-4-phenylpentanoate by the appropriate quantity of methyl (RS)-5-[3-(3-isothiazolylmethoxy)phenyl]-4-(2-methylphenyl)-5-oxopentanoate, there is prepared (RS)-5-[3-(3-isothiazolylmethoxy)phenyl]-4-(2-methylphenyl)-5-oxopentanoic acid, m.p. 102–104° C. [Elemental analysis:- C,66.8;H,5.33;N,3.44%. Calculated:- C,66.8;H,5.35; N,3.54%]. (xxxxi) By proceeding in a similar manner, but replacing the methyl (RS)-5-(3-benzyloxyphenyl)-5-oxo-4-phenylpentanoate by the appropriate quantity of methyl (RS)-5-(3-benzyloxy-5-hydroxyphenyl)-4-(2,3-dimethylphenyl)-5-oxopentanoate, there is prepared (RS)-5-(3-benzyloxy-5-hydroxyphenyl)-4-(2,3-dimethylphenyl)-5-oxopentanoic acid. (xxxxii) By proceeding in a similar manner, but replacing the methyl (RS)-5-(3-benzyloxyphenyl)-5-oxo-4-phenylpentanoate by the appropriate quantity of methyl (RS)-5-(3-benzyloxy-4-methylphenyl)-4-(2-methylphenyl)-5-oxopentanoate, and using a solution of potassium hydroxide in methanol (15% w/v) at reflux for 1 hour, there is prepared (RS)-5-(3-benzyloxy-4-methyl-phenyl)-4-(2-methylphenyl)-5-oxopentanoic acid, in the form of a white solid after trituration with pentane, m.p. 94–98° C. [Elemental analysis:- C,77.1; H,6.58%. Calculated:- C,77.6;H,6.51%]. (xxxxiii) By proceeding in a similar manner but replacing the methyl (RS)-5-(3-benzyloxyphenyl)-5-oxo-4-phenylpentanoate by the appropriate quantity of methyl (RS)-4-(2-methylphenyl)-5-oxo-5-[3-( 4-pyridy)methoxy)phenyl]pentanoate, there is prepared (RS)-4-(2-methylphenyl)-5-oxo-5-[3-(4-pyridylmethoxy)phenyl]pentanoic acid, m.p. 124–125° C. [Elemental analysis:- C,74.0;H,6.05;N,3.43%. Calculated:- C,74.0;H,5.95; N,3.60%]. (xxxxiv) By proceeding in a similar manner but replacing the methyl (RS)-5-(3-benzyloxyphenyl)-5-oxo-4-phenylpentanoate by the appropriate quantity of methyl (RS)-4-(2-methylphenyl)-5-[3-(3-methyl-2-thienylmethoxy)phenyl]-5-oxopentanoate, there is prepared (RS)-4-(2-methyl-phenyl)-5-[3-(3-methyl-2-thienylmethoxy)phenyl]-5-oxopentanoic acid, m.p. 88–90° C. [Elemental analysis:- C,70.3;H,5.98%; $C_{24}H_{24}O_4S$ requires C,70.6; H,5.92%]. (xxxxv) By proceeding in a similar manner but replacing the methyl (RS)-5-(3-benzyloxyphenyl)-5-oxo-4-phenylpentanoate by the appropriate quantity of methyl (RS)-4-(2-methylphenyl)-5-oxo-5-[3-(3-pyridylmethoxy) phenyl]pentanoate, there is prepared (RS)-4-(2-methylphenyl)-5-oxo-5-[3-(3-pyridylmethoxy) phenyl]pentanoic acid hydrate in the form of an oil. [Elemental analysis:- C,72.9;H,6.44; N,3.27%; Calculated for $C_{24}H_{23}NO_4$.0.3$H_2O$:- C,72.9;H,6.03;N,3.54%]. (xxxxvi) By proceeding in a similar manner, but replacing the methyl (RS)-5-(3-benzyloxyphenyl)-5-oxo-4-phenylpentanoate by the appropriate quantity of methyl (RS)-5-(3-benzyloxyphenyl)-4-(2,5-dimethylphenyl)-5-oxopentanoate, and using a solution of potassium hydroxide in methanol (15% w/v) at reflux for 0.75 hours, there is prepared (RS)-5-(3-benzyloxyphenyl)-4-(2,5-dimethylphenyl)-5-oxopentanoic acid, in the form of a white solid after trituration with diisopropyl ether, m.p. 146–148° C. [Elemental analysis:- C,77.2;H,6.5%. Calculated:- C,77.6;H,6.51%]. (xxxxvii) By proceeding in a similar manner, but replacing the methyl (RS)-5-(3-benzyloxyphenyl)-5-oxo-4-phenylpentanoate by the appropriate quantity of methyl (RS)-5-(3-benzyloxy-6-hydroxyphenyl)-4-(2-methylphenyl)-5-oxopentanoate, there is prepared (RS)-5-(3-benzyloxy-6-hydroxyphenyl)-4-(2-methylphenyl)-5-oxopentanoic acid, in the form of a yellow oil.

EXAMPLE 25
Compounds CR and CS

A mixture of methyl (RS)-5-(3-benzyloxy-phenyl)-4-(3-methylpyrid-4-yl)-5-oxopentanoate (3.26 g), dioxan (50 mL), water (9 mL) and concentrated hydrochloric acid (6 mL) is stirred at 60° C. for 1 hour and then evaporated to dryness under reduced pressure. The residue is treated with saturated aqueous sodium bicarbonate solution to give a solution of pH 7 and extracted with ethyl acetate. Evaporation, followed by crystallisation from a mixture of ethyl acetate and pentane affords (RS)-5-(3-benzyloxyphenyl)-4-(3-methylpyrid-4-yl)-5-oxopentanoic acid (1.56 g) in the form of a cream coloured solid, m.p. 55–57° C. [Elemental analysis:- C,73.7;H,5.92; N,3.41%. Calculated:- C,74.0;H,5.95;N,3.60%].

By proceeding in a similar manner, but replacing the methyl (RS)-5-(3-benzyloxyphenyl)-4-(3-methylpyridin-4-yl)-5-oxopentanoate by the appropriate quantity of methyl (RS)-5-[3-(1,2,4-oxadiazol-3-ylmethoxy)phenyl]-4-(2-methylphenyl)-5-oxopentanoate and carrying out the reaction for 4 hours, there is prepared, after flash chromatography on silica eluting with a mixture of dichloromethane and methanol (96.5:3.5 v/v), (RS)-5-[3-(1,2,4-oxadiazol-3-ylmethoxy)phenyl]-4-(2-methylphenyl)-5-oxopentanoic acid, in the form of a colourless oil.

EXAMPLE 26
Compounds CT–CZ and DA–DO

A stirred solution of benzyl (3-benzyloxyphenyl) ketone (10 g) in tetrahydrofuran (100 mL) cooled at 0° C. is treated with potassium tert-butoxide (370 mg). After 40 minutes at 0° C., the mixture is treated with methyl acrylate (2.9 g) and stirring is continued at ambient temperature. The reaction is then concentrated under reduced pressure, partitioned between water and ethyl acetate and the organic layer is dried over magnesium sulphate. Concentration gives methyl (RS)-5-(3-benzyloxyphenyl)-5-oxo-4-phenylpentanoate (11.6 g), in the form of a colourless oil.

By proceeding in a similar manner, but using the appropriate quantities of the corresponding starting materials, there are prepared:- methyl (RS)-5-[3-(benzyloxy)phenyl]-4-(2-chlorophenyl)-5-oxopentanoate, in the form of a yellow oil; methyl (RS)-5-[3-(benzyloxy)phenyl]-4-(2-methoxyphenyl)-5-oxopentanoate, in the form of an orange oil; methyl (RS)-5-[3-(benzyloxy)phenyl]-4-(2-methylphenyl)-5-oxo-pentanoate, in the form of a pale yellow oil; methyl (RS)-5-[3-(benzyloxy)phenyl]-4-(2-ethylphenyl)-5-oxo-pentanoate, in the form of a pale yellow oil; methyl (RS)-5-[3-(benzyloxy)phenyl]-4-(2-chloro-6-fluorophenyl)-5-oxo-pentanoate, in the form of a yellow oil; methyl (RS)-5-[3-(benzyloxy)phenyl]-4-(2,6-dichlorophenyl)-5-oxo-pentanoate, in the form of a pale yellow oil; methyl (RS)-5-[3-(benzyloxy)phenyl]-4-(3,4-dichlorophenyl)-5-oxo-pentanoate, in the form of an orange oil; methyl (RS)-5-[3-(benzyloxy)phenyl]-4-(4-chlorophenyl)-5-oxopentanoate, in the form of a yellow oil; methyl (RS)-5-[3-(benzyloxy)phenyl]-4-(4-methylphenyl)-5-oxopentanoate, in the form of a yellow oil; methyl (RS)-5-[3-(benzyloxy)phenyl]-4-(3-chlorophenyl)-5-oxo-pentanoate, in the form of a white solid, m.p. 110–111° C.; methyl (RS)-5-[3-(benzyloxy)phenyl]-4-(3-methoxyphenyl)-5-oxopentanoate, in the form of a pale yellow oil; methyl (RS)-5-(4-benzyloxyphenyl)-5-oxo-4-phenylpentanoate, in the form of a colourless solid, m.p. 74–76° C.; methyl (RS)-5-(3-benzyloxyphenyl)-5-oxo-4-(2-pyridyl)pentanoate, in the form of a brown oil; methyl (3RS,4RS)-5-(3-benzyloxyphenyl)-3-methyl-5-oxo-4-phenylpentanoate, in the form of an oil; methyl (2RS,4RS)-5-(3-benzyloxyphenyl)-2-methyl-5-oxo-4-phenylpentanoate, in the form of an oil; methyl (RS)-5-[3-(2-methoxybenzyloxy)phenyl]-5-oxo-4-phenylpentanoate, in the form of a colourless oil; methyl (RS)-5-[3-(3,4-methylenedioxybenzyloxy)phenyl]-5-oxo-4-phenylpentanoate, in the form of an oil; methyl (RS)-5-(3-benzyloxy-2-methylphenyl)-4-(2-methylphenyl)-5-oxopentanoate; methyl (RS)-5-(3,5-benzyloxyphenyl)-4-(2-methylphenyl)-5-oxopentanoate; methyl (RS)-5-(3-benzyloxy-4-methylphenyl)-4-(2-methylphenyl)-5-oxopentanoate; and methyl (RS)-5-(3-benzyloxyphenyl)-4-(2,5-dimethylphenyl)-5-oxopentanoate.

EXAMPLE 27
Compounds DP–DS

A stirred solution of benzyl 3-benzyloxyphenyl ketone (3.02 g) in dry tetrahydrofuran (70 mL) at −40° C. is treated with potassium tert-butoxide (1.12 g), portionwise during 10 minutes. The reaction is stirred at −40° C. for 1 hour and is then treated dropwise with a solution of methyl bromoacetate (1.04 g) in tetrahydrofuran (10 mL). The mixture is allowed to stir at ambient temperature for 18 hours. After this time, the reaction is concentrated to dryness and partitioned between ethyl acetate and water. The organic layer is dried over magnesium sulphate and concentrated under reduced pressure. The residue is recrystallised from a mixture of ethyl acetate and pentane, to give methyl (RS)-4-(3-benzyloxyphenyl)-4-oxo-3-phenylbutanoate (1.4 g), m.p. 88–89° C.

By proceeding in a similar manner but using the appropriate quantities of the corresponding starting materials, there are prepared:

ethyl (RS)-6-(3-benzyloxyphenyl)-6-oxo-5-phenylhexanoate, in the form of a light green oil; ethyl (RS)-7-(3-benzyloxyphenyl)-7-oxo-6-phenylheptanoate, in the form of a colourless oil; and ethyl (RS)-6-(3-benzyloxyphenyl)-6-oxo-5-phenylhex-2-enoate, in the form of an oil.

EXAMPLE 28
Compounds DT–DZ and EA–EL

A stirred solution of methyl (RS)-5-[3-(hydroxy)phenyl]-4-(2-methylphenyl)-5-oxo-pentanoate (1.68 g) in dimethylformamide (20 mL) is treated with 60% sodium hydride in oil (237 mg). After 15 minutes the mixture is treated with 4-chlorobenzyl chloride (953 mg) and heated at 60° C. for 1 hour. The reaction mixture is evaporated, the residue is dissolved in diethyl ether, washed with water, dried, and evaporated, to give methyl (RS)-5-[3-(4-chlorobenzyloxy)phenyl]-4-(2-methylphenyl)-5-oxopentanoate (2.05 g), in the form of a colouriess oil. [NMR(CDCl$_3$):- 2.0–2.5(4H, m),2.5(3H,s), 3.65(3H,s), 4.8(1H,m),5.0(2H,q),7.0–7.5 (12H)].

By proceeding in a similar manner, but using the appropriate quantities of the corresponding starting materials, there are prepared: ethyl (RS)-5-[3-(4-chlorobenzyloxy)phenyl]-4-(2-methylphenyl)-5-oxopentanoate; methyl (RS)-5-(3-cyclopentylmethoxyphenyl)-4-(2-methylphenyl)-5-oxopentanoate; methyl (RS)-4-(2-methylphenyl)-5-oxo-5-[3-(3-thienylmethoxy)phenyl]pentanoate; methyl (RS)-5-[3-(2-fluorobenzyloxy)phenyl]-4-(2-methylphenyl)-5-oxopentanoate; methyl (RS)-5-[3-(2-furylmethoxy)phenyl]-4-(2-methylphenyl)-5-oxopentanoate; methyl (RS)-5-[3-(3-furylmethoxy)phenyl]-4-(2-methylphenyl)-5-oxopentanoate; methyl (RS)-5-[3-(3-chlorobenzyloxy)phenyl]-4-(2-methylphenyl)-5-oxopentanoate; methyl (RS)-5-[3-(4-methoxybenzyloxy)phenyl]-4-(2-methylphenyl)-5-oxopentanoate; methyl (RS)-4-(2-methylphenyl)-5-oxo-5-[3-(2-pyridylmethoxy)phenyl]pentanoate; methyl (RS)-4-(2-methylphenyl)-5-oxo-5-[3-(2-thienylmethoxy)phenyl]pentanoate; methyl (RS)-5-[3-(3-methoxybenzyloxy)phenyl]-4-(2-methylphenyl)-5-oxopentanoate; methyl (RS)-5-[3-(3-isothiazolylmethoxy)phenyl]-5-oxo-4-(2-methylphenyl)pentanoate; methyl (RS)-5-[3-(4-pyridylmethoxy)phenyl]-5-oxo-4-(2-methylphenyl)pentanoate; methyl (RS)-5-[3-(3-nitrobenzyloxy)phenyl]-5-oxo-4-(2-methylphenyl)pentanoate; methyl (RS)-5-[3-(3-pyridylmethoxy)phenyl]-5-oxo-4-(2-methylphenyl)pentanoate; methyl (RS)-5-(3-methoxyphenyl)-4-(2-methylphenyl)-5-oxopentanoate; methyl (RS)-5-(3-isopropoxyphenyl)-4-(2-methylphenyl)-5-oxopentanoate; and methyl (RS)-5-[3-(1,2,4-oxadiazol-3-ylmethoxy)phenyl]-4-(2-methylphenyl)-5-oxopentanoate.

EXAMPLE 29
Compound EM

A solution of triphenylphosphine (1.13 g) in tetrahydrofuran (30 mL) is treated with diisopropyl azodicarboxylate (0.84 mL) at 0–5° C. The suspension is then treated with methyl (RS)-5-(3-hydroxyphenyl)-5-oxo-4-(2-methylphenyl)pentanoate (671 mg) and 3-methyl-2-thienylmethanol (275 mg), and stirred at 5° C. for 15 minutes. The solution is evaporated and the residue is subjected to flash chromatography on silica gel, eluting with a mixture of pentane and ethyl acetate (5:1 v/v), to give methyl (RS)-5-[3-(3-methyl-2-thienylmethoxy)phenyl]-4-(2-methylphenyl)-5-oxopentanoate (350 mg), in the form of an oil. [NMR(CDCl$_3$):- 2.0–2.5(4H,m), 2.25(3H,s),2.5(3H,s), 3.65(3H,s), 4.8(1H,m),5.1 (2H,q),6.85–7.5(10H)].

EXAMPLE 30
Compound EN

A solution of methyl (RS)-5-[3-(3-nitro-benzyloxy)phenyl]-5-oxo-4-(2-methylphenyl)pentanoate (1.2 g) in methyl acetate (30 mL) is treated with palladium on carbon catalyst (5%; 200 mg) and shaken under hydrogen at atmospheric pressure and room temperature for 3 hours. The mixture is filtered and evaporated giving methyl (RS)-5-[3-(3-aminobenzyloxy)- phenyl]-5-oxo-4-(2-methylphenyl)pentanoate (1.3 g) in the form of a brown oil.

EXAMPLE 31
Compound EO

A solution of [3-benzyloxy-5-(4-methoxybenzyloxy)](2-methylbenzyl) ketone (18.8 g) in dry tetrahydrofuran (200 mL) is treated with potassium tert-butoxide and stirred at ambient temperature for 15 minutes. It is then treated with methyl acrylate (4 g) and stirring is continued for 2 hours. After this time, the mixture is concentrated and partitioned between ethyl acetate (250 mL) and water (150 mL). The organic layer is dried over magnesium sulphate and concentrated. The residue is chromatographed on silica gel, eluting with ethyl acetate/pentane (1/4), to give methyl (RS)-5-[3-benzyloxy-5-(4-methoxybenzyloxy)phenyl]-4-(2-methylphenyl)-5-oxopentanoate (15.3 g), in the form of a pale yellow oil.

EXAMPLE 32
Compound EP

A solution of methyl (RS)-5-[3-benzyloxy-5-(4-methoxybenzyloxy)phenyl]-4-(2-methylphenyl)-5-oxopentanoate (0.54 g) in dichloromethane (10 mL), pH 7.3 phosphate buffer and tert-butanol (0.1 mL) is treated at 0° C. with 2,3-dichloro-5,6-dicyanobenzoquinone (0.34 g) and stirred at ambient temperature for 48 hours. It is then diluted with water (100 mL) and extracted with dichloromethane (3×30 mL). The combined organic extracts are washed with brine (50 mL), dried over magnesium sulphate and concentrated. The resulting oil (0.4 g) is dissolved in a solution of potassium hydroxide in methanol (20 mL; 15% w/v) and heated at reflux for 5 hours and is then allowed to cool. The mixture is concentrated, diluted with water (30 mL) and acidified to pH1 by treatment with concentrated hydrochloric acid. The mixture is extracted with ethyl acetate (3×50 mL) and the combined organic extracts are washed with brine and dried over magnesium sulphate, and concentrated. The resulting residue is chromatographed on silica gel, eluting with a mixture of ethyl acetate and pentane (1:1 v/v). The resulting oil is triturated with a mixture of diisopropyl ether and pentane, to give (RS)-5-(3-benzyloxy-5-hydroxyphenyl)-4-(2-methylphenyl)-5-oxopentanoic acid in the form of a white solid (80 mg), m.p. 116–117° C. [Elemental analysis:- C,73.80; H,5.90%; Calculated:- C,74.24;H,5.98%].

EXAMPLE 33
Compounds EQ and ER

A mixture of 1-(3-benzyloxyphenyl)-4-cyano-2-phenylbutan-1-one (2.2 g), toluene (80 mL), trimethyltin chloride (6.17 g) and sodium azide is stirred at 115° C. for 30 hours. The cooled reaction mixture is filtered and the insoluble material is washed with a little ethyl acetate. The combined filtrate plus washings are evaporated and the resulting orange oily solid (3 g) is subjected to flash chromatography on silica gel, eluting with a mixture of dichloromethane and methanol (29:1 v/v), followed by crystallisation from a mixture of ethyl acetate and cyclohexane, to give 5-[4-(3-benzyloxyphenyl)-4-oxo-3-phenylbutyl]-1H-tetrazole (0.86 g), in the form of a white solid, m.p. 136–138° C. [Elemental analysis:- C,72.5;H,5.63; N,14.0%; Calculated:- C,72.3;H,5.56; N,14.1%].

By proceeding in a similar manner, but replacing the 1-(3-benzyloxyphenyl)-4-cyano-2-phenylbutan-1-one by the appropriate quantity of 1-(3-benzyloxyphenyl)-3-cyano-2-(2-methyl-phenyl)propan-1-one, there is prepared 5-[3-(3-benzyloxyphenyl)-3-oxo-2-(2-methylphenyl)propyl]-1H-tetrazole, in the form of an oil. [Elemental analysis:- C,72.6;H,5.61; N,13.9%; Calculated:- C,72.4;H,5.53;N, 14.07%].

EXAMPLE 34
Compounds ES and ET

A mixture of (RS)-6-(3-benzyloxyphenyl)-5-(2-methylphenyl)-3,4-dihydro-1,2-oxathiine-2,2-dioxide (1.6 g), aqueous sodium hydroxide solution (10 mL; 1 N) and 1,4-dioxane (20 mL) is heated at reflux for 3 hours. The cooled reaction mixture is partitioned between ethyl acetate (50 mL) and water (50 mL), and the aqueous phase is acidified with dilute hydrochloric acid (2 N) and extracted with ethyl acetate (2×50 mL). The combined extracts are washed with water, dried over magnesium sulphate and evaporated, and the residual brown oil is subjected to chromatography on silica gel, eluting with a mixture of dichloromethane and methanol (9:1 v/v) to remove starting material, then eluting with a mixture of dichloromethane and methanol (4:2 v/v), to give (RS)-4-(3-benzyloxyphenyl)-3-(2-methylphenyl)-4-oxobutylsulphonic acid hydrate (0.95 g), in the form of a brown oil. [Elemental analysis:- C,65.1;H,6.37%; Calculated for $C_{24}H_{24}O_5S \cdot H_2O$:- C,65.1;H,5.92%].

By proceeding in a similar manner, but replacing the (RS)-6-(3-benzyloxyphenyl)-5-(2-methylphenyl)-3,4-dihydro-1,2-oxathiine-2,2-dioxide by the appropriate quantity of (RS)-6-[3-(3-thienylmethoxy)phenyl]-5-(2-methylphenyl)-3,4-dihydro-1,2-oxathiine-2,2-dioxide, there is prepared (RS)-4-[3-(3-thienylmethoxy)phenyl]-3-(2-methylphenyl)-4-oxobutylsulphonic acid, in the form of a pale brown hygroscopic solid, which turns into a brown oil on contact with the atmosphere. [NMR $\{(CD_3)_2SO\}$:- 1.4–2.5(4H,m), 2.41(3H,s), 5.1(2H,q),5.3(1H,t),6.96–7.6 (10H,m)].

EXAMPLE 35
Compounds EU and EV

A stirred solution of benzyl 3-benzyloxy-phenyl ketone (4.6 g) in tetrahydrofuran (100 mL) is treated with potassium tert-butoxide (1.9 g). After stirring for 20 minutes it is treated with phenyl vinylsulphonate (3.04 g), dropwise, and stirring is continued for a further 3 days. The reaction mixture is then concentrated under reduced pressure and partitioned between water and ethyl acetate. The organic layer is dried over magnesium sulphate and evaporated and the resulting residue is triturated with a mixture of ethyl acetate and petroleum ether (1:4 v/v), to give (RS)-6-(3-benzyloxyphenyl)-5-(2-methylphenyl)-3,4-dihydro-1,2-oxathiine-2,2-dioxide, in the form of a white solid (1.6 g), m.p. 257–259° C.

By proceeding in a similar manner, but replacing the benzyl 3-benzyloxyphenyl ketone by the appropriate quantity of 1-[3-(3-thienylmethoxy)phenyl]-2-(2-methylphenyl) ethan-1-one, there is prepared (RS)-6-[3-(3-thienylmethoxy)-phenyl]-5-(2-methylphenyl)-3,4-dihydro-1,2-oxathiine-2,2-dioxide, in the form of a cream coloured solid, m.p. 56–57° C.

EXAMPLE 36
Compound EW

By proceeding in a manner similar to that described hereinbefore in Example 34 but replacing the (RS)-6-(3-benzyloxyphenyl)-5-(2-methylphenyl)-3,4-dihydro-1,2-oxathiine-2,2-dioxide by the appropriate quantity of diethyl (RS)-4-(3-benzyloxy)phenyl-3-(2-methylphenyl)-4-oxobutylphosphonate, and heating at reflux for 8 hours, there is prepared ethyl (RS)-4-(3-benzyloxyphenyl)-3-(2-methylphenyl)-4-oxobutylphosphonate (0.38 g), in the form of a brown gum.

EXAMPLE 37
Compound EX

By proceeding in a manner similar to that described hereinbefore in Example 35, but replacing the benzyl 3-benzyloxyphenyl ketone by the appropriate quantity of 1-[3-(3-thienyl-methoxy)phenyl]-2-(2-methylphenyl)ethan-1-one and the phenyl vinylsulphonate by the appropriate quantity of diethyl vinylphosphonate, there is prepared diethyl (RS)-4-(3-benzyloxyphenyl)-3-(2-methylphenyl)-4-oxobutylphosphonate, in the form of a colourless oil.

EXAMPLE 38
Compounds EY–EZ and FA–FL

A mixture of ethyl (RS)-4-(3-benzyloxy-phenoxy)-4-phenylbutanoate (1 g), aqueous potassium hydroxide solution (5 mL;10% w/v) and methanol (50 mL) is stirred at reflux for 30 minutes. The reaction mixture is then evaporated to dryness and the residue is partitioned between ethyl acetate (100 mL) and dilute hydrochloric acid (50 mL; 1 N). The organic layer is washed with water, dried over magnesium sulphate, filtered and concentrated under reduced pressure to give a brown oil, which slowly crystallises. Recrystallisation from cyclohexane gives (RS)-4-(3-benzyloxyphenoxy)-4-phenylbutanoic acid (0.55 g), in the form of a beige solid, m.p. 100–104° C. [Elemental analysis:- C,76.3;H,6.21%; Calculated:- C,76.2;H,6.12%].

By proceeding in a similar manner, but replacing the ethyl (RS)-4-(3-benzyloxyphenoxy)-4-phenylbutanoate with the appropriate esters, there are prepared:- (RS)-4-(2-carboxy-5-benzyloxyphenoxy)-4-phenylbutanoic acid, in the form of a white solid after recrystallisation from ethyl acetate/cyclohexane, m.p. 124–126° C. [Elemental analysis:- C,71.1;H,5.44%; Calculated:- C,70.9; H,5.46%]; (RS)-4-[2-(N-ethylcarbamoyl)-5-benzyloxyphenoxy]-4-phenylbutanoic acid in the form of a white solid after recrystallisation from ethyl acetate/cyclohexane, m.p. 137–139° C. [Elemental analysis:- C,72.2; H,6.33;N,3.29%; Calculated:- C,72.0;H,6.28; N,3.23%];

(RS)-4-(2-acetyl-5-benzyloxyphenoxy)-4-phenylbutanoic acid in the form of a white solid after recrystallisation from ethyl acetate/cyclohexane, m.p. 112–115° C. [Elemental analysis:- C,74.1; H,6.00%; Calculated:- C,74.2;H,5.98%]; (RS)-4-[3-(3-thienyl-methoxy)phenoxy)]-4-phenylbutanoic acid in the form of a white solid after recrystallisation from cyclohexane, m.p. 105–107° C. [Elemental analysis:- C,67.2; H,5.44%; Calculated:- C,67.6,H 5.44%]; (RS)-4-(3-benzyloxy)phenoxy-4-(2-methylphenyl)butanoic acid in the form of a yellow oil [Elemental analysis:- C,76.5;H,6.95%; Calculated:- C,76.6; H,6.43%]; (RS)-4-[2-acetyl-5-(3-thienylmethoxy)phenoxy]-4-(2-methylphenyl)butanoic acid in the form of a white solid after recrystallisation from cyclohexane/ethyl acetate, m.p. 116–121° C. [Elemental analysis:- C,68.4;H,5.69%; Calculated:- C,67.9;H,5.70%]; (RS)-4-[2-acetyl-5-(3-thienylmethoxy)phenoxy]-4-phenylbutanoic acid in the form of a white solid after recrystallisation from cyclohexane/ethyl acetate, m.p. 134–135° C. [Elemental analysis:- C,67.5; H,5.37%; Calculated:- C,67.3;H 5.40%]; (RS)-4-[2-acetyl-5-(3-pyridylmethoxy)phenoxy]-4-phenylbutanoic acid in the form of a colourless oil [Elemental analysis:- C,67.5;H, 5.84;N,3.22%; Calculated:- C,68.0;H,5.91;N,3.31%]; (RS)-4-[2-carbamoyl-5-benzyloxyphenoxy]-4-phenylbutanoic acid in the form of a white solid after recrystallisation from a mixture of ethyl acetate and acetonitrile, m.p. 170–171° C. [Elemental analysis:- C,71.1;H,5.67;N,3.36%; Calculated:- C,71.1; H,5.72; N,3.44%]; (RS)-4-[2-cyano-5-benzyloxyphenoxy]-4-phenylbutanoic acid in the form of a white solid after recrystallisation from ethyl acetate/cyclohexane, m.p. 134–137° C. [Elemental analysis:- C,74.3; H,5.29;N,3.42%; Calculated:- C,74.4;H,5.46; N,3.61%]; (RS)-4-[2-(N,N-dimethylcarbamoyl)-5-benzyloxy-phenoxy]-4-phenylbutanoic acid in the form of a yellow semi-solid [Elemental analysis:- C,71.3; H,6.38; N,3.04%; Calculated:- C,71.3;H,6.33; N,3.20%]; (RS)-4-[2-(3-pyrazolyl)-5-(3-thienylmethoxy)phenoxy]-4-(2-methylphenyl)butanoic acid in the form of an off-white solid after recrystallisation from ethyl acetate/cyclohexane, m.p. 189–190° C. [Elemental analysis:- C,66.9; H,5.39;N,6.21; Calculated:- C,66.9; H,5.39; N,6.25]; and (RS)-4-[2-cyano-5-(3-thienylmethoxy)phenoxy]-4-(2-methylphenyl)butanoic acid in the form of a white solid after recrystallisation from a mixture of ethyl acetate and cyclohexane, m.p. 167–169° C. [Elemental analysis:- C,67.4;H,5.11; N,3.41; Calculated:- C,67.2;H,5.19;N,3.44].

EXAMPLE 39
Compound FM

A mixture of 3-benzyloxyphenol (3 g), ethyl (RS)-4-chloro-4-phenylbutanoate (4.53 g), potassium carbonate (4.14 g), potassium iodide (100 mg) and methyl ethyl ketone (100 mL) is heated at reflux for 40 hours. The mixture is evaporated to dryness and the residue is partitioned between ethyl acetate (200 mL) and water (200 mL). The organic layer is dried over magnesium sulphate, filtered, and concentrated in vacuo. Flash chromatography of the resulting oil, eluting with a mixture of ethyl acetate and cyclohexane (1:19 v/v), gives ethyl (RS)-4-(3-benzyloxyphenoxy)-4-phenylbutanoate (1 g), in the form of a yellow oil.

EXAMPLE 40
Compounds FN–FW

A stirred suspension of sodium hydride (340 mg) in dry dimethylformamide (100 mL) is treated portionwise with methyl 4-benzyloxy-2-hydroxybenzoate (2 g). After stirring at ambient temperature for 30 minutes, it is treated with ethyl (RS)-4-chloro-4-phenylbutanoate (1.9 g) in one portion and stirred for 16 hours at ambient temperature, and then for two hours at 80° C. The reaction mixture is then concentrated in vacuo and the residue is partitioned between ethyl acetate (100 mL) and water (100 mL). The organic layer is dried over magnesium sulphate, filtered and concentrated in vacuo. Flash chromatography of the resulting oil, eluting with 5–10% ethyl acetate/cyclohexane, affords ethyl (RS)-4-(2-methoxycarbonyl-5-benzyloxyphenoxy)-4-phenylbutanoate (2 g), in the form of a yellow oil.

By proceeding in a similar manner, but replacing methyl 4-benzyloxy-2-hydroxybenzoate with 3-benzyloxyphenol and ethyl (RS)-4-chloro-4-phenylbutanoate with ethyl (RS)-4-chloro-4-(2-methyl)phenylbutanoate, there is prepared ethyl (RS)-4-[(3-benzyloxy)phenoxy]-4-(2-methylphenyl) butanoate. By proceeding in a similar manner, but replacing methyl 4-benzyloxy-2-hydroxybenzoate with 3-(3-thienylmethoxy)phenol, there is prepared ethyl (RS)-4-[3-(3-thienylmethoxy)phenoxy]-4-phenylbutanoate. By proceeding in a similar manner, but replacing methyl 4-benzyloxy-2-hydroxybenzoate with 2-hydroxy-4-(3-thienylmethoxy)acetophenone, there is prepared ethyl (RS)-4-[2-acetyl-5-(3-thienylmethoxy)phenoxy)]-4-phenylbutanoate. By proceeding in a similar manner but replacing methyl 4-benzyloxy-2-hydroxybenzoate with 2-hydroxy-4-benzyloxy-N-ethylbenzamide there is obtained ethyl (RS)-4-[2-(N-ethylcarbamoyl)-5-benzyloxyphenoxy]-4-phenyl-butanoate. By proceeding in a similar manner but replacing methyl 4-benzyloxy-2-hydroxybenzoate with 2-hydroxy-4-(3-thienylmethoxy)acetophenone and ethyl (RS)-4-chloro-4-phenylbutanoate with ethyl (RS)-4-chloro-4-(2-methylphenyl)butanoate, there is prepared ethyl (RS)-4-[2-acetyl-5-(3-thienylmethoxy)phenoxy]-4-(2-methylphenyl)-butanoate. By proceeding in a similar manner, but replacing methyl 4-benzyloxy-2-hydroxybenzoate with 2-hydroxy-4-(3-pyridylmethoxy) acetophenone, there is prepared ethyl (RS)-4-[2-acetyl-5-(3-pyridylmethoxy)phenoxy]-4-phenylbutanoate. By proceeding in a similar manner, but replacing methyl 4-benzyloxy-2-hydroxybenzoate with 4-benzyloxy-2-hydroxybenzamide, there is prepared ethyl (RS)-4-[2-carbamoyl-5-benzyloxyphenoxy]-4-phenylbutanoate. By proceeding in a similar manner, but replacing methyl 4-benzyloxy-2-hydroxybenzoate with 4-benzyloxy-2-hydroxy-N,N-dimethylbenzamide, there is prepared ethyl (RS)-4-[2-N,N-dimethylcarbamoyl-5-benzyloxyphenoxy]-4-phenylbutanoate. By proceeding in a similar manner. but replacing methyl 4-benzyloxy-2-hydroxybenzoate with 4-(3-thienylmethoxy)-2-hydroxybenzamide and ethyl (RS)-4-chloro-4-phenylbutanoate with ethyl (RS)-4-chloro-4-(2-methylphenyl)butanoate, there is prepared ethyl (RS)-4-[2-carbamoyl-5-(3-thienylmethoxy)phenoxy]-4-(2-methylphenyl)butanoate.

EXAMPLE 41
Compound FX

A mixture of 4-benzyloxy-2-hydroxyaceto-phenone (1.2 g), ethyl (RS)-4-chloro-4-phenyl-butanoate (1.21 g), potassium carbonate (760 mg), potassium iodide (35 mg) and dimethylformamide (30 mL) is stirred at 100° C. for 8 hours. It is evaporated to dryness and the resulting residue is partitioned between ethyl acetate (200 mL) and water (200 mL). The organic layer is dried over magnesium sulphate, filtered and concentrated in vacuo. Flash chromatography of the resulting oil, eluting with 15–30% ethyl acetate/hexane, affords ethyl (RS)-4-(2-acetyl-5-benzyloxy-phenoxy)-4-phenylbutanoate (0.73 g), in the form of a yellow oil.

EXAMPLE 42
Compounds FY and FZ

A mixture of ethyl (RS)-4-(2-carbamoyl-5-benzyloxyphenoxy)-4-phenylbutanoate (1.9 g) and acetic anhydride (50 mL) is stirred at reflux for 2 hours. The reaction mixture is evaporated to low bulk and the residue is dissolved in ethyl acetate (50 mL). This solution is washed with aqueous sodium hydrogen carbonate and water, dried, and evaporated. Flash chromatography, eluting with a mixture of cyclohexane and dichloromethane (15:85 v/v), gives ethyl (RS)-4-(2-cyano-5-benzyloxyphenoxy)-4-phenylbutanoate (0.6 g).

By proceeding in a similar manner, but replacing ethyl (RS)-4-(2-carbamoyl-5-benzyloxy-phenoxy)-4-phenylbutanoate by ethyl (RS)-4-(2-carbamoyl-5-(3-thienylmethoxy)phenoxy)-4-(2-methylphenyl)butanoate, there is prepared ethyl (RS)-4-[2-cyano-5-(3-thienylmethoxy)phenoxy]-4-(2-methylphenyl)butanoate.

EXAMPLE 43
Compound GA

A stirred suspension of sodium hydride (0.1 g of a 60% dispersion in oil) in anhydrous toluene (25 mL) is treated with a mixture of ethyl (RS)-4-[2-acetyl-5-(3-thienylmethoxy)phenoxy]-4-(2-methylphenyl)butanoate (1 g) and ethyl formate (1 mL) in anhydrous toluene (5 mL). The resulting mixture is stirred at reflux for 2 hours, during which time a yellow precipitate forms. After cooling to room temperature the mixture is filtered and the residue is washed with a little cyclohexane and partitioned between dilute hydrochloric acid (10 mL; 1 M) and ethyl acetate (50 mL). The organic layer is dried and evaporated and the residue is dissolved in ethanol (25 mL) and treated with hydrazine hydrate (0.12 g). After standing at room temperature overnight, the mixture is partitioned between water (50 mL) and ethyl acetate (50 mL). The organic layer is dried and evaporated flash chromatography, eluting with a mixture of ethyl acetate and cyclohexane (1:4 v/v), to give ethyl (RS)-4-[2-(3-pyrazolyl)-5-(3-thienylmethoxy)phenoxy]-4-(2-methylphenyl)butanoate (0.25 g) in the form of a colourless oil.

EXAMPLE 44
Compounds GB–GE (RS)-5-(3-Benzyloxyphenyl)-4-(2-methylphenyl)-5-oxopentanoic acid is separated into its enantiomers, (R)-5-

(3-benzyloxyphenyl)-4-(2-methylphenyl)-5-oxopentanoic acid and (S)-5-(3-benzyloxyphenyl)-4-(2-methylphenyl)-5-oxopentanoic acid, by chiral HPLC, under the following conditions:- Chiralcel OD column; mobile phase of isopropanol/methanol/acetic acid/heptane (1:1:1:97 v/v); flow rate 1 mL/minute; temperature ambient; UV detection 270 nm.

By proceeding in a similar manner, (RS)-4-[2-acetyl-5-(3-thienylmethoxy)phenoxy]-4-(2-methyl-phenyl)butanoic acid is separated into its enantiomers, (R)-4-[2-acetyl-5-(3-thienylmethoxy)-phenoxy]-4-(2-methylphenyl)butanoic acid and (S)-4-[2-acetyl-5-(3-thienylmethoxy)phenoxy]-4-(2-methylphenyl)butanoic acid, by chiral HPLC, under the following conditions:- Chiralcel OD column; mobile phase of isopropanol/acetic acid/heptane (10:1:100 v/v); flow rate 1 mL/minute; temperature ambient; UV detection 270 nm.

EXAMPLE 45
Compounds GF–GI

A solution of ethyl (RS)-4-[2-acetyl-5-(5-pyrimidinylmethoxy)phenoxy]-4-(2-methylphenyl)-butanoate (1.1 g) in dioxan (10 mL) and sodium hydroxide (5.3 mL; 1 M) is stirred at 25° C. for 45 minutes. The solution is evaporated, the residue is diluted with water, and brought to pH 6 by treatment with hydrochloric acid (2 M). The precipitate is extracted with ethyl acetate, washed with water, dried and evaporated. The residual oil is subjected to flash chromatography on silica gel, eluting with a mixture of dichloromethane and methanol (95:5 v/v), followed by trituration with diethyl ether to give (RS)-4-(2-acetyl-5-(5-pyrimidinylmethoxy)-phenoxy]-4-(2-methylphenyl) butanoic acid (0.44 g) in the form of a colourless solid, m.p.142–144° C. [NMR($CDCl_3$):- 2.2–2.7(4H,m),2.45(3H, s), 2.7 (3H,s),4.9(2H,q),5.5(1H,q),6.2–7.8(7H),8.7(2H,s), 9.2(1H,s)].

By proceeding in a similar manner, but using the appropriate quantities of the corresponding starting materials, there are prepared:- (RS)-4-(2-methylphenyl)-4-[2-(2-pyridyl)-5-(3-thienylmethoxy)phenoxy]butanoic acid, m.p. 65–67° C.; (RS)-4-(2-methylphenyl)-4-[2-{3-(2-pyridyl)pyrazol-5-yl}-5-(3-thienylmethoxy)phenoxy]-butanoic acid, m.p. 211–213° C.; and (RS)-4-(2-methylphenyl)-4-[2-thiocarbamoyl-5-(3-thienylmethoxy)phenoxy]butanoic acid, m.p. 149–150° C.

EXAMPLE 46
Compound GJ

A solution of ethyl (RS)-4-[2-acetyl-5-(3-thienylmethoxy)phenoxy]-4-(2-methylphenyl)-butanoate (0.5 g) in ethanol (5 mL) is treated with pyridine-2-carboxaldehyde (0.12 g) and aqueous sodium hydroxide solution (0.95 g; 33% w/w) and stirred at 25° C. for 90 minutes. The solution is diluted with water and then brought to pH 7 by treatment with hydrochloric acid (2 M), forming a yellow gum. This gum is extracted with ethyl acetate, and the extract is washed with water, dried and evaporated. The resulting residue is subjected to flash chromatography on silica gel, eluting with a mixture of ethyl acetate and pentane (65:35 v/v), followed by trituration with pentane, to give (E)-(RS)-4-(2-methylphenyl)-4-[2-{3-(2-pyridyl) prop-2-enoyl}-5-(3-thienylmethoxy)phenoxy]butanoic acid (0.22 g) in the form of a yellow solid, m.p. 65–70° C. [NMR ($CDCl_3$):- 2.1–2.9 (4H,m),2.4(3H,s),4.9(2H,q),5.6(1H,q), 6.2–7.6(12H),7.7(1H,d,J=16 Hz),7.8(1H,t), 8.0(1H,d,J=16 Hz),8.6(1H,d)].

EXAMPLE 47
Compounds GK and GL

A stirred solution of 2-hydroxy-4-(5-pyrimidinylmethoxy)acetophenone (0.65 g) in dry dimethylformamide (15 mL) is treated with sodium hydride (0.16 g; 60% w/v dispersion in mineral oil; 4 mmol). After 30 minutes the suspension is treated with ethyl (RS)-4-chloro-4-(2-methyl-phenyl)butanoate (0.96 g) and heated to 90° C. for 6 hours. The reaction mixture is evaporated and the residue is dissolved in ethyl acetate, washed with water, dried and evaporated. The residual oil is subjected to flash chromatography on silica gel, eluting with ethyl acetate, to give ethyl (RS)-4-[2-acetyl-5-(5-pyrimidinylmethoxy) phenoxy]-4-(2-methylphenyl)butanoate (1.19 g) in the form of a brown oil. [NMR($CDCl_3$):- 1.2(3H,m), 2.2–2.7(4H,m), 2.5(3H,s), 2.7(3H,s), 4.1(2H,t), 4.9(2H,q), 5.5(1H,q), 6.2–7.8(7H), 8.7 (2H,s), 9.2(1H,s).

By proceeding in a similar manner, but using the appropriate quantities of the corresponding starting materials, there is prepared ethyl (RS)-4-(2-methylphenyl)-4-[2-(2-pyridyl)-5-(3-thienylmethoxy)phenoxy]butanoate in the form of a colourless oil

EXAMPLE 48
Compound GM

A stirred solution of ethyl (RS)-4-(2-methyl-phenyl)-4-[2-acetyl-5-(3-thienylmethoxy)phenoxy]-butanoate (0.90 g) in toluene (25 mL) is treated with ethyl pyridine-2-carboxylate (0.30 g) and sodium hydride (0.12 g; 60% w/v dispersion in mineral oil; 3 mmol) and heated at reflux for 4 hours. The solution is then evaporated, and the residual brown gum is dissolved in ethanol (40 mL) treated with acetic acid (0.48 g) and hydrazine hydrate (0.10 g) and heated at reflux for 2 hours. The solution is evaporated and the residual gum is subjected to flash chromatography on silica gel, eluting with a mixture of pentane and ethyl acetate (1:2 v/v), to give ethyl (RS)-4-(2-methylphenyl)-4-[2-{3-(2-pyridyl)pyrazol-5-yl}-5-(3-thienylmethoxy)-phenoxy] butanoate (0.20 g) in the form of a light brown oil. [NMR ($CDC_3$):- 1.2(3H,t),2.2–2.7 (4H,m),2.5(3H,s), 4.1(2H,q),4.9 (2H,q),5.6(1H,m), 6.3–7.7(13H,m),7.8(1H,t),8.0(1H,d)].

EXAMPLE 49
Compound GN

A stirred solution of ethyl (RS)-4-[2-carbamoyl-5-(3-thienylmethoxy)phenoxy]-4-(2-methylphenyl)butanoate (2.44 g) in tetrahydrofuran (49 mL) is treated with 2,4-bis (4-methoxyphenyl)-1,3-dithia-2,4-diphosphetane-2,4-disulphide (1.08 g) and maintained at 25° C. for 24 hours. The solution is then evaporated and the residual oil is subjected to flash chromatography on silica gel, eluting with a mixture of pentane and ethyl acetate (2:1 v/v), followed by trituration with diethyl ether, to give ethyl (RS)-4-(2-methylphenyl)-4-[5-(3-thienylmethoxy)-2-thiocarbamoylphenoxy]butanoate (1.79 g) in the form of a yellow solid, m.p. 134–135° C. [NMR($CDCl_3$):- 1.2(3H,t), 2.2–2.6(4H,m), 2.4(3H,s),4.1(2H,q), 4.9(2H,q),5.6(1H,m), 6.2–7.8(9H,m),8.7(1H,d)].

EXAMPLE 50
Compounds GO–GZ and HA–HL

By proceeding in a manner similar to that described hereinbefore in Example 38, and using the appropriate quantities of the corresponding esters as starting materials, there are prepared;

(RS)-4-[5-benzyloxy-2-(methylthio)phenoxy]-4-phenylbutanoic acid hydrate, in the form of a white solid, m.p. 104–105° C. after recrystallisation from a mixture of petroleum ether (b.p.40–60° C.) and ethyl acetate [Elemental analysis:- C,69.5; H,5.82;S,8.0%; Calculated for $C_{24}H_{24}O_4S$:0.25$H_2O$:- C,69.8;H,5.98;S,7.76%]; (E)-(RS)-4-[5-benzyloxy-2-(2-carboxyethenyl)phenoxy]-4-(2-methylphenyl)butanoic acid hydrate, in the form of a white solid, m.p. 151–153° C., after recrystallisation from a mixture of t-butyl methyl ether and pentane [Elemental analysis:- C,71.2;H,5.86%; Calculated for $C_{28}H_{28}O_6$.0.5$H_2O$:- C,71.2;H,5.97%]; (RS)-4-[2-(1-methyl-2-carboxyethenyl)-5-(3-thienylmethoxy)phenoxy]-4-(2-methylphenyl)butanoic acid (E:Z ratio 3:1), in the form of a white solid, m.p. 167–170° C., after recrystallisation from a mixture of cyclohexane and ethyl acetate [Elemental analysis:- C,66.8; H,5.65%; Calculated:- C,66.9;H,5.62%]; (RS)-4-[5-benzyloxy-2-hydroxyiminomethylphenoxy]-4-(2-methylphenyl)butanoic acid, (E:Z ratio 4:1), in the form of a yellow oil [Elemental analysis:- C,71.5;H,6.59;N, 2.56%; Calculated:- C,71.6; H,6.01;N,3.34%]; (RS)-4-[2-{N-(carboxymethoxy)iminomethyl}-5-(3-thienyl-methoxy)phenoxy]-4-(2-methylphenyl)butanoic acid in the form of an off-white solid, m.p. 114–116° C. after recrystallisation from a mixture of isopropanol and pentane [Elemental analysis:- C,62.4; H,5.20;N,2.96%; Calculated:- C,62.1; H,5.21; N,2.90%]; (RS,RS)-4-[2-(1-hydroxyethyl)-5-(3-thienyl-methoxy)phenoxy]-4-(2-methylphenyl)butanoic acid in the form of a colourless oil [Elemental analysis:- C,67.7;H, 6.63%; Calculated:- C,67.6;H,6.14%]; (RS)-4-(2-methylphenyl)-4-[2-(propen-2-yl)-5-(3-thienylmethoxy) phenoxy]butanoic acid in the form of a white solid, m.p. 98–100° C., after recrystallisation from heptane [Elemental analysis:- C,71.1;H,6.27%; Calculated:- C,71.1; H,6.20%]; (RS)-4-[2-(5-carboxy-3-pyrazolyl)-5-(3-pyridylmethoxy) phenoxy]-4-(2-methylphenyl)butanoic acid characterised as the hydrochloride salt in the form of a white solid, m.p. 199–200° C., [Elemental analysis:- C,60.8;H,4.79; N,7.79%; Calculated for $C_{27}H_{25}N_3O_6$:HCl.0.5$H_2O$:- C,60.8; H,5.07;N,7.88%]; (RS)-4-[2-(5-carboxy-3-pyrazolyl)-5-(3-thienylmethoxy)phenoxy]-4-(2-methylphenyl)butanoic acid, in the form of a white solid, m.p. 209–210° C. [Elemental analysis:- C,62.4;H,4.97;N, 5.39%; Calculated for $C_{26}H_{24}O_6N_2S$.0.5$H_2O$:- C,62.3;H, 5.02; N,5.59%]; (RS)-4-[2-acetyl-5-(3-thienylmethoxy) phenoxy]-4-(2-bromophenyl)butanoic acid in the form of a white solid, m.p. 158–160° C., after recrystallisation from a mixture of cyclohexane and diethyl ether [Elemental analysis:- C,56.3;H,4.42; Br,16.4%; Calculated:- C,56.5;H, 4.32;Br,16.3%; (RS)-4-(2-methylphenyl)-4-[2-nitro-5-(3-thienylmethoxy)phenoxy]butanoic acid in the form of a pale yellow solid, m.p. 175–177° C., after recrystallisation from a mixture of ethyl acetate and cyclohexane [Elemental analysis:- C,61.8; H,4.87;N,3.24%; Calculated:- C,61.8;H, 4.95; N,3.28%]; (RR,RS,SR,SS)-4-(2-methylphenyl)-4-[2-methyl-sulphinyl-5-(3-thienylmethoxy)phenoxy]butanoic acid, in the form of a yellow foam, by stirring the reaction mixture at ambient temperature for sixteen hours [Elemental analysis:- C,62.8; H,5.63;S,11.8%; Calculated:- C,62.2;H, 5.41; S,14.41%]; (RS)-4-[2-acetyl-5-(3-thienylmethoxy) phenoxy]-4-(2-chloro-6-fluorophenyl)butanoic acid in the form of a beige solid, m.p. 129–130° C., after recrystallisation from a mixture of cyclohexane and ethyl acetate [Elemental analysis:- C,59.8; H,4.41;S,6.71; Cl,7.79%; Calculated:- C,59.7;H, 4.36;S,6.93;Cl,7.66%]; (RS)-4-(5-benzyloxy-2-formylphenoxy)-4-(2-methylphenyl)butanoic acid in the form of a yellow solid, m.p. 112–114° C., after recrystallisation from a mixture of diisopropyl ether and pentane [Elemental analysis:- C,74.1; H,6.04%; Calculated:- C,74.2;H,5.98%]; (RS)-4-[2-formyl-5-(3-thienylmethoxy) phenoxy]-4-(2-methylphenyl)butanoic acid, in the form of a yellow solid, m.p. 124–126° C. [Elemental analysis:- C,66.9; H,5.43;S,7.82%; Calculated:- C,67.1;H,5.63;S, 7.81%]; (RS)-4-(2-methylphenyl)-4-[5-(3-thienylmethoxy)-2-(trifluoroacetyl)phenoxy]butanoic acid in the form of a white solid, m.p. 103–104° C., after flash chromatography on silica gel, eluting with a mixture of ethyl acetate and cyclohexane (2:3 v/v), followed by recrystallisation from cyclohexane [Elemental analysis:- C,60.0; H,4.32%; Calculated:- C,60.3;H 4.42%]; (RS)-4-(2-methylphenyl)-4-[2-pentafluoroethyl-5-(3-thienylmethoxy)phenoxy]butanoic acid in the form of a white solid, m.p. 109–110° C. [using aqueous potassium carbonate solution (10% w/v) instead of the potassium hydroxide solution, and recrystallising from heptane] [Elemental analysis:- C,57.7;H,4.26%; Calculated:- C,57.6; H,4.23%]; (RS)-4-[2-cyano-3-methyl-5-(3-thienylmethoxy)phenoxy]-4-(2-methylphenyl)butanoic acid in the form of a white solid, m.p. 125–126° C., after recrystallisation from a mixture of ethyl acetate and cyclohexane [Elemental analysis:- C,68.0; H,5.55;N,2.94%; Calculated:- C,68.4;H,5.50; N,3.32%]; (RS)-4-[2-carbamoyl-5-(3-thienylmethoxy)phenoxy]-4-(2-methylphenyl)butanoic acid in the form of a white solid, m.p. 203–205° C., after recrystallisation from a mixture of ethyl acetate and acetonitrile [Elemental analysis:- C,64.7;H,5.48;N,3.09%; Calculated:- C,64.9; H,5.45;N, 3.29%]; (RS)-4-[2-{N-(3-imidazol-1-ylpropyl)carbamoyl}-5-(3-thienylmethoxy)phenoxy]-4-(2-methylphenyl)butanoic acid in the form of a white solid, m.p. 146–148° C., after recrystallisation from acetonitrile [Elemental analysis:- C,65.1; H,5.85;N,7.55%; Calculated:- C,65.2;H,5.86; N,7.87%]; (RS)-4-[2-{N-(2-carboxyethyl)carbamoyl}-5-(3-thienylmethoxy)phenoxy]-4-(2-methylphenyl)butanoic acid in the form of a white solid, m.p. 147–149° C., after recrystallisation from a mixture of ethyl acetate and cyclohexane [Elemental analysis:- C,62.6;H,5.46;N,2.80%; Calculated:- C,62.8;H,5.47;N,2.82%]; (RS)-4-[2-{N-(carboxymethyl)carbamoyl}-5-(3-thienylmethoxy) phenoxy]-4-(2-methylphenyl)butanoic acid in the form of a white solid, m.p. 138–140° C., after recrystallisation from a mixture of ethyl acetate and cyclohexane [Elemental analysis:- C,61.9;H,5.31;N,2.74%; Calculated:- C,62.1;H, 5.21;N,2.90%]; (RS)-4-[2-(N-(2-cyanoethyl)carbamoyl}-5-(3-thienylmethoxy)phenoxy]-4-(2-methylphenyl)butanoic acid in the form of a white solid, m.p. 139–141° C., after recrystallisation from a mixture of ethyl acetate and cyclohexane [Elemental analysis:- C,65.3;H,5.55;N,5.77%; Calculated:- C,65.3;H,5.48;N,5.85%]; and (RS)-4-[2-(5-carboxy-1-methyl-3-pyrazolyl)-5-(3-thienylmethoxy) phenoxy]-4-(2-methylphenyl)butanoic acid in the form of a white solid, m.p. 205–207° C., [Elemental analysis:- C,63.7;H,5.41; N,5.20%; Calculated:- C,64.0;H,5.17; N,5.53%].

EXAMPLE 51

Compounds HM and HN

A mixture of ethyl (RS)-4-[2-{N-(cyano-methyl) carbamoyl}-5-(3-thienylmethoxy)phenoxy]-4-(2-methylphenyl)butanoate (1.80 g), aqueous potassium carbonate solution (20 mL; 10% w/v) and methanol (200 mL) is stirred at ambient temperature for 16 hours. The reaction mixture is concentrated in vacuo and the residue is dissolved in water (50 mL) and acidified to pH1 by treatment with hydrochloric acid (1 N), then extracted with ethyl acetate (150 mL). The organic extract is washed with water (50 mL), dried over magnesium sulphate, and evaporated to dryness. Flash chromatography of the residue on silica gel, eluting with a mixture of methanol and dichloromethane (1:19 v/v) gives two products:- (RS)-4-[2-{N-(carbamoylmethyl)carbamoyl}-5-(3-thienylmethoxy)

phenoxy]-4-(2-methylphenyl)butanoic acid, in the form of a white solid, m.p. 202–204° C., after recrystallisation from a mixture of ethyl acetate and acetonitrile [Elemental analysis:- C,62.3;H,5.44; N,5.66%; Calculated:- C,62.2;H, 5.43;N,5.81%]; and (RS)-4-[2-{N-(methoxycarbonylmethyl)carbamoyl}-5-(3-thienylmethoxy)phenoxy]-4-(2-methylphenyl)butanoic acid, in the form of a white solid, m.p. 156–158° C., after recrystallisation from a mixture of ethyl acetate and acetonitrile [Elemental analysis:- C,62.8;H,5.48;N,2.90%; Calculated:- C,62.8;H,5.47;N,2.82%].

EXAMPLE 52
Compounds HO–HZ and IA–IB

By proceeding in a manner similar to that described hereinbefore in Example 40, and using the appropriate quantities of the corresponding starting materials, there are prepared:- ethyl (RS)-4-[5-benzyloxy-2-(methylthio) phenoxy]-4-phenylbutanoate, in the form of a yellow oil; ethyl (RS)-4-(2-methylphenyl)-4-[2-methylthio-5-(3-thienylmethoxy)phenoxy]butanoate, in the form of a yellow oil; ethyl (RS)-4-[2-acetyl-5-(3-thienylmethoxy)phenoxy]-4-(2-chloro-6-fluorophenyl)butanoate, in the form of an orange oil; ethyl (RS)-4-(5-benzyloxy-2-formylphenoxy)-4-(2-methylphenyl)butanoate, in the form of a yellow oil; ethyl (RS)-4-[2-formyl-5-(3-thienylmethoxy)phenoxy]-4-(2-methylphenyl)butanoate, in the form of a yellow oil; ethyl (RS)-4-[5-(3-thienylmethoxy)-2-trifluoroacetylphenoxy]-4-(2-methylphenyl)butanoate, in the form of a yellow oil; ethyl (RS)-4-[2-carbamoyl-3-methyl-5-(3-thienylmethoxy)phenoxy]-4-(2-methylphenyl) butanoate, in the form of a colourless oil; ethyl (RS)-4-[2-acetyl-5-(3-thienylmethoxy)phenoxy]-4-(2-bromophenyl) butanoate, in the form of a colourless oil; ethyl (RS)-4-(2-methylphenyl)-4-[2-nitro-5-(3-thienylmethoxy)phenoxy] butanoate, in the form of a yellow oil; ethyl (RS)-4-[2-{N-methoxycarbonylmethyl)carbamoyl}-5-(3-thienylmethoxy) phenoxy]-4-(2-methylphenyl)butanoate, in the form of a yellow oil; ethyl (RS)-4-[2-{N-(3-imidazol-1-ylpropyl) carbamoyl}-5-(3-thienylmethoxy)phenoxy]-4-(2-methylphenyl)butanoate, in the form of a yellow oil; ethyl (RS)-4-[2-{N-(2-cyanoethyl)carbamoyl}-5-(3-thienylmethoxy)phenoxy]-4-(2-methylphenyl)butanoate, in the form of a yellow oil; ethyl (RS)-4-[2-{N-cyanomethyl) carbamoyl}-5-(3-thienylmethoxy)phenoxy]-4-(2-methylphenyl)butanoate, in the form of a yellow oil; ethyl (RS)-4-[2-{N-(2-methoxycarbonylethyl)carbamoyl]-5-( 3-thienylmethoxy)phenoxy]-4-(2-methylphenyl)butanoate, in the form of a yellow oil; ethyl 4-[2-(1-methoxycarbonyl-2-phenylethylcarbamoyl)-5-(3-thienylmethoxy)phenoxy]-4-(2-methylphenyl)butanoate, thought to be the diastereomers (1R, 4RS), in the form of a yellow oil; ethyl 4-[2-(1-methoxycarbonyl-2-phenylethylcarbamoyl)-5-(3-thienylmethoxy)phenoxy]-4-(2-methylphenyl)butanoate, thought to be the diastereomers (1S, 4RS), in the form of a yellow oil; methyl 2-[2-hydroxy-4-(3-thienylmethoxy) benzoylamino]-3-phenylpropionate, thought to be the (R)-enantiomer, in the form of a yellow oil; and methyl 2-[2-hydroxy-4-(3-thienyl-methoxy)benzoylamino]-3-phenylpropionate, thought to be the (S)-enantiomer, in the form of a yellow oil.

EXAMPLE 53
Compound IC

A solution of ethyl (RS)-4-(2-methylphenyl)-4-[2-methylthio-5-(3-thienylmethoxy)phenoxy]butanoate in acetone (20 mL), at 0° C. is treated dropwise with a solution of potassium peroxymonosulphate (1.01 g of commercial 2KHSO$_5$:KHSO$_4$:K$_2$SO$_4$). The reaction mixture is stirred at 0° C. for 20 minutes, then treated with saturated aqueous sodium bisulphate solution (20 mL), and extracted with dichloromethane (2×50 mL). The combined organic extracts are dried over magnesium sulphate, filtered and concentrated in vacuo, to give ethyl (RS,RS)-4-(2-methylphenyl)-4-[2-methyl-sulphinyl-5-(3-thienylmethoxy)phenoxy)-butanoate (0.75 g) in the form of a yellow oil.

EXAMPLE 54
Compounds ID and IE

A stirred suspension of sodium hydride (0.272 g; 60% w/v dispersion in mineral oil; 6.8 mmol) in tetrahydrofuran (100 mL) at 0° C. under nitrogen is treated, dropwise, with methyl (diethylphosphono)acetate (1.43 g) and stirred for 15 minutes. It is then treated with a solution of ethyl (RS)-4-(5-benzyloxy-2-formylphenoxy)-4-(2-methylphenyl)butanoate (1.96 g) in tetrahydrofuran (5 mL) in one portion, and the reaction mixture is stirred at ambient temperature for 15 minutes. The mixture is treated with water (100 mL) and extracted with ethyl acetate (3×100 mL), and the combined organic extracts are washed with brine (50 mL), dried over magnesium sulphate, and filtered and the solvent is removed in vacuo, to give ethyl (E)-(RS)-4-(2-methylphenyl)-4-[2-(2-methoxycarbonylethenyl)-5-benzyloxyphenoxy] butanoate, in the form of a yellow oil.

By proceeding in a similar manner but replacing the ethyl (RS)-4-(5-benzyloxy-2-formyl-phenoxy)-4-(2-methylphenyl)butanoate used as starting material by the appropriate quantity of ethyl (RS)-4-[2-acetyl-5-(3-thienylmethoxy)-phenoxy]-4-(2-methylphenyl)butanoate, there is prepared ethyl (RS)-4-[2-(2-methoxycarbonyl-1-methylethenyl)-5-(3-thienylmethoxy)phenoxy]-4-(2-methylphenyl)butanoate (E:Z ratio 3:1), in the form of a yellow oil.

EXAMPLE 55
Compounds IF and IG

A mixture of ethyl (RS)-4-(5-benzyloxy-2-formylphenoxy)-4-(2-methylphenyl)butanoate (0.49 g), hydroxylamine hydrochloride (0.1 g) and pyridine (0.1 g) in ethanol (10 mL) is heated at reflux for 1 hour. The solvent is then removed in vacuo and the residue is partitioned between water (50 mL) and ethyl acetate (50 mL). The aqueous layer is extracted with ethyl acetate (2×50 mL) and the combined organic extracts are washed with brine (50 mL), dried over magnesium sulphate and filtered and the solvent is removed in vacuo, to give a yellow oil. Flash chromatography on silica gel, eluting with a mixture of petroleum ether (b.p.40–60° C.) and ethyl acetate (7:1 v/v), gives ethyl (RS)-4-(5-benzyloxy-2-hydroxyiminomethylphenoxy)-4-(2-methylphenyl) butanoate (E:Z ratio 4:1), (0.24 g).

By proceeding in a similar manner, but replacing the ethyl (RS)-4-(5-benzyloxy-2-formyl-phenoxy)-4-(2-methylphenyl)butanoate used as starting material by the appropriate quantity of ethyl (RS)-4-[2-formyl-5-(3-thienylmethoxy))phenoxy]-4-(2-methylphenyl)butanoate, there is prepared ethyl (RS)-4-[2-hydroxyiminomethyl-5-(3-thienylmethoxy))phenoxy]-4-(2-methylphenyl)butanoate (E:Z ratio 4:1).

EXAMPLE 56
Compound IH

A stirred solution of ethyl (RS)-4-(5-benzyloxy-2-hydroxyiminomethylphenoxy)-4-(2-methylphenyl) butanoate (3.68 g) in tetrahydrofuran (100 mL) at ambient temperature is treated portionwise with sodium hydride (0.33 g; 60% w/v dispersion in mineral oil; 8.25 mmol) during 30 minutes. It is then treated with ethyl bromoacetate (1.58 g) and stirred for one hour at ambient temperature then for 5 hours at 80° C. It is then treated with a further portion of ethyl bromoacetate (0.40 g) and heating at 80° C. is continued for one hour.

The solvent is then removed in vacuo and the residue is partitioned between saturated aqueous potassium carbonate solution (50 mL) and ethyl acetate (50 mL). The aqueous layer is extracted with ethyl acetate (2×50 mL) and the combined organic extracts are washed with brine (50 mL), dried over magnesium sulphate and filtered and the solvent is removed in vacuo, to give a yellow oil. Flash chromatography on silica gel, eluting with a mixture of petroleum ether (b.p.40–60° C.) and ethyl acetate (2:1 v/v) gives ethyl (RS)-4-[2-{N-(ethoxycarbonylmethoxy)iminomethyl}-5-(3-thienylmethoxy)phenoxy]-4-(2-methylphenyl)butanoate (E:Z ratio 4:1) (2.66 g), in the form of a yellow oil.

EXAMPLE 57
Compound II

A stirred solution of ethyl (RS)-4-[2-acetyl-5-(3-thienylmethoxy)phenoxy]-4-(2-methylphenyl)butanoate (1 g) in methanol (50 mL) is treated, portionwise, with sodium borohydride (0.1 g), and stirred at ambient temperature for one hour. It is then treated with dilute acetic acid (50 mL; 1 N) and extracted with ethyl acetate (2×50 mL). The combined organic extracts are washed with water (2×50 mL) dried over magnesium sulphate, filtered and concentrated in vacuo. Flash chromatography on silica gel, eluting with a mixture of ethyl acetate and cyclohexane (1:5 v/v) gives ethyl (RS,RS)-4-[2-(1-hydroxyethyl)-5-(3-thienylmethoxy)phenoxy]-4-(2-methylphenyl)butanoate.

EXAMPLE 58
Compound IJ

A stirred suspension of methyltriphenylphosphonium bromide (2.4 g) in tetrahydrofuran (50 mL) at ambient temperature is treated with a solution of butyllithium in hexanes (2.6 mL; 2.5 M). After two hours, the reaction mixture is treated with a solution of ethyl (RS)-4-[2-acetyl-5-(3-thienylmethoxy)phenoxy]-4-(2-methylphenyl)-butanoate (1 g) in tetrahydrofuran (2 mL) and stirred for a further two hours. It is then partitioned between hydrochloric acid (50 mL; 1 N) and ethyl acetate (100 mL). The organic layer is washed with water (50 mL), dried over magnesium sulphate, filtered and concentrated in vacuo. The residue is subjected to flash chromatography on silica gel, eluting with a mixture of ethyl acetate and cyclohexane (1:9 v/v) to give ethyl (RS)-4-(2-methylphenyl)-4-[2-(propen-2-yl)-5-(3-thienylmethoxy)phenoxyl]butanoate (0.7 g), in the form of a colourless oil.

EXAMPLE 59
Compounds IK and IL

A stirred suspension of sodium hydride (0.64 g; 60% w/v dispersion in mineral oil;16 mmol) in toluene (100 mL) is treated, dropwise, with a solution of ethyl (RS)-4-[2-acetyl-5-(3-pyridylmethoxy)phenoxy]-4-(2-methylphenyl) butanoate (6.5 g) and diethyl oxalate (6.57 g) in toluene (20 mL), and the mixture is heated at reflux for 5 hours. It is then evaporated to dryness, and the resulting residue is dissolved in ethanol (100 mL) and treated with hydrazine hydrate (0.75 g) and glacial acetic acid (3.6 g) and heated at reflux for 3 hours. The mixture is then partitioned between ethyl acetate (100 mL) and aqueous potassium carbonate solution (100 mL;10% w/v). The organic layer is washed with water (100 mL), dried over magnesium sulphate and evaporated to dryness. The resulting residue is subjected to flash chromatography on silica gel, eluting with ethyl acetate, to give ethyl (RS)-4-[2-(5-ethoxycarbonyl-3-pyrazolyl)-5-(3-pyridylmethoxy)phenoxy]-4-(2-ethylphenyl)butanoate (2.6 g).

By proceeding in a similar manner but replacing the ethyl (RS)-4-[2-acetyl-5-(3-pyridylmethoxy)phenoxy]-4-(2-methylphenyl)butanoate used as starting material by the appropriate quantity of ethyl (RS)-4-[2-acetyl-5-(3-thienylmethoxy)phenoxy]-4-(2-methylphenyl)butanoate, there is prepared ethyl (RS)-4-[2-(5-ethoxycarbonyl-3-pyrazolyl)-5-(3-thienylmethoxy)phenoxy]-4-(2-methylphenyl)butanoate.

EXAMPLE 60
Compound IM

A solution of ethyl (RS)-4-(2-methylphenyl)-4-[2-trifluoroacetyl-5-(3-thienylmethoxy)-phenoxy]butanoate (1.3 g) and diethylaminosulphur trifluoride (0.64 mL) in dichloromethane is stirred at −5° C. for 30 minutes, and then at ambient temperature for 16 hours. The reaction mixture is treated with a further portion of diethylaminosulphur trifluoride (0.32 mL) and stirred for 1 hour. It is then treated with saturated aqueous sodium bicarbonate solution (10 mL) and stirred for 15 minutes, then it is diluted with dichloromethane (50 mL) and the organic phase is washed with water (50 mL), dried over magnesium sulphate, filtered and evaporated to dryness. The resulting residue is subjected to flash chromatography on silica gel, eluting with a mixture of ethyl acetate and cyclohexane (1:19 v/v), to give ethyl (RS)-4-(2-methylphenyl)-4-[2-pentafluoroethyl-5-(3-thienylmethoxy)phenoxy]butanoate (0.6 g), in the form of a yellow oil.

EXAMPLE 61
Compound IN

By proceeding in a manner similar to that described hereinbefore in Example 42, but replacing the ethyl (RS)-4-(5-benzyloxy-2-carbamoylphenoxy)-4-(2-methylphenyl) butanoate with the appropriate quantity of ethyl (RS)-4-[2-carbamoyl-3-methyl-5-(3-thienylmethoxy)phenoxy]-4-(2-methylphenyl)butanoate, there is prepared ethyl (RS)-4-[2-cyano-3-methyl-5-(3-thienylmethoxy)phenoxy]-4-(2-methylphenyl)butanoate.

EXAMPLE 62
Compound IO

A mixture of (RS)-4-[2-(5-carboxy-3-pyrazolyl)-5-(3-thienylmethoxy)phenoxy]-4-(2-methylphenyl)butanoic acid (0.5 g), iodomethane (0.25 mL), potassium carbonate (0.55 g) and dimethylformamide (20 mL) is stirred at ambient temperature for 36 hours. The solvent is then removed in vacuo and the resulting residue is dissolved in ethyl acetate (50 mL), and this solution is washed with water (3×50 mL), dried over magnesium sulphate, filtered and concentrated in vacuo. The resulting residue is subjected to flash chromatography on silica gel, eluting with a mixture of petroleum ether (b.p. 40–60° C.) and ethyl acetate (2:1 v/v), to give methyl (RS)-4-[2-(5-methoxycarbonyl-1-methyl-3-pyrazolyl)-5-(3-thienylmethoxy)phenoxy]-4-(2-methylphenyl)butanoate (0.37 g), in the form of a colourless oil.

EXAMPLE 63
Compound IP (a) A solution of (RS)-4-[2-cyano-5-(3-thienylmethoxy) phenoxy]-4-(2-methylphenyl)-butanoic acid (500 mg) in dichloromethane (50 mL) is treated with 1,1'- carbonyldiimidazole (215 mg) and stirred at 25° C. for 2 hours, by the end of which period the evolution of carbon dioxide gas has ceased. The resulting solution is designated "solution A".

(b) A solution of benzenesulphonamide (1.16 g) in dimethylformamide (50 mL) is treated with sodium hydride (201 mg; 60% w/v dispersion in mineral oil; 5 mmol) and stirred for 2 hours. The solution is then treated, dropwise, with "solution A" prepared as hereinbefore in part (a), and stirred for 18 hours at 25° C. The solution is then evaporated and the resulting residue is partitioned between ethyl acetate and water. The organic layer is dried and evaporated, and the residual oil is subjected to flash chromatography on silica gel, eluting with a mixture of pentane and ethyl acetate (2:1 v/v), to give (RS)-N-[4-{2-cyano-5-(3-thienylmethoxy) phenoxy}-4-(2-methylphenyl)butanoyl] benzenesulphonamide (250 mg), in the form of a colourless solid, m.p. 68–70° C. [NMR(CDCl$_3$):- 2.0–2.8(4H,m), 2.3 (3H,s),4.9(2H,q),5.3(1H,q),6.1–8.0(10H)].

EXAMPLE 64
Compounds IQ and IR (RS)-4-[2-cyano-5-(3-thienylmethoxy)phenoxy]-4-(2-methylphenyl)butanoic acid is separated into its enantiomers, (R)-4-[2-cyano-5-(3-thienylmethoxy) phenoxy]-4-(2-methylphenyl)butanoic acid and (S)-4-[2-cyano-5-(3-thienylmethoxy)phenoxy]-4-(2-methylphenyl) butanoic acid, by chiral HPLC, under the following conditions:- Chiralcel OD column; mobile phase of isopropanol/acetic acid/heptane (10:1:100 v/v); flow rate 1 mL/minute; temperature ambient; UV detection 270 nm.

The (R)-enantiomer is thought to be the more mobile of the two.

EXAMPLE 65
Compound IQ

A mixture of sodium 4-hydroxy-4-(2-methyl-phenyl) butanoate, thought to be the (R)-enantiomer, (3 g) and sodium hydride (1.5 g; 60% w/v dispersion in mineral oil; 37.5 mmol) in tetrahydrofuran (50 mL) is stirred at ambient temperature for 1 hour under an atmosphere of argon, and is then warmed to 55° C. It is then treated with 2-fluoro-4-(3-thienylmethoxy)benzonitrile (3 g), in one portion, and stirring is continued at 55° C. for 15 hours. The mixture is then cooled, diluted with hydrochloric acid (200 mL; 1 N) and extracted with ethyl acetate (4×100 mL). The combined extracts are dried over magnesium sulphate and concentrated in vacuo, to give an oily residue. This residue is boiled in isopropyl ether, and the resulting mixture is filtered while hot, and then allowed to cool. The yellow solid which separates is collected and recrystallized from a mixture of ethyl acetate and hexane, to give 4-[2-cyano-5-(3-thienylmethoxy)phenoxy]-4-(2-methylphenyl)butanoic acid, thought to be the (R)-enantiomer, (1.5 g) in the form of a white fluffy solid, m.p. 145° C. Chiral HPLC assay showed a 98% enantiomeric excess. [Elemental analysis:- C,67.82;H,5.18; N,3.24%; Calculated:- C,67.80;H,5.19;N, 3.44%].

EXAMPLE 66
Compound IS

A mixture of sodium 4-hydroxy-4-(2-methyl-phenyl) butanoate, thought to be the (R)-enantiomer, (3 g) and sodium hydride (1.5 g; 60% w/v dispersion in mineral oil; 37.5 mmol) in tetrahydrofuran (50 mL) is stirred at ambient temperature for 1 hour under an atmosphere of argon and is then warmed to 55° C. It is then treated with 2-fluoro-4-(3-pyridyl-methoxy)benzonitrile (3 g), in one portion, and stirring is continued at 55° C. for 15 hours. The reaction mixture is then cooled, concentrated in vacuo, and diluted with water (100 mL). The pH of the mixture is adjusted to 5 by treatment with concentrated hydrochloric acid and is then extracted with ethyl acetate (4×100 mL). The combined extracts are dried over magnesium sulphate and concentrated in vacuo, to give an oily residue. This residue is recrystallized from isopropyl ether to give 4-[2-cyano-5-(3-pyridylmethoxy)phenoxy]-4-(2-methylphenyl)butanoic acid, thought to be the (R)-enantiomer, (1.5 g) in the form of a white solid, m.p. 130–134° C. Chiral HPLC assay showed a 98% enantiomeric excess. [Elemental analysis:- C,71.12; H,5.49;N,6.62%; Calculated:- C,71.64; H,5.47;N, 6.97%].

EXAMPLE 67
Compound IT

A mixture of 4-[2-cyano-5-(3-pyridylmethoxy)-phenoxy]-4-(2-methylphenyl)butanoic acid, thought to be the (R)-enantiomer, (50 mg), dicyclohexylamine (0.5 mL) and diethyl ether (10 mL) is stirred at ambient temperature for 18 hours. The resulting precipitate is collected and washed with diethyl ether, to give dicyclohexylammonium 4-[2-cyano-5-(3-pyridylmethoxy)phenoxy]-4-(2-methylphenyl)butanoate, thought to be the (R)-enantiomer, (30 mg) in the form of a white solid, m.p. 92–93° C.

EXAMPLE 68
Compound IU

A solution of triphenylphosphine (0.57 g) in tetrahydrofuran (10 mL) cooled at 0° C. is treated with diisopropyl azodicarboxylate (0.42 mL) and stirred for 20 minutes at 0° C. It is then treated, dropwise, with a solution of t-butyl 4-hydroxy-4-(2-methylphenyl)butanoate, thought to be the (R)-enantiomer, (0.35 g) and 2-hydroxy-4-(3-thienylmethoxy)benzonitrile (0.25 g) in tetrahydrofuran (10 mL). Stirring is continued at 0° C. for 30 minutes and then at ambient temperature for 18 hours. The solvent is evaporated in vacuo and the oil is subjected to flash chromatography on silica gel, eluting with a mixture of cyclohexane and dichloromethane (1:3 v/v), to give a yellow oil (0.46 g). This oil is dissolved in methanol (5 mL) and tetrahydrofuran (5 mL). The resulting solution is treated with aqueous sodium hydroxide solution (3 mL; 5 N) and stirred at ambient temperature for 24 hours, and then it is concentrated to dryness in vacuo. The resulting residue is diluted with hydrochloric acid (50 mL; 1 N) and extracted with ethyl acetate (2×50 mL) and the combined extracts are dried over magnesium sulphate and concentrated to dryness in vacuo, to give a solid, which is recrystallized twice from a mixture of ethyl acetate and cyclohexane, to give 4-[2-cyano-5-(3-thienylmethoxy)phenoxy]-4-(2-methylphenyl)butanoic acid, thought to be the (S)-enantiomer, (0.22 g) in the form of a white fluffy solid, m.p. 143° C. Chiral HPLC assay showed a 99% enantiomeric excess. [Elemental analysis:- C,67.67;H,5.14;N,3.28%; Calculated:- C,67.80;H,5.19;N, 3.44%].

EXAMPLE 69
Compound IV

A stirred solution of ethyl (RS)-5-(3-benzylthiophenyl)-4-(2-methylphenyl)-5-oxopentanoate (0.56 g) and 1 N sodium hydroxide (3.4 mL) in dioxan (11 mL) is heated at 70° C. for 1.5 hours. The reaction mixture is evaporated and the residue dissolved in water (6 mL). The pH of the solution is adjusted to pH 1 by addition of 2 N hydrochloric acid and the mixture extracted with ether (20 mL). The organic phase is washed twice with water (6 mL), dried over magnesium sulphate and evaporated. The residual orange oil (0.59 g) is triturated with pentane and crystallised from cyclohexane to give (RS)-5-(3-benzylthiophenyl)-4-(2-methylphenyl)-5-oxopentanoic acid hemihydrate as a pale yellow solid (0.37 g), m.p.105–107° C. [Elemental analysis:- C,72.4; H,5.94%. Calculated for $C_{25}H_{24}O_3S.0.5H_2O$:- C,72.4; H,5.91%].

EXAMPLE 70
Compound IW

A mixture of (RS)-4-(2-methylphenyl)-5-oxo-(1-pyrid-3-ylmethoxy)pentanoic acid (0.3 g) and hydrogen peroxide (0.1 mL, 27.5% w/w) in acetic acid (3 mL) is heated at 60° C. for 12 hours. The reaction mixture is evaporated and the residue partitioned between ethyl acetate and water. The organic phase is washed with water, dried over magnesium sulphate and evaporated in vacuo. The residue is purified by flash chromatography on silica eluting with a mixture of dichloromethane and methanol, (95:5 v/v). Fractions homogeneous in the required product are combined and evaporated. The residue is crystallised from ether to give (RS)-4-(2-methylphenyl)-5-oxo-(1-oxopyrid-3-ylmethoxy)pentanoic acid hemihydrate as an off-white solid. [Elemental analysis:- C,69.5; H,5.69; N,3.09%. Calculated for $C_{24}H_{23}NO_5.0.5H_2O$:- C,69.5; H,6.08; N,3.33%].

EXAMPLE 71
Compound IX

A mixture of (RS)-4-[2-formyl-5-(3-thienylmethoxy)phenoxy]-4-(2-methylphenyl)butanoic acid (0.7 g), O-benzylhydroxylamine hydrochloride (0.48 g) and pyridine (1 mL) in ethanol (50 mL) is heated at 65° C. for 5 hours. The reaction mixture is evaporated. The residue is dissolved dichloromethane (80 mL), washed with 1 N hydrochloric acid, then with water, dried over magnesium sulphate and evaporated. The resulting oil is purified by flash chromatography on silica eluting with a mixture of dichloromethane and methanol (95:5 v/v). Fractions homogeneous in the required product are combined, evaporated and the solid residue triturated with pentane to give (RS)-4-[2-(benzyloxyiminomethyl)-5-(3-thienylmethoxy)phenoxy]-4-(2-methylphenyl)butanoic acid hydrate (0.2 g) as a cream coloured solid, m.p. 35–37° C. [Elemental analysis:- C,69.2; H,5.60; N,2.58; S,6.26%. Calculated for $C_{25}H_{23}NO_8.0.3H_2O$: - C,69.2; H,5.72; N,2.69; S,6.16%]

EXAMPLE 72
Compound IY

A stirred solution of ethyl (RS)-4-(2-carboxycarbonyl-5-(3-thienylmethoxy)phenoxy)-4-(2-methylphenyl)butanoate (0.37 g) and 1 N sodium hydroxide (2.7 mL) in dioxan (6.6 mL) is heated at 60° C. for 1.5 hours. The reaction mixture is evaporated and the residue dissolved in water (5 mL). The pH of the solution is adjusted to 1 by addition of 1 N hydrochloric acid and the mixture extracted with ethyl acetate (20 mL). The organic phase is dried over magnesium sulphate and evaporated. The residual yellow oil is triturated with ether to give (RS)-4-(2-Carboxycarbonyl-5-(3-thienylmethoxy)phenoxy)-4-(2-methylphenyl)butanoic acid as a yellow solid (0.29 g), m.p. 173–175° C. [Elemental analysis:- C,63.2; H,5.07%. Calculated:- C,63.4; H,4.88%].

EXAMPLE 73
Compound IZ

A solution of tert-butyl 4-[2-benzoyl-5-(pyridin-3-ylmethoxy)phenoxy]-4-(2-methylphenyl)butanoate, thought to be the (R)-enantiomer, (1 g) in a mixture of methanol (10 mL) and tetrahydrofuran (10 mL) is treated with 5 M aqueous sodium hydroxide solution (7.5 mL) and the reaction stirred at ambient temperature for 24 hours. The reaction is concentrated to low volume, acidified to pH 5 with dilute hydrochloric acid, and extracted into dichloromethane (2×30 mL). The combined organic layers are washed with brine, dried over magnesium sulphate, filtered and concentrated under reduced pressure to leave a yellow gum. Trituration with diethyl ether and recrystallization of the resultant solid from acetonitrile containing a little decolourizing charcoal gives 4-[2-benzoyl-5-(pyridin-3-ylmethoxy)phenoxy]-4-(2-methylphenyl)butanoic acid, thought to be the (R)-enantiomer, (0.2 g) as a pale yellow solid, m.p. 185–186° C. [Elemental analysis:- C, 74.83; H, 5.65; N, 2.91%; Calculated:- C, 75.01; H, 5.72; N,2.87%].

EXAMPLE 74
Compound JA

A stirred solution of methyl 3-[3-(3-carboxy-1-(2-methylphenyl)propoxy)-4-nitrophenoxymethyl]benzoate (0.86 g) in a mixture of methanol (50 mL) and 50% aqueous potassium hydroxide solution (10 mL) is heated at reflux for 2 hours. The reaction mixture is evaporated in vacuo and the residue partitioned between ethyl acetate (50 mL) and 2 N hydrochloric acid (50 mL). The organic phase is washed three times with water (50 mL),dried over magnesium sulphate and evaporated to give a yellow solid (0.8 g) which is purified by flash chromatography on silica eluting initially with a mixture of cyclohexane and ethyl acetate (7:3 v/v) to remove the starting material then eluting with a mixture of cyclohexane and ethyl acetate (1:1 v/v). Fractions homogeneous in the required product are combined and evaporated to give a clear yellow oil (0.19 g) which is triturated with a mixture of ether and pentane to give (RS)-3-[3-(3-carboxy-1-(2-methylphenyl)propoxy)-4-nitrophenoxymethyl]benzoic acid as a pale yellow solid (0.11 g), m.p. 85–87° C. [Elemental analysis:- C,64.5; H,5.10; N,2.60%. Calculated for $C_{25}H_{23}NO_8.0.3H_2O$: -C,64.5; H,4.98; N,3.01%].

EXAMPLE 75
Compound JB

A solution of dry sodium (RS)-4-hydroxy-4-(2-methylphenyl)butanoate (0.18 g) in dry tetrahydrofuran (50 mL) is treated with sodium hydride and stirred at 60° C. for 15 minutes. tert-Butyl 3-[(4-cyano-3-fluoro-phenoxymethyl)phenyl]propionate (0.2 g) is added and the mixture heated at reflux for 4 hours. After standing at room temperature for 18 hours the reaction mixture is filtered. Ethyl acetate (50 mL) and 1 N hydrochloric acid (50 mL) are added to the filtrate and the organic phase is separated. The organic phase is washed with water (10 mL), dried over magnesium sulphate, evaporated and the residue purified by flash chromatography on silica eluting with a mixture of dichloromethane and methanol (95:5 v/v). Fractions homogeneous in the required product are combined and evaporated. The residue is dissolved in ether and the solution washed with 1% sodium bicarbonate solution, 0.5 N hydrochloric acid, water, dried over magnesium sulphate and evaporated. The resulting colourless gum is crystallised from a mixture of cyclohexane and ethyl acetate to give (RS)-4-{5-[3-(2-carboxyethyl)benzyloxy]-2-cyanophenoxy}-4-(2-methylphenyl)butanoic acid (0.12 g) m.p. 136–137° C. [Elemental analysis:- C,71.4; H,6.23; N,2.91%. Calculated:- C,71.0; H,5.75; N,2.96%].

EXAMPLE 76
Compound JC

A solution of ethyl (RS)-4-[2-(4,5-dihydrooxazol-2-yl)-5-(3-thienylmethoxy)phenoxy]-4-(2-methylphenyl)butanoate (500 mg) in methanol (50 mL) containing 10% w/v potassium carbonate (5 mL) is stirred at ambient temperature for 16 hours. The reaction mixture is concentrated under reduced pressure and partitioned between water (100 mL) and ethyl acetate (100 mL) then acidified to pH 5 with 1 N HCl. The organic phase is washed three times with water (50 mL), dried over magnesium sulphate, filtered and concentrated under reduced pressure. Recrystallisation from cyclohexane/ethyl acetate gives (RS)-4-[2-(4,5-dihydrooxazol-2-yl))-5-(3-thienylmethoxy)phenoxy]-4-(2-methylphenyl)butanoic acid hydrate as a white solid (160 mg), m.p. 107–109° C. [Elemental analysis:- C,65.9, H, 5.69, N, 2.94%. Calculated for $C_{25}H_{25}NO_5S.0.2H_2O$:- C,66.0, H, 5.59, N, 3.01%].

EXAMPLE 77
Compounds JD and JE

A solution of ethyl 4-[2-(1-methoxycarbonyl-2-phenylethylcarbamoyl)-5-(3-thienylmethoxy)phenoxy]-4-(2-methylphenyl)butanoate, thought to be the diastereomers (1R, 4RS), (0.48 g) in methanol (100 mL) is treated with 10% aqueous potassium carbonate solution (10 mL). The reaction mixture is stirred at room temperature for 18 hours and evaporated. The residue is dissolved in water (50 mL), the solution acidified to pH 1 by addition of 1 N hydrochloric acid and extracted with ethyl acetate (120 mL). The organic phase is washed with water (100 mL), brine (100 mL), dried over magnesium sulphate and evaporated. The semi-solid residue (0.44 g) is boiled with acetonitrile (20 mL), the mixture cooled to room temperature and filtered to remove 2-[2-hydroxy-4-(3-thienylmethoxy)benzoylamino]-3-phenylpropionic acid (0.047 g) as a white solid, m.p. 178–180° C. [Elemental analysis:- C,63.52; H,4.76; N,3.15%. Calculated :- C,63.46; H,4.82; N,3.52%]. The filtrate is evaporated to give 4-[2-(1-carboxy-2-phenylethylcarbamoyl)-5-(3-thienylmethoxy)phenoxy]-4-(2-methylphenyl)butanoic acid, thought to be the diastereomers (1R, 4RS), (0.3 g), as an oily semi-solid. [Elemental analysis:- C,66.54; H,5.45; N,2.35%. Calculated :- C,67.00; H,5.45; N,2.44%].

By proceeding in a similar manner but replacing the ethyl 4-[2-(1-methoxycarbonyl-2-phenylethylcarbamoyl)-5-(3-thienylmethoxy)phenoxy]-4-(2-methylphenyl)butanoate, thought to be the diastereomers (1R, 4RS), by the appropriate quantity of ethyl 4-[2-(1-methoxycarbonyl-2-phenylethylcarbamoyl)-5-(3-thienylmethoxy)-phenoxy]-4-(2-methylphenyl)butanoate, thought to be the diastereomers (1S, 4RS), there is prepared ethyl 4-[2-(1-carboxy-2-phenylethylcarbamoyl)-5-(3-thienylmethoxy)phenoxy]-4-(2-methylphenyl)butanoic acid, thought to be the diastereomers (1S, 4RS), m.p. 149–150° C. [Elemental analysis:- C,74.8; H,5.24; N,2.84%. Calculated:- C,75.1; H,5.26; N,2.92%].

EXAMPLE 78
Compound JF

A solution of ethyl (RS)-4-[2-(oxazol-2-yl)-5-(3-thienylmethoxy)phenoxy]-4-(2-methylphenyl)butanoate (140 mg) in methanol (25 mL) containing 10% w/v potassium carbonate (2 mL) is stirred at reflux for 2 hours. The reaction mixture is partitioned between 1 N HCl (50 mL) and ethyl acetate (50 mL) then the organic phase is washed with water (2×50 mL), dried over magnesium sulphate, filtered and concentrated under reduced pressure. Recrystallisation from cyclohexane/ethyl acetate gives (RS)-4-[2-(oxazol-2-yl)-5-(3-thienylmethoxy)phenoxy]-4-(2-methylphenyl)butanoic acid as a white solid (70 mg), m.p. 112–114° C. [Elemental analysis:- C,66.8, H, 5.16, N, 3.12%. Calculated:- C,66.5, H, 5.04, N, 3.01%]

EXAMPLE 79
Compound JG

A solution of methyl (RS)-2-[2-(3-ethoxycarbonyl-1-(2-methylphenyl)propoxy)-4-(3-thienylmethoxy)benzoylamino]acrylate (200 mg) in methanol (20 mL) containing 10% w/v potassium carbonate (2 mL) is stirred at ambient temperature for 16 hours and at reflux for 3 hours. The reaction mixture is partitioned between 1N HCl (50 mL) and ethyl acetate (50 mL) then the organic phase is washed with water (2×50 mL), dried over magnesium sulphate, filtered and concentrated under reduced pressure. Recrystallisation from cyclohexane/ethyl acetate gives (RS)-2-[2-(3-carboxy-1-(2-methylphenyl)propoxy)-4-(3-thienylmethoxy)benzoylamino]acrylic acid as a white, fluffy solid (20 mg), m.p. 140–143° C. [Elemental analysis:- C,61.9, H, 5.32, N, 2.53%. Calculated:- C,61.9, H, 5.16, N, 2.78%]

EXAMPLE 80
Compound JH

A solution of ethyl (RS)-4-[2-(4-methoxycarbonyloxazol-2-yl)-5-(3-thienylmethoxy)phenoxy]-4-(2-methylphenyl)butanoate (300 mg) in methanol (25 mL) containing 10% w/v potassium carbonate (2 mL) is stirred at reflux for 3 hours. The reaction mixture is partitioned between 1N HCl (50 mL) and ethyl acetate (50 mL) then the organic phase is washed with water (50 mL), dried over magnesium sulphate, filtered and concentrated under reduced pressure. Recrystallisation from cyclohexane/ethyl acetate gives (RS)-4-[2-(4-carboxyoxazol-2-yl)-5-(3-thienylmethoxy)phenoxy]-4-(2-methylphenyl)butanoic acid (100 mg), in the form of a white solid, m.p. 178–179° C. [Elemental analysis:- C,62.4, H, 4.57, N, 2.79%. Calculated for $C_{26}H_{23}NO_7S.0.2H_2O$:- C,62.2, H,4.78, N,2.79%].

EXAMPLE 81
Compound JI

A solution of ethyl (RS)-4-(2-cyano-5-(3-thienylmethoxy)phenoxy)-4-(2-chloro-6-fluorophenyl)butanoate (360 mg) in methanol (10 mL) containing 1 N sodium hydroxide (3 mL) is stirred at ambient temperature for 16 hours. The reaction mixture is poured into 0.5 N HCl (20 mL) and extracted twice with ethyl acetate (20 mL). The combined organic phases are washed with brine (20 mL), dried over magnesium sulphate, filtered and concentrated under reduced pressure to leave a dark yellow oil. Crystallisation from a mixture of cyclohexane and ethyl acetate gives (RS)-4-(2-chloro-6-fluorophenyl)-4-(2-cyano-5-(3-thienylmethoxy)phenoxy)-butanoic acid (210 mg) in the form of a beige solid, m.p. 128–130° C.

EXAMPLE 82
Compound JJ

A solution of tert-butyl (R)-4-(2-methylphenyl)-4-(2-nitro-5-(3-pyridylmethoxy)phenoxy)butanoate (800 mg) in methanol (20 mL) containing 5 N sodium hydroxide (10 mL) is stirred at ambient temperature for 48 hours. The reaction mixture is poured into water (50 mL), acidified to pH 5 with 1 N HCl and extracted three times with ethyl acetate (50 mL). The combined organic phases are washed with brine (50 mL), dried over magnesium sulphate, filtered and concentrated under reduced pressure The residual brown gum is purified by flash chromatography on silica eluting with ethyl acetate. Fractions homogeneous in the required product are combined and evaporated to give a yellow oil. Trituration with pentane afforded (R)-4-(2-methylphenyl)-4-(2-nitro-5-(3-pyridylmethoxy)phenoxy)butanoic acid as a white solid (150 mg), m.p. 117–119° C. [Elemental analysis:- C,65.4, H, 5.21, N, 6.64%. Calculated:- C,65.3, H, 5.17, N, 6.59%]

EXAMPLE 83
Compound JK

A solution of ethyl (RS)-4-(2-cyano-5-(3-thienylmethoxy)phenoxy)-4-(2,5-dimethylphenyl)butanoate (500 mg) in methanol (20 mL) containing 1 N sodium hydroxide (5 mL) is stirred at ambient temperature for 16 hours. The reaction mixture is poured into 0.5 N HCl (20 mL) and extracted three times with ethyl acetate (20 mL). The combined organic phases are washed with brine (20 mL), dried over magnesium sulphate, filtered and concentrated under reduced pressure to leave a brown oil. Crystallisation with cyclohexane gives (RS)-4-(2-cyano-5-(3-thienylmethoxy)phenoxy)-4-(2,5-dimethylphenyl) butanoic acid, (170 mg) in the form of an off-white solid, m.p. 135–136° C. [Elemental analysis:- C,68.4, H, 5.46, N, 3.33%. Calculated:- C,68.7, H, 5.57, N, 3.00%]

EXAMPLE 84
Compound JL

A solution of sodium (RS)-4-(benzo[1,3]dioxol-4-yl)-4-hydroxybutanoate (1.23 g) is added to a stirred suspension of sodium hydride (0.6 g, 60% dispersion in mineral oil) in tetrahydrofuran (50 mL). The mixture is stirred at room temperature for 1.5 hours when 2-fluoro-4-(3-pyridylmethoxy)benzonitrile (1.07 g) is added in one portion. The reaction mixture is heated at 55–60° C. for 18 hours and evaporated. The residue is dissolved in water (100 mL), the solution acidified to pH 2 with 1 N hydrochloric acid and the mixture extracted with ethyl acetate (100 mL). The organic phase is washed with water (100 mL), with brine (100 mL), dried over magnesium sulphate and evaporated. The yellow semi-solid residue is recrystallised from acetonitrile to give (RS)-4-(benzo[1,3]dioxol-4-yl)-4-[2-cyano-5-(3-pyridylmethoxy)phenoxy]butanoic acid (0.80 g) as a cream solid, m.p. 181–183° C. [Elemental analysis:- C,66.32; H,4.57; N,6.52%. Calculated :- C,66.66; H,4.66; N,6.48%]

EXAMPLE 85
Compound JM

A solution of sodium (RS)-4-(2,3-dimethylphenyl)-4-hydroxybutanoate (1 g) is added to a stirred suspension of sodium hydride (0.5 g, 60% dispersion in mineral oil) in tetrahydrofuran (50 mL) under nitrogen. The mixture is stirred at room temperature for 3 hours when 2-fluoro-4-(3-pyridylmethoxy)benzonitrile (1 g) is added in one portion. The reaction mixture is heated at 55–60° C. for 18 hours and evaporated. The residue is dissolved in water (100 mL), the solution acidified to pH 1 with 1 N hydrochloric acid. The precipitated solid Is filtered, washed with water, ethyl acetate and ether, dried, and recrystallised from ethyl acetate to give (RS)-4-[2-cyano-5-(3-pyridylmethoxy)-phenoxy]-4-(2,3-dimethylphenyl)butanoic acid (0.85 g) as a white solid, m.p. 187–189° C. [Elemental analysis:- C,71.76; H,6.59; N,5.67%. Calculated:- C,72.10; H,6.73; N,5.81%]

EXAMPLE 86
Compound JN

A solution of (RS)-4-[2-cyano-5-(3-pyridylmethoxy)phenoxy]-4-(2-methyl-5-(2-(trimethylsilyl)ethoxymethoxy)phenyl)butanoic acid (1.8 g) in tetrahydrofuran (150 mL) is treated with 1 N hydrochloric acid (10 mL) and the mixture heated at reflux for 1 hour. The reaction mixture is evaporated and the residue partitioned between ethyl acetate (200 mL) and water (100 mL). The organic phase is washed with water (100 mL), brine (100 mL), dried over magnesium sulphate and evaporated. The residual brown gum (1.25 g) is recrystallised from acetonitrile to give (RS)-4-[2-cyano-5-(3-pyridylmethoxy)phenoxy]-4-(5-hydroxy-2-methylphenyl)butanoic acid (0.5 g) as a cream solid, m.p. 198–200° C. [Elemental analysis:- C,68.32; H,5.45; N,6.93%. Calculated:- C,68.89; H,5.30; N,6.69%]

EXAMPLE 87
Compound JO

To a stirred suspension of sodium hydride (0.69 g, 60% dispersion in mineral oil) in dry tetrahydrofuran (50 mL) is added a solution of sodium (RS)-5-hydroxy-5-(2-methylphenyl)pentanoate (1.23 g) in dry tetrahydrofuran (100 mL). The mixture is stirred at room temperature for 1.5 hours when 2-fluoro-4-(3-thienylmethoxy)benzonitrile (1.57 g) is added in one portion. The reaction mixture is heated at 55–60° C. for 18 hours and evaporated. The residue is dissolved in water (100 mL), the solution acidified to pH 1 with 1 N hydrochloric acid and the mixture extracted three times with ethyl acetate (100 mL). The combined extracts are washed with brine (100 mL), dried over magnesium sulphate and evaporated to give (RS)-5-[2-cyano-5-(3-thienylmethoxy)phenoxy]-5-(2-methylphenyl)pentanoic acid as a white waxy solid (0.4 g), mp.p.106–108° C. [Elemental analysis:- C,67.15; H,5.84; N,2.75; S,6.99%. Calculated for $C_{24}H_{23}NO_4S.0.5EtOAc$:- C,66.66; H,4.66; N,6.48%].

EXAMPLE 88
Compound JP

A solution of ethyl (RS)-4-(2-cyano-3-fluoro-5-(3-thienylmethoxy)phenoxy)-4-(2-methylphenyl)butanoate (200 mg) in methanol (20 mL) containing 1 N sodium hydroxide (5 mL) is stirred at ambient temperature for 16 hours. The reaction mixture is poured into 0.5 N HCl (30 mL) and extracted three times with ethyl acetate (30 mL). The combined organic phases are washed with brine (20 mL), dried over magnesium sulphate, filtered and concentrated under reduced pressure to leave a brown oil. Crystallisation with cyclohexane gives (RS)-4-(2-cyano-3-fluoro-5-(3-thienylmethoxy)phenoxy)-4-(2-methylphenyl)butanoic acid, (70 mg) in the form of a white solid, m.p. 150–151° C. [Elemental analysis:- C,64.9, H, 4.74, N, 3.29%. Calculated:- C,64.8, H, 4.81, N, 3.13%]

EXAMPLE 89
Compound JQ

A solution of ethyl (RS)-2,4-dioxo-4-[2-(1-(2-methylphenyl)ethoxy)-4-(3-thienylmethoxy)phenyl]butanoate (0.38 g) in 15% methanolic potassium hydroxide (25 mL) is stirred at reflux for 1 hour before being cooled and concentrated under reduced pressure. The residue is dissolved in water, acidified to pH 1 with concentrated hydrochloric acid and extracted with ethyl acetate. The organic layer is dried over magnesium sulphate, filtered and concentrated under reduced pressure. The residue is recrystallised from cyclohexane to give (RS)-2,4-dioxo-4-[2-(1-(2-methylphenyl)ethoxy)-4-(3-thienylmethoxy)-phenyl]butanoic acid (35 mg) as a yellow solid, m.p. 124–6° C. [Elemental analysis:- C, 65.82; H, 5.03%; Calculated for $C_{24}H_{22}O_6S$:- C, 65.74; H, 5.06%].

EXAMPLE 90
Compound JR

To a stirred suspension of ethyl (RS)-4-[2-(5-ethoxycarbonylpyrazol-3-yl)-5-(3-thienylmethoxy)phenoxy]-4-(2-methylphenyl)butanoate (4 g) in 15% potassium hydroxide in methanol (100 mL, w/v) at room temperature is added water (10 mL). The solid slowly dissolves and after stirring for 15 minutes the reaction mixture is partitioned between ethyl acetate (200 mL) and 2 N hydrochloric acid (200 mL). The organic phase is washed with water (200 mL), dried over magnesium sulphate and evaporated. The residue is recrystallised from a mixture of ethyl acetate and cyclohexane to give (RS)-4-[2-(5-ethoxycarbonylpyrazol-3-yl)-5-(3-thienylmethoxy)phenoxy]-4-(2-methylphenyl)butanoic acid hydrate (1.9 g), m.p.167–168° C. [Elemental analysis:- C,63.9; H,5.39; N,5.22%. Calculated for $C_{28}H_{28}N_2O_6S.0.5H_2O$:- C,63.5; H,5.48; N,5.29%].

EXAMPLE 91
Compound JS tert-Butyl (R)-4-[2-(5-ethoxycarbonylpyrazol-3-yl)-5-(3-pyridylmethoxy)phenoxy]-4-(2-methylphenyl)butanoate (1.7 g) is stirred in trifluoroacetic acid (10 mL) at ambient temperature for 15 minutes. The reaction mixture is basified with saturated sodium bicarbonate solution and a solid is precipitated which is taken up in ethyl acetate (50 mL) and washed with water (50 mL). The organic phase is dried over magnesium sulphate, filtered and concentrated in vacuo. Recrystallisation from ethyl acetate/cyclohexane affords (R)-4-[2-(5-ethoxycarbonylpyrazol-3-yl)-5-(3-pyridylmethoxy)-phenoxy]-4-(2-methylphenyl)butanoic acid (0.35 g) in the form of a white solid, m.p. 108–110° C. [Elemental analysis:- C,67.9, H, 5.92, N, 7.64%. Calculated:- C,67.6, H, 5.63, N, 8.16%]

EXAMPLE 92
Compound JT

A solution of (R)-4-[2-(5-ethoxycarbonylpyrazol-3-yl)-5-(3-pyridylmethoxy)phenoxy]-4-(2-methylphenyl)butanoic acid (150 mg) in methanol (50 mL) containing 10% w/v potassium hydroxide (5 mL) is stirred at reflux for 1 hour. The reaction mixture is partitioned between 1 N acetic acid (50 mL) and ethyl acetate (50 mL). Some precipitation occurred in the organic phase which is washed with water (50 mL) and concentrated under reduced pressure. Trituration with hot ethyl acetate followed by cooling affords a solid which is filtered then washed with ethyl acetate to give (R)-4-[2-(5-carboxypyrazol-3yl)-5-(3-pyridylmethoxy)phenoxy]-4-(2-methylphenyl) butanoic acid hydrate (40 mg) as a white solid, m.p. 144–146° C. [Elemental analysis:- C,64.1, H, 5.02, N, 8.27%. Calculated for $C_{27}H_{25}N_3O_6.H_2O$:- C,64.2, H, 5.35, N, 8.32%].

EXAMPLE 93
Compound JU (RS)-2,2-difluoro-3-hydroxy-3-(2-methylphenyl)propanoic acid (1.5 g) is added portionwise to a stirred suspension of sodium hydride (1.1 g, 60% dispersion in mineral oil) in THF (80 mL) at ambient temperature under nitrogen. After 20 minutes 2-fluoro-4-(3-pyridylmethoxy)benzonitrile (1.6 g) is added in one portion and the reaction stirred at 60° C. for 16 hours. The reaction is concentrated in vacuo and the residue acididfied with 1 N HCl to pH 1 and extracted with ethyl acetate (100 mL). A white solid precipitates from the ethyl acetate which is filtered off to give (RS)-4-[2-cyano-5-(3-pyridylmethoxy)phenoxy]-2,2-difluoro-4-(2-methylphenyl)propanoic acid (0.64 g), m.p. 265–267° C. [Elemental analysis:- C,64.7, H, 4.19, N, 6.43%. Calculated:- C,65.1, H, 4.72, N, 6.60%]

EXAMPLE 94
Compound JV

A solution of ethyl (RS)-4-[2-(5-ethoxycarbonylisoxazol-3-yl)-5-(3-thienylmethoxy)phenoxy]-4-(2-methylphenyl)butanoate (2.56 g) in methanol (30 mL) is treated with 50% aqueous potassium hydroxide solution (10 mL, w/v) and the mixture is heated to reflux for 3 hours. The reaction mixture is acidified to pH 1 by addition of concentrated hydrochloric acid (50 mL). Water (75 mL) and ethyl acetate (75 mL) are added and the organic phase separated. The aqueous phase is further extracted with ethyl acetate (3×50 mL). The combined organic phases are dried over magnesium sulphate and evaporated. During the evaporation a white solid is formed. This is filtered and the remaining solution evaporated to dryness to give an orange oil (2.08 g). This material is partitioned between ethyl acetate (50 mL) and water (50 mL), the pH of the aqueous layer is adjusted to pH 9 by addition of potassium carbonate, and the aqueous layer is separated. Glacial acetic acid is added to the aqueous solution to adjust the pH to pH 4 and the orange oil collected by decantation. Trituration with a mixture of ethyl acetate and cyclohexane gives (RS)-4-[2-(5-carboxyisoxazol-3-yl)-5-(3-thienylmethoxy)phenoxy]-4-(2-methylphenyl)butanoic acid (0.42 g) as a cream solid, m.p.162–164° C. [Elemental analysis:- C,62.98; H,4.70; N,2.65%. Calculated:- C,63.30; H,4.70; N,2.84%].

EXAMPLE 95
Compound JW tert-Butyl (R)-4-[2-(5-methoxycarbonylpyrazol-3-yl)-5-(3-pyridylmethoxy)phenoxy]-4-(2-methylphenyl)butanoate (2 g) is dissolved in trifluoroacetic acid (10 mL) and allowed to stand at room temperature for 2 minutes. The solution is quenched with saturated aqueous sodium hydrogen carbonate solution (100 mL) and the product extracted into ethyl acetate (100 mL). This solution is washed with water, dried, and evaporated. The residue is purified by flash chromatography on silica eluting initially with a mixture of ethyl acetate and cyclohexane (3:2 v/v) to remove trace high running impurities, and then eluting with a mixture of methanol and dichloromethane (1:4 v/v). Fractions heterogeneous in the required product are combined and evaporated. The residue is recrystallised from a mixture ethyl acetate and cyclohexane to give (R)-4-[2-(5-methoxycarbonylpyrazol-3-yl)-5-(3-pyridylmethoxy)phenoxy]-4-(2-methylphenyl)butanoic acid (0.4 g) as a white solid, m.p. 155–156° C. [Elemental analysis:- C,66.90; H,5.49; N,8.11%. Calculated:- C,67.00; H,5.43; N,8.43%].

EXAMPLE 96
Compound JX (R)-4-[2-(5-methoxycarbonylpyrazol-3-yl)-5-(3-pyridylmethoxy)phenoxy]-4-(2-methylphenyl)butanoic acid (0.2 g) is dissolved in methanol (20 mL) and concentrated aqueous ammonia (20 mL). After standing at room temperature overnight .the solution is evaporated to dryness and the residue triturated successively with ether and ethyl acetate to give (R)-4-[2-(5-carbamoylpyrazol-3-yl)-5-(3-pyridylmethoxy)-phenoxy]-4-(2-methylphenyl)butanoic acid (0.035 g) as a white powder, mp 180–192° C.

EXAMPLE 97
Compound JY

A solution of ethyl (RS)-4-[(2-acetyl-5-(3-thienylmethoxy)-phenoxy]-4-(2-cyanophenyl)butanoate (250 mg) in methanol (10 ml) containing 1N sodium hydroxide (3 mL) is stirred at ambient temperature for 16 hours. The reaction mixture is poured into 0.5 N hydrochloric acid (20 mL) and extracted twice with ethyl acetate (20 mL). The combined organic phases are washed with brine (20 mL), dried over magnesium sulphate and concentrated under reduced pressure to leave a dark yellow oil. Crystallization from a mixture of cyclohexane and ethyl acetate affords (RS)-4-[(2-acetyl-5-(3-thienylmethoxy)phenoxy]-4-(2-cyanophenyl)butanoic acid (20 mg) in the form of a beige solid, m.p. 132–134° C. [Elemental analysis:- C, 66.0, H, 4.87, N, 3.02%. Calculated:- C, 66.2, H, 4.86, N, 3.22%].

2-Hydroxy-4-(3-thienylmethoxy)acetophenone (2.5 g) is added portionwise stirred suspension of sodium hydride (440 mg, 60% dispersion in mineral oil) in dry dimethyl formamide (30 mL). After stirring at ambient temperature for 30 minutes, ethyl (RS)-4-chloro-4-(2-cyanophenyl) butanoate (2.87 g) is added in one portion and the reaction mixture stirred for 16 hours at 100° C. The reaction is concentrated in vacuo and the residue partitioned between ethyl acetate (100 mL) and water (100 mL). The organic phase is dried over magnesium sulphate, filtered and concentrated in vacuo. The residual oil is purified by flash chromatography on silica eluting with a mixture of ethyl acetate and pentane (1:2, v/v). Fractions homogeneous in the required product are combined and evaporated to give ethyl (RS)-4-[2-acetyl-5-(3-thienyl-methoxy)phenoxy]-4-(2-cyanophenyl)butanoate (250 mg) as an orange oil.

A solution of 2-cyanobenzaldehyde (5 g) in dichloromethane (10 mL) is added dropwise to a stirred 1 M solution of titanium (IV) chloride in dichloromethane (38 mL) at 0° C. under nitrogen. The mixture is stirred for 5 minutes and [1-ethoxycyclopropyloxy)trimethyl]silane (8.42 mL) is added dropwise maintaining the temperature at 0–5° C. The mixture is stirred for 16 hours at ambient temperature then quenched with water (200 mL). The mixture is extracted three times with dichloromethane (100 mL) and the combined organic extracts are washed with brine (100 mL), dried over magnesium sulphate and evaporated to give ethyl (RS)-4-chloro-4-(2-cyanophenyl)butanoate (5.5 g) as a yellow oil.

EXAMPLE 98
Compound JZ

Sodium (R)-4-Hydroxy-4-(2-methylphenyl)butanoate (0.39 g) is added in one portion to a stirred suspension of sodium hydride (0.11 g, 60% dispersion in mineral oil) in tetrahydrofuran (30 mL) and the mixture is stirred at 50° C. for 1 hour. A solution of 2-fluoro-4-(isothiazol-4-ylmethoxy) benzonitrile (0.21 g) in tetrahydrofuran (20 mL) is added and the reaction mixture is stirred at reflux for 16 hours. The reaction mixture is concentrated in vacuo and water is added to the residue. The solution is acidified with 1 N hydrochloric acid and extracted with ethyl acetate (50 mL). The organic phase is washed with water (50 mL), with brine (50 mL), dried over magnesium sulphate and evaporated. The residue is purified by flash chromatography on silica eluting with a mixture of dichloromethane and methanol (19:1 v/v). Fractions homogeneous in the required product are combined and evaporated to give (R)-4-[(2-cyano-5-(isothiazol-4-ylmethoxy)phenoxy]-4-(2-methylphenyl)butanoic acid, (0.02 g) in the form of a yellow oil. [NMR (CDCl$_3$) (300 MHz): -2.2–2.4 (m, 2H), 2.45 (s, 3H), 2.6–2.65 (m), 2.75–2.8 (m,1H), 5.0 (q, 2H), 5.5 (dd,1H), 6.15 (d,1H), 6.5 (dd, 1H), 7.2 (m, 3H), 7.4 (m,1H), 7.45 (d,1H), 8.45 (d, 2H)].

EXAMPLE 99
Compound KA

A mixture of ethyl 3-(2,4-dibenzyloxy)phenyl propanoate (1.4 g) and 15% w/v potassium hydroxide in methanol (25 mL) is refluxed for 2 hours. The reaction is concentrated in vacuo to give a yellow solid which is partitioned between ethyl acetate (50 mL) and water (50 mL). Acidification with 1 N HCl leads to the formation of a precipitate which is filtered off to give 3-(2,4-dibenzyloxy)phenyl propanoic acid (0.52 g) as a white solid, m.p. 142–144° C. [Elemental Analysis:- C, 75.9, H, 6.06% Calculated for C, 76.2, H, 6.12%].

EXAMPLE 100
Compound KB

A mixture of ethyl 2,4-dibenzyloxyphenoxyacetate (2 g), 10% w/v potassium hydroxide (10 mL) and methanol (50 mL) is stirred at ambient temperature for 1 hour. The reaction is concentrated in vacuo and acidified with 1 N HCL then extracted with ethyl acetate (2×100 mL). The organic layer is washed with water (2×100 mL), dried over magnesium sulphate, filtered and concentrated in vacuo to give a white powder. Recrystallisation from ethyl acetate/ cyclohexane affords 2,4-dibenzyloxyphenoxyacetic acid (0.4 g) as a white solid, m.p. 72° C. [Elemental Analysis:- C, 72.4, H, 5.50% Calculated for C, 72.5H, 5.53%].

EXAMPLE 101
Compound KC

A stirred suspension of sodium (R)-4-hydroxy-4-(2-methylphenyl)butanoate (190 mg) in THF (15 mL) is treated with 60% sodium hydride (35 mg) and maintained at 25° for 0.5 hours. The mixture is treated with 2-fluoro-4-(thiophen-3-ylmethoxy)nitrobenzene (220 mg) and maintained at 50° C. for 3 hours. The solution is evaporated. The residue is dissolved in ethyl acetate, washed with water, dried and evaporated. The residue is purified by flash chromatography on silica, eluting with dichloromethane followed by ethyl acetate, followed by recrystallisation from ethyl acetate/ pentane to give (R)-4-[2-nitro-5-(thiophen-3-ylmethoxy) phenoxy]-4-(2-methylphenyl)butyric acid (70 mg), a tan coloured solid, mp. 130–131° C. $^1$H NMR (CHCl$_3$) 2.2–2.9 (4H,m), 2.4 (3H,s), 4.9 (2H, q), 5.5 (1H, q), 6.2 (1H,s), 6.5 (1H,d), 7.0–7.4 (7H,m), 7.9 (1H,d).

EXAMPLE 102
Compounds KD and KE

A stirred solution of (R,S)-4-[2-cyano-5-(thiophen-3-ylmethoxy)phenoxy]-4-(2-methylphenyl)butyric acid (500 mg) in dichloromethane (80 mL) is treated with 1,1-carbonyidiimidazole (215 mg) and stirred at 25° C. for 2 hours. This solution is added to a solution of the sodium salt of methanesulphon-amide (which is prepared by adding 60% sodium hydride (201 mg) to a solution of methane-sulphonamide (684 mg) in DMF (50 mL). Stirred at 25° C. for 18 hours. The solution is evaporated. The residue is dissolved in ethyl acetate, washed with water, dried, and evaporated. The residual oil is purified by flash chromatography on silica, eluting with pentane/ ethyl acetate: 2/1, followed by trituration with pentane to give (R,S)-N-{4-[2-cyano-5-(thiophen-3-ylmethoxy)phenoxy]-4-(2-methylphenyl)butyryl}methane sulphonamide (500 mg), colourless solid, mp.78–80° C. [Elemental analysis: C,59.7; H,5.14; N,5.41%. Calculated for $C_{24}H_{24}N_2O_5S_2$: C,59.5; H,4.99; N,5.78%].

The following is prepared similarly according to the instant method:

(R,S)-N-{4-[2-Cyano-5-(thiophen-3-ylmethoxy) phenoxy]-4-(2-methylphenyl)butyryl}trifluoromethane sulphonamide, colourless solid, mp.193–195° C. [Elemental analysis: C,53.3; H,4.29; N,5.78%. Calculated for $C_{24}H_{24}N_2O_5S_2$: C,53.5; H,3.93; N,5.20%].

EXAMPLE 103
Compound KF

A stirred solution of ethyl (R,S)-4-[2-(3-methoxycarbonylpropionyl)-5-(thiophen-3-ylmethoxy)

phenoxy]-4-(2-methylphenyl)butanoate (1.8 g) in dioxan (20 mL) and 2 M NaOH (5.15 mL) is heated at 40° C. for 1.5 hours. The solution is evaporated. The residue is dissolved in water, brought to pH 1 with 1 M HCl, and extracted with ethyl acetate. The organic layer is washed with water, dried, and evaporated. The residue is recrystallised from ethyl acetate/cyclohexane to give (R,S)-4-[2-(3-carboxypropionyl)-5-(thiophen-3-ylmethoxy)phenoxy]-4-(2-methylphenyl)butyric acid (1 g), a colourless solid, mp. 150–152° C. [Elemental analysis: C,65.0; H,5.52%. Calculated for $C_{26}H_{26}O_7S$: C,64.7; H,5.43%].

EXAMPLE 104
Compound KG

A stirred solution of ethyl (R,S)-4-[2-(1,2,4-oxadiazol-3-yl)-5-(thiophen-3-ylmethoxy)phenoxy]-4-(2-methylphenyl) butanoate (61 mg) in dioxan (2 mL) and 1 M HCl (0.38 mL) is heated at 80° C. for 5 hours. The solution is evaporated. The residue is dissolved in ethyl acetate, washed with water, dried and evaporated. The residue is purified by flash chromatography on silica, eluting with ether/pentane: 3/1, to give (R,S)-4-[2-(1,2,4-oxadiazol-3-yl)-5-(thiophen-3-ylmethoxy)phenoxy]-4-(2-methylphenyl)-butyric acid (18 mg), a colourless solid, mp. 145–149° C. $^1$H NMR ($CHCl_3$) 2.2–3.0 (4H,m), 2.4 (3H,s), 4.9 (2H, q), 5.5 (1H, q), 6.2 (1H,s), 6.6 (1H,d), 7.0–7.4 (7H,m), 7.9 (1H,d), 8.8 (1H,s).

EXAMPLE 105
Compound KH

A stirred solution of ethyl (R,S)-4-[2-(thiazol-2-yl)-5-(thiophen-3-ylmethoxy)phenoxy]-4-(2-methylphenyl) butanoate (500 mg) in dioxan (8.6 mL) and 1 M NaOH (2.5 mL) is heated at 60° C. for 1.5 hours. The solution is evaporated. The residue is dissolved in water, brought to pH 1 with 1 M HCl, and extracted with ethyl acetate. The organic layer is washed with water, dried, and evaporated. The residual solid is triturated with ether giving (R,S)-4-[2-(thiazol-2-yl)-5-(thiophen-3-ylmethoxy)phenoxy]-4-(2-methylphenyl)butyric acid, a colourless solid (320 mg), mp. 174–176° C. [Elemental analysis: C,64.0; H,5.32; N, 2.62%. Calculated for $C_{25}H_{23}NO_4S_2$: C,64.5; H,4.98; N,3.01%].

Reference Example 1

A solution of methyl 2-hydroxy-4-(4-chlorobenzyloxy) benzoate (5.2 g) in dry dimethylformamide (DMF) (50 mL) is treated with NaH (60% dispersion, 0.71 g) and stirred at 25° C. for 20 minutes. Benzyl bromide (2.12 mL) is added and the solution heated at 60° C. for 2 hours. The solution is evaporated. The residue is dissolved in ethyl acetate, washed with water, dried, and evaporated. The residue is recrystallized from ethyl acetate to yield methyl 2-benzyloxy-4-(4-chlorobenzyloxy)benzoate as colourless crystals (5.1 g, 75%), m.p. 99–101° C. $^1$H NMR (DMSO) 3.8(3H,s),5.18 (2H,s), 5.21(2H,s), 6.7(1H,d), 6.85(1H,s), 7.3–7.5(9H,m), 7.75(1H,d).

By proceeding in a similar manner, but using the appropriate amount of a hydroxy substituted benzoate precursor, there are prepared:
methyl 2-benzyloxy-4-(3-phenylpropyloxy)benzoate; methyl 2,4-di-(4-chlorobenzyloxy)benzoate; methyl 2-benzyloxy-4-(2-(3-indolyl)ethoxy)benzoate (solid); methyl 2-(3-phenylpropyloxy)-4-benzyloxybenzoate, m.p. 50–51° C.; methyl 2-benzyloxy-4-(2-naphthylmethoxy) benzoate (solid); methyl 2-benzyloxy-4-(1-naphthylmethoxy)benzoate; methyl 2-benzyloxy-4-(3,4-methylenedioxybenzyloxy)benzoate; methyl 2-(2-pyridylmethoxy)-4-benzyloxybenzoate, m.p. 120–121° C.; methyl 2-(2-phenylethoxy)-4-benzyloxybenzoate (solid); methyl 2-cyclohexylmethoxy-4-benzyloxybenzoate, (colourless solid); methyl 2-(4-chlorobenzyloxy)-4-benzyloxybenzoate, m.p. 95–97° C.; methyl 2-benzyloxy-4-(2-phenylethoxy)benzoate; methyl 2-benzyl-oxy-4-(4-isopropylbenzyloxy)benzoate (solid); methyl 2-benzyloxy-4-(4-nitrobenzyloxy)benzoate, m.p. 132–134° C.; methyl 2-benzyloxy-4-(4-fluorobenzyloxy)benzoate, m.p. 130–132° C.; methyl 2-isopropyloxy-4-benzyloxybenzoate (solid); methyl 2-(4-pyridylmethoxy)-4-benzyloxybenzoate, m.p. 75° C.; methyl 2-benzyloxy-4-(3,4-dichlorobenzyloxy) benzoate, m.p. 94–96° C.; methyl 2-benzyloxy-4-(4-methoxybenzyloxy)benzoate; and methyl 2-benzyloxy-4-(3-methoxybenzyloxy)benzoate. m.p. 75–76° C.

Reference Example 2

A solution of methyl 2,4-dihydroxybenzoate (6.73 g) in acetone (250 mL) is treated with potassium iodide (2.66 g), tetrabutylammonium chloride (0.05 g), potassium carbonate (5.53 g), and 4-chlorobenzyl chloride (7.08 g), and stirred at reflux for 24 hours. The mixture is filtered, and the filtrate evaporated. The residue is taken up in ethyl acetate, washed with water, dried, and evaporated. The residue is recrystalized from ethyl acetate to yield methyl 2-hydroxy-4-(4-chlorobenzyloxy)benzoate as colourless crystals (5.3 g, 45%), m.p. 119–121° C. $^1$H NMR (DMSO) 3.9(3H,s), 5.2(2H,s), 6.6(2H,m), 7.5(4H,m), 7.7(1H,d).

By proceeding in a similar manner, but using the appropriate amount of a hydroxy substituted benzoate precursor, there are prepared:
methyl 2-hydroxy-4-(3-phenylpropyloxy)benzoate; methyl 2-hydroxy-4-(2-(3-indolyl)ethoxy)benzoate; methyl 2-hydroxy-4-benzyloxybenzoate, m.p. 101–102° C.; methyl 2-hydroxy-4-(2-naphthylmethoxy)benzoate; methyl 2-hydroxy-4-(1-naphthylmethoxy)benzoate; methyl 2-hydroxy-4-(3,4-methylenedioxybenzyloxy)benzoate (solid); methyl 2-hydroxy-4-(2-phenylethoxy)benzoate; methyl 2-hydroxy-4-(4-isopropylbenzyloxy)benzoate, m.p. 68–70° C.; methyl 2-hydroxy-4-(4-nitrobenzyloxy) benzoate, m.p. 178–180° C.; methyl 2-hydroxy-4-(4-fluorobenzyloxy)benzoate, m.p. 82–84° C.; methyl 2-hydroxy-4-(3,4-dichlorobenzyloxy)benzoate, m.p. 134–136° C.; methyl 2-hydroxy-4-(4-methoxybenzyloxy) benzoate; and methyl 2-hydroxy-4-(3-methoxybenzyloxy) benzoate.

Reference Example 3

A mixture of triphenylphosphine (15.7 g) and carbon tetrabromide (9.93 g) in dry dichloromethane (100 mL) is cooled to 0° C. and stirred for 30 minutes. A solution of 2,4-dibenzyloxybenzaldehyde (4.76 g) in dichloromethane (30 mL) is added and the solution stirred at 0° C. for 2 hours. The solution is treated with pentane to precipitate triphenylphosphine oxide. The filtrate is evaporated to give 1-(2,4-dibenzyloxyphenyl)-2,2-dibromoethylene as a yellow oil (4.85 g, 67%).

Reference Example 4

A solution of 2,4-dibenzyloxybenzoic acid (3.34 g) and methyl glycinate hydrochloride (1.25 g) in DMF (40 mL) is treated with triethylamine (2.23 g) and 1-hydroxybenzotriazole (1.53 g) at 0° C. The mixture is stirred for 10 minutes, treated with 1-(3-dimethylaminopropyl)-3-ethylcarbodiimide, hydrochloride (2.05 g) and allowed to warm to 25° C. The solution is evaporated. The residue is partitioned between ethyl acetate and water. The organic layer is washed with 1 M HCl, 1 M NaOH, water, dried and evaporated. The residue is recrystallized from methanol to yield methyl N-(2,4-dibenzyloxybenzoyl)glycinate as a solid (900 mg). H NMR (CDCl₃) 3.7(3H,s), 4.2(2H,d), 5.1 (2H,s), 5.2(2H,s), 6.6(1H, s), 6.7(1H,d), 7.3–7.5(10H,m), 8.2(1H,d), 8.4(1H,t).

Reference Example 5

A suspension of 4-benzyloxy-2-(1-o-tolylethoxy)benzoyl chloride (2.73 g) and glycine methyl ester hydrochloride (1.21 g) in dichloromethane (50 mL) is treated with triethylamine (2.78 g) dropwise at 25° C. The mixture is stirred for 24 hours. The solution is washed with water, 1 M HCl, brine, dried and evaporated. The residual oil is purified by flash chromatography, eluting initially with dichloromethane and then with ether. Fractions homogeneous in the required product are combined and evaporated to yield a red gum. Trituration with cyclohexane/ether yields a solid. Recrystallization from ethyl acetate yields N-(4-benzyloxy-2-(1-o-tolylethoxy)benzoyl)glycinate as a colourless solid (240 mg), m.p. 137–139° C. H NMR (CDCl₃) 1.8(3H,d), 2.4(3H, s), 3.8(3H,s), 4.3(2H,d), 4.9(2H,s), 5.6(1H,q), 6.2(1H,s), 6.6(1H,d), 7.1–7.4(9H,m), 8.15(1H,d), 8.7(1H,t).

Reference Example 6

A solution of 4-benzyloxy-2-(1-o-tolylethoxy)benzoic acid (2.5 g) in dichloromethane (50 mL) is treated with a 2 M solution of oxalyl chloride in dichloromethane (6.5 mL) and stirred at 25° C. for 3.5 hours. The mixture is evaporated to give 4-benzyloxy-2-(1-o-tolylethoxy)benzoyl chloride as a brown liquid (2.73 g).

Reference Example 7

A solution of methyl 4-benzyloxy-2-(1-o-tolylethoxy) benzoate (2.8 g) in 15% KOH in MeOH (50 mL) is refluxed for 3 hours. The solution is evaporated, the residue treated with water, brought to pH 1 with concentrated HCl, extracted with dichloromethane. The extract is dried and evaporated to give 4-benzyloxy-2-(1-o-tolylethoxy)benzoic acid as a colourless solid, m.p. 110–113° C.

Reference Example 8

A solution of triphenylphosphine(5.48 g) in dry THF (35 mL) is treated with diisopropyl azodicarboxylate (4.23 g) at 0–5° C. and stirred for 15 minutes. The suspension is treated dropwise with a solution of methyl 4-benzyloxy-2-hydroxybenzoate (2.7 g) and 1-o-tolylethanol (1.42 g) in dry THF (35 mL) during 25 minutes at 0–5° C. and then stirred at 0–5° C. for 1 hour and at 25° C. for 24 hours. The mixture is evaporated and the residual gum purified by flash chromatography on silica, eluting with dichloromethane. Fractions homogeneous in the required product are combined and evaporated to yield methyl 4-benzyloxy-2-(1-o-tolyiethoxy)benzoate as a colourless oil (2.83 g, 72%). ¹H NMR (CDCl₃) 1.6(3H,d), 2.4(3H,s), 3.9(3H,s), 4.9(2H,s), 5.5(1H,q), 6.3(1H,s), 6.5(1H,d), 7.1–7.6(9H,m), 7.8(1H,d).

Reference Example 9

A solution of ethyl 4-(2,4-dibenzyloxyphenyl)-2,4-dioxobutanoate (3.23 g) in ethanol (10 mL) is treated with hydrazine hydrate (0.4 mL), refluxed for 2 hours and then cooled to room temperature. The mixture is filtered to yield ethyl 3-(2,4-dibenzyloxyphenyl)-pyrazole-5-carboxylate as a solid (1.5 g).

Reference Example 10

A suspension of potassium ethoxide (0.63 g) in ether (50 mL) is treated with diethyl oxalate (1.2 g), cooled to 0° C, treated with 2,4-dibenzyloxyacetophenone (2.5 g) and stirred at 25° C. for 24 hours. The mixture is partitioned between ether and 0.1 M HCl. The ether layer is washed with water, dried, and evaporated to yield 4-(2,4-dibenzyloxyphenyl)-2,4-dioxobutanoate as an oil (3.23 g).

Reference Example 11

Ethyl 5-(4-benzyloxyphenyl)-2H-pyrazole-3-carboxylate (6 g) is added portionwise to a stirred suspension of sodium hydride (0.75 g) in tetrahydrofuran (250 mL) at room temperature. Stirring is continued at this temperature for a further 30 minutes when benzyl bromide (3.57 g) is added in one portion. The reaction mixture is heated to reflux for 5 hours, then evaporated in vacuo. The residue is treated with water (250 mL), the resulting yellow solid washed well with water, then dissolved in tetrahydrofuran and filtered to remove a small amount of insoluble white solid. The filtrate is evaporated and the residual yellow solid purified by flash chromatography on silica eluting initially with dichloromethane then with a mixture of ethyl acetate and dichloromethane (1:9 v/v) to give ethyl 2-benzyl-5-(4-benzyloxyphenyl)-2H-pyrazole-3-carboxylate (1.2 g) and ethyl 1-benzyl-5-(4-benzyloxyphenyl)-2H-pyrazole-3-carboxylate (2 g).

A suspension of ethyl 4-benzyloxyphenyl-2,4-dioxobutanoate (35.86 g) in ethanol (300 mL) is treated with hydrazine hydrate (6 mL) and the mixture is heated at reflux for 2 hours. The reaction mixture is cooled to room temperature, filtered, and the solid washed with ethanol to give ethyl 5-(4-benzyloxyphenyl)-2H-pyrazole-3-carboxylate (25 g), m.p. 160–170° C.

Diethyl oxalate (17.7 g) is added in one portion to a stirred suspension of potassium ethoxide (10.2 g) in anhydrous ether (1000 mL). The stirred mixture is cooled to 0° C., treated with 4-benzyloxyacetophenone (25 g) portionwise, and stirring continued for 3 hours. After standing at room temperature for 18 hours the reaction mixture is poured onto 1 N hydrochloric acid (500 mL) and the organic phase separated. The organic phase is washed with water, dried over magnesium sulphate and evaporated to give ethyl 4-benzyloxypheyl-2,4-dioxobutanoate (35 g).

A mixture of 4-hydroxyacetophenone (30 g), potassium carbonate (33.4 g), potassium iodide (1 g) and benzyl bromide (41.4 g) in methyl ethyl ketone (500 mL) is heated at reflux for 18 hours. The cooled reaction mixture is filtered and the filtrate evaporated. The residue is crystallised from cyclohexane to give 4-benzyloxyacetophenone (45 g, 90%).

Reference Example 12

A stirred solution of methyl benzoylamino (dimethoxyphosphoryl)acetate (4.25 g) in dry tetrahydrofuran (30 mL) is treated with sodium hydride (0.66 g, 60% dispersion in mineral oil) under nitrogen. After stirring for 15 minutes a solution of 2,4-dibenzyloxybenzaldehyde (4.74 g) in dry tetrahydrofuran (15 mL) is added dropwise. The reaction mixture is stirred at room temperature for 18 hours, evaporated and the residue partitioned between ethyl acetate (100 mL) and water (75 mL). The organic phase is washed with brine (50 mL), dried over magnesium sulphate and evaporated. The residual yellow oil is purified by flash chromatography on silica eluting with initially with dichloro-methane then with a mixture of dichloromethane and ethyl acetate (9:1 v/v). Fractions homogeneous in the required products are evaporated to give methyl (E)-2-benzoylamino-3-(2,4-dibenzyloxyphenyl)acrylate (1 g) as a yellow foam, and methyl (Z)-2-benzoylamino-3-(2,4-dibenzyloxyphenyl)-acrylate (1.6 g) as a yellow oil.

A stirred solution of methyl amino(dimethoxyphosphoryl) acetate (6 g) in dichloromethane (50 mL) is treated with benzoyl chloride (5 g) and the mixture allowed to stand at room temperature for 4 hours. The reaction mixture is washed twice with saturated aqueous sodium bicarbonate solution (75 mL), brine (50 mL), dried over magnesium sulphate and evaporated. The residual pale yellow oil is dissolved in ether (5 mL) and pentane added to give methyl benzoylamino(dimethoxyphosphoryl)acetate (4.25 g) as a white solid.

A solution of (±)-N-(benzyloxycarbonyl)-α-phosphonoglycine trimethyl ester (20 g) in methanol (300 mL) is treated with palladium on carbon catalyst (5%, 2 g) and shaken under hydrogen at atmospheric pressure and room temperature for 18 hours. The mixture is filtered and evaporated giving methyl amino(dimethoxyphosphoryl) acetate as an oil (12 g).

Reference Example 13

A stirred solution of triethyl 2-phosphono-3-phenylpropionate (5.17 g) in dry tetrahydrofuran (50 mL) is treated with a solution of n-butyl lithium in hexanes (8 mL, 2.5 M) at −78° C. After stirring for 15 minutes a solution of 2,4-dibenzyloxybenzaldehyde (5 g) in dry tetrahydrofuran (50 mL) is added dropwise over 5 minutes at −78° C. The reaction mixture is stirred at −78° C. for 1 hour and allowed to warm to room temperature. After standing at room temperature for 18 hours the reaction mixture is evaporated and the residue partitioned between ethyl acetate (120 mL) and water (75 mL). The organic phase is washed with brine (50 mL), dried over magnesium sulphate and evaporated. The residue is purified by flash chromatography on silica eluting with dichloromethane. Fractions homogeneous in the required product are evaporated to give ethyl (E)-2-benzyl-3-(2,4-dibenzyloxyphenyl)acrylate (1.5 g) as a yellow oil.

Reference Example 14

A mixture of 2,4-dibenzyloxybenzaldehyde (1 g), methyl cyanoacetate (0.27 mL), piperidine (0.1 mL) and ethanol (30 mL) is stirred at ambient temperature for 20 minutes and the solvent is removed under reduced pressure. The residue is recrystallized from ethanol to give methyl (E)-3-(2,4-dibenzyloxyphenyl)-2-cyanoacrylate as a yellow solid (400 mg).

Reference Example 15

A mixture of 2,4-dibenzyloxyacetophenone (33.2 g) and diethyl oxalate (21.9 g) in ethanol (250 mL) is treated with sodium (2.53 g) added in small portions over 2 hours. The resulting mixture is stirred at room temperature for 18 hours and filtered. The solid is washed with a little ethanol and then washed thoroughly with ether. A portion of this solid (5 g) and hydroxylamine hydrochloride (0.84 g) are suspended in ethanol (100 mL) and 1 N hydrochloric acid is added until the pH of the mixture reaches pH 1. The stirred mixture is heated at reflux for 3 hours, during which time all the solids dissolve, then left at room temperature for 18 hours. The resulting solid is filtered and washed with ether to give ethyl 3-(2,4-dibenzyloxyphenyl)-isoxazole-5-carboxylate (2.2 g).

Reference Example 16

Benzyl 2-benzyloxy-4-iodobenzoate (7.6 g) is added to triethylamine (120 mL) followed by phenylacetylene (2.94 g) then tetrakis(triphenylphosphine)palladium(0) (0.664 g) and copper (I) bromide (0.248 g). The resulting mixture is stirred at room temperature for 3 hours. The triethylamine is distilled off and the residue partitioned between ether (600 mL) and saturated aqueous ammonium chloride solution. The organic phase is dried over magnesium sulphate and evaporated. The residue is purified by flash chromatography on silica eluting with a mixture of pentane and ethyl acetate (5:1 v/v). Fractions homogeneous in the required product are combined and evaporated to give benzyl 2-benzyloxy-4-phenylethynyl-benzoate (2 g) as a cream solid, m.p. 98–100° C.

Sodium hydride (4.7 g, 60% dispersion in mineral oil) is added portionwise over 15 minutes to a solution of 4-iodosalicylic acid (15.4 g) in dry dimethylformamide (150 mL). After stirring for 40 minutes benzyl bromide (19.9 g) is added and the mixture heated at 60° C. for 1.5 hours. The reaction mixture is evaporated and the residue partitioned between chloroform and water. The organic phase is dried over magnesium sulphate, evaporated and the residue triturated with ether to give benzyl 2-benzyloxy-4-iodobenzoate (14.2 g) as a cream coloured solid.

Reference Example 17

2,4-Dibenzyloxyphenol (3.1 g) is added to a stirred suspension of sodium hydride (0.44 g, 60% dispersion in mineral oil) and the mixture is heated at reflux for 30 minutes. Refluxing is allowed to abate when ethyl bromoacetate (1.8 g) is added and the mixture heated at reflux for 1 hour. The reaction mixture is evaporated and the residue partitioned between ethyl acetate and water. The organic phase is washed with water, dried over magnesium sulphate and evaporated to give a light brown oil which is purified by column chromatography on silica eluting with dichloromethane. Fractions homogeneous in the required product are combined and evaporated. The residue is triturated with pentane to give ethyl (2,4-dibenzyloxyphenoxy)acetate (3.2 g) as a white powder, m.p. 62–64° C. [Elemental analysis:- C,73.3; H,6.13%. Calculated:- C,73.5; H,6.13%].

Reference Example 18

A solution of methyl (RS)-5-(3-benzyloxyphenyl)-5-oxo-4-(2-methylphenyl)-pentanoate (46 g) in methanol (250 mL), methyl acetate (250 mL) and concentrated hydrochloric acid (25 mL) is treated with palladium on carbon catalyst (5%; 1.5 g) and shaken under hydrogen at atmospheric pressure and room temperature for 2 hours. The suspension is filtered, and evaporated. The residue is dissolved in ethyl acetate, washed with water, dried and evaporated, and the residue is recrystallised from a mixture of ethyl acetate and cyclohexane, giving methyl (RS)-5-(3-hydroxyphenyl)-5-oxo-4-(2-methylphenyl)pentanoate as colourless crystals (21.7 g), m.p. 101–103° C.

Reference Example 19

A suspension of magnesium turnings (9 g) in dry diethyl ether (100 mL) containing a few crystals of iodine is treated with a solution of benzyl chloride (22.8 g) in diethyl ether (150 mL) at such a rate in the form of to maintain gentle reflux. After the addition is complete, the mixture is treated with 3-benzyloxybenzonitrile (12.7 g) and heated to reflux for 5 hours. The mixture is then treated with hydrochloric acid (1 N) until it is at pH 1, and stirring is continued for 1 hour at ambient temperature. The reaction mixture is separated and the aqueous layer extracted with diethyl ether (3×100 mL). The combined organic extracts are washed with water (3×100 mL), dried over magnesium sulphate and concentrated under reduced pressure. The resulting residue is recrystallised from methanol, to give benzyl 3-benzyloxyphenyl ketone (14.8 g), in the form of a white solid, m.p. 58–60° C. [Elemental analysis:- C,76.2; H,4.99%; Calculated:- C,76.28;H,4.99%].

By proceeding in a similar manner, but using the appropriate quantities of the corresponding starting materials, there are prepared:- 1-[3-(2-methoxybenzyloxy)phenyl]-2-phenylethanone; 1-[3-(3,4-methylenedioxybenzyloxy) phenyl]-2-phenylethanone; and 1-(3-phenoxyphenyl)-2-phenylethanone.

Reference Example 20

A stirred solution of 3-cyanophenol (20 g) in dry N,N-dimethylformamide (200 mL) is treated with sodium hydride (5.6 g; 60% dispersion in mineral oil), portionwise during 40 minutes, followed by dropwise addition of benzyl bromide (20 mL). The mixture is heated at 90° C. for 4 hours, cooled and concentrated under reduced pressure. The residue is partitioned between ethyl acetate and water and the organic layer washed with 1 N sodium hydroxide (100 mL) followed by drying over magnesium sulphate and concentration. The residue is recrystallised from methanol to give 3-benzyloxybenzonitrile (24 g), in the form of a cream solid, m.p. 38–40° C.

By proceeding in a similar manner, but using the appropriate quantities of the corresponding starting materials, there are prepared:
3-(2-methoxybenzyloxy)benzonitrile; and 3-(3,4-methylenedioxybenzyloxy)benzonitrile.

Reference Example 21

A stirred solution of benzyl 3-benzyloxyphenyl ketone (3.02 g) in tetrahydrofuran (40 mL) at 0° C. is treated with potassium tert-butoxide (56 mg), followed by acrylonitrile (0.66 mL). The mixture is stirred at room temperature overnight and then concentrated under reduced pressure and partitioned between water and ethyl acetate. The organic layer is dried over magnesium sulphate and evaporated, to give a brown oil (4.3 g), which is subjected to flash chromatography on silica gel, eluting with a mixture of ethyl acetate and pentane (1:4 v/v), to give 1-(3-benzyloxyphenyl)-4-cyano-2-phenylbutanone (2.2 g), in the form of a light green oil. [Elemental analysis:- C,81.3;H, 6.06;N,3.65%; Calculated:-C,81.1;H,5.96;N,3.94%].

Reference Example 22

A stirred solution of 1-(3-benzyloxyphenyl)-2-(2-methylphenyl)ethan-1-one (4 g) in tetrahydrofuran (100 mL) is treated with potassium tert-butoxide (200 mg). After stirring for 30 minutes, it is treated with bromoacetonitrile (0.98 mL), dropwise, and stirring is continued for a further 28 hours. The mixture is then treated with further quantities of potassium tert-butoxide (200 mg) and bromoacetonitrile (0.98 mL) and allowed to stand at room temperature overnight. It is then concentrated under reduced pressure and partitioned between water and ethyl acetate. The organic layer is dried over magnesium sulphate and evaporated, to give a brown oil, which is subjected to flash chromatography on silica gel, eluting with a mixture of ethyl acetate and pentane (1:9 v/v), to give 1-(3-benzyloxyphenyl)-3-cyano-2-(2-methylphenyl)propan-1-one, in the form of a colourless oil (0.67 g).

Reference Example 23

A mixture of 2,4-dihydroxyacetophenone (29 g), 3-(chloromethyl)thiophene (30 g), potassium carbonate (32 g) and potassium iodide (0.1 g) in 2-butanone (250 mL) is stirred at reflux overnight. The reaction mixture is partitioned between ethyl acetate (300 mL) and dilute hydrochloric acid (300 mL; 1 M), and the organic layer is washed with water, dried, and evaporated. Crystallisation of the residue from cyclohexane gives 2-hydroxy-4-(3-thienylmethoxy)acetophenone (21 g) in the form of a white solid.

By proceeding in a similar manner, but replacing 3-(chloromethyl)thiophene with 3-(chloromethyl)pyridine, there is prepared 2-hydroxy-4-(3-pyridylmethoxy) acetophenone, in the form of a white solid.

Reference Example 24

A mixture of methyl 2,4-dihydroxybenzoate (50 g), benzyl chloride (37 mL), tetrabutylammonium bromide (0.25 g), potassium carbonate (44.4 g) and potassium iodide (18.4 g) in acetone is stirred at reflux overnight. The reaction mixture is evaporated to dryness and the residue is partitioned between water (300 mL) and ethyl acetate (300 mL). The organic layer is washed with aqueous sodium hydrogen carbonate solution and water, dried and evaporated. Crystallisation of the residue from ethyl acetate gives methyl 4-benzyloxy-2-hydroxybenzoate (45.1 g), in the form of a white solid.

By proceeding in a similar manner, but replacing benzyl chloride by 3-(chloromethyl)thiophene and performing the reaction at room temperature, there is prepared methyl 2-hydroxy-4-(3-thienylmethoxy)benzoate.

Reference Example 25

A mixture of methyl 4-benzyloxy-2-hydroxybenzoate (20 g) and concentrated aqueous ammonia (30 mL) in ethanol (100 mL) is heated on the steam bath in a sealed pressure vessel overnight. The contents of the pressure vessel are dissolved in methanol and the solution is evaporated to dryness. The residue is subjected to flash chromatography, eluting first with dichloromethane to remove unreacted starting material, and then with a mixture of ethyl acetate and dichloromethane (3:7 v/v), to obtain 2-hydroxy-4-benzyloxybenzamide (4 g), in the form of a white solid.

By proceeding in a similar manner, but replacing concentrated aqueous ammonia with concentrated aqueous ethylamine, there is prepared 4-benzyloxy-N-ethyl-2-hydroxybenzamide.

By proceeding in a similar manner, but replacing concentrated aqueous ammonia with ethanolic dimethylamine, there is prepared 4-benzyloxy-N,N-dimethyl-2-hydroxybenzamide.

By proceeding in a similar manner, but replacing methyl 4-benzyloxy-2-hydroxybenzoate by methyl 4-(3-thienyimethoxy)-2-hydroxybenzoate and concentrated aqueous ammonia by ethanolic ammonia solution, there is prepared 2-hydroxy-4-(3-thienylmethoxy)benzamide.

Reference Example 26

A stirred solution of 2,4-dihydroxyacetophenone (1.03 g) in dry acetone (40 mL) is treated with potassium carbonate (1.88 g), potassium iodide (1.13 g), tetrabutylammonium bromide (0.22 g), and 5-chloromethylpyrimidine (0.95 g) and heated at reflux for 18 hours. The suspension is filtered, the filtrate is evaporated and the resulting residual solid is recrystallised from a mixture of cyclohexane and ethyl acetate to give 2-hydroxy-4-(5-pyrimidinylmethoxy) acetophenone (0.65 g) in the form of a colourless solid, m.p.

133–134° C. [NMR(CDCl₃):- 2.6(3H,s),5.1(2H,s),6.5–7.7 (3H),8.7(2H,s),9.2(1H,s), 12.7(1H,s)].

By proceeding in a similar manner, but using the appropriate quantities of the corresponding starting materials, there is prepared 2-(2-pyridyl)-5-(3-thienylmethoxy)phenol, m.p. 115–117° C.

Reference Example 27

A mixture of 2-(2,4-dimethoxyphenyl)pyridine (14 g) in pyridine hydrochloride (121 g) is heated to 160° C. and the resulting melt is heated at 160° C. for 7 hours. The mixture is then cooled, diluted with dichloromethane, washed with hydrochloric acid (2 M) and water, dried and evaporated. The residual oil is subjected to flash chromatography on silica gel, eluting with a mixture of pentane and ethyl acetate (1:1 v/v), to give 2-(2,4-dihydroxyphenyl)pyridine (8.0 g) in the form of a solid, m.p. 170–172° C. [NMR(CDCl₃):- 6.3(1H,s),6.4(1H,d),7.3(1H,m), 7.8(1H,d),7.9(1H,t),8.0(1H,d),8.5(1H,d).

Reference Example 28

A stirred suspension of magnesium (8.11 g) in dry tetrahydrofuran (100 mL) is heated, and then treated with a solution of 1-bromo-2,4-dimethoxybenzene (48 mL) in tetrahydrofuran (100 mL) at such a rate as to maintain reflux. The resulting solution is then cooled and added, dropwise, to a solution of 2-bromopyridine (50.3 g) and bis-triphenylphosphinepalladium(II) chloride (3.5 g) in tetrahydrofuran (100 mL) at reflux, and the mixture is maintained at reflux for 6 hours. The solution is then evaporated and the residue is dissolved in ethyl acetate, washed with water, dried and evaporated to give a dark oil. This is subjected to flash chromatography on silica gel, eluting with a mixture of pentane and ethyl acetate (2:1 v/v) to give 2-(2,4-dimethoxyphenyl)pyridine (28 g) in the form of an oil. [NMR(CDCl₃):- 3.84(3H,s),3.86(3H,s), 6.55(1H,s),6.6(1H,d),7.2(1H,m),7.7(1H,t),7.77 (1H,d),7.8(1H,d),8.7(1H,d)].

Reference Example 29

A stirred solution of titanium(IV) chloride in dichloromethane (95 mL;

1 M) at 0° C. under nitrogen is treated, dropwise, with a solution of 2-chloro-6-fluorobenzaldehyde (15 g) in dichloromethane (20 mL). The mixture is stirred for 5 minutes, and then treated, dropwise, with (1-ethoxycyclopropyloxy) trimethylsilane (21.1 mL), maintaining the temperature at between 0° C. and 5° C. The mixture is stirred for 16 hours at room temperature, and then it is treated with water (200 mL) and extracted with dichloromethane (3×100 mL), and the combined organic extracts are washed with brine (50 mL), dried over magnesium sulphate, and evaporated, to give (RS)-4-chloro-4-(2-chloro-6-fluorophenyl)butanoate, in the form of a yellow oil.

By proceeding in a similar manner, but replacing the 2-chloro-6-fluorobenzaldehyde with the appropriate quantity of 2-bromobenzaldehyde, there is prepared ethyl (RS)-4-(2-bromophenyl)-4-chlorobutanoate, in the form of a yellow oil.

Reference Example 30

A stirred mixture of 5-benzyloxy-2-mercaptophenol (10 g), potassium carbonate (6 g) and acetone (200 mL) at 0° C. is treated, dropwise, with iodomethane (6.1 g) and stirred for 2 hours at 0° C. The reaction mixture is evaporated to dryness and the residue is partitioned between ethyl acetate (200 mL) and water (200 mL). The organic layer is dried over magnesium sulphate, filtered and concentrated in vacuo to give 5-benzyloxy-2-methylthiophenol, in the form of a brown oil.

By proceeding in a similar manner, but replacing the 5-benzyloxy-2-mercaptophenol with the appropriate quantity of 2-mercapto-5-(3-thienylmethoxy)phenol, there is prepared 2-methylthio-5-(3-thienylmethoxy)phenol, in the form of a yellow oil, after flash chromatography on silica gel, using a mixture of petroleum ether and ethyl acetate (9:1 v/v) as eluent.

Reference Example 31

A mixture of 6-benzyloxy-1,3-benzoxathiol-2-one (35 g), aqueous sodium hydroxide solution (200 mL; 2 N) and methanol (50 mL) is stirred at ambient temperature for 16 hours and then it is heated at reflux for 30 minutes. The reaction mixture is then evaporated to dryness and the residue is acidified to pH 1 by treatment with concentrated hydrochloric acid (20 mL). The residue is diluted with water (200 mL) and then extracted with diethyl ether (3×200 mL). The combined organic extracts are washed with brine (100 mL), dried over magnesium sulphate, filtered and concentrated in vacuo, to give 5-benzyloxy-2-mercaptophenol, in the form of a yellow oil which solidified on standing overnight.

By proceeding in a similar manner, but replacing the 6-benzyloxy-1,3-benzoxathiol-2-one with the appropriate quantity of 6-(3-thienylmethoxy)-1,3-benzoxathiol-2-one, there is prepared 5-(3-thienylmethoxy)-2-mercaptophenol.

A mixture of 6-hydroxy-1,3-benzoxathiol-2-one (15 g) and potassium carbonate (13.8 g) in dimethylformamide (200 mL) is stirred for 20 minutes, and is then treated, dropwise, with 3-chloromethylthiophene (11.8 g). The mixture is stirred at 60° C. for 16 hours. The reaction mixture is then concentrated in vacuo, and partitioned between water (200 mL) and ethyl acetate (200 mL). The aqueous layer is extracted with ethyl acetate (100 mL) and with diethyl ether (100 mL), and the combined aqueous layers are washed with brine, dried over magnesium sulphate, and evaporated to give a yellow solid, which is recrystallised from ethanol (200 mL) to give 6-(3-thienylmethoxy)-1,3-benzoxathiol-2-one (8.9 g), in the form of pale yellow crystals.

By proceeding in a similar manner, but replacing the 3-chloromethylthiophene by the appropriate quantity of benzyl chloride, there is prepared 6-benzyloxy-1,3-benzoxathiol-2-one.

Reference Example 32

A solution of 2,4-dihydroxybenzaldehyde (42.6 g) in dimethylformamide (250 mL) at ambient temperature is treated with sodium hydride (13.5 g; 60% w/v dispersion in mineral oil; 338 mmol), portionwise during 30 minutes. It is then treated with 3-chloromethylthiophene and the reaction mixture is heated at 60° C. for 3 hours. The mixture is concentrated in vacuo and the residue is partitioned between hydrochloric acid (200 mL; 0.5 N) and ethyl acetate (200 mL). The aqueous layer is extracted with ethyl acetate (3×100 mL) and the combined organic extracts are washed with brine (50 mL), dried over magnesium sulphate, filtered and the solvent is removed in vacuo. Flash chromatography on silica gel, using a mixture of petroleum ether (b.p. 40–60° C.) and ethyl acetate (4:1 v/v) as eluent, gives 2-hydroxy-4-(3-thienylmethoxy)benzaldehyde (11.8 g), in the form of a white solid.

By proceeding in a similar manner, but using the appropriate quantities of the corresponding starting materials, there are prepared 4-benzyloxy-2-hydroxybenzaldehyde and 5-(3-thienylmethoxy)-2-trifluoroacetylphenol.

Reference Example 33

By proceeding in a manner similar to that described hereinbefore in Reference Example 24 but replacing the methyl 4-benzyloxy-2-hydroxybenzoate by the appropriate quantity of ethyl 2-hydroxy-6-methyl-4-(3-thienylmethoxy)benzoate, and the concentrated aqueous ammonia solution by ethanolic ammonia solution, there is prepared 2-hydroxy-6-methyl-4-(3-thienylmethoxy)benzamide.

Reference Example 34

By proceeding in a manner similar to that described hereinbefore in Reference Example 23 but replacing the methyl 2,4-dihydroxybenzoate by the appropriate quantity of ethyl 2,4-dihydroxy-6-methylbenzoate, there is prepared ethyl 2-hydroxy-6-methyl-4-(3-thienylmethoxy)benzoate.

Reference Example 35

A mixture of 2-fluoro-4-(3-thienylmethoxy)nitrobenzene (4.21 g), aqueous potassium hydroxide solution (50 mL; 50% w/v) and t-butanol (20 mL) is heated at reflux for 4 hours. It is then evaporated to dryness and the residue is partitioned between ethyl acetate (100 mL) and hydrochloric acid (100 mL; 1 N). The organic phase is washed with water (3×100 mL), dried over magnesium sulphate, filtered and evaporated, to give 2-nitro-5-(3-thienylmethoxy)phenol, in the form of a yellow solid.

Reference Example 36

A mixture of 1-[N-(methoxycarbonylmethyl)carbamoyl]-2-[2-(trimethylsilyl)ethoxy]methoxy-4-(3-thienylmethoxy)benzene (3.3 g), tetrabutylammonium fluoride (20 mL of a 1 M solution in tetrahydrofuran) and tetrahydrofuran (30 mL) is stirred at ambient temperature for one hour and at reflux for 45 minutes, then it is cooled to ambient temperature and concentrated in vacuo. The resulting residue is partitioned between ethyl acetate (100 mL) and saturated brine (100 mL), and the organic layer is washed with brine (2×50 mL), dried over magnesium sulphate, filtered and concentrated in vacuo. Flash chromatography of the residual oil on silica gel, eluting with a mixture of methanol and dichloromethane (2:98 v/v) gives 2-[N-(methoxycarbonylmethyl)carbamoyl]-5-(3-thienylmethoxy)phenol (2.3 g), in the form of a white solid.

By proceeding in a similar manner, but replacing the 1-[N-(methoxycarbonylmethyl)carbamoyl]-2-[2-(trimethylsilyl)ethoxy]methoxy-4-(3-thienylmethoxy)benzene used as starting material by the appropriate quantities of the corresponding starting materials, there are prepared;
2-[N-(3-imidazol-1-ylpropyl)carbamoyl]-5-(3-thienylmethoxy)phenol, in the form of a yellow oil; 2-[N-(2-methoxycarbonylethyl)carbamoyl]-5-(3-thienylmethoxy)phenol, in the form of a yellow oil; 2-[N-(2-cyanoethyl)carbamoyl]-5-(3-thienylmethoxy)phenol, in the form of a yellow oil; and 2-[N-(cyanomethyl)carbamoyl]-5-(3-thienylmethoxy)phenol, in the form of a yellow oil Reference Example 37

A mixture of 4-(3-thienylmethoxy)-2-[2-(trimethylsilyl)ethoxy]methoxybenzoic acid (3.09 g), methyl aminoacetate hydrochloride (0.99 g), 1-hydroxybenzotriazole (1.28 g), triethylamine (0.8 g) and dimethylformamide (50 mL) is stirred at ambient temperature for 16 hours. It is then concentrated in vacuo and the resulting residue is dissolved in ethyl acetate (100 mL), washed quickly with hydrochloric acid (2×50 mL; 1 N), and then washed with saturated aqueous sodium bicarbonate solution (50 mL) and with water (50 mL), then dried over magnesium sulphate, filtered and concentrated in vacuo, to give 1-[N-(methoxycarbonylmethyl)carbamoyl]-4-(3-thienylmethoxy)-2-[2-(trimethylsilyl)ethoxy]methoxybenzene, in the form of a yellow oil.

By proceeding in a similar manner, but replacing the methyl aminoacetate hydrochloride by the appropriate quantities of the corresponding starting materials, there are prepared:
1-[N-(3-imidazol-1-ylpropyl)carbamoyl]-4-(3-thienylmethoxy)-2-[2-(trimethylsilyl)ethoxy]methoxybenzene, in the form of a yellow oil; 1-[N-(2-methoxyarbonylethyl)carbamoyl]-4-(3-thienylmethoxy)-2-[2-(trimethylsilyl)ethoxy]methoxybenzene, in the form of a yellow oil; 1-[N-(cyanomethyl)carbamoyl]-4-(3-thienylmethoxy)-2-(2-trimethylsilylethoxy)methoxybenzene, in the form of a yellow oil; 1-[N-(cyanoethyl)carbamoyl]-4-(3-thienylmethoxy)-2-(2-trimethylsilylethoxy)methoxybenzene, in the form of a yellow oil; methyl 2-[2-(trimethylsilyl)ethoxy-4-(3-thienylmethoxy)benzoylamino]-3-phenylpropionate, thought to be the (R)-enantiomer, in the form of a yellow oil; and methyl 2-[2-(trimethylsilyl)ethoxy-4-(3-thienylmethoxy)benzoylamino]-3-phenylpropionate, thought to be the (S)-enantiomer, in the form of a yellow oil.

Reference Example 38

A mixture of methyl 4-(3-thienylmethoxy)-2-(2-trimethylsilylethoxy)methoxybenzoate (12.1 g) and aqueous potassium carbonate solution (50 mL; 10% w/v) in methanol (200 mL) is heated at reflux for 7 hours. It is then concentrated in vacuo and the residue is treated with water (200 mL) and acidified to pH 1 by treatment with hydrochloric acid (1 N), and the resulting solid is quickly filtered off and is then washed with water. The white solid is then azeotroped with cyclohexane in a Dean-Stark apparatus until no more water is removed. The solid is filtered off, to give 4-(3-thienylmethoxy)-2-(2-trimethylsilylethoxy)methoxybenzoic acid (6.03 g), in the form of a white solid.

Reference Example 39

A stirred suspension of sodium hydride (1.53 g; 60% w/v dispersion in mineral oil; 38.3 mmol) in dimethylformamide (100 mL) is treated, portionwise, with methyl 2-hydroxy-4-(3-thienylmethoxy)benzoate (8.44 g) and stirred for 40 minutes. The mixture is treated with 2-(trimethyl-silyl)ethoxymethyl chloride (6.39 g), in one portion, and stirred at ambient temperature for three hours. It is then evaporated to dryness and the resulting residue is partitioned between water (100 mL) and ethyl acetate (100 mL). The organic layer is washed with brine (150 mL), dried over magnesium sulphate, filtered and concentrated in vacuo, to give methyl 4-(3-thienylmethoxy)-2-(2-trimethylsilylethoxy)methoxybenzoate, in the form of a yellow oil.

Reference Example 40

A solution of triphenylphosphine (20 g) in tetrahydrofuran (300 mL) cooled at 0° C. is treated dropwise during 5 minutes with diisopropyl azodicarboxylate (15 mL) and stirred for 15 minutes at 0° C. It is then treated, dropwise, with a solution of 2-fluoro-4-hydroxybenzonitrile (7 g) and 3-thienylmethanol (7 g) in tetrahydrofuran (200 mL) during 2 hours, and stirring is continued at ambient temperature for 18 hours. The mixture is concentrated in vacuo and the residue is dissolved in ethyl acetate (500 mL). This solution is washed with water (200 mL) and aqueous sodium hydroxide solution (1 N), dried over magnesium sulphate and concentrated in vacuo, to give an oil, which is passed through a pad of silica gel (thickness 5 cm) with the aid of dichloromethane. The resulting filtrate is concentrated in vacuo, to give an oil which crystallizes on standing. Recrystallization from isopropyl ether gives 2-fluoro-4-(3-thienylmethoxy)benzonitrile (6 g), in the form of a white solid, m.p. 63–65° C.

Reference Example 41

A solution of triphenylphosphine (20 g) in tetrahydrofuran (300 mL) cooled at 0° C. is treated dropwise during 5 minutes with diisopropyl azodicarboxylate (15 mL) and stirred for 15 minutes at 0° C. It is then treated, dropwise, with a solution of 2-fluoro-4-hydroxybenzonitrile (7 g) and 3-pyridylmethanol (7 g) in tetrahydrofuran (200 mL) during 2 hours, and stirring is continued at ambient temperature for 18 hours. The mixture is concentrated in vacuo and the residue is dissolved in ethyl acetate (500 mL) and the solution is washed with hydrochloric acid (3×100 mL; 1 N) and the remaining organic layer is discarded. The combined acid washings are basified to pH 10 by treatment with solid sodium hydroxide and extracted with ethyl acetate (3×100 mL). This organic extract is dried over magnesium sulphate and concentrated in vacuo, and the residue is recrystallized from isopropyl ether, to give 2-fluoro-4-(3-pyridylmethoxy) benzonitrile (10 g), in the form of a white solid, m.p. 105–110° C.

Reference Example 42

A mixture of 4-(2-methylphenyl)-4-oxobutanoic acid (40 g), concentrated sulphuric acid (4 mL) and t-butanol (4 mL) in dichloromethane (200 mL) is cooled to 0° C., and isobutylene (about 400 mL) is condensed into the mixture. It is then stirred at 0° C. until t.l.c. shows reaction is complete. The excess isobutylene is allowed to evaporate, and then the mixture is treated carefully with saturated aqueous sodium bicarbonate solution (200 mL), with vigorous stirring. The organic layer is separated, filtered through a pad of silica gel with the aid of more dichloromethane, and concentrated in vacuo, to give t-butyl 4-(2-methylphenyl)-4-oxobutanoate (5 g), in the form of a pale yellow oil.

Reference Example 43

A solution of t-butyl 4-(2-methylphenyl)-4-oxobutanoate (12 g) in dry diethyl ether (50 mL) is dried over molecular sieves (4 Å; 10 g) for 3 hours, and then it is transferred to a dry flask and placed under an argon atmosphere. The solution is cooled to −20° C., treated rapidly with bis[(1S, 2R,3S,5S)-pinan-3-yl]chloroborane (25 g) and sealed under an atmosphere of argon. The reaction mixture is stored at −20° C. for 48 hours, and then it is warmed to ambient temperature. It is then diluted with diethyl ether (50 mL) and treated with diethanolamine (10 g). The mixture is stirred vigorously at ambient temperature for 5 hours, then it is poured into pentane (500 mL) and filtered through a pad of diatomaceous earth. The filtrate is concentrated in vacuo at 0.5 mmHg/50° C. for 3 hours, and the resulting residue is subjected to flash chromatography on silica gel, eluting with a mixture of methanol and dichloromethane (1:19 v/v), to give t-butyl 4-hydroxy-4-(2-methylphenyl)butanoate, thought to be the (R)-enantiomer, (10 g) in the form of a colourless oil. $^{25}[\alpha]_D$=+49° (c=0.01 ;CHCl$_3$); [NMR (CDCl$_3$) (300 MHz):- 1.45(s,9H), 2.00(m,2H), 2.32(s,3H), 2.40(m,2H),4.99(m,1H),7.10–7.50(m,4H).

The enantiomeric excess is determined to be greater than 99%, by reacting the product with (R)-(−)-α-methoxy-α-(trifluoromethyl)phenylacetyl chloride and considering the NMR (CDCl$_3$) spectrum of the resulting ester.

By proceeding in a similar manner, but replacing the bis[(1S,2R,3S,5S)pinan-3-yl]-chloroborane by an appropriate quantity of bis[(1R,2S,3R,5R)pinan-3-yl]chloroborane, there is prepared tert-butyl 4-hydroxy-4-(2-methylphenyl) butanoate, thought to be the (S)-enantiomer, in the form of a colourless oil, $^{25}[\alpha]_D$=−45° (c=0.02;CHCl$_3$).

Reference Example 44

A solution of t-butyl 4-hydroxy-4-(2-methylphenyl) butanoate, thought to be the (R)-enantiomer, (0.5 g) in tetrahydrofuran (3 mL) and methanol (3 mL) is treated with aqueous sodium hydroxide solution (5 N; 0.5 mL) and stirred at ambient temperature for 8 hours. The reaction mixture is concentrated to dryness. The resulting residue is treated with isopropanol (10 mL) and stirred for 30 minutes, and the resulting precipitate is collected and washed with isopropyl ether, to give sodium 4-hydroxy-4-(2-methylphenyl)butanoate, thought to be the (R)-enantiomer, (300 mg) in the form of a white solid, m.p. above 250° C.; $^{25}[\alpha]_D$=+34° (c=0.01; CH$_3$OH); [NMR(DMSO-d$_6$) (300 MHz):- 1.58–1.75 (m,2H),2.11(m,2H),2.22(s,3H),4.75(m, 1H),7.05–7.48 (m.4H).

Reference Example 45

A mixture of 3-fluoro-4-nitrophenol (5.0 g) 3-chloromethylthiophene (4.2 g) and potassium carbonate (4.4 g) in dimethylformamide (25 mL) is stirred at 90° C. for 16 hours. The solvent is removed in vacuo and the residue is partitioned between ethyl acetate (50 mL) and water (50 mL). The organic phase is washed with water (2×50 mL), dried over magnesium sulphate, and evaporated to give 3-fluoro-4-nitrophenyl-5-(3-thienylmethoxy)benzene (7.66 g), in the form of a yellow solid.

Reference Example 46

A stirred solution of 2,4-dihydroxybenzaldehyde (31.8 g) in dry dimethylformamide (150 mL) at ambient temperature is treated with sodium hydride (11.96 g; 60% w/v dispersion in mineral oil; 300 mmol), portionwise, during 30 minutes. After a further period of 15 minutes, the mixture is treated, dropwise, with a solution of 3-chloromethylthiophene (35 g) in dimethylformamide (50 mL). The mixture is stirred at 70° C. for 2 hours, then it is cooled and the solvent is evaporated. The residue is partitioned between ethyl acetate (200 mL) and hydrochloric acid (200 mL; 0.5 M), and the aqueous layer is extracted further with ethyl acetate (2×100 mL). The combined organic extracts are washed with brine (100 mL), dried over magnesium sulphate, and concentrated in vacuo. The residue is subjected to flash chromatography on silica gel, eluting with a mixture of ethyl acetate and pentane (1:4 v/v), to give a colourless oil, which crystallises on standing. This solid is recrystallised from diisopropyl ether, to give 2-hydroxy-4-(3-thienylmethoxy)benzaldehyde (8 g), in the form of a white solid.

A mixture of 2-hydroxy-4-(3-thienylmethoxy) benzaldehyde (7.7 g), nitroethane (4.74 mL), sodium acetate (5.4 g) and glacial acetic acid (6.6 mL) is heated at reflux for 14 hours. The mixture is then cooled, diluted with water (50 mL) and extracted with ethyl acetate (3×50 mL). The combined organic extracts are washed with saturated aqueous sodium bicarbonate solution (3×50 mL), dried over magnesium sulphate, and concentrated in vacuo. The resulting residue is subjected to flash chromatography on silica gel, eluting with a mixture of ethyl acetate and pentane (3:7 v/v), to give 2-hydroxy-4-(3-thienylmethoxy)benzonitrile (7.6 g), in the form of a pale yellow solid.

Reference Example 47

A mixture of methyl (RS)-5-(3-iodophenyl)-4-(2-methylphenyl)-5-oxopentanoate (1.7 g), bis(triphenylphosphine)palladium (II) chloride (0.1 g), tetrakis(triphenylphosphine)palladium (0) (0.13 g) and benzylthiotrimethylstannane (1.17 g) in toluene (37 mL) is heated at reflux for 24 hours. The reaction mixture is washed twice with 10% aqueous potassium fluoride (20 mL), with water (20 mL), dried over magnesium sulphate and evaporated. The residue (2.87 g) is purified by flash chromatography on silica eluting with a mixture of pentane and ethyl acetate (98:2 v/v). Fractions homogeneous in the required product are combined and evaporated to give ethyl (RS)-5-(3-benzylthiophenyl)-4-(2-methylphenyl)-5-oxopentanoate as an orange oil (0.57 g).

A solution of 1-(3-iodophenyl)-2-(2-methylphenyl) ethanone (3.21 g) in dry tetrahydrofuran (30 mL) is treated with methyl acrylate (0.9 mL) and potassium tertiary butoxide (0.107 g). The reaction mixture is heated at reflux for 18 hours, evaporated and the residue partitioned between ethyl acetate (60 mL) and water (30 mL). The organic phase is dried over magnesium sulphate, evaporated and the residual solid washed with pentane to give methyl (RS)-5-(3-iodophenyl)-4-(2-methylphenyl)-5-oxopentanoate as a fawn coloured solid (3.39 g), m.p. 106–108° C.

A solution of 2-methylbenzyl chloride (4.57 mL) in ether (61 mL) is added dropwise to magnesium (1.64 g) at a rate to maintain reflux. The mixture is stirred for 15 minutes, decanted from the excess magnesium and this solution is added dropwise to a stirred solution of N-methoxy-N-methyl-3-iodoenzamide (4.9 g) in ether (30 mL) at 5–10° C. giving a cream coloured precipitate. The suspension is treated with 2 N hydrochloric acid (50 mL) and the organic phase separated, washed with water (50 mL) and dried over magnesium sulphate. 1-(3-Iodophenyl)-2-(2-methylphenyl) ethanone (0.69 g) is precipitated in the filtrate during filtration. Evaporation of the solution gives an oily solid which is triturated with a mixture of pentane and ethyl acetate (9:1 v/v) to give a further quantity of 1-(3-iodophenyl)-2-(2-methylphenyl)ethanone (2.69 g), m.p.115–117° C. [Elemental analysis:- C.,53.9; H,3.90%. Calculated:- C,53.6; H,3.90%].

A stirred solution of N-methoxymethylamine (3.47 g) and triethylamine (10.4 mL) in dichloromethane (100 mL) at 5° C. is treated dropwise with 3-iodobenzoyl chloride (9.8 g). The reaction mixture is stirred at room temperature for 2 hours, washed twice with water (70 mL), dried over magnesium sulphate, and evaporated to give N-methoxy-N-methyl-3-iodobenzamide (9.8 g) as a brown oil.

A stirred suspension of 3-iodobenzoic acid (8.84 g) in thionyl chloride (44 mL) is heated at reflux for 30 minutes. The dark brown solution is evaporated to give 3-iodobenzoyl chloride (9.8 g) as a brown oil.

Reference Example 48

A stirred solution of ethyl (RS)-4-(2-acetyl-5-(3-thienylmethoxy)phenoxy)-4-(2-methylphenyl)butanoate (0.5 g) in pyridine (2.5 mL) is treated with selenium dioxide (0.204 g) and the mixture is heated at 100° C. for 4 hours. A further quantity of selenium dioxide (0.1 g) is added and the mixture is heated at 100° C. for 18 hours. The suspension is filtered and the filtrate evaporated to give an orange oil (0.76 g) which is dissolved in ethyl acetate (20 mL) and washed twice with 1 N acetic acid (10 mL), with water (10 mL) and dried over magnesium sulphate. Evaporation gives an orange oil (0.58 g) which is purified by flash chromatography on silica eluting with a mixture of dichloromethane and methanol (9:1 v/v). Fractions homogeneous in the required product are combined and evaporated to give ethyl (RS)-4-(2-carboxycarbonyl-5-(3-thienylmethoxy)phenoxy)-4-(2-methylphenyl)butanoate (0.38 g) as a yellow gum.

Reference Example 49

Diisopropyl azodicarboxylate (6.45 mL) is added dropwise to a stirred, cooled (0° C.) solution of triphenylphosphine (8.6 g) in dry tetrahydrofuran (60 mL). After a further 30 minutes, a solution of 2'-hydroxy-4'-(pyridin-3-ylmethoxy)benzophenone (5 g) and tert-butyl 4-hydroxy-4-(2-methylphenyl)butanoate, thought to be the (S)-enantiomer, (5.13 g) in dry tetrahydrofuran (60 mL) is added dropwise over 25 minutes and stirring continued for a further 3 hours at °C. The reaction is allowed to warm to ambient temperature overnight before being concentrated under vacuo. The resultant oil is purified by flash chromatography on silica eluting with a mixture of dichloromethane and ethyl acetate (9:1 v/v). Fractions homogeneous in the required product are combined and concentrated under reduced pressure to give t-butyl 4-[2-benzoyl-5-(pyridin-3-ylmethoxy)phenoxy]-4-(2-methylphenyl)butanoate, thought to be the (R)-enantiomer, as a colourless oil (8.66 g).

A mixture of 2,4-dihydroxybenzophenone (21.4 g), 3-chloromethylpyridine hydrochloride (25 g), potassium carbonate (80 g), potassium iodide (0.5 g) and tetrabutylammonium bromide (0.2 g) in methyl ethyl ketone is heated at reflux with mechanical stirring for 18 hours. The reaction mixture is filtered through hyflo and the solids washed with several portions of methyl ethyl ketone. The filtrate and the washings are combined and concentrated under reduced pressure to leave a brown oil which is dissolved in ethyl acetate (250 mL) and washed four times with water (200 mL). The organic layer is dried over magnesium sulphate, filtered and concentrated under reduced pressure to leave a residue which is crystallised from cyclohexane containing a little decolourizing charcoal to give 2'-hydroxy-4'-(pyridin-3-ylmethoxy)benzophenone (21.2 g) as a pale yellow solid, m.p. 88–90° C.

Reference Example 50

Dry sodium 4-hydroxy-4-(2-methylphenyl)butanoate, thought to be the (R)-enantiomer, (1 g) is added portionwise to a stirred suspension of sodium hydride (0.6 g, 60% dispersion in mineral oil) in dry tetrahydrofuran (50 mL) under nitrogen. The reaction mixture is stirred at 50° C. for 15 minutes when methyl 3-(3-fluoro-4-nitrophenoxymethyl] benzoate (1.4 g) is added in one portion. After stirring at 50–60° C. for 18 hours the reaction mixture is evaporated to dryness and the residue partitioned between ethyl acetate (50 mL) and 1 N hydrochloric acid (50 mL). The organic phase is washed three times with water (50 mL), dried over magnesium sulphate and evaporated to give a yellow-brown oil (2.47 g) which is purified by flash chromatography on silica eluting initially with a mixture of cyclohexane and ethyl acetate (4:1 v/v) then eluting with a mixture of cyclohexane and ethyl acetate (3:1 v/v). Fractions homogeneous in the required product are combined and evaporated to give methyl 3-[3-(3-carboxy-1-(2-methylphenyl) propoxy)-4-nitrophenoxymethyl]benzoate (0.86 g) as a clear yellow oil.

2-Fluoro-4-hydroxynitrobenzene (3 g) is added portionwise to a stirred suspension of sodium hydride (0.9 g, 60% dispersion in mineral oil) in dry dimethylformamide (50 mL) under nitrogen. After stirring for 20 minutes methyl 3-bromomethylbenzoate is added in one portion and stirring continued for 3 hours. The reaction mixture is evaporated to dryness and the residue partitioned between ethyl acetate (50 mL) and water (50 mL). The organic phase is washed three times with water (50 mL), dried over magnesium sulphate and evaporated to give a yellow solid which is crystallised from a mixture of ethyl acetate and cyclohexane (1:3 v/v) to give methyl 3-(3-fluoro-4-nitrophenoxymethyl)benzoate (4.95 g) as a white solid.

Reference Example 51

Diisopropyl azodicarboxylate (2.6 g) is added portionwise to a stirred solution of triphenylphosphine (3.4 g) in dry tetrahydrofuran (40 mL) at 0° C. under nitrogen. The reaction mixture is stirred at 0° C. for 15 minutes then treated with a solution of 2-fluoro-4-hydroxybenzonitrile (0.87 g) and t-butyl 3-(3-hydroxymethylphenyl)propionate (1.5 g) in dry tetrahydrofuran (10 mL) whilst maintaining the temperature at 0–5° C. Stirring is continued at this temperature for 1 hour when the reaction mixture is allowed to warm up to room temperature. The reaction mixture is evaporated to low bulk and partitioned between ethyl acetate (100 mL) and water (100 mL). The organic phase is washed with water (50 mL), dried over magnesium sulphate and evaporated. The residue is purified by flash chromatography on silica eluting with a mixture of cyclohexane and ethyl acetate (4:1 v/v). Fractions homogeneous in the required product are combined and evaporated to give tert-butyl 3-[3-(4-cyano-3-fluoro-phenoxymethyl)phenyl]propionate (0.3 g).

A stirred solution of tert-butyl 3-(3-formylphenyl)acrylate (5 g) in methanol (150 mL) at 0° C. is treated with sodium borohydride (0.38 g) portionwise. After stirring at 0° C. for 20 minutes the reaction mixture is partitioned between ethyl acetate (200 mL) and water (100 mL). The organic phase is separated, dried over magnesium sulphate and evaporated to give tert-butyl 3-(3-hydroxymethylphenyl)acrylate which is dissolved in dry toluene (50 mL) and treated with tris (triphenylphosphine)rhodium(I) chloride (80 mg) and triethylsilane (8 mL). The mixture is stirred at room temperature for 3 hours, left standing at room temperature for 18 hours and evaporated. The residue is purified by flash chromatography on silica eluting with a mixture of cyclohexane and ethyl acetate (4:1 v/v). Fractions homogeneous in the required product are combined and evaporated to give tert-butyl 3-(3-hydroxymethylphenyl)propionate (1.5 g).

To a stirred mixture of 3-bromobenzaldehyde (20 g), tert butyl acrylate (40 mL), triethylamine (44 mL) and tris(2-methylphenyl)phosphine (3.4 g) in dry dimethylformamide (300 mL) is added palladium (II) acetate in one portion. The resulting dark brown mixture is heated at 100° C. for 18 hours then evaporated in vacuo. The residual semi-solid is partitioned between ethyl acetate (250 mL) and 2 N hydrochloric acid (250 mL). the organic phase is washed three times with water (250 mL), dried over magnesium sulphate and evaporated. The resulting dark brown oil (28.1 g) is purified by flash chromatography on silica eluting initially with a mixture of cyclohexane and dichloromethane (4:1 v/v) then with a mixture of cyclohexane and dichloromethane (1:1 v/v). Fractions homogeneous in the required product are combined and evaporated to give tert-butyl 3-(3-formylphenyl)acrylate as a yellow oil (14.08 g).

Reference Example 52

Burgess reagent (1.3 g) is added to a solution of ethyl (RS)-4-[2-(2-hydroxyethylcarbamoyl)-5-(3-thienylmethoxy)phenoxy]-4-(2-methylphenyl)butanoate (2.5 g) in THF (50 mL) under nitrogen and the mixture refluxed for 30 minutes. The reaction is cooled to ambient temperature then partitioned between ethyl acetate (100 mL) and water (100 mL). The organic phase is dried over magnesium sulphate, filtered and evaporated to dryness. The residue is purified by flash chromatography on silica eluting with a mixture of ethyl acetate and cyclohexane (1:1 v/v). Fractions homogeneous in the required product are combined and evaporated to give ethyl (RS)-4-[2-( 4,5-dihydrooxazol-2-yl)-5-(3-thienylmethoxy)phenoxy]-4-(2-methylphenyl)butanoate (1.5 g) as a white solid.

2-Hydroxy-N-(2-hydroxyethyl)-4-(3-thieny(methoxy) benzamide (2.93 g) is added portionwise to a stirred suspension of sodium hydride (0.44 g of a 60% dispersion in mineral oil) in DMF (100 mL) at ambient temperature. The reaction is stirred at ambient temperature for 30 minutes then a solution of ethyl (R,S)-4-chloro-4-(2-methylphenyl) butanoate (3.6 g) in DMF (5 mL) is added in one portion and the reaction stirred for 4 hours at 100° C. The reaction is left at ambient temperature for 16 hours then concentrated in vacuo. The residue is partitioned between ethyl acetate (150 mL) and water (100 mL). The organic phase is washed with water (100 mL), dried over magnesium sulphate, filtered and concentrated in vacuo. The residue is purified by flash chromatography on silica eluting with a mixture of ethyl acetate and cyclohexane (1:1 v/v). Fractions homogeneous in the required product are combined and evaporated to give ethyl (RS)-4-(2-(N-2-hydroxyethylcarbamoyl)-5-(3-thienylmethoxy)phenoxy)-4-(2-methylphenyl) butanoate (3.9 g) as a yellow oil.

A mixture of methyl 2-hydroxy-5-(3-thienylmethoxy) benzoate (9.96 g) and ethanolamine (250 mL) is refluxed for 1 hour. The ethanolamine is neutralised with 2N HCl and the mixture extracted with ethyl acetate (2×250 mL). The combined organic extracts are washed with water (2×100 mL), dried over magnesium sulphate, filtered and concentrated under reduced pressure to give a yellow solid. Trituration with diethyl et her gives 2-Hydroxy-N-(2-hydroxyethyl)-4-(3-thienylmeth oxy)benzamide (6.8 g) in the form of a white solid.

Reference Example 53

A solution of ethyl (RS)-4-[2-(4,5-dihydrooxazol-2-yl)-5-(3-thienylmethoxy)phenoxy]-4-(2-methylphenyl)butanoate (900 mg) and nickel peroxide (5.04 g) in toluene (50 mL) is stirred at 100° C. for 2 hours. The reaction is left at ambient temperature for 16 hours then filtered through a pad of hyflo and the filtrate concentrated in vacuo. The residue is purified by flash chromatography on silica eluting with a mixture of ethyl acetate and cyclohexane (15:85 v/v). Fractions homogeneous in the required product are combined and evaporated to give ethyl (RS)-4-[2-(oxazol-2-yl)-5-(3-thienylmethoxy)phenoxy]-4-(2-methylphenyl)butanoate (140 mg) and starting material (400 mg).

Reference Example 54

Methyl (RS)-2-[2-hydroxy-4-(3-thienylmethoxy)phenyl]-4,5-dihydrooxazole-4-carboxylate (200 mg) is added portionwise to a stirred suspension of sodium hydride (0.04 g, 60% dispersion in mineral oil) in DMF (25 mL) at ambient temperature. The reaction is stirred at ambient temperature for 30 minutes then a solution of ethyl (R,S)-4-chloro-4-(2-methylphenyl) butanoate (240 mg) in DMF (5 mL) is added in one portion and the reaction stirred for 4 hours at 100° C. The reaction is left at ambient temperature for 16 hours then concentrated in vacuo. The residue is partitioned between ethyl acetate (50 mL) and water (50 mL). The organic phase is washed with water (50 mL), dried over magnesium sulphate, filtered and concentrated in vacuo. The residue is purified by flash chromatography on silica eluting with a mixture of ethyl acetate and cyclohexane (15:85 v/v). Fractions homogeneous in the required product are combined and evaporated to give methyl (RS)-2-[2-(3-ethoxycarbonyl-1-(2-methylphenyl)propoxy)-4-(3-thienylmethoxy)benzoylamino]acrylate (250 mg) as a colourless oil.

Thionyl chloride (7.14 g) is added to a stirred solution of methyl (RS)-3-hydroxy-2-[4-(3-thienylmethoxy)-2-(2-trimethylsilylethoxymethoxy)benzoyl]propionate (6.5 g) in dichloromethane (100 mL) at ambient temperature. The reaction is left to stand at room temperature for 18 hours. The reaction mixture is partitioned between ethyl acetate (250 mL) and 55% w/v potassium carbonate. The organic phase is washed with water (200 mL), dried over magnesium sulphate, filtered and concentrated in vacuo. The residue is recrystallised from ethyl acetate/cyclohexane to give methyl (RS)-2-[2-hydroxy-4-(3-thienylmethoxy)phenyl]-4,5-dihydrooxazole-4-carboxylate (1.9 g) in the form of an off white solid.

A mixture of 4-(3-thienylmethoxy)-2-(2-trimethylsilylethoxymethoxy)benzoic acid (6 g), (RS) serine methyl ester hydrochloride (2.7 g), 1-hydroxybenzotriazole (2.6 g), triethylamine (2.4 mL), 1-(3-dimethylaminopropyl)-3-ethyl carbodiimide hydrochloride (3.6 g) and DMF (100 mL) is stirred at ambient temperature for 16 hours. The reaction is concentrated in vacuo and the residue partitioned between ethyl acetate (150 mL) and 1N HCl (100 mL). The organic phase is washed with water (2×100 mL) then dried over magnesium sulphate, filtered and concentrated in vacuo. The residue is purified by flash chromatography on silica eluting initially with a mixture of ethyl acetate and cyclohexane (3:7 v/v) then with a mixture of ethyl acetate and cyclohexane (1:1 v/v). Fractions homogeneous in the required product are combined and evaporated to give methyl (RS)-3-hydroxy-2-[4-(3-thienylmethoxy)-2-(2-trimethylsilylethoxymethoxy)benzoyl]aminopropionate (6.5 g) as a colourless oil.

Reference Example 55

Methyl 2-[2-hydroxy-4-(3-thienylmethoxy)phenyl]oxazole-4-carboxylate (400 mg) is added portionwise to a stirred suspension of sodium hydride (100 mg, 60% dispersion in mineral oil) in dry DMF (30 mL). After stirring at 60° C. for 15 minutes, ethyl (R,S)-4-chloro-4-(2-methylphenyl) butanoate (0.6 g) is added in one portion and the reaction stirred for 2 hours at 90° C. The reaction is concentrated in vacuo and the residue partitioned between ethyl acetate (100 mL) and water (100 mL). The organic phase is dried over magnesium sulphate, filtered and concentrated in vacuo. The residue is purified by flash chromatography on silica eluting with a mixture of ethyl acetate and pentane (1:4 v/v). Fractions homogeneous in the required product are combined and evaporated to give ethyl (RS)-4-[2-(4-methoxycarbonyloxazol-2-yl)-5-(3-thienylmethoxy) phenoxy]-4-(2-methylphenyl)butanoate (300 mg) as an yellow oil.

A mixture of methyl 2-[2-hydroxy-4-(3-thienylmethoxy) phenyl]-4,5-dihydrooxazole-4-carboxylate (1 g) and (2,3-dichloro-5,6-dicyanobenzoquinone (0.8 g) in toluene (100 mL) is stirred at reflux for 2 hours. The reaction is concentrated in vacuo and the residue passed through a pad of silica eluting with 20% ethyl acetate in cyclohexane. The eluant is concentrated in vacuo and the residue partitioned between ethyl acetate (100 mL) and 1N HCl (50 mL). The organic phase is washed with water (20 mL), dried over magnesium sulphate and concentrated in vacuo to give methyl 2-[2-hydroxy-4-(3-thienylmethoxy)phenyl]oxazole-4-carboxylate (400 mg).

Reference Example 56

2-Hydroxy-4-(3-thienylmethoxy)benzonitrile (0.5 g) is added portionwise to a stirred suspension of sodium hydride (90 mg, 60% dispersion in mineral oil) in dry DMF (100 mL). After stirring at ambient temperature for 30 minutes, ethyl (RS)-4-chloro-4-(2-chloro-6-fluorophenyl)butanoate (0.62 g) is added in one portion and the reaction stirred for 48 hours at 90° C. The reaction mixture is concentrated in vacuo and the residue partitioned between ethyl acetate (100 mL) and water (100 mL). The organic phase is dried over magnesium sulphate, filtered and concentrated in vacuo. The residue is purified by flash chromatography on silica eluting with a mixture of ethyl acetate and pentane (1:2 v/v). Fractions homogeneous in the required product are combined and evaporated to give ethyl (RS)-4-(2-chloro-6-fluorophenyl)-4-(2-cyano-5-(3-thienylmethoxy)phenoxy) butanoate (360 mg) as an orange oil.

A solution of 2-chloro-6-fluorobenzaldehyde (15 g) in dichloromethane (20 mL) is added dropwise to a stirred 1M solution of titanium (IV) chloride in dichloromethane (95 mL) at 0° C. under nitrogen. The mixture is stirred for 5 minutes and [(1-ethoxycyclopropyloxy)trimethyl]silane (21.1 mL) is added dropwise maintaining the temperature at 0–5° C. The mixture is stirred for 16 hours at ambient temperature then quenched with water (200 mL). The mixture is extracted three times with dichloromethane (100 mL) and the combined organic extracts are washed with brine (50 mL), dried over magnesium sulphate and evaporated to give ethyl (RS)-4-chloro-4-(2-chloro-6-fluorophenyl)butanoate (24.3 g) as a yellow oil.

Reference Example 57

3-(3-Fluoro-4-nitrophenoxymethyl)pyridine (1.53 g) is added to a stirred suspension of sodium hydride (0.48 g, 60% dispersion in mineral oil) in THF (50 mL) at ambient temperature. A solution of tert-butyl (R)-4-hydroxy-4-(2-methylphenyl)butanoate (3.08 g) in THF (30 mL) is added dropwise to the mixture over 2 hours. The reaction mixture is concentrated under reduced pressure and the residue partitioned between water (100 mL) and ethyl acetate (100 mL). The aqueous layer is extracted three times with ethyl acetate (100 mL) and the combined organic phases were dried over magnesium sulphate, filtered and concentrated in vacuo. The residue is purified by flash chromatography on silica eluting with ethyl acetate. Fractions homogeneous in the required product are combined and evaporated to give tert-butyl (R)-4-(2-methylphenyl)-4-(2-nitro-5-(3-pyridylmethoxy)phenoxy)butanoate (0.85 g) as a yellow gum.

3-Fluoro-4-nitrophenol (7.5 g) is added to a stirred suspension of sodium hydride (2.2 g, 60% dispersion in mineral oil) in DMF (50 mL). The mixture is stirred at ambient temperature for 30 minutes. To this mixture is added a solution prepared by the addition of sodium hydride (2.2 g, 60% dispersion in mineral oil) to a stirred suspension of 3-chloromethylpyridine hydrochloride (8.2 g) in DMF (50 mL). The resulting mixture is stirred at 90° C. for 16 hours then cooled to ambient temperature. The reaction mixture is concentrated in vacuo and the residue partitioned between dichloromethane (100 mL) and water (100 mL). The aqueous phase is extracted four times with dichloromethane (100 mL). The combined organic phases are washed with brine (100 mL), dried over magnesium sulphate, filtered and concentrated in vacuo to give an orange solid. Recrystallisation from ethyl acetate gives 3-(3-fluoro-4-nitrophenoxymethyl)pyridine (4.6 g) as pale orange/brown cystals.

Reference Example 58

2-Hydroxy-4-(3-thienylmethoxy)benzonitrile (1.5 g) is added portionwise to a stirred suspension of sodium hydride (440 mg, 60% dispersion in mineral oil) in dry DMF(50 mL). After stirring at ambient temperature for 30 minutes, ethyl (RS)-4-chloro-4-(2,5-dimethylphenyl)butanoate (2.5 g) is added in one portion and the reaction stirred for 48 hours at 90° C. The reaction is concentrated in vacuo and the residue partitioned between ethyl acetate (50 mL) and water (50 mL). The aqueous layer is extracted twice with ethyl acetate (50 mL). The combined organic phases are dried over magnesium sulphate, filtered and concentrated in vacuo. The residue is purified by flash chromatography on silica eluting with a mixture of ethyl acetate and pentane (1:2 v/v). Fractions homogeneous in the required product are combined and evaporated to give ethyl (RS)-4-(2-cyano-5-(3-thienylmethoxy)phenoxy)-4-(2,5-dimethylphenyl) butanoate (500 mg) as a pale brown oil.

A solution of 2,5-dimethylbenzaldehyde (10 g) in dichloromethane (20 mL) is added dropwise to a stirred 1M solution of titanium (IV) chloride in dichloromethane (75 mL) at 0° C. under nitrogen. The mixture is stirred for 5 minutes and [(1-ethoxycyclopropyloxy)trimethyl]silane (16.6 mL) is added dropwise maintaining the temperature at 0–5° C. The mixture is stirred for 16 hours at ambient temperature then quenched with water (200 mL). The mixture is extracted three times with dichloromethane (100 mL) and the combined organic extracts are washed with brine (50 mL), dried over magnesium sulphate and evaporated to give ethyl (RS)-4-chloro-4-(2,5-dimethylphenyl) butanoate (17.3 g) as a yellow oil.

Reference Example 59

A solution of ethyl (RS)-4-(benzo[1,3]dioxol-4-yl)-4-hydroxybutanoate (2.52 g) in ethanol (56 mL) is treated with 1 N sodium hydroxide solution (10 mL). The reaction mixture is stirred at room temperature for 4 hours, evaporated and the residue azeotroped with toluene to give sodium (RS)-(benzo[1,3]dioxol-4-yl)-4-hydroxybutanoate (2.22 g) as a brown gum.

A mixture of 2,3-methylenedioxybenzaldehyde (1.5 g) and [1-ethoxycyclopropyl)oxy]trimethylsilane (2.7 g) in dry dichloromethane (15 mL) is added dropwise to a stirred suspension of zinc iodide (10 mg) in dry dichloromethane (20 mL) under nitrogen. The temperature of the reaction mixture reaches 25–35° C. The reaction flask is wrapped in aluminium foil and stirring is continued for 3 hours. The reaction mixture is treated with dry pyridine (20 drops) and stirring continued for 15 minutes. The reaction mixture is evaporated, washed twice with water (50 mL), twice with brine (50 mL), dried over magnesium sulphate and evaporated to give ethyl (RS)-4-(benzo[1,3]dioxol-4-yl)-4-hydroxybutanoate (6.01 g) as a yellow oil.

Reference Example 60

A solution of ethyl (RS)-4-(2,3-dimethylphenyl)-4-hydroxybutanoate (3.66 g) in ethanol (100 mL) is treated with 1 N sodium hydroxide solution (15.5 mL). The reaction mixture is stirred at room temperature for 18 hours, evaporated and the residue azeotroped with toluene to give sodium (RS)-4-(2,3-dimethylphenyl)-4-hydroxy-butanoate (3.2 g) as a brown solid.

A mixture of 2,3-dimethylbenzaldehyde (2 g) and (1-ethoxycyclopropyl)oxy]trimethylsilane (3.6 mL) in dry dichloromethane (20 mL) is added dropwise to a stirred suspension of zinc iodide (<100 mg) in dry dichloromethane (25 mL) under nitrogen. The reaction flask is wrapped in aluminium foil and stirring is continued for 3 hours. The reaction mixture is treated with dry pyridine (10 mL) and stirring continued for 15 minutes. The reaction mixture is washed three times with water (50 mL), twice with brine (50 mL), dried over magnesium sulphate and evaporated to give ethyl (RS)-4-(2,3-dimethylphenyl)-4-hydroxybutanoate (3.6 g) as a yellow oil.

Reference Example 61

Sodium (RS)-4-hydroxy-4-(2-methyl-5-(2-(trimethylsilyl)ethoxymethoxyphenyl)butanoate (1.81 g) is added to a stirred suspension of sodium hydride (0.6 g, 60% dispersion in mineral oil) in tetrahydrofuran (50 mL). The mixture is stirred at room temperature for 5 minutes then at 50° C. for 1.5 hours when 2-fluoro-4-(3-pyridylmethoxy) benzonitrile (1.07 g) is added in one portion. The reaction mixture is heated at reflux for 18 hours and evaporated. The residue is dissolved in water, the solution acidified to pH 1 with 1 N hydrochloric acid and the mixture extracted with ethyl acetate (200 mL). The organic phase is washed with water (200 mL), brine (200 mL), dried over magnesium sulphate and evaporated to give (RS)-4-[2-cyano-5-(3-pyridylmethoxy)-phenoxy]-4-(2-methyl-5-(2-(trimethylsilyl)ethoxymethoxy)phenyl)butanoic acid (1.86 g) as a cream solid.

A solution of ethyl (RS)-4-hydroxy-4-(2-methyl-5-(2-(trimethylsilyl)ethoxymethoxyphenyl)butanoate (3.68 g) in ethanol (50 mL) is treated with 1 N sodium hydroxide solution (10 mL). The reaction mixture is stirred at room temperature for 4.5 hours, evaporated and the residue azeotroped with toluene to give sodium (RS)-4-hydroxy-4-(2-methyl-5-(2-(trimethylsilyl)ethoxymethoxyphenyl) butanoate (3.24 g) as a yellow gum.

A mixture of 2-methyl-5-(2-(trimethylsilyl) ethoxymethoxy)benzaldehyde (3.44 g) and [1-ethoxycyclopropyl)oxy]trimethylsilane (2.7 g) in dry dichloromethane (15 mL) is added dropwise to a stirred suspension of zinc iodide (10 mg) in dry dichloromethane (25 mL) under nitrogen. The temperature of the reaction mixture reaches 25–35° C. The reaction flask is wrapped in aluminum foil and stirring is continued for 3 hours. The reaction mixture is treated with dry pyridine (20 drops) and stirring continued for 15 minutes. The reaction mixture is evaporated, washed twice with water (100 mL), brine (100 mL), dried over magnesium sulphate and evaporated to give ethyl (RS)-4-hydroxy-4-(2-methyl-5-(2-(trimethylsilyl) ethoxymethoxyphenyl)butanoate (8.25 g) as a light-brown oil.

5-hydroxy-2-methylbenzaldehyde (3.4 g) is added portionwise to a stirred suspension of sodium hydride (1.2 g, 60% dispersion in mineral oil). The reaction mixture is stirred at room temperature for 45 minutes, 2-(trimethylsilyl)ethoxymethyl chloride (5 g) is added slowly and stirring continued for a further 3 hours. The mixture is evaporated and the residue partitioned between ethyl acetate (50 mL) and water (150 mL). The organic phase is washed with brine (150 mL) dried over magnesium sulphate and evaporated to give 2-methyl-5-(2-(trimethylsilyl)ethoxymethoxy)benzaldehyde (6.87 g) as a red-brown oil.

A stirred mixture of 5-methoxy-2-methylbenzaldehyde (24.9 g) and pyridine hydrochloride (100 g) is heated at 170° C. for 7 hours. Water (250 mL) is added cautiously to the reaction mixture at 140° C. and the very dark mixture is extracted twice with chloroform (250 mL), filtration through hyflo removes a small amount of insoluble black solid and aids separation. The organic phase is washed with 1 N hydrochloric acid (250 mL), with water (250 mL), with brine (250 mL), dried over magnesium sulphate and evaporated. The residue is washed with pentane to give 5-hydroxy-2-methylbenzaldehyde (10.66 g) as a cream solid, m.p. 116–118° C.

A solution of 2-(5-methoxy-2-methylphenyl)-[1,3] dioxolane (18.25 g) in tetrahydrofuran (180 mL) is treated with 1 N hydrochloric acid (27 mL). The reaction mixture is heated at reflux for 2 hours, evaporated and the residue is partitioned between ethyl acetate (150 mL) and water (150 mL). The organic phase is washed with water (150 mL), with brine (150 mL), dried over magnesium sulphate and evaporated to give 5-methoxy-2-methylbenzaldehyde (12 g) as an orange oil.

A stirred solution of 2-(2-bromo-5-methoxyphenyl)-[1,3] dioxolane (25.92 g) in tetrahydrofuran (400 mL) at −70° C. is treated dropwise with a solution of n-butyl lithium in hexanes (48.0 mL, 2.5 M). After stirring for 10 minutes methyl iodide (21.29 g) is added dropwise whilst maintaining the temperature at −65° C. The reaction mixture is stirred at −65° C. for 1 hour, allowed to warm to room temperature and stirring is continued for a further hour. The reaction mixture is evaporated and the residue partitioned between ethyl acetate (50 mL) and water (50 mL). The organic phase is washed with brine (500 mL), dried over magnesium sulphate and evaporated to give 2-(5-methoxy-2-methylphenyl)-[1,3]dioxolane (18.25 g) as a yellow oil.

A mixture of 2-bromo-5-methoxy-benzaldehyde (45.25 g), ethylene glycol (52.22 g) and 4-toluenesulphonic acid (0.4 g) in toluene (400 mL) is heated at reflux for 5 hours using a Dean and Stark apparatus to remove water formed in the reaction. The reaction mixture is washed five times with water (500 mL) and evaporated giving 2-(2-bromo-5-methoxyphenyl)-[1,3]dioxolane (51.9 g) as a yellow liquid.

A stirred solution of 3-methoxybenzaldehyde (27.23 g) in dichloromethane (150 mL) at 0° C. is treated with a solution of bromine (32 g) in dry dichloromethane (50 mL) over 30 minutes. The reaction mixture is stirred at room temperature for 4 hours, combined with a previous preparation carried out on the same scale, and washed with saturated sodium metabisulphite solution (400 mL), with water (400 mL), brine (400 mL) and dried over magnesium sulphate. Evaporation and recrystallisation of the residue from petroleum ether (b.p. 40–60° C.) gives 2-bromo-5-methoxybenzaldehyde (45.25 g) as a white solid, m.p. 73–74° C.

Reference Example 62

A suspension of 6-(2-methylphenyl)tetrahydropyran-2-one (2.5 g) in a mixture of tetrahydrofuran (20 mL) and methanol (20 mL) is treated with 5 M sodium hydroxide solution under nitrogen. The reaction mixture is stirred at room temperature for 24 hours, diluted with water (100 mL) and extracted with ethyl acetate (100 mL). The aqueous phase is washed three times with ethyl acetate (50 mL) and evaporated in vacuo. The residue is azeotroped with toluene to give sodium (RS)-5-hydroxy-4-(2-methylphenyl) pentanoate (1.57 g) as a white solid.

To a stirred suspension of 5-oxo-5-(2-methylphenyl) pentanoic acid (10 g) in water (100 mL) is added potassium hydroxide pellets (6.35 g). The temperature of the mixture is maintained at 2–20° C. whilst sodium borohydride (1.47 g) is added over 15 minutes. The reaction mixture is left at room temperature for 18 hours when 1 N hydrochloric acid (100 mL) is cautiously added followed by water (50 mL) and ethyl acetate (100 mL). The organic phase is separated and the aqueous phase extracted twice with ethyl acetate (100 mL). The combined organic phases are washed with brine (100 mL), dried over magnesium sulphate and evaporated to give 6-(2-methylphenyl)-tetrahydropyran-2-one (5.27 g) as a yellow oil.

A stirred solution of glutaric anhydride (22.82 g) in dry tetrahydrofuran (300 mL) at −78° C. is treated with a solution of 2-methylphenyl magnesium chloride in tetrahydrofuran (200 mL, 0.1 M) over 45 minutes. The mixture is stirred at −78° C. for 2.5 hours and the grey suspension is poured into 1 N hydrochloric acid (300 mL). The mixture is extracted with ethyl acetate (300 mL). The organic phase is dried over magnesium sulphate and evaporated to give 5-oxo-5-(2-methylphenyl)pentanoic acid (36.74 g) as a red-brown oil.

Reference Example 63

2-Fluoro-6-hydroxy-4-(3-thienylmethoxy)benzonitrile (200 mg) is added to a stirred suspension of sodium hydride (36 mg, 60% dispersion in mineral oil) in dry DMF (10 mL). After stirring at ambient temperature for 30 minutes, a solution of ethyl (R,S)-4-chloro-4-(2-methylphenyl) butanoate (220 mg) in DMF (5 mL) is added in one portion and the reaction stirred for 3 hours at ambient temperature. The reaction mixture is concentrated in vacuo and the residue partitioned between diethyl ether (20 mL) and water (20 mL). The aqueous layer is extracted four times with diethyl ether (20 mL). The combined organic phases are washed with brine (20 mL), dried over magnesium sulphate, filtered and concentrated in vacuo. The residue is purified by flash chromatography on silica eluting with a mixture of ethyl acetate and pentane (1:2 v/v). Fractions homogeneous in the required product are combined and evaporated to give ethyl (RS)-4-(2-cyano-3-fluoro-5-(3-thienylmethoxy) phenoxy)-4-(2-methylphenyl) butanoate (200 mg) as a pale yellow oil.

A mixture of 2-fluoro-6-hydroxy-4-(3-thienylmethoxy) benzaldehyde (1 g), nitroethane (0.6 g) sodium acetate (0.66 g) and glacial acetic acid (1 mL) is heated at reflux for 2 hours. The reaction mixture is cooled to ambient temperature, water (50 mL) is added and the mixture is extracted three times with ethyl acetate (50 mL). The combined organic phases are washed with saturated brine (50 mL), dried over magnesium sulphate, filtered and concentrated under reduced pressure to leave a brown oil. The residue is purified by flash chromatography on silica eluting with a mixture of ethyl acetate and pentane (1:2 v/v). Fractions homogeneous in the required product are combined and evaporated to give 2-fluoro-6-hydroxy-4-(3-thienylmethoxy)benzonitrile (250 mg), as a yellow solid.

Sodium hydride (0.52 g, 60% dispersion in mineral oil) is added portionwise over 30 minutes to a solution of 2,4-dihydroxy-6-fluorobenzaldehyde (2 g) in DMF (50 mL) at 0° C. The mixture is stirred at 0° C. for 30 minutes then a solution of 3-chloromethylthiophene (1.72 g) in DMF (50 mL) is added and the mixtured stirred at 60° C. for 16 hours. The reaction is concentrated in vacuo and the residue partitioned between diethyl ether (50 mL) and water (50 mL). The aqueous phase is extracted four times with diethyl ether (50 mL) and the combined organic phases washed with brine (50 mL). The organic phase is dried over magnesium sulphate, filtered and concentrated in vacuo. The residue is purified by flash chromatography on silica eluting with a mixture of ethyl acetate and pentane (1:4 v/v). Fractions homogeneous in the required product are combined and evaporated to give a pale yellow solid which is triturated with diisopropyl ether to give 6-fluoro-2-hydroxy-4-(3-thienylmethoxy)benzaldehyde (1.1 g) as a yellow solid.

Dimethylformamide (DMF) (12.7 g) is added to vigorously stirred phosphorous oxychloride (14.4 g) at 0° C. The reaction mixture is stirred at this temperature for 30 minutes, then 3,5-dihydroxyfluorobenzene (6 g) is added. The sticky red syrup is allowed to warm to room temperature and stirred for 2 hours, then left to stand for 14 hours. Water (100 mL) is added and the mixture extracted three times with ethyl acetate (100 mL). The combined organic phases are washed with brine (100 mL), dried over magnesium sulphate and evaporated. The residue is purified by flash chromatography on silica eluting with a mixture of ethyl acetate and pentane (1:2 v/v). Fractions homogeneous in the required product are combined and evaporated to give an orange solid which is triturated with ethyl acetate to give 2,4-dihydroxy-6-fluorobenzaldehyde (2 g) as a yellow solid.

Reference Example 64

To a stirred suspension of sodium hydride (0.24 g of a 60% w/w dispersion in mineral oil) in toluene (30 mL) is added a solution of (RS)-2-(1-(2-methylphenyl)ethoxy)-4-(3-thienylmethoxy)acetophenone (1.42 g) and diethyl oxalate (2.45 g) in toluene (20 mL) dropwise. The reaction is heated at reflux for two hours and concentrated under reduced pressure to leave ethyl (RS)-2,4-dioxo-4-[2-(1-(2-methylphenyl)ethoxy)-4-(3-thienylmethoxy)phenyl]butanoate as a brown oil.

To a stirred, cooled (0° C.) solution of triphenylphosphine (8.4 g) in dry tetrahydrofuran (60 mL) is added diisopropyl azodicarboxylate (6.5 mL) dropwise. When a cream suspension is formed, a solution of 2-hydroxy-4-(3-thienylmethoxy)acetophenone (3.5 g) and (RS)-1-(2-methylphenyl)ethanol (2.2 g) in tetrahydrofuran (75 mL) is added dropwise and the reaction stirred at ambient temperature for 48 hours. The reaction is partitioned between ethyl acetate and 1 N aqueous sodium hydroxide. The organic layer is washed with water, dried over magnesium sulphate and concentrated under reduced pressure. The residue is chromatographed on silica gel eluting with dichloromethane to give (RS)-2-(1-(2-methylphenyl)ethoxy)-4-(3-thienylmethoxy)acetophenone (2.61 g) as a colourless oil.

Reference Example 65

A solution of tert-butyl (R)-4-(2-acetyl-5-(3-pyridylmethoxy)phenoxy)-4-(2-methylphenyl)butanoate (1.46 g) and diethyl oxalate (1.46 g) in toluene (20 mL) is added dropwise to a stirred suspension of sodium hydride (0.15 g, 60% dispersion in mineral oil) in toluene (50 mL) at ambient temperature. The mixture is stirred at reflux for three hours, cooled to ambient temperature and concentrated in vacuo. The residue is taken up in ethanol (100 mL), treated with hydrazine hydrate (0.16 mL) and acidified to pH 5 by the addition of glacial acetic acid. The mixture is refluxed for 3 hours, cooled to ambient temperature then concentrated in vacuo. The residue is partitioned between ethyl acetate (100 mL) and water (100 mL) and the organic phase washed with water (100 mL), dried over magnesium sulphate and passed through a pad of silica eluting with ethyl acetate. The fractions containing product are concentrated in vacuo to give t-butyl (R)-4-[2-(5-ethoxycarbonylpyrazol-3-yl)-5-(3-pyridylmethoxy)phenoxy]-4-(2-methylphenyl)butanoate (1.7 g).

Diisopropyl azodicarboxylate (8 g) is added portionwise to a stirred solution of triphenylphosphine (10.5 g) in THF (100 mL) at 0° C. under nitrogen. Stirring is continued at 0° C. for 15 minutes. A solution of 2-acetyl-5-(3-pyridylmethoxy)phenol (4.5 g) and tert-butyl (S)-4-hydroxy-4-(2-methylphenyl)butanoate (4.9 g) in THF (100 mL) is added at such a rate that the temperature does not exceed 5° C. The reaction is allowed to warm to ambient temperature stirred for 16 hours, then concentrated in vacuo. The residue is partitioned between ethyl acetate (200 mL) and water (200 mL) and the organic phase dried over magnesium sulphate, filtered and concentrated in vacuo.The residue is purified by flash chromatography on silica eluting initially with a mixture of ethyl acetate and cyclohexane (1:1 v/v) then with ethyl acetate. Fractions homogeneous in the required product are combined and evaporated to give t-butyl (R)-4-(2-acetyl-5-(3-pyridylmethoxy)phenoxy)-4-(2-methylphenyl)butanoate (2 g).

Reference Example 66

A solution of ethyl bromodifluoroacetate (5.6 g) and 2-methylbenzaldehyde (3 g) in THF (25 mL) is added dropwise to a refluxing suspension of activated zinc dust (2.1 g) in THF (25 mL) and refluxing continued for a further 4 hours. The reaction is allowed to cool to ambient temperature, filtered through hyflo and concentrated in vacuo to give a yellow solid. The solid is taken up in ethyl acetate (50 mL) and washed with brine which leads to the formation of a white precipitate which is filtered off then partitioned between ethyl acetate (50 mL) and 1 N HCl (50 mL). The organic phase is washed with water, dried over magnesium sulphate, filtered and concentrated in vacuo to give (RS)-2,2-difluoro-3-hydroxy-3-(2-methylphenyl)propanoic acid as a yellow solid (2.4 g)

Reference Example 67

A solution of ethyl (RS)-4-[2-acetyl-5-(3-thienylmethoxy)phenoxy]-4-(2-methylphenyl)butanoate (2.91 g) and diethyl oxalate (2.82 g) in dry toluene are stirred at room temperature whilst adding sodium hydride (0.28 g, 60% dispersion in mineral oil) portionwise. The reaction mixture is heated at reflux for 5 hours then left at room temperature for 18 hours. Evaporation gives an orange oil which is dissolved in ethanol (100 mL) and treated with glacial acetic acid (1.5 mL). Hydroxylamine hydrochloride (0.49 g) is added and the mixture heated at reflux for 5 hours. The reaction mixture is partitioned between ethyl acetate (100 mL) and water (100 mL). The aqueous phase is extracted with three times ethyl acetate (50 mL). The combined organic phases are washed with brine (50 mL), with water (50 mL), dried over magnesium sulphate and evaporated. The residue is purified by flash chromatography on silica eluting with a mixture of ethyl acetate and pentane (1:1 v/v). Fractions homogeneous in the required product are combined and evaporated to give ethyl (RS)-4-[2-(5-ethoxycarbonylisoxazol-3-yl)-5-(3-thienylmethoxy)phenoxy]-4-(2-methylphenyl)butanoate (2.56 g) as an orange oil.

Reference Example 68

A solution of diisopropyl azodicarboxylate (40 g) in anhydrous THF (20 mL) is added dropwise with stirring under ice cooling to a solution of triphenylphosphine (52 g) in anhydrous THF (200 mL). The resulting thick white suspension is treated dropwise over about 1 h under ice cooling with a mixture of 2-acetyl-5-(3-pyridylmethoxy)phenol (23 g) and tert-butyl (R)-4-hydroxy-4-(2-methyl)butanoate (30 g) in anhydrous THF (100 mL). After stirring under ice cooling for 2 hours and then standing at room temperature overnight the mixture is partitioned between ethyl acetate (500 mL) and water (500 mL). The layers are separated and the organic layer washed with water, dried, and evaporated. The residue is partially purified by flash chromatography on silica eluting with a mixture of ethyl acetate and cyclohexane (60 to 100%). Fractions containing the required product are combined and evaporated to give impure tert-butyl (R)-4-[2-(acetyl-5-(3-pyridylmethoxy)phenoxy]-4-methylphenyl)butanoate (72 g). This material is mixed with dimethyl oxalate (17.7 g) in anhydrous toluene (200 mL) and heated at reflux under a Dean-Stark water separator. When no more water separates the mixture is allowed to cool and sodium hydride (4.8 g, 60% dispersion) is added. The mixture is gradually returned to reflux; when a vigorous reaction sets in the heat is removed. When this reaction subsides the mixture is stirred at reflux for a further 15 minutes and then evaporated to dryness. The residue is dissolved in methanol (200 mL), treated with hydrazine hydrate (5 g) and taken to pH 6 with glacial acetic acid (about 7 g). The mixture is refluxed for 1 hour, further hydrazine hydrate (2 g) is added, and reflux continued for another 1 hour. The residue obtained after evaporation is partitioned between ethyl acetate (500 mL) and water (500 mL). The layers are separated and the organic layer washed with water, dried, and evaporated. The residue is purified by flash chromatography on silica eluting with a mixture of ethyl acetate and cyclohexane (3:2 v/v. Fractions homogeneous in the required product are combined and evaporated to give tert-Butyl (R)-4-[2-(5-methoxycarbonylpyrazol-3-yl)-5-(3-pyridylmethoxy)-phenoxy]-4-(2-methylphenyl)butanoate (20.4 g).

Reference Example 69

(R)-t-butyl 4-[2-(5-methoxycarbonyl-3-pyrazolyl)-5-(3-pyridylmethoxy)phenoxyl-4-(2-methylphenyl)butanoate (2 g) is dissolved in trifluoroacetic acid (10 mL) and allowed to stand at room temperature for 2 minutes. The solution is quenched with saturated aqueous sodium hydrogen carbonate solution (100 mL) and the product extracted into ethyl acetate (100 mL). This solution is washed with water, dried, and evaporated. The residue is purified by flash chromatography eluting with 60% ethyl acetate in cyclohexane to remove trace high running impurities, and then 20% methanol in dichloromethane to obtain the required product. Crystallisation from ethyl acetate/cyclohexane mixture gives (R)-4-[2-(5-methoxycarbonyl-3-pyrazolyl)-5-(3-pyridylmethoxy)phenoxy]-4-(2-methylphenyl)butanoic acid (0.4 g) of a white solid, mp 155–6° C.

Reference Example 70

2-Hydroxy-4-(3-thienylmethoxy)benzonitrile (2.5 g) is added portionwise to a stirred suspension of sodium hydride (0.44 g, 60% dispersion in mineral oil) in dry dimethyl formamide (30 mL). After stirring at ambient temperature for 30 minutes, ethyl (RS)-4-chloro-4-(2-cyanophenyl)butanoate (2.87 g) is added in one portion and the reaction stirred for 16 hours at 100° C. The reaction is concentrated in vacuo and the residue partitioned between ethyl acetate (100 mL) and water (100 mL). The organic phase is dried over magnesium sulphate, filtered and concentrated in vacuo. The residual oil is purified by flash chromatography on silica eluting with a mixture of ethyl acetate and pentane (1:2 v/v). Fractions homogeneous in the required product are combined and evaporated to give ethyl (RS)-4-(2-cyanophenyl)-4-[2-cyano-5-(3-thienylmethoxy)phenoxy]butanoate (250 mg) as an orange oil.

A solution of 2-cyanobenzaldehyde (5 g) in dichloromethane (10 mL) is added dropwise to a stirred 1M solution of titanium (IV) chloride in dichloromethane (38 mL) at 0° C. under nitrogen. The mixture is stirred for 5 minutes and [(1-ethoxycyclopropyloxy)trimethyl]silane (8.42 mL) is added dropwise maintaining the temperature at 0–5° C. The mixture is stirred for 16 hours at ambient temperature then quenched with water (200 mL). The mixture is extracted three times with dichloromethane (100 mL) and the combined organic extracts are washed with brine (100 mL), dried over magnesium sulphate and evaporated to give ethyl (RS)-4-chloro-4-(2-cyanophenyl)butanoate (5.5 g) as a yellow oil.

Reference Example 71

Diisopropyl azodicarboxylate (1.19 g) is added to a stirred solution of triphenylphosphine (1.55 g) in tetrahydrofuran (30 mL) at 0° C. under nitrogen and stirring is continued at 0° C. for 30 minutes. A solution of isothiazol-4-ylmethanol (0.34 g) and 2-fluoro-4-hydroxybenzonitrile (0.4 g) in tetrahydrofuran (30 mL) is added at such a rate that the temperature did not exceed 0° C. After the addition is complete stirring is continued at 0° C. for 30 minutes then at ambient temperature for 24 hours. The reaction mixture is concentrated in vacuo and the residue is partitioned between ethyl acetate (50 mL) and water (50 mL). The organic phase is washed with water (50 mL), with brine (50 mL), dried over magnesium sulphate and evaporated. The residue is purified by flash chromatography on silica eluting with dichloromethane. Fractions homogeneous in the required product are combined and evaporated to give 2-fluoro-4-(isothiazol-4-ylmethoxy)benzonitrile (0.24 g), m.p. 102–105° C.

Isothiazole-4-carboxylic acid (0.65 g) is added portionwise to a stirred mixture of lithium aluminum hydride (0.19 g) in tetrahydrofuran (50 mL) at ambient temperature under nitrogen the reaction mixture is heated at reflux for 4 hours then cooled to 0° C. Sodium hydroxide solution (3% w/v) is added dropwise and the mixture stirred at 0° C. for 1 hour then filtered through hyflo. The filtrate is evaporated and azeotroped with toluene to give isothiazol-4-ylmethanol (0.35 g).

Reference Example 72

A stirred solution of 1-(3-benzyloxyphenyl)-2-phenylethanone in tetrahydrofuran (30 mL) is treated with a solution of lithium diisopropylamine in tetrahydrofuran (5.5 mL, 2 M) at −35° C. under nitrogen. The resulting clear yellow solution is cooled to −70° C. and treated with a solution of bromine (1.6 g) in dichloromethane (5 mL). Stirring is continued at −70° C. and treated with a solution of bromine (1.6 g) in dichloromethane (5 mL). Stirring is continued at −70° C. for 5 minutes. Water (30 mL) is added and the reaction mixture allowed to warm to room temperature. The reaction mixture is extracted twice with ether (50 mL), the combined extracts are washed with brine (40 mL), dried over magnesium sulphate and evaporated to give (RS)-1-(3-benzyloxyphenyl)-2-bromo-2-phenylethanone (3.92 g) in the form of a yellow oil.

Wilkinson's catalyst (18 mg) is added to a stirred solution of ethyl 3-(2,4-dibenzyloxy)phenyl propen-2-oate (1.52 g) in toluene (10 mL) at ambient temperature under nitrogen. Neat triethylsilane (1.6 mL) is added and the reaction stirred at ambient temperature for 16 hours. The reaction is concentrated in vacuo to give a dark brown oil which is purified by flash chromatography on silica eluting with a mixture of ethyl acetate and petrol ether (5:1 v/v ). Fractions homogeneous in the required product are combined and evaporated to give ethyl 3-(2,4-dibenzyloxy)phenyl propanoate (1.48 g) as a colourless oil.

Sodium hydride (1.32 g, 60% dispersion in mineral oil) is suspended in THF (75 mL) and cooled to −10° C. Neat triethylphosphonoacetate (7.4 g) is added dropwise and stirred at −10° C. for 15 minutes. A solution of 2,4-dibenzyloxybenzaldehyde (10 g) is added dropwise to the reaction. A thick viscous oil is formed and the reaction is left at 0° C. for one hour then quenched with saturated ammonium chloride solution (100 mL) and extracted with ethyl acetate (3×100 mL). The ethyl acetate extracts are combined, washed with water (2×100 mL), dried over magnesium sulphate, filtered and concentrated in vacuo to give ethyl 3-(2,4-dibenzyloxy)phenylpropen-2-oate (12 g) as a yellow oil.

Reference Example 74

A mixture of 2,4-dibenzyloxyphenol (3.1 g) and sodium hydride (0.44 g, 60% dispersion in mineral oil) in THF (75 mL) is refluxed for 30 minutes then refluxing is allowed to abate. Neat ethyl bromoacetate (1.8 g) is added and refluxing continued for 1 hour. The reaction is concentrated in vacuo and the residue partitioned between ethyl acetate (100 mL) and water (100 mL). The organic phase is washed with water (100 mL), dried o ver magnesium sulphate, filtered and concentrated in vacuo to give a light brown oil. Flash chromatography of the residue eluting with dichloromethane affords ethyl 2,4-dibenzyloxyphenoxyacetate (3.2 g) after trituration with pentane.

Reference Example 75

A stirred solution of methyl 4-[2-hydroxy-4-(thiophen-3-ylmethoxy)phenyl]-4-oxobutanoate (1.6 g) in DMF (20 mL) is treated with 60% sodium hydride (0.2 g) and stirred at 25° for 0.3 hours. The mixture is treated with ethyl (R,S)-4-chloro-4-(2-methylphenyl)butanoate (1.2 g) and heated at 80° C. for 6 hours. The solution is evaporated (hivac). The residue is dissolved in ethyl acetate, washed with water, dried and evaporated. The residue is purified by flash chromatography on silica, eluting with ethyl acetate/pentaned: 1/1 to give (R,S)-4-[2-(3-methoxycarbonylpropionyl)-5-(thiophen-3-ylmethoxy) phenoxy]-4-(2-methylphenyl)butyric acid, ethyl ester (1.9 g), an orange oil.

A stirred solution of 4-(2,4-dihydroxyphenyl)-4-oxobutyric acid, methyl ester 6.76 g) in methyl ethyl ketone (150 mL) is treated with potassium carbonate (4.17 g), potassium iodide (5 g) tetrabutyl ammonium chloride (1 g) and 3-chloromethylthiophene (4 g), and refluxed for 24 hours. The reaction mixture is filtered, the filtrate is evaporated. The residue is dissolved in ethyl acetate, washed with water, dried, and evaporated. The residue is recrystallised from ethyl acetate/cyclohexane to give 4-(2-hydroxy-4-(thiophen-3-ylmethoxy)phenyl]-4-oxo-butyric acid, methyl ester (7.16 g), a pale cream solid, mp. 100–102° C.

Reference Example 76

A stirred solution of (R,S)-4-[2-(amino-hydroxyiminomethyl)-5-(thiophen-3-ylmethoxy)phenoxy]-4-(2-methylphenyl)butyric acid, ethyl ester (400 mg) in trimethyl orthoformate (8 mL) is refluxed for 2 hours. The solution is evaporated. The residue is purified by flash chromatography on silica, eluting with pentane/ether: 2/1 to give (R,S)-4-[2-(1,2,4-oxadiazol-3-yl)-5-(thiophen-3-ylmethoxy)phenoxy]-4-(2-methylphenyl)butyric acid, ethyl ester (74 mg).

A solution of ethyl (R,S)-4-[2-cyano-5-(thiophen-3-ylmethoxy)phenoxy]-4-(2-methylphenyl)butanoate (2.3 g) and hydroxylamine hydrochloride (0.4 g) in ethanol (80 mL) is treated with a solution of NaOH (0.23 g) in water (8 mL) and refluxed for 60 hours. The solution is evaporated. The residue is dissolved in ethyl acetate, washed with water, dried and evaporated. The residual yellow oil is purified by flash chromatography on silica, eluting with pentane/ethyl acetate: 3/1 to give ethyl (R,S)-4-[2-(amino-hydroxyiminomethyl)-5-(thiophen-3-ylmethoxy)phenoxy]-4-(2-methylphenyl)butanoate (0.63 g).

Reference Example 77

A stirred solution of ethyl (R,S)-4-[2-(2-thiocarbamoyl)-5-(thiophen-3-ylmethoxy)phenoxy]-4-(2-methylphenyl) butanoate (1.17 g) in ethanol (12 mL) and DMF (6 mL) is treated with 50% aq. chloroacetaldehyde (1.17 g) and refluxed for 24 hours. The solution is evaporated. The residue is partitioned between ethyl acetate and water. The organic layer is washed with water, dried and evaporated. The residual solid is purified by flash chromatography on silica eluting with ethyl acetate/pentane: 1/3, followed by trituration with ether to give (R,S)-4-[2-(thiazol-2-yl)-5-(thiophen-3-ylmethoxy)phenoxy]-4-(2-methylphenyl) butyric acid, ethyl ester, a colourless solid (1.02 g), m.p. 127–129° C.

A stirred solution of ethyl (R,S)-4-[2-(2-carbamoyl)-5-(thiophen-3-ylmethoxy)phenoxy]-4-(2-methylphenyl) butanoate (2.44 g) in THF (49 mL) is treated with Lawesson's reagent (1.08 g) and maintained at 25° C. for 24 hours. The solution is evaporated. The residual gum is purified by flash chromatography on silica, eluting with pentane/ethyl acetate: 2/1, followed by trituration with ether to give (R,S)-4-[2-(2-thiocarbamoyl)-5-(thiophen-3-ylmethoxy) phenoxy]-4-(2-methylphenyl)butyric acid, ethyl ester, a pale yellow solid (1.79 g), mp. 134–135° C.

Compounds of formula I and their pharmaceutically acceptable salts exhibit pharmacological activity and accordingly are of use for the preparation of pharmaceutical compositions for the treatment of humans and other animals.

Compounds of formula I exhibit useful pharmacological activity and accordingly are incorporated into pharmaceutical compositions and used in the treatment of patients suffering from certain medical disorders. More especially, they are endothelin inhibitors, in particular endothelin A inhibitors.

The present invention provides compounds of formula I, and compositions containing compounds of formula I, which are of use in a method for the treatment of a patient suffering from, or subject to, conditions which can be ameliorated by the administration of an inhibitor of endothelin. For example, compounds within the present invention are useful for the treatment of diseases and conditions characterized by, or having an etiology involving pathogenic endothelin levels. Examples of disease states and conditions which can be ameliorated by the administration of inhibitors of endothelin such as compounds of formula I include vascular ischaemia, for example cerebrovascular disease including cerebral ischaemia such as stroke and subarachnoid hemorrhage, coronary disorders such as myocardial infarction including acute myocardial infarction, coronary heart disease, angina including unstable and vasospastic angina, preeclampsia, essential and pulmonary hypertension and congestive heart failure, renal disorders such as acute renal insufficiency and chronic renal insufficiency, cyclosporin induced nephrotoxicity, erythropoetin induced renal complications and hypertension, gastrointestinal disorders such as ulceration and irritable bowel syndrome, poor peripheral skeletal muscle disorders such as peripheral vascular disease, intermittent claudication and critical limb ischaemia, glaucoma, atherosclerosis and related diseases, hypertension, asthma, migraine, endotoxin shock, Raynauds disease, benign prostatic hyperplasia, bone loss such as osteoporosis and restenosis after angioplasty. Compounds of the present invention are also useful as a therapy for promoting wound healing.

According to a further feature of the invention there is provided a method for the treatment of a human or animal patient suffering from, or subject to, conditions which can be ameliorated by the administration of an inhibitor of endothelin, especially ETA, for example conditions as hereinbefore described, which comprises the administration to the patient of an effective amount of compound of formula I or a composition containing a compound of formula I. "Effective amount" is meant to describe an amount of compound of the present invention effective in inhibiting endothelin and thus producing the desired therapeutic effect.

The present invention also includes within its scope pharmaceutical formulations which comprise at least one of the compounds of formula I in association with a pharmaceutically acceptable carrier or coating.

In practice compounds of the present invention may generally be administered parenterally, rectally or orally. The compounds of the invention may also be administered topically to treat peripheral vascular diseases.

The products according to the invention may be presented in forms permitting administration by the most suitable route and the invention also relates to pharmaceutical compositions containing at least one product according to the invention which are suitable for use in human or veterinary medicine. These compositions may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs, creams, ointments or syrups, and can contain one or more agents chosen from the group comprising sweeteners, flavorings, colorings, or stabilizers in order to obtain pharmaceutically acceptable preparations.

The choice of vehicle and the content of active substance in the vehicle are generally determined in accordance with the solubility and chemical properties of the product, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation or microfiltration.

Suitable compositions containing the compounds of the invention may be prepared by conventional means. For example, compounds of the invention may be dissolved or suspended in a suitable carrier for use in a nebulizer or a suspension or solution aerosol, or may be absorbed or adsorbed onto a suitable solid carrier for use in a dry powder inhaler.

Solid compositions for rectal administration include suppositories formulated in accordance with known methods and containing at least one compound of formula I.

Compositions for topical administration include creams and ointments formulated in accordance with known methods, such as a topical carrier such as Plastibase® (mineral oil gelled with polyethylene) and containing at least one compound of formula I.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.01 to about 100 mg/kg, preferably about 0.02 to about 50 mg/kg, and more preferably about 0.1 to about 25 mg/kg body weight (or from about 1 to about 5000 mg, preferably from about 5 to about 2000 mg) in single of 2 to 4 divided daily doses. In each particular case, the doses will be determined in accordance with the factors distinctive to the subject to be treated, such as age, weight, general state of health and other characteristics which can influence the efficacy of the medicinal product.

The products according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. It goes without saying that, for other patients, it will be necessary to prescribe not more than one or two doses per day.

The compounds of the present invention can also be administered in combination with endothelin converting enzyme inhibitors, angiotensin II receptor antagonists, renin inhibitors, angiotensin converting enzyme inhibitors, α- and β-adrenoceptor agonists and antagonists, diuretics, potassium channel activators, calcium channel antagonists, nitrates, antiarrhythmic agents, positive inotropic agents, serotonin receptor agonists and antagonists, platelet activating factor antagonists, histamine receptor antagonists, proton pump inhibitors, antithrombotic and thrombolytic agents, lipid lowering agents, antibiotic agents and phosphodiesterase inhibitors. If formulated as a fixed dose, such combination products employ the compounds of the present invention within the dosage range described below and the other pharmaceutically active agent within its approved dosage range. The compounds of the present invention may also be formulated with or useful in conjunction with antifungal and immunosuppressive agents such as amphotericin B, cyclosporins and the like to counteract the hypertension and nephrotoxicity secondary to such compounds. The compounds of the present invention may also be used in conjunction with haemodialysis.

Compounds within the scope of the present invention exhibit marked pharmacological activities according to tests described in the literature which tests results are believed to correlate to pharmacological activity in humans and other mammals. The following pharmacological test results are typical characteristics of compounds of the present invention.

In Vitro Tests
A) Preparation of $ET_A$ Receptors

A10 cells are grown to confluence in Dulbecco's modified essential medium containing 10% foetal calf serum. Two days after the final medium change cells are harvested by scraping from the base of the flask and centrifuged at 1500 rpm for 10 minutes at 4° C. in an bench centrifuge. The resulting pellets are washed in 50 mM Hepes buffer pH 7.3 containing calcium chloride (1 mM) and magnesium chloride (5 mM) and resuspended at a density of 140,000 cells/mL in the same. Cell suspensions are then frozen using a mixture of methanol and solid carbon dioxide and stored at −20° C. until required. For use in the assay cells are diluted to the required density with Hepes buffer pH 7.3.

B) Preparation of $ET_B$ Receptors

Rats are killed by cervical dislocation and the cerebellum tissue is removed into ice cold Tris buffer pH 7.4 containing sucrose (0.25 M), ethylenediaminetetracetic acid (3 mM), and a cocktail of protease inhibitors. After homogenizing using a glass/teflon manual homogenizer, the samples are centrifuged at 4° C. for 17 minutes at 1000 g, and the resulting supernatants are retained. This material is centrifuged at 4000 g for 35 minutes at 4° C. and the pellets are resuspended in 50 mM Tris buffer pH 7.4, and the protein concentration is measured. Aliquots of 100 mL are frozen in a mixture of methanol and solid carbon dioxide and stored at −20° C. until required. For use in the assay samples are diluted to the required concentration with Tris buffer pH 7.4 containing 0.1% bovine serum albumin.

C) Assay Methodology

Assays are performed using Millipore 96 well filtration plates with 0.22 μm filters in a final volume of 250 mL. Mixtures consisting of test compound and [$^{125}$I]-ET-1 (20 pM) in Tris buffer pH 7.4 containing 0.1% bovine serum albumin are treated with either A10 cells or cerebellum protein. Total and non-specific binding are measured in the absence and presence of unlabelled ET-1 (100 nM). Approximately 60,000 A10 cells are used per well or 5 μg of cerebellum protein. Plates are incubated for 2 hours at 37° C. before the reaction is terminated by vacuum filtration. Plates are washed twice with assay buffer at 4° C. and the filters are punched out for gamma counting.

Results

The $IC_{50}$ values (50% inhibition of ET-1 binding) for compounds of the invention in the antagonism of ET-1 at $ET_A$ and $ET_B$ receptors are from about $10^{-9}$ M to about $10^{-4}$ M.

In Vivo Tests

Compounds are evaluated in vivo after administration either intravenously or orally to pithed rats (prepared according to the method described by Gillespie, J. S. & Muir, T. C., (1967), Br. J. Pharmacol. Chemother., 30, 78–87). The degree of inhibition produced by the test compounds of the biphasic depressor and pressor responses to ET-1 given intravenously is measured.

What is claimed is:

1. A compound of formula I wherein
 $R^1$ is —CN;
 $R^2$ is aryl lower alkoxy or aryl lower alkylthio;
 $R^3$ is hydroxy, alkoxy, aryloxy, cycloalkyl(lower alkyl)oxy, cycloalkenyl(lower alkyl)oxy, aryl lower alkoxy, aryl lower alkylthio, or aralkynyl;
 $R^4$ is —Y—CH($R^{15}$)(alkyl or alkenyl)$R^{16}$;
 $R^5$ is alkyl, alkenyl or halo;
 $R^{15}$ is aryl;
 $R^{16}$ is carboxy;
 Y is oxygen or carbonyl; and
 m, n and p are independently zero or 1, and o is 1;
with the proviso that at least one of m and n is 1,
or a pharmaceutically acceptable salt, or prodrug thereof.

2. A compound of claim 1 wherein
 $R^2$ is aryl lower alkoxy;
 $R^4$ is —O—CH(aryl)(alkyl)$R^{16}$;
 $R^5$ is halo; and
 m, o and p are 1 and n is zero.

3. A compound of claim 1 wherein
 $R^2$ is lower alkoxy;
 $R^4$ is —O—CH(aryl)(alkyl)$R^{16}$; and
 m and o are 1 and n and p are zero.

4. A compound according to claim 1 wherein
 $R^2$ is substituted on the phenyl moiety at the 4-position relative to $R^1$ and $R^4$ is substituted on the phenyl moiety at the 2-position relative to $R^1$.

5. A compound according claim 1 wherein
p is 1; and
$R^5$ is substituted on the phenyl moiety at the ortho position relative to $R^1$.

6. A compound of claim 1 wherein $R^{15}$ is phenyl or phenyl substituted at the ortho position relative to the attachment of the phenyl group to the rest of the $R^4$ moiety, and is optionally further substituted.

7. A compound of claim 1 wherein $R^{15}$ is phenyl substituted at the ortho position relative to the attachment of the phenyl group to the rest of the $R^4$ moiety by methyl, and is optionally further substituted.

8. A compound of claim 1 wherein $R^{15}$ is phenyl substituted by one or more substituents selected from lower alkyl, halo, $CF_3$, CN or lower alkoxy.

9. A compound according to claim 1 wherein
$R^2$ and $R^3$ are independently aryl lower alkoxy.

10. A compound according to claim 1 wherein
Y is oxygen.

11. A compound according to claim 1 wherein
n is zero.

12. A compound according to claim 1 wherein
$R^4$ is $—Y—CH(R^{15})(C_{1-3}alkyl)R^{16}$.

13. A compound of formuna Ia

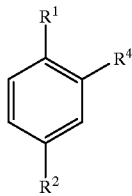

wherein $R^1$, $R^2$ and $R^4$ are as defined in claim 1, or a pharmaceutically acceptable salt or prodrug thereof.

14. A compound according to claim 13 wherein $R^4$ is $—OCH(R^{15})(alkyl)R^{16}$ wherein $R^{15}$ is aryl and $R^{16}$ is carboxy.

15. A compound according to claim 14 wherein $R^{15}$ is phenyl substituted in the ortho position relative to the attachment of the phenyl group to the rest of the $R^4$ moiety by a lower alkyl or chloro substituent and is optionally further substituted by one or more of halo, lower alkyl, $CF_3$, CN or lower alkoxy.

16. A compound according to claim 14 wherein within $—OCH(R^{15})(alkyl)R^{16}$ the alkyl portion is $—CH_2CH_2—$.

17. A compound of formula Ib

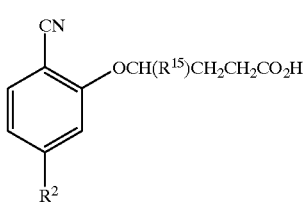

wherein $R^2$ and $R^{15}$ are a defined in claim 1, or a pharmaceutically acceptable salt or prodrug thereof.

18. A compound according to claim 1 which is:

(RS)-4-[2-Cyano-5-benzyloxyphenoxy]-4-phenyl-butanoic acid;

Ethyl (RS)-4-(2-cyano-5-benzyloxyphenoxy)-4-phenylbutanoate; or (RS)-4-{5-[3-(2-Carboxyethyl)benzyloxy]-2-cyano-phenoxy}-4-(2-methylphenyl)butanoic acid, or a phamaceutically acceptable salt or prodrug thereof.

19. A pharmaceutical composition comprising a pharmaceutically effective amount of a compound according to claim 1 and a pharmaceutically acceptable carrier or excipient.

20. A method for treating pulmonary hypertension comprising administering to a patient suffering from pulmonary hypertension an effective amount of a compound of claim 1.

* * * * *